(12) United States Patent
Haruyama et al.

(10) Patent No.: US 12,043,618 B2
(45) Date of Patent: Jul. 23, 2024

(54) ORGANIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Takuya Haruyama, Kanagawa (JP); Sachiko Kawakami, Kanagawa (JP); Naoaki Hashimoto, Kanagawa (JP); Yusuke Takita, Kanagawa (JP); Tsunenori Suzuki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 18/096,204

(22) Filed: Jan. 12, 2023

(65) Prior Publication Data

US 2023/0150988 A1 May 18, 2023

Related U.S. Application Data

(63) Continuation of application No. 16/609,284, filed as application No. PCT/IB2018/052746 on Apr. 20, 2018, now Pat. No. 11,555,030.

(30) Foreign Application Priority Data

May 2, 2017 (JP) .................................. 2017-091582

(51) Int. Cl.
*C07D 407/12* (2006.01)
*H10K 50/11* (2023.01)
(Continued)

(52) U.S. Cl.
CPC ............ *C07D 407/12* (2013.01); *H10K 50/11* (2023.02); *H10K 50/84* (2023.02); *H10K 77/10* (2023.02);
(Continued)

(58) Field of Classification Search
None
See application file for complete search history.

(56) References Cited

U.S. PATENT DOCUMENTS 7,906,226 B2   3/2011   Matsuura et al.
8,105,701 B2   1/2012   Matsuura et al.
(Continued)

FOREIGN PATENT DOCUMENTS

CN   105683173 A    6/2016
CN   106170481 A   11/2016
(Continued)

OTHER PUBLICATIONS

Niimi, Kazuki, et al. "[2,2'] Bi [naphtho [2, 3-b] furanyl]: a versatile organic semiconductor with a furan-furan junction." Chemical Communications 48.47 (2012): 5892-5894. (Year: 2012).*
(Continued)

*Primary Examiner* — Robert S Loewe
(74) *Attorney, Agent, or Firm* — Husch Blackwell LLP

(57) ABSTRACT

An organic compound has a benzonaphthofuran skeleton and is represented by General Formula (G1). In General Formula (G1), A represents a pyrene skeleton. In the case where the pyrene skeleton has a substituent, the substituent is a diarylamino group including two substituted or unsubstituted aryl groups each having 6 to 13 carbon atoms, a substituted or unsubstituted aryl group having 6 to 13 carbon atoms, an alkyl group having 1 to 7 carbon atoms, a substituted or unsubstituted monocyclic saturated hydrocarbon group having 3 to 20 carbon atoms, or a substituted or
(Continued)

unsubstituted polycyclic saturated hydrocarbon group having 7 to 10 carbon atoms. The two aryl groups of the diarylamino group may be the same or different. In X1 represented by General Formula (G1-1), one of R6 and R7 is bonded to N in General Formula (G1), and the other of R6 and R7 represents an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms.

3 Claims, 37 Drawing Sheets

(51) Int. Cl.
　　*H10K 50/84*　　(2023.01)
　　*H10K 77/10*　　(2023.01)
　　*H10K 85/60*　　(2023.01)
　　H10K 50/15　　(2023.01)
　　H10K 50/16　　(2023.01)
　　H10K 50/17　　(2023.01)
　　H10K 101/10　　(2023.01)

(52) U.S. Cl.
　　CPC ....... *H10K 85/633* (2023.02); *H10K 85/6574* (2023.02); *H10K 50/15* (2023.02); *H10K 50/16* (2023.02); *H10K 50/171* (2023.02); *H10K 2101/10* (2023.02)

(56) References Cited

U.S. PATENT DOCUMENTS

| | | | |
|---|---|---|---|
| 8,470,455 | B2 | 6/2013 | Matsuura et al. |
| 8,822,434 | B2 | 9/2014 | Liang et al. |
| 9,093,649 | B2 | 7/2015 | Kawakami et al. |
| 9,303,053 | B2 | 4/2016 | Liang et al. |
| 9,526,739 | B2 | 12/2016 | Liang et al. |
| 9,586,924 | B2 | 3/2017 | Kawakami et al. |
| 9,899,603 | B2 | 2/2018 | Kawakami et al. |
| 10,424,741 | B2 | 9/2019 | Lee et al. |
| 2014/0326985 | A1 | 11/2014 | Mizuki et al. |
| 2014/0353646 | A1 | 12/2014 | Mizuki et al. |
| 2015/0031900 | A1 | 1/2015 | Kawakami et al. |
| 2015/0329514 | A1 | 11/2015 | Kawakami et al. |
| 2015/0349284 | A1 | 12/2015 | Seo et al. |
| 2016/0126500 | A1 | 5/2016 | Uesaka et al. |
| 2016/0166591 | A1 | 6/2016 | Liang et al. |
| 2016/0284998 | A1 | 9/2016 | Kawamura et al. |
| 2017/0040535 | A1 | 2/2017 | Ogita et al. |
| 2017/0229648 | A1 | 8/2017 | Kawakami et al. |
| 2019/0378992 | A1 | 12/2019 | Skulason et al. |

FOREIGN PATENT DOCUMENTS

| | | |
|---|---|---|
| CN | 106432157 A | 2/2017 |
| DE | 112014003458 T5 | 4/2016 |
| DE | 102016214546 A1 | 2/2017 |
| EP | 1 718 122 A1 | 11/2006 |
| EP | 3 196 198 A1 | 7/2017 |
| JP | 08-092134 A | 4/1996 |
| JP | 2010-182699 A | 8/2010 |
| JP | 2015-013805 A | 1/2015 |
| JP | 2015-013807 A | 1/2015 |
| JP | 2015-042636 A | 3/2015 |
| JP | 2015-181169 A | 10/2015 |
| JP | 2017-036267 A | 2/2017 |
| JP | 2018-084206 A | 5/2018 |
| KR | 2014-0095072 A | 7/2014 |
| KR | 2016-0034937 A | 3/2016 |
| KR | 2016-0130874 A | 11/2016 |
| KR | 2017-0017761 A | 2/2017 |
| KR | 2017-0055444 A | 5/2017 |
| KR | 2017-0134793 A | 12/2017 |
| TW | 201326364 | 7/2013 |
| TW | 201509937 | 3/2015 |
| TW | 201538498 | 10/2015 |
| TW | 201731840 | 9/2017 |
| WO | WO 2011/103552 A2 | 8/2011 |
| WO | WO 2013/042775 A1 | 3/2013 |
| WO | WO 2013/077405 A1 | 5/2013 |
| WO | WO 2015/011614 A1 | 1/2015 |
| WO | WO 2015/194791 A2 | 12/2015 |
| WO | WO 2016/042772 A1 | 3/2016 |

OTHER PUBLICATIONS

Supporting information for Niimi, Kazuki, et al. "[2,2'] Bi [naphtho [2, 3-b] furanyl]: a versatile organic semiconductor with a furan-furan junction." Chemical Communications 48.47 (2012): 5892-5894. (Year: 2012).*
Rong, Ming-Guang, et al. "De novo synthesis of phenols and naphthols through oxidative cycloaromatization of dienynes." Organic letters 20.19 (2018): 6289-6293. (Year: 2018).*
International Search Report (Application No. PCT/IB2018/052746) dated Jul. 24, 2018.
Written Opinion (Application No. PCT/IB2018/052746) dated Jul. 24, 2018.
Chinese Office Action (Application No. 201880025312.4) dated Sep. 29, 2022.

* cited by examiner

ORGANIC COMPOUND, LIGHT-EMITTING ELEMENT, LIGHT-EMITTING DEVICE, ELECTRONIC DEVICE, AND LIGHTING DEVICE

This application is a continuation of copending U.S. application Ser. No. 16/609,284, filed on Oct. 29, 2019 which is a 371 of international application PCT/IB2018/052746 filed on Apr. 20, 2018 which are all incorporated herein by reference.

TECHNICAL FIELD

One embodiment of the present invention relates to an organic compound, a light-emitting element, a light-emitting device, an electronic device, and a lighting device. Note that one embodiment of the present invention is not limited to the above technical field. That is, one embodiment of the present invention relates to an object, a method, a manufacturing method, or a driving method. One embodiment of the present invention relates to a process, a machine, manufacture, or a composition of matter. Specific examples include a semiconductor device, a display device, a liquid crystal display device, and the like.

BACKGROUND ART

A light-emitting element including an electroluminescent (EL) layer between a pair of electrodes (also referred to as an organic EL element) has characteristics such as thinness, light weight, high-speed response to input signals, and low power consumption; thus, a display including such a light-emitting element has attracted attention as a next-generation flat panel display.

In a light-emitting element, voltage application between a pair of electrodes causes, in an EL layer, recombination of electrons and holes injected from the electrodes, which brings a light-emitting substance (organic compound) contained in the EL layer into an excited state. Light is emitted when the light-emitting substance returns to the ground state from the excited state. The excited state can be a singlet excited state (S*) and a triplet excited state (T*). Light emission from a singlet excited state is referred to as fluorescence, and light emission from a triplet excited state is referred to as phosphorescence. The statistical generation ratio thereof in the light-emitting element is considered to be S*:T*=1:3. Since the spectrum of light emitted from a light-emitting substance depends on the light-emitting substance, the use of different types of organic compounds as light-emitting substances makes it possible to obtain light-emitting elements which exhibit various colors.

In order to improve element characteristics of such a light-emitting element, improvement of an element structure, development of a material, and the like have been actively carried out (see Patent Document 1, for example).

REFERENCE

[Patent Document 1] Japanese Published Patent Application No. 2010-182699

DISCLOSURE OF INVENTION

In development of light-emitting elements, organic compounds used in the light-emitting element are very important for improving the characteristics. Thus, an object of one embodiment of the present invention is to provide a novel organic compound. That is, an object is to provide a novel organic compound that is effective in improving the element characteristics and reliability. Another object of one embodiment of the present invention is to provide a novel organic compound that can be used in a light-emitting element. Another object of one embodiment of the present invention is to provide a novel organic compound that can be used in an EL layer of a light-emitting element. Another object is to provide a highly efficient, highly reliable, and novel light-emitting element using a novel organic compound of one embodiment of the present invention. Another object is to provide a novel light-emitting element using a novel organic compound of one embodiment of the present invention and emitting blue light with high color purity. Another object is to provide a novel light-emitting device, a novel electronic device, or a novel lighting device. Note that the description of these objects does not disturb the existence of other objects. In one embodiment of the present invention, there is not necessarily a need to achieve all the objects. Other objects will be apparent from and can be derived from the description of the specification, the drawings, the claims, and the like.

One embodiment of the present invention is an organic compound which has a benzonaphthofuran skeleton and is represented by General Formula (G1) below.

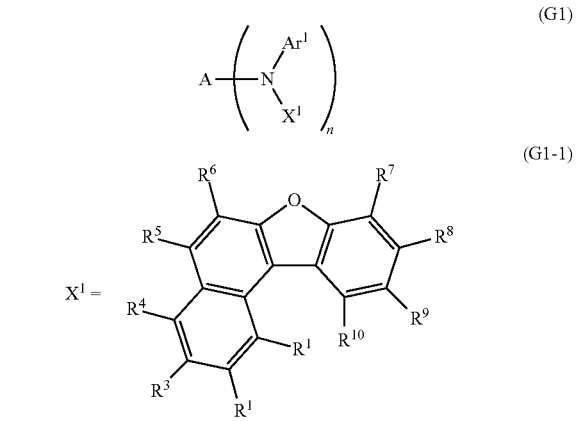

In General Formula (G1), A represents a pyrene skeleton. In the case where the pyrene skeleton has a substituent, the substituent is a diarylamino group including two substituted or unsubstituted aryl groups each having 6 to 13 carbon atoms, a substituted or unsubstituted aryl group having 6 to 13 carbon atoms, an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. The two aryl groups of the diarylamino group may be the same or different. In $X^1$ represented by General Formula (G1-1), one of $R^6$ and $R^7$ is bonded to N in General Formula (G1), and the other of $R^6$ and $R^7$ represents an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. $Ar^1$ represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms. In addition, n represents 1 to 4, and in the case where n is 2 or more, amine skeletons may be the same or different.

Another embodiment of the present invention is an organic compound represented by General Formula (G2) below.

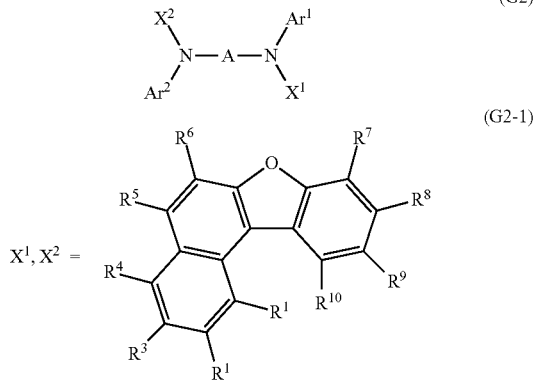

In General Formula (G2), A represents a substituted or unsubstituted pyrene skeleton. $X^1$ and $X^2$ represented by General Formula (G2-1) are independent of each other. One of $R^6$ and $R^7$ is bonded to N in General Formula (G2), and the other of $R^6$ and $R^7$ represents an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. Each of $Ar^1$ and $Ar^2$ independently represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

In each of the above embodiments, the other of $R^6$ and $R^7$ is preferably a monocyclic saturated hydrocarbon group having 3 to 20 carbon atoms. The monocyclic saturated hydrocarbon group having 3 to 20 carbon atoms is further preferably a cyclohexyl group.

Another embodiment of the present invention is as follows. In General Formula (G2), A represents a substituted or unsubstituted pyrene skeleton. $X^1$ and $X^2$ represented by General Formula (G2-1) are independent of each other. One of $R^6$ and $R^7$ is bonded to N in General Formula (G2), and the other of $R^6$ and $R^7$ represents a trialkylsilyl group having 3 to 18 carbon atoms or a substituted or unsubstituted triarylsilyl group having 18 to 30 carbon atoms. Each of $Ar^1$ and $Ar^2$ independently represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

Another embodiment of the present invention is an organic compound represented by General Formula (G3) below.

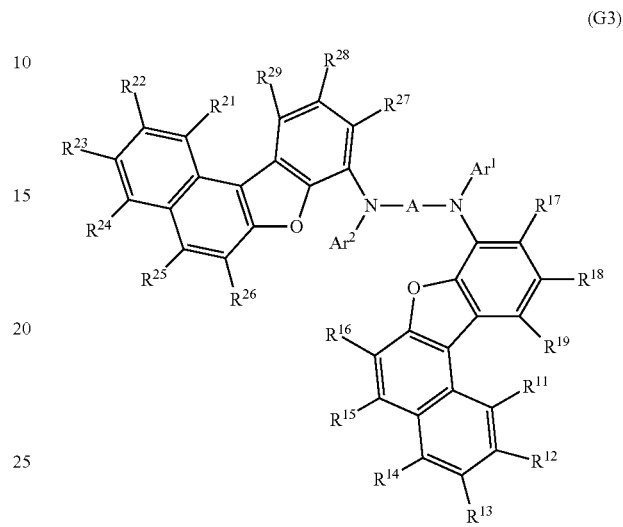

In General Formula (G3), A represents a substituted or unsubstituted pyrene skeleton. $R^{16}$ and $R^{26}$ each represent an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. Each of $R^{11}$ to $R^{15}$, $R^{17}$ to $R^{19}$, $R^{21}$ to $R^{25}$, and $R^{27}$ to $R^{29}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

In the above embodiment, $R^{16}$ and $R^{26}$ are each preferably a monocyclic saturated hydrocarbon group having 3 to 20 carbon atoms. The monocyclic saturated hydrocarbon group having 3 to 20 carbon atoms is further preferably a cyclohexyl group.

Another embodiment of the present invention is an organic compound represented by General Formula (G4) below.

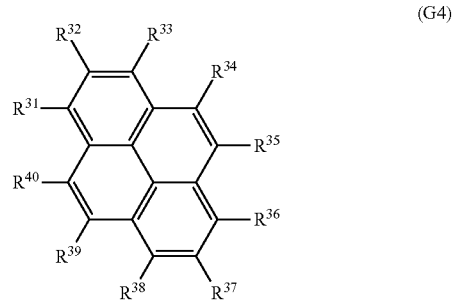

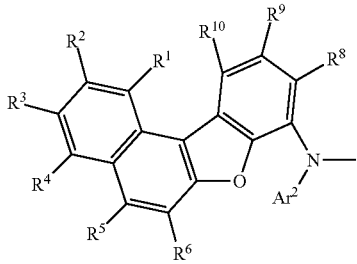

(G4-1)

In General Formula (G4), at least one of $R^{31}$, $R^{33}$, $R^{35}$, and $R^{38}$ has a group represented by General Formula (G4-1). In the case where two or more of $R^{31}$, $R^{33}$, $R^{35}$, and $R^{38}$ have the group represented by General Formula (G4-1), they may have the same structure or different structures. $R^6$ represents an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. Each of all those which, out of $R^{31}$ to $R^{40}$, do not have the group represented by General Formula (G4-1) and $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

In each of the above embodiments, $R^6$ is preferably a monocyclic saturated hydrocarbon group having 3 to 20 carbon atoms. The monocyclic saturated hydrocarbon group having 3 to 20 carbon atoms is further preferably a cyclohexyl group.

The above-described organic compound of one embodiment of the present invention has a structure in which an amine is bonded to the pyrene skeleton and the amine and the benzonaphthofuran skeleton are bonded. The amine is bonded to one of 6- and 8-positions of the benzonaphthofuran skeleton, and the other of the 6- and 8-positions of the benzonaphthofuran skeleton (the position to which the amine is not bonded) has a specific substituent, i.e., an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. Note that such a structure enables the emission spectrum to be narrowed. The narrowed emission spectrum can improve the element characteristics of, for example, a top-emission light-emitting element having a microcavity structure. In addition, the use of such a material in manufacturing a light-emitting element can improve the reliability of the light-emitting element. Furthermore, such a structure improves the sublimability of a compound and can therefore reduce decomposition of the compound at the time of evaporation. Suppression of decomposition at the time of evaporation makes it possible to provide a highly reliable light-emitting element. It is preferable that the above-described specific substituent be a monocyclic saturated hydrocarbon group having 3 to 20 carbon atoms because the above effect is significant and the yield of synthesis is high. It is particularly preferable that the specific substituent be a cyclohexyl group.

Another embodiment of the present invention is an organic compound represented by Structural Formula (100) or Structural Formula (101).

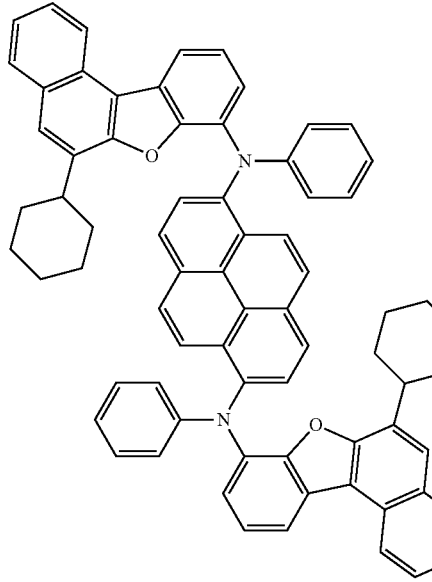

(100)

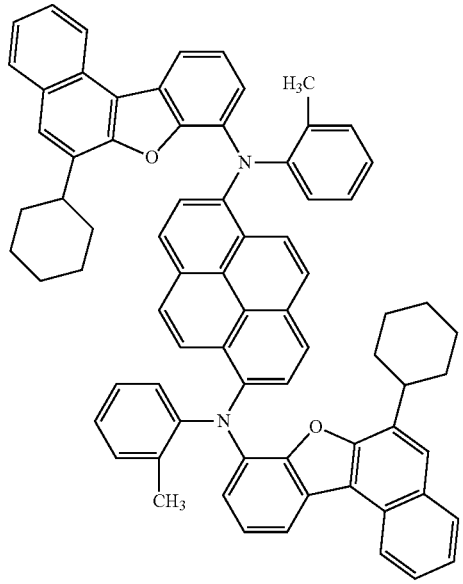

(101)

Another embodiment of the present invention is a light-emitting element containing the organic compound of one embodiment of the present invention. Note that the present invention also includes a light-emitting element containing a host material in addition to the above organic compound.

Another embodiment of the present invention is a light-emitting element containing the organic compound of one embodiment of the present invention. Note that the present invention also includes a light-emitting element in which an EL layer provided between a pair of electrodes or a light-emitting layer included in the EL layer contains the organic compound of one embodiment of the present invention. In addition to the above light-emitting elements, a light-emitting device including a transistor, a substrate, or the like is also included in the scope of the invention. Furthermore, in addition to the light-emitting device, an electronic device and a lighting device that include a microphone, a camera, an operation button, an external connection portion, a housing, a cover, a support, a speaker, or the like are also included in the scope of the invention.

One embodiment of the present invention includes, in its scope, a light-emitting device including a light-emitting element, and a lighting device including the light-emitting device. Accordingly, the light-emitting device in this specification refers to an image display device and a light source (including a lighting device). In addition, the light-emitting device includes, in its category, all of a module in which a connector such as a flexible printed circuit (FPC) or a tape carrier package (TCP) is connected to a light-emitting device, a module in which a printed wiring board is provided at the end of a TCP, and a module in which an integrated circuit (IC) is directly mounted on a light-emitting element by a chip on glass (COG) method.

According to one embodiment of the present invention, a novel organic compound can be provided. In other words, a novel organic compound that is effective in improving the element characteristics can be provided. According to one embodiment of the present invention, a novel organic compound that can be used in a light-emitting element can be provided. According to one embodiment of the present invention, a novel organic compound that can be used in an EL layer of a light-emitting element can be provided. According to one embodiment of the present invention, a highly efficient, highly reliable, and novel light-emitting element using a novel organic compound of one embodiment of the present invention can be provided. According to one embodiment of the present invention, a novel light-emitting element using a novel organic compound of one embodiment of the present invention and emitting blue light with high color purity can be provided. In addition, a novel light-emitting device, a novel electronic device, or a novel lighting device can be provided. Note that the description of these effects does not disturb the existence of other effects. In one embodiment of the present invention, there is not necessarily a need to achieve all the effects. Other effects will be apparent from and can be derived from the description of the specification, the drawings, the claims, and the like.

BEST MODE FOR CARRYING OUT THE INVENTION

Figure 1A:
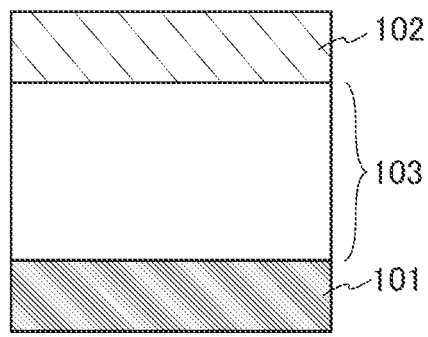
FIGS. 1A to 1E illustrate structures of light-emitting elements.

Embodiments of the present invention will be described below with reference to the drawings. Note that the present invention is not limited to the following description, and the modes and details of the present invention can be modified in various ways without departing from the spirit and scope of the present invention. Therefore, the present invention should not be construed as being limited to the description in the following embodiments.

Note that the position, size, range, or the like of each component illustrated in drawings and the like is not accurately represented in some cases for easy understanding. Therefore, the disclosed invention is not necessarily limited to the position, size, range, or the like disclosed in the drawings and the like.

In the description of modes of the present invention with reference to the drawings in this specification and the like, the same components in different diagrams are commonly denoted by the same reference numeral.

Embodiment 1

In this embodiment, organic compounds each of which is one embodiment of the present invention are described.

Note that an organic compound described in this embodiment has a structure which has a benzonaphthofuran skeleton and is represented by General Formula (G1) below.

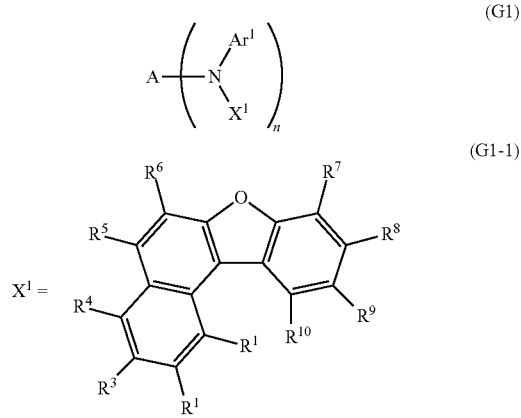

In General Formula (G1), A represents a pyrene skeleton. In the case where the pyrene skeleton has a substituent, the substituent is a diarylamino group including two substituted or unsubstituted aryl groups each having 6 to 13 carbon atoms, a substituted or unsubstituted aryl group having 6 to 13 carbon atoms, an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. The two aryl groups of the diarylamino group may be the same or different. In $X^1$ represented by General Formula (G1-1), one of $R^6$ and $R^7$ is bonded to N in General Formula (G1), and the other of $R^6$ and $R^7$ represents an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. $Ar^1$ represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms. In addition, n represents 1 to 4, and in the case where n is 2 or more, amine skeletons may be the same or different.

An organic compound described in this embodiment is represented by General Formula (G2) below.

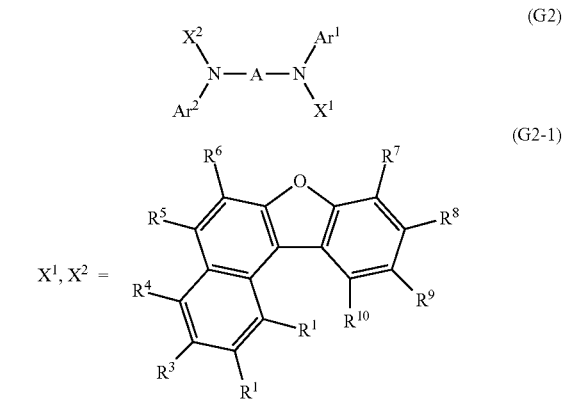

In General Formula (G2), A represents a substituted or unsubstituted pyrene skeleton. $X^1$ and $X^2$ represented by General Formula (G2-1) are independent of each other. One of $R^6$ and $R^7$ is bonded to N in General Formula (G2), and the other of $R^6$ and $R^7$ represents an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. Each of $Ar^1$ and $Ar^2$ independently represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

In each of the above structures, the other of $R^6$ and $R^7$ is preferably a monocyclic saturated hydrocarbon group having 3 to 20 carbon atoms. The monocyclic saturated hydrocarbon group having 3 to 20 carbon atoms is further preferably a cyclohexyl group.

Another embodiment of the present invention is as follows. In General Formula (G2), A represents a substituted or unsubstituted pyrene skeleton. $X^1$ and $X^2$ represented by General Formula (G2-1) are independent of each other. One of $R^6$ and $R^7$ is bonded to N in General Formula (G2), and the other of $R^6$ and $R^7$ represents a trialkylsilyl group having 3 to 18 carbon atoms or a substituted or unsubstituted triarylsilyl group having 18 to 30 carbon atoms. Each of $Ar^1$ and $Ar^2$ independently represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

In the case where one of $R^6$ and $R^7$ in General Formula (G2-1) is a trialkylsilyl group having 3 to 18 carbon atoms, examples of the trialkylsilyl group include a trimethylsilyl group, a triethylsilyl group, a tri(n-propyl)silyl group, a triisopropylsilyl group, a tri(n-butyl)silyl group, a tri(sec-butyl)silyl group, a triisobutylsilyl group, a tri(tert-butyl)silyl group, a tri(n-pentyl)silyl group, a triisopenthylsilyl group, a tri(sec-pentyl)silyl group, a tri(tert-pentyl)silyl group, a trineopentylsilyl group, a tri(n-hexyl)silyl group, a triisohexylsilyl group, a tri(sec-hexyl)silyl group, a tri(tert-hexyl)silyl group, a trineohexylsilyl group, a tri(3-methylpentyl)silyl group, a tri(2-methylpentyl)silyl group, a tri(2-ethylbutyl)silyl group, a tri(1,2-dimethylbutyl)silyl group, a tri(2,3-dimethylbutyl)silyl group, and the like. In the case where one of $R^6$ and $R^7$ is a substituted or unsubstituted triarylsilyl group having 18 to 30 carbon atoms, examples of the triarylsilyl group include a triphenylsilyl group, a tri(1-naphthyl)silyl group, a tri(2-naphthyl)silyl group, a tri(ortho-tolyl)silyl group, a tri(meta-tolyl)silyl group, a tri(para-tolyl)silyl group, a trimesitylsilyl group, a tri(para-tert-butylphenyl)silyl group, and the like.

An organic compound described in this embodiment is represented by General Formula (G3) below.

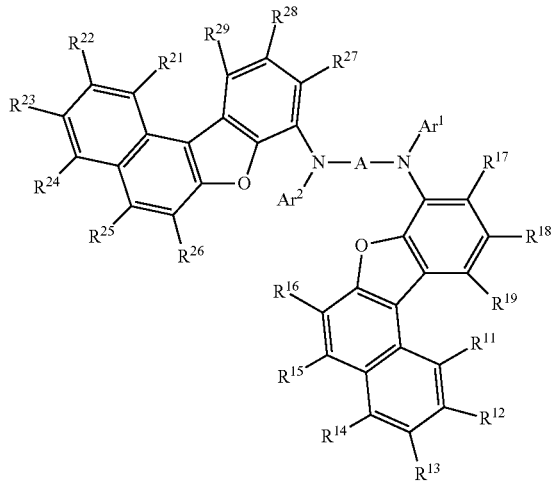

(G3)

In General Formula (G3), A represents a substituted or unsubstituted pyrene skeleton. $R^{16}$ and $R^{26}$ each represent an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. Each of $R^{11}$ to $R^{15}$, $R^{17}$ to $R^{19}$, $R^{21}$ to $R^{25}$, and $R^{27}$ to $R^{29}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

In the above structure, $R^{16}$ and $R^{26}$ are each preferably a monocyclic saturated hydrocarbon group having 3 to 20 carbon atoms. The monocyclic saturated hydrocarbon group having 3 to 20 carbon atoms is further preferably a cyclohexyl group.

An organic compound described in this embodiment is represented by General Formula (G4) below.

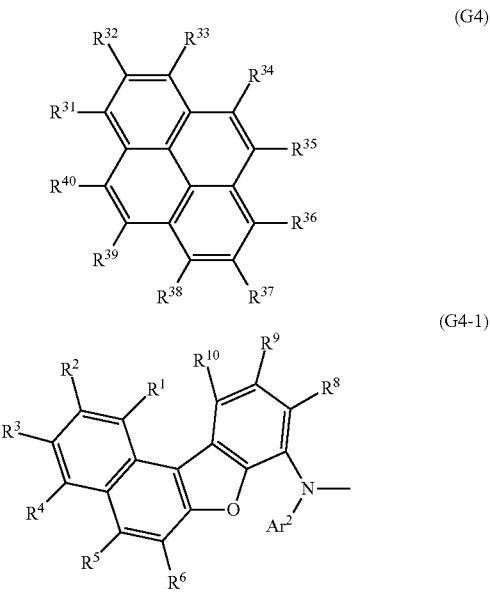

(G4)

(G4-1)

In General Formula (G4), at least one of $R^{31}$, $R^{33}$, $R^{35}$, and $R^{38}$ has a group represented by General Formula (G4-1). In the case where two or more of $R^{31}$, $R^{33}$, $R^{35}$, and $R^{38}$ have the group represented by General Formula (G4-1), they may have the same structure or different structures. $R^6$ represents an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. Each of all those which, out of $R^{31}$ to $R^{40}$, do not have the group represented by General Formula (G4-1) and $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

In each of the above structures, $R^6$ is preferably a monocyclic saturated hydrocarbon group having 3 to 20 carbon atoms. The monocyclic saturated hydrocarbon group having 3 to 20 carbon atoms is further preferably a cyclohexyl group.

In the case where the pyrene skeleton represented by A in each of General Formulae (G1) to (G3) has a substituent, examples of the substituent include a diarylamino group including two substituted or unsubstituted aryl groups each having 6 to 13 carbon atoms, a substituted or unsubstituted aryl group having 6 to 13 carbon atoms, an alkyl group having 1 to 7 carbon atoms, a substituted or unsubstituted monocyclic saturated hydrocarbon group having 3 to 20 carbon atoms, and a substituted or unsubstituted polycyclic saturated hydrocarbon group having 7 to 10 carbon atoms. Specific examples of the substituent include those which are represented by Structural Formulae (01) to (58) below.

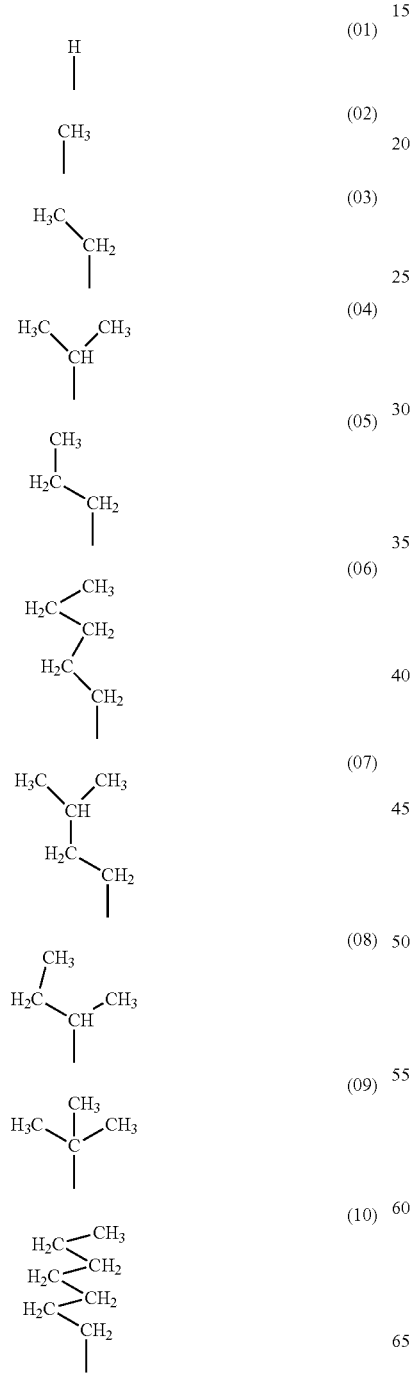

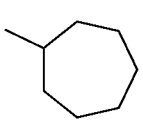

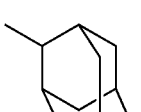

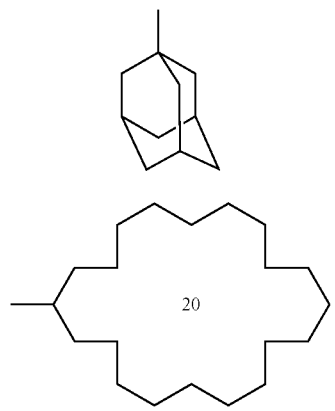

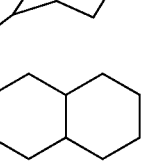

(23)
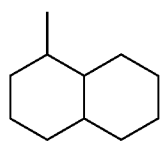
(24)
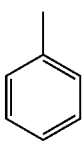
(25)
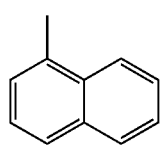
(26)
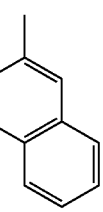
(27)
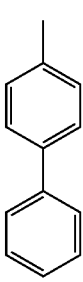
(28)
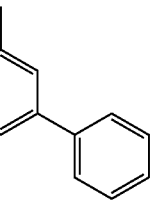
(29)
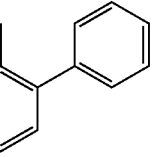
(30)
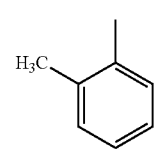
(31)
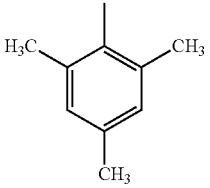
(32)
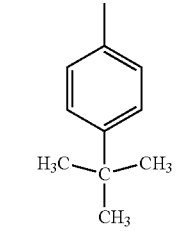
(33)
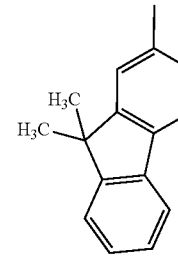
(34)
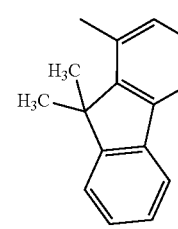
(35)
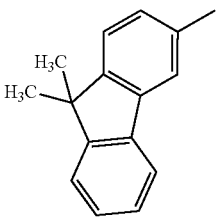
(36)
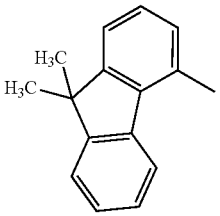
(37)
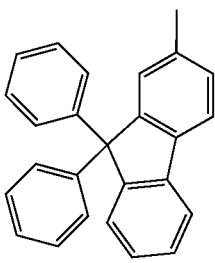

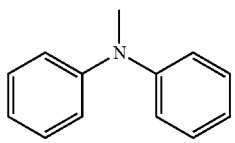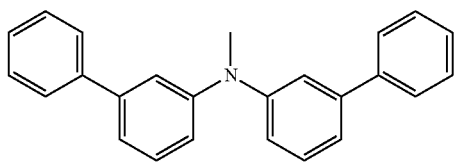

-continued

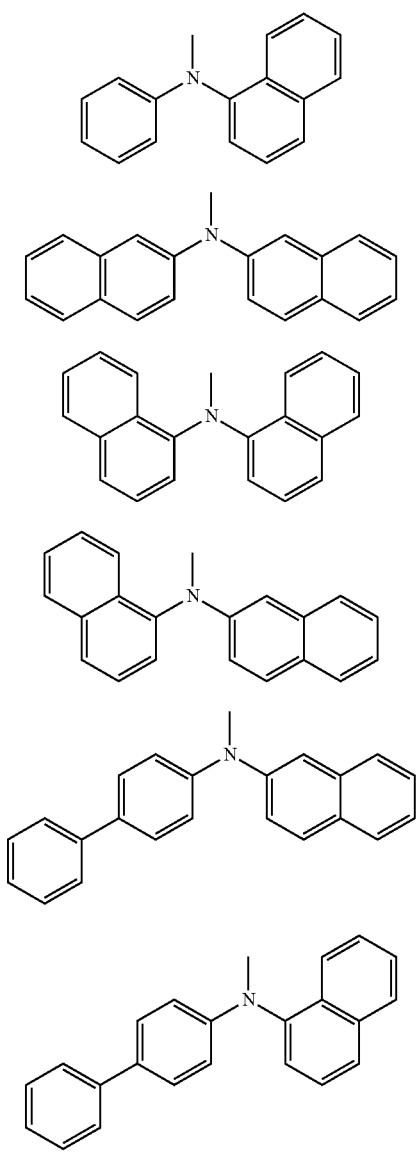

(53)
(54)
(55)
(56)
(57)
(58)

In any of General Formulae (G1) to (G3), in the case where the diarylamino group including two substituted or unsubstituted aryl groups each having 6 to 13 carbon atoms, the substituted or unsubstituted aryl group having 6 to 13 carbon atoms, the substituted or unsubstituted monocyclic saturated hydrocarbon group having 3 to 20 carbon atoms, or the substituted or unsubstituted polycyclic saturated hydrocarbon group having 7 to 10 carbon atoms has a substituent, examples of the substituent include an alkyl group having 1 to 7 carbon atoms, such as a methyl group, an ethyl group, a propyl group, an isopropyl group, a butyl group, an isobutyl group, a sec-butyl group, a tert-butyl group, a pentyl group, or a hexyl group; a cycloalkyl group having 5 to 7 carbon atoms, such as a cyclopentyl group, a cyclohexyl group, a cycloheptyl group, or a 8,9,10-trinorbornanyl group; an aryl group having 6 to 12 carbon atoms, such as a phenyl group, a naphthyl group, or a biphenyl group; and the like.

Specific examples of the monocyclic saturated hydrocarbon group having 3 to 20 carbon atoms in any of General Formulae (G1) to (G4) include a cyclopropyl group, a cyclopentyl group, a cyclohexyl group, a cycloheptyl group, a 2-methylcyclohexyl group, a cyclooctyl group, a cyclononyl group, a cyclodecyl group, a cycloicosyl group, and the like.

Specific examples of the polycyclic saturated hydrocarbon group having 7 to 10 carbon atoms in any of General Formulae (G1) to (G4) include a 8,9,10-trinorbornanyl group, a decahydronaphthyl group, an adamantyl group, and the like.

Specific examples of the aryl group having 6 to 13 carbon atoms in any of General Formulae (G1) to (G4) include a phenyl group, an o-tolyl group, an m-tolyl group, a p-tolyl group, a mesityl group, an o-biphenyl group, an m-biphenyl group, a p-biphenyl group, a 1-naphthyl group, a 2-naphthyl group, a fluorenyl group, a 9,9-dimethylfluorenyl group, and the like.

Specific examples of the alkyl group having 1 to 7 carbon atoms in any of General Formulae (G1) to (G4) include a methyl group, an ethyl group, a propyl group, an isopropyl group, a butyl group, an isobutyl group, a sec-butyl group, a tert-butyl group, a pentyl group, an isopentyl group, a sec-pentyl group, a tert-pentyl group, a neopentyl group, a hexyl group, an isohexyl group, a 3-methylpentyl group, a 2-methylpentyl group, a 2-ethylbutyl group, a 1,2-dimethylbutyl group, a 2,3-dimethylbutyl group, an n-heptyl group, and the like.

In addition, the other of $R^6$ and $R^7$ in General Formula (G1-1) or (G2-1) or $R^6$ in General Formula (G4-1) represents an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms, and specific examples thereof include those which are represented by Structural Formulae (02) to (23) below.

(02)

(03)

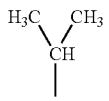
(04)

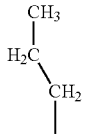
(05)

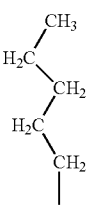
(06)

-continued
(07) 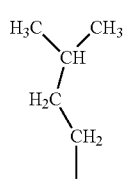
(08) 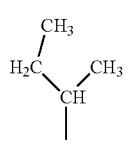
(09) 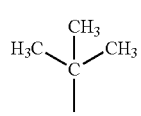
(10) 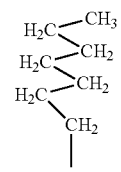
(11) 
(12) 
(13) 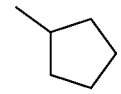
(14) 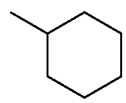
(15) 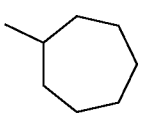
(16) 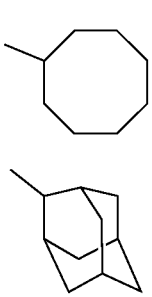
(17) 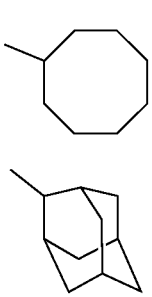
(18) 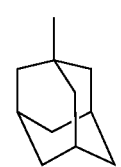
-continued
(19) 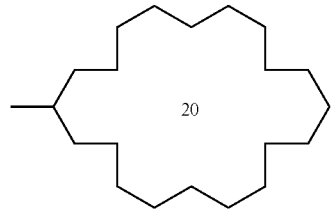
(20) 
(21) 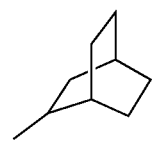
(22) 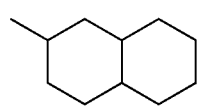
(23) 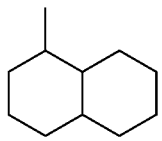
In addition, $Ar^1$ in General Formula (G1), $Ar^1$ and $Ar^2$ in General Formula (G2), $Ar^1$ and $Ar^2$ in General Formula (G3), or $Ar^2$ in General Formula (G4) represent(s) a substituted or unsubstituted aryl group having 6 to 13 carbon atoms, and specific examples thereof include those which are represented by Structural Formulae (24) to (37) below.
(24) 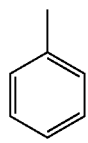
(25) 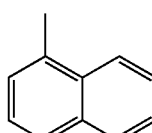
(26) 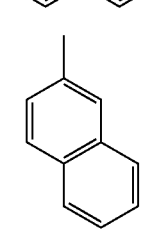

(27) 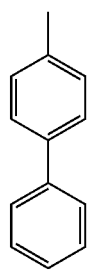

(28) 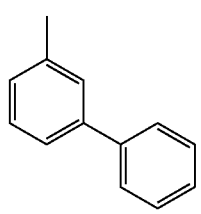

(29) 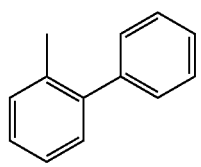

(30) 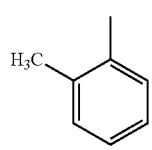

(31) 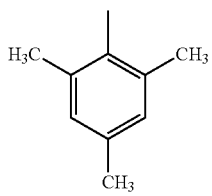

(32) 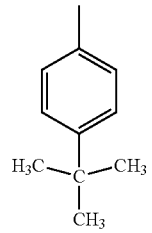

(33) 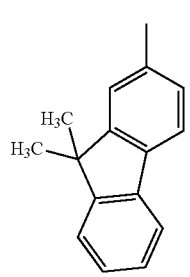

(34) 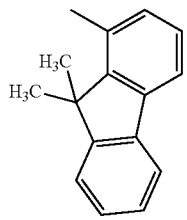

(35) 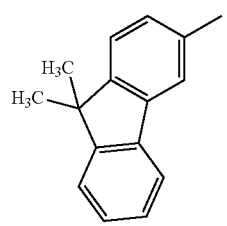

(36) 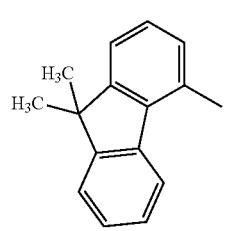

(37) 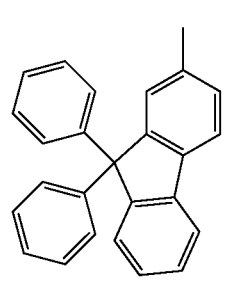

In addition, each of $R^1$ to $R^5$ and $R^8$ to $R^{10}$ in any of General Formulae (G1-1), (G2-1), and (G4-1) independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms, and specific examples thereof include those which are represented by Structural Formulae (01) to (32) below.

(01) H

(02) CH₃

(03) H₃C—CH₂—

(04) H₃C   CH₃
      \\ /
       CH
       |

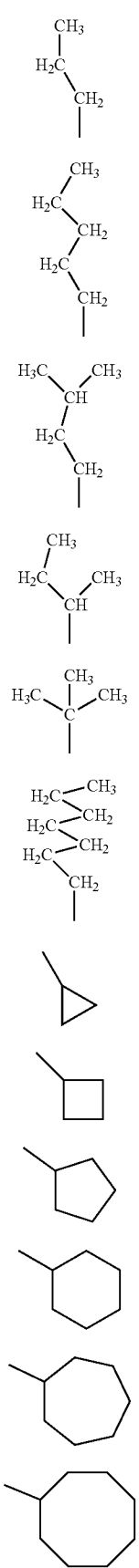
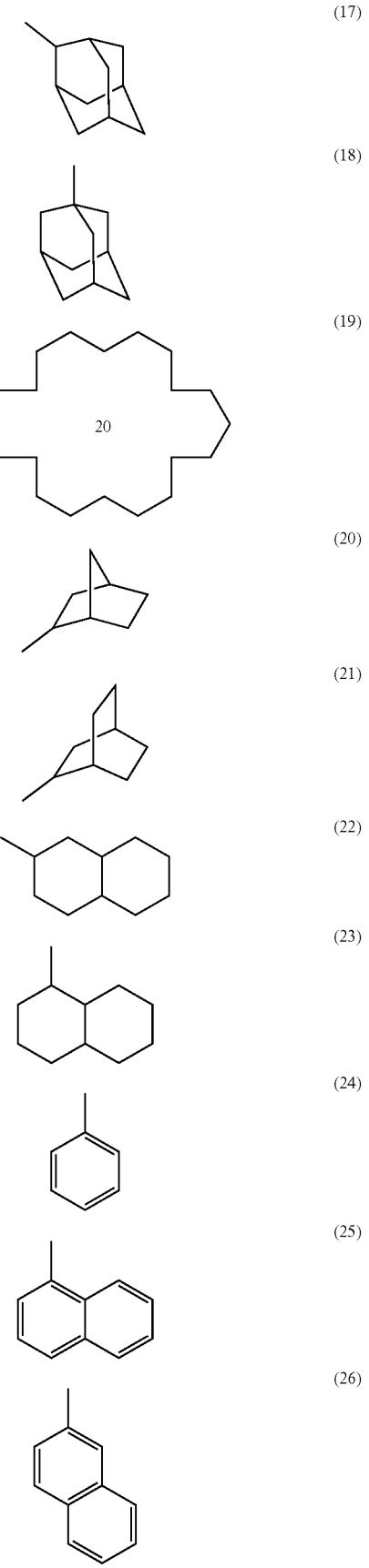

(27)

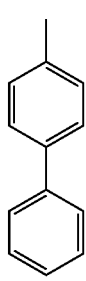

(28)

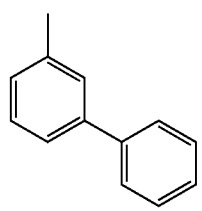

(29)

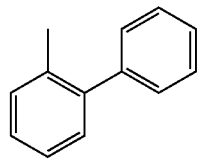

(30)

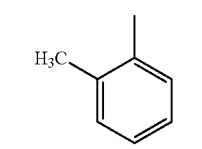

(31)

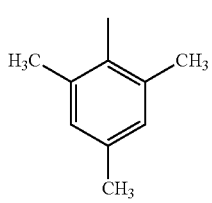

(32)

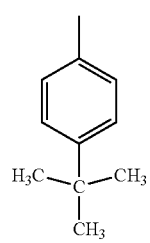

The above-described organic compound of one embodiment of the present invention, which is represented by any of General Formulae (G1) to (G4), has a structure in which an amine is bonded to the pyrene skeleton and the amine and the benzonaphthofuran skeleton are bonded. The amine is bonded to one of 6- and 8-positions of the benzonaphthofuran skeleton, and the other of the 6- and 8-positions of the benzonaphthofuran skeleton (the position to which the amine is not bonded) has a specific substituent, i.e., an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. Note that such a structure enables the emission spectrum to be narrowed. The narrowed emission spectrum can improve the element characteristics of, for example, a top-emission light-emitting element having a microcavity structure. In addition, the use of such a material in manufacturing a light-emitting element can improve the reliability of the light-emitting element. Furthermore, such a structure improves the sublimability of a compound and can therefore reduce decomposition of the compound at the time of evaporation. Suppression of decomposition at the time of evaporation makes it possible to provide a highly reliable light-emitting element. It is preferable that the above-described specific substituent be a monocyclic saturated hydrocarbon group having 3 to 20 carbon atoms because the above effect is significant and the yield of synthesis is high. It is particularly preferable that the specific substituent be a cyclohexyl group.

Next, specific structural formulae of the above-described organic compounds, each of which is one embodiment of the present invention, are shown below. Note that the present invention is not limited to these formulae.

(100)

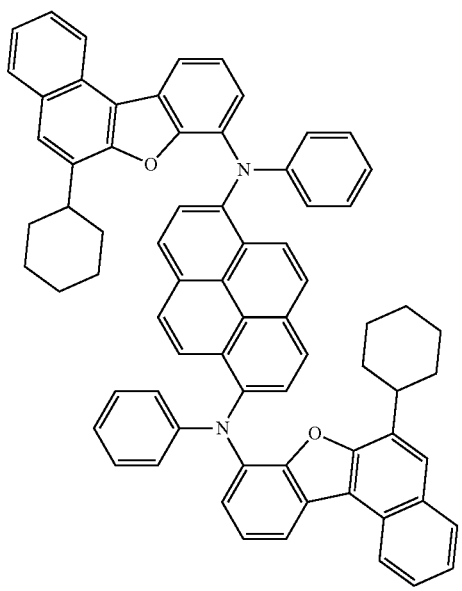

(101)

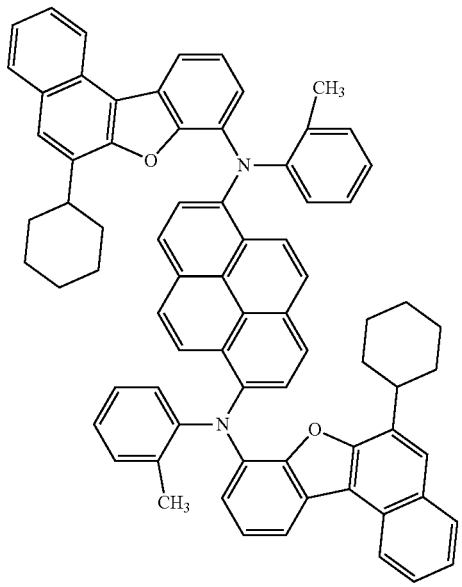

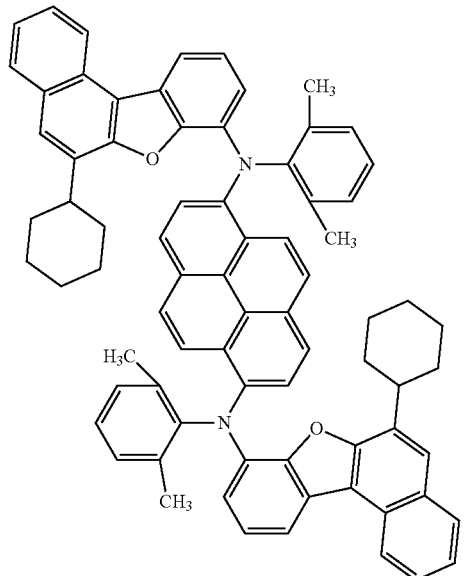
(102)
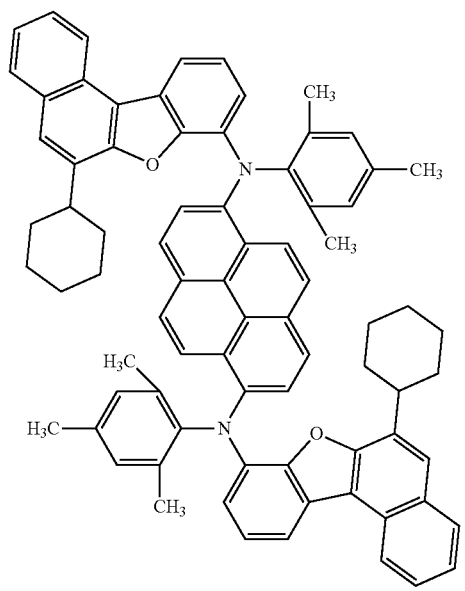
(103)
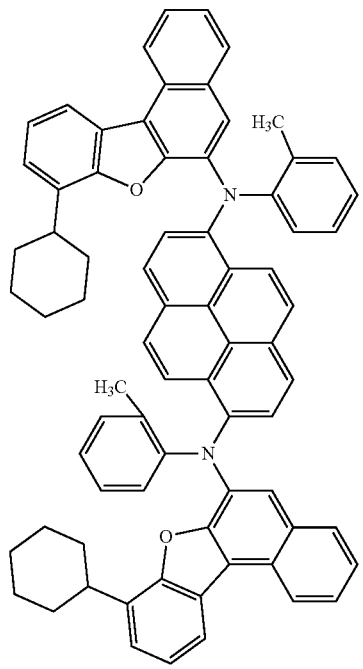
(104)
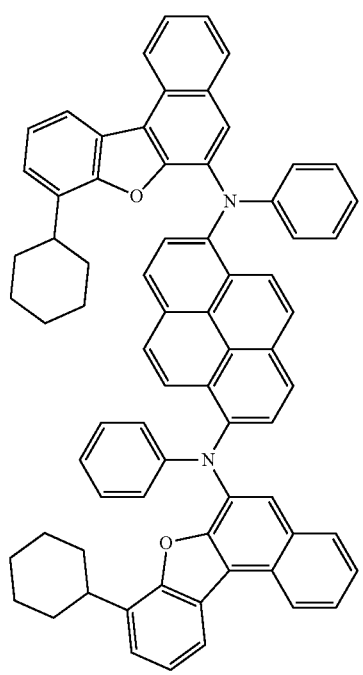
(105)

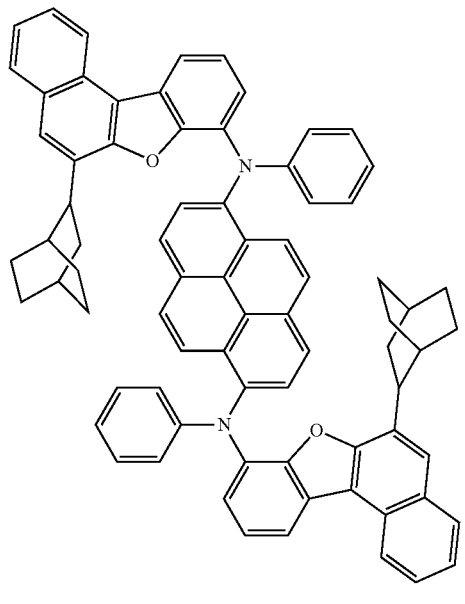
(106)
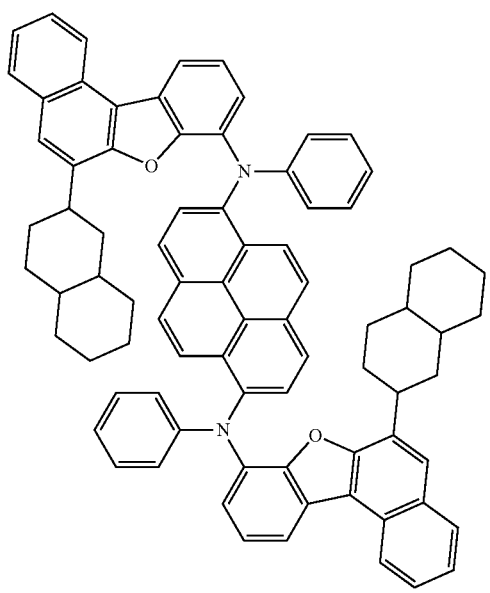
(108)
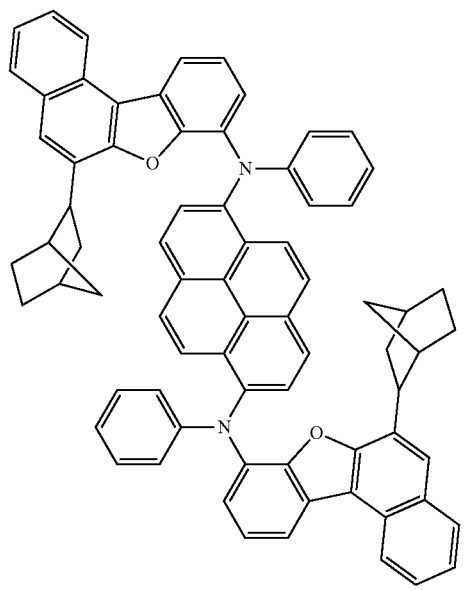
(107)
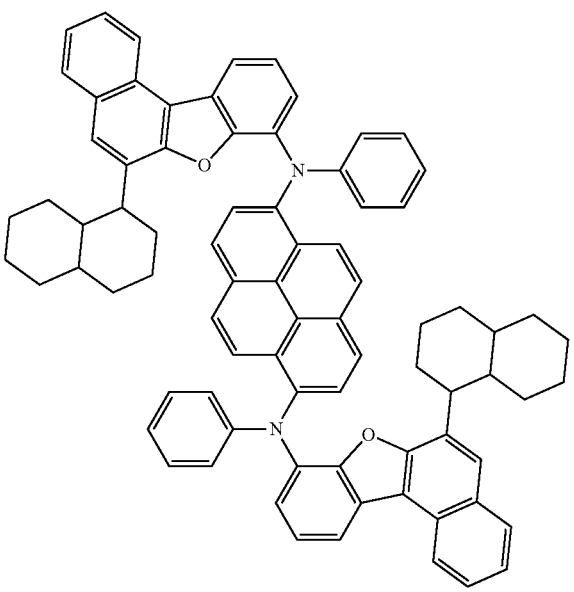
(109)

(110)
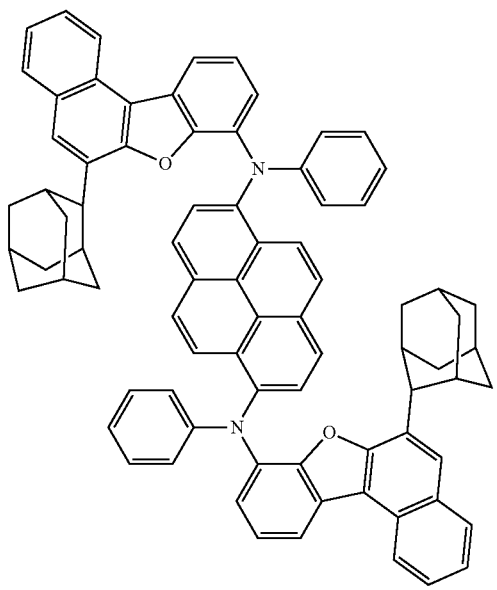
(111)
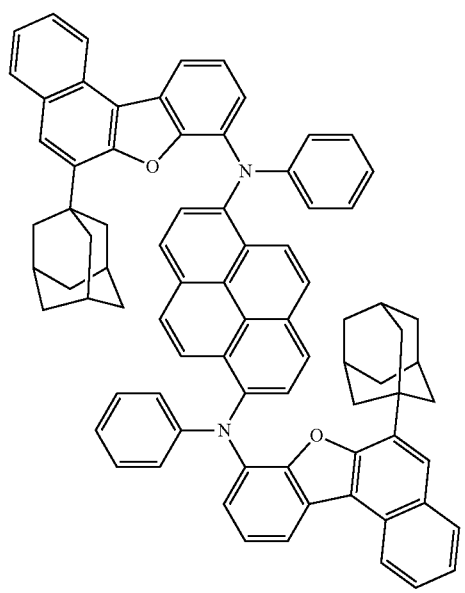
(112)
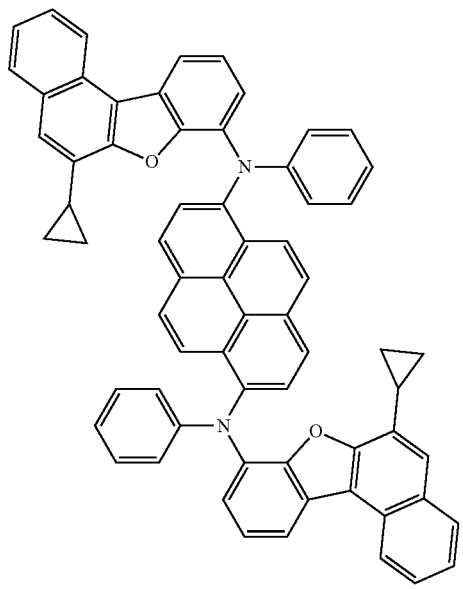
(113)
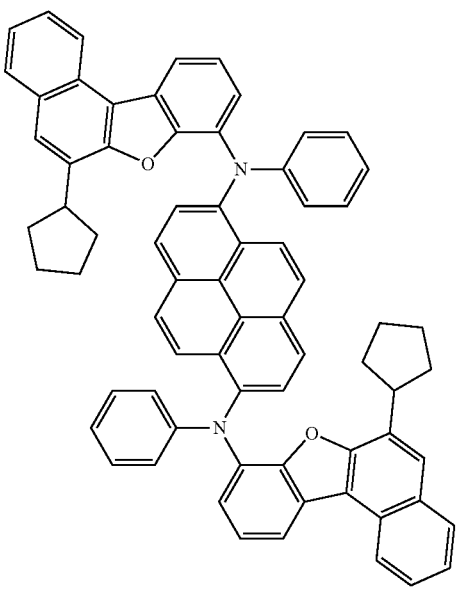

(114)
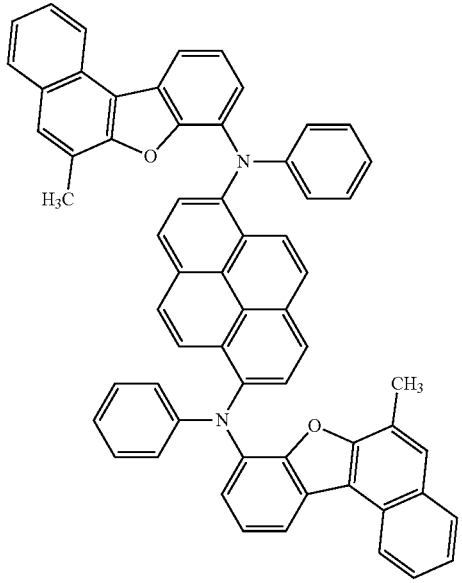
(116)
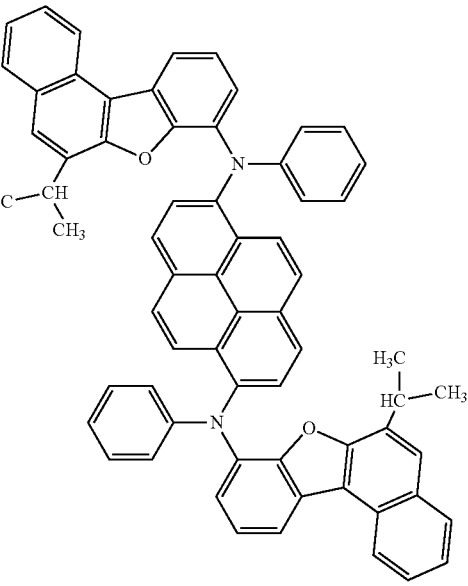
(115)
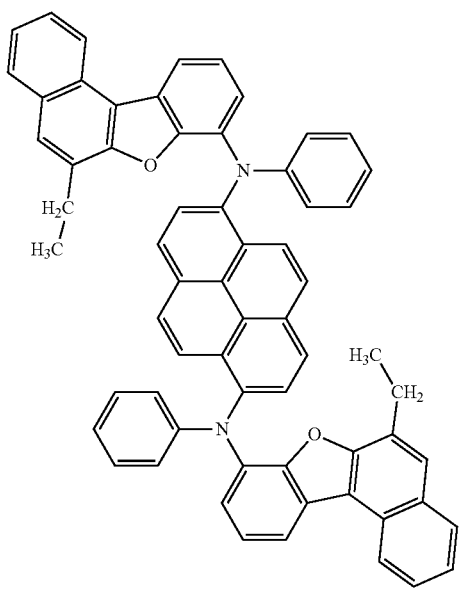
(117)
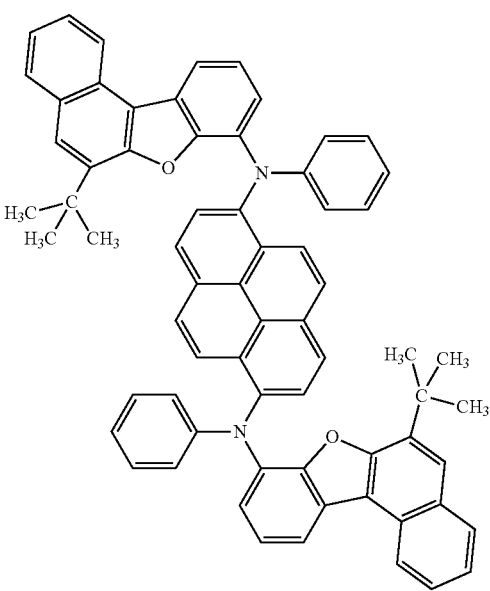

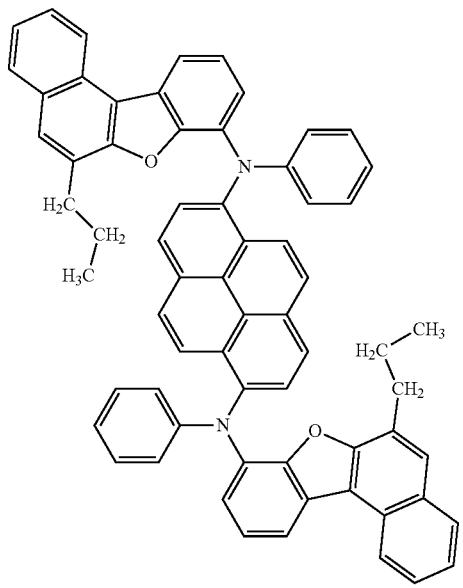
(118)
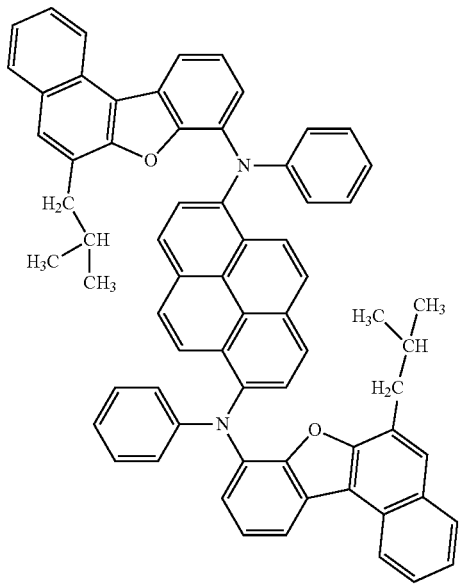
(120)
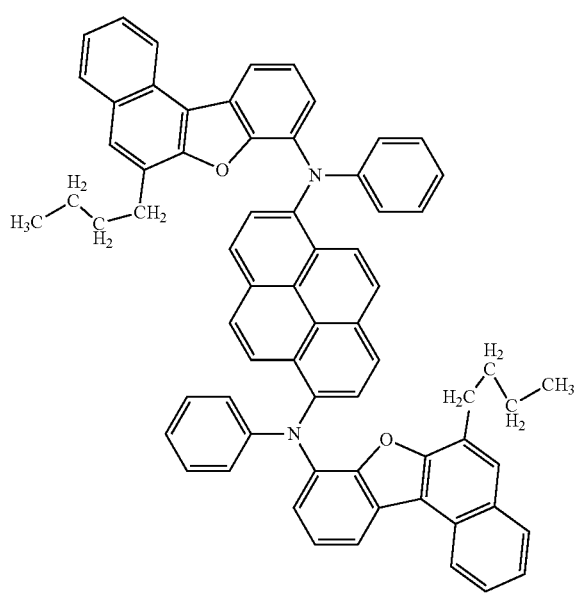
(119)
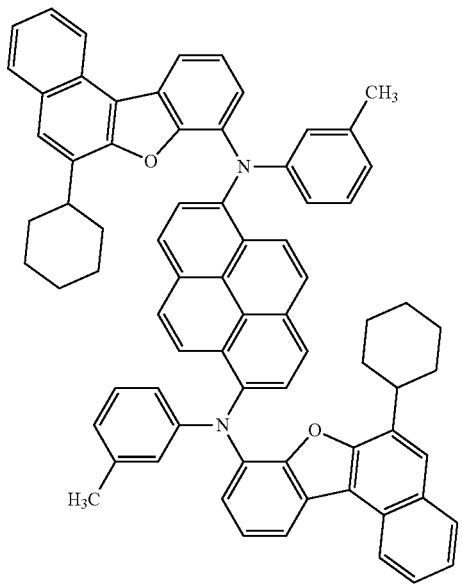
(121)

(122)
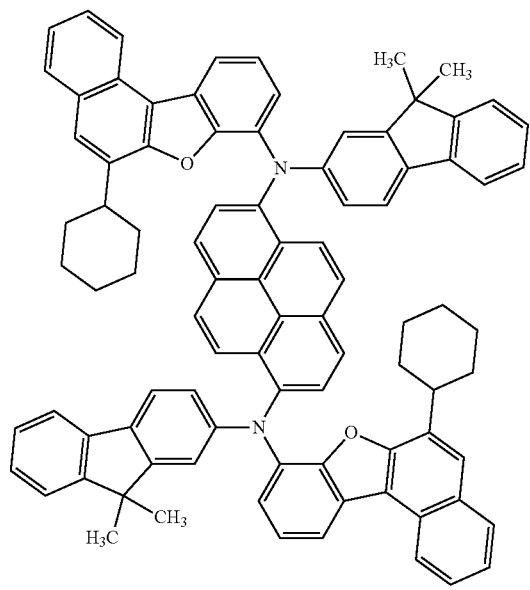
(124)
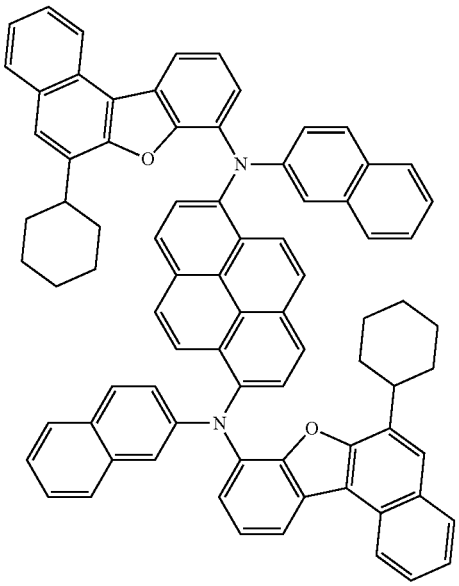
(123)
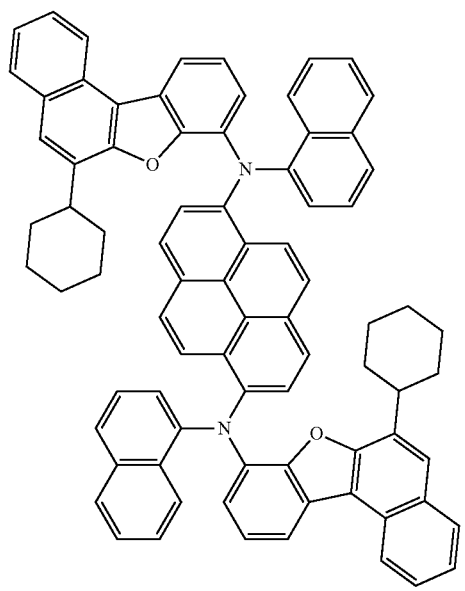
(125)
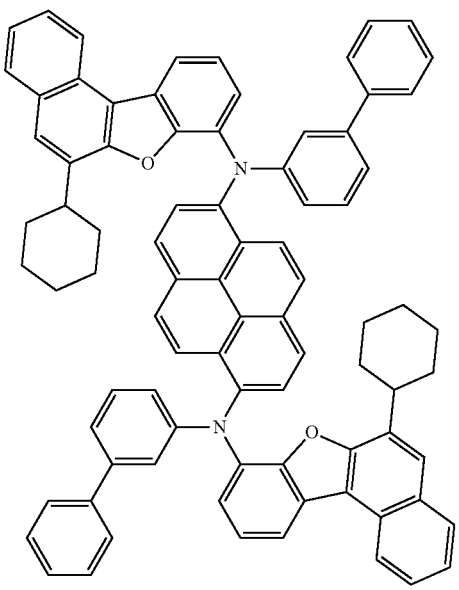

(126)
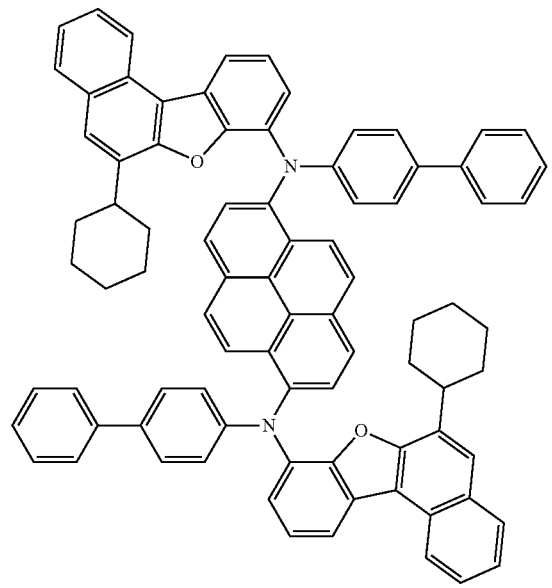
(128)
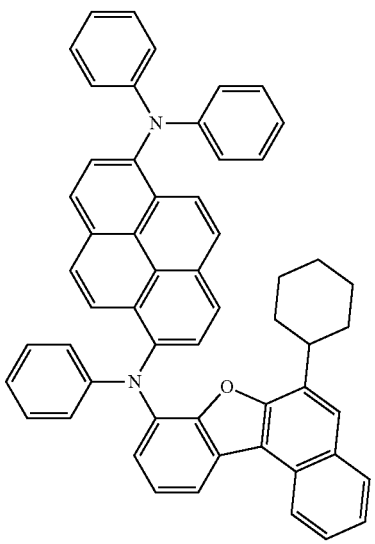
(127)
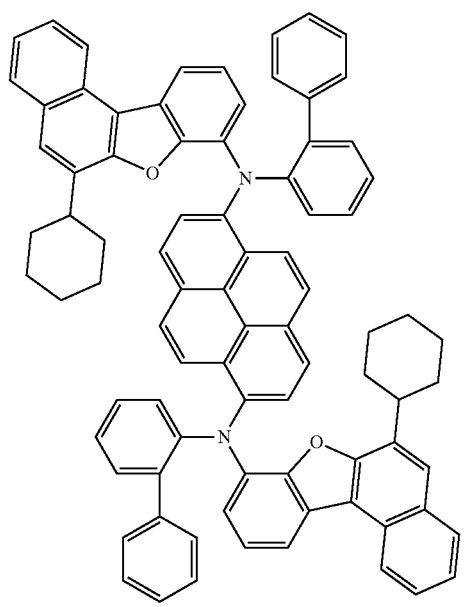
(129)
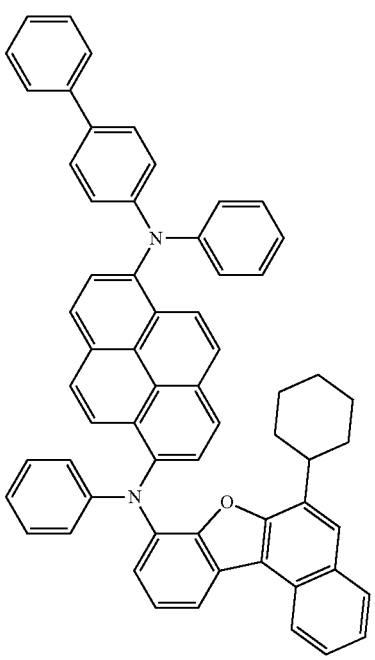

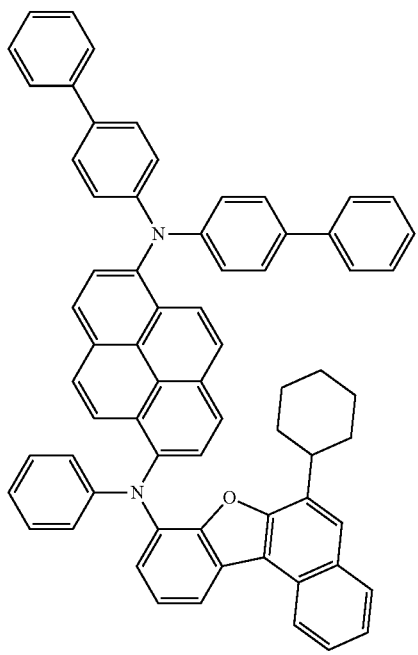
(130)
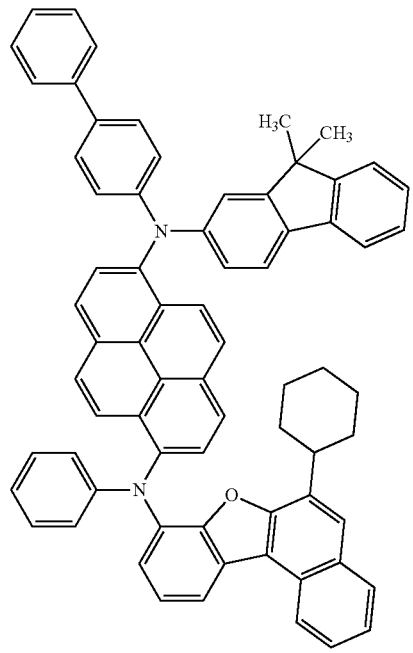
(132)
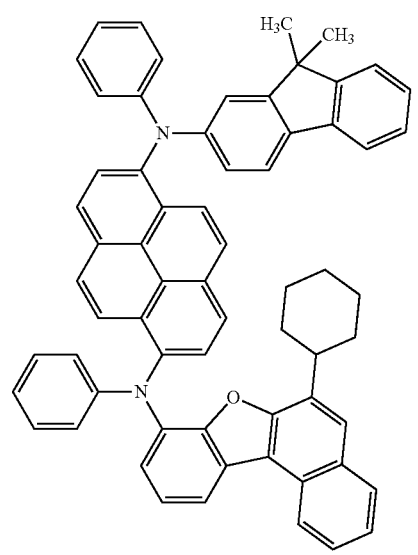
(131)
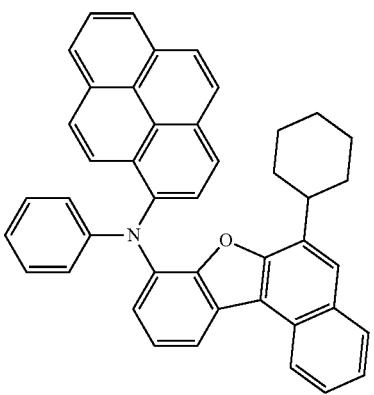
(133)

(134)
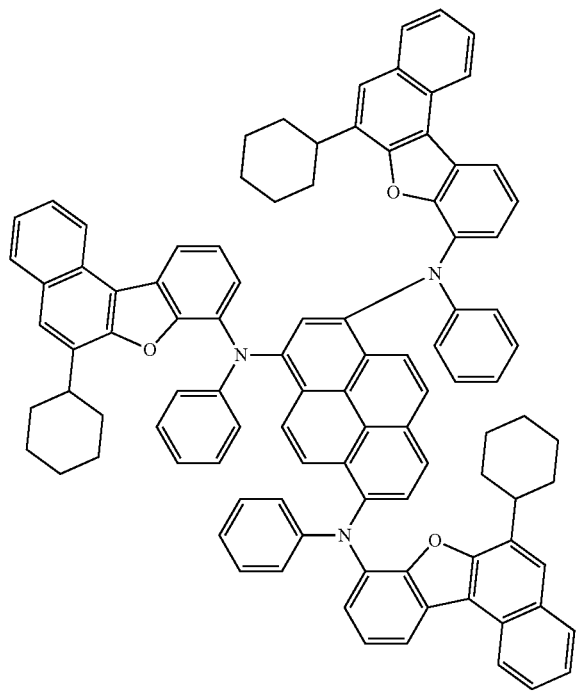
(136)
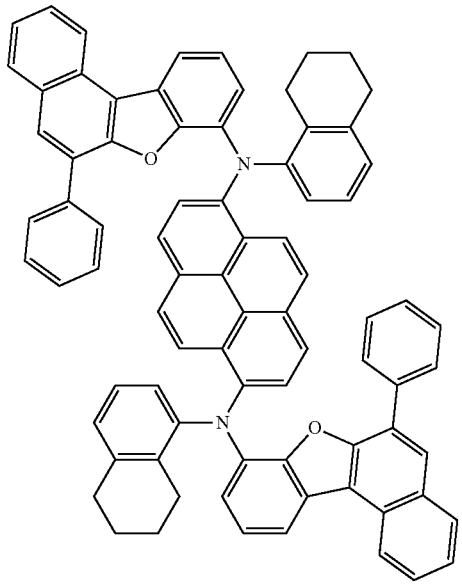
(135)
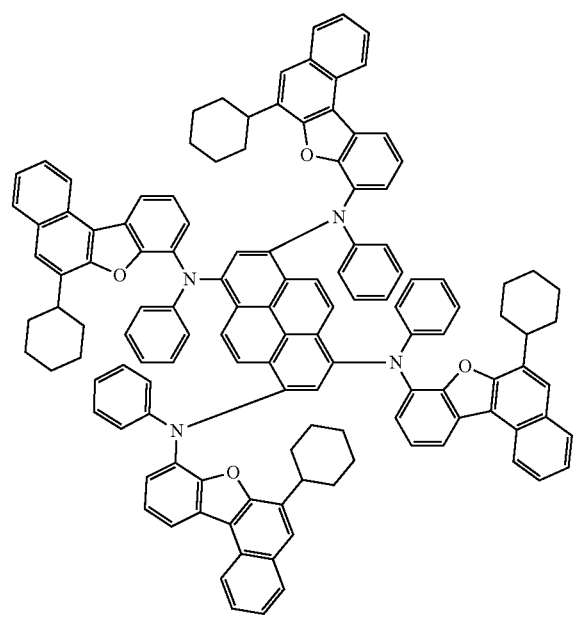
(137)
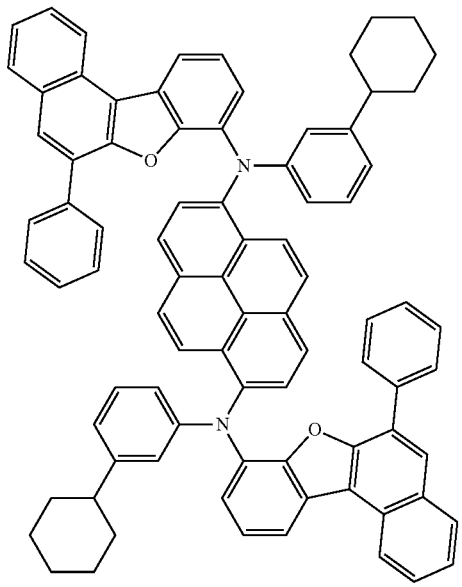

(138)
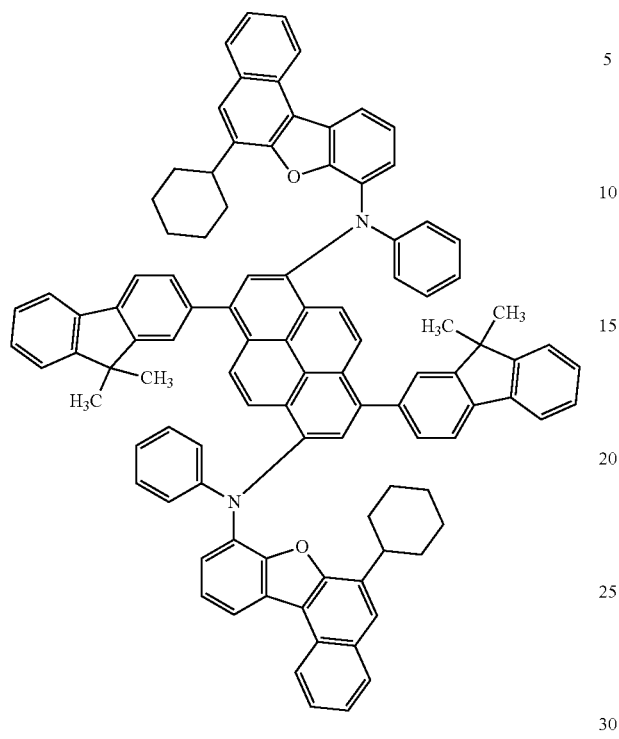
(139)
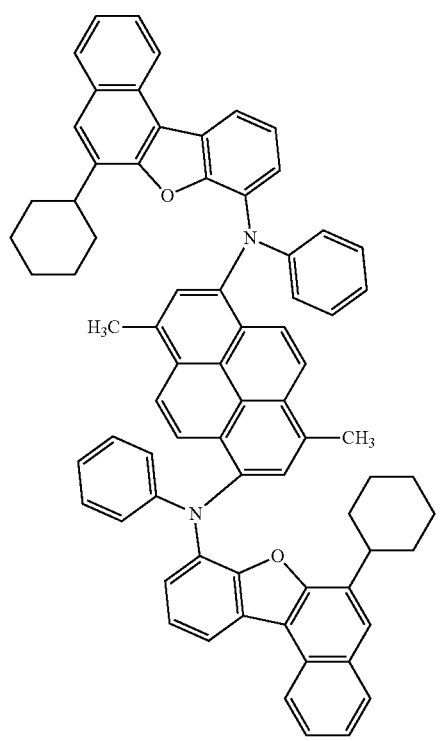
(140)
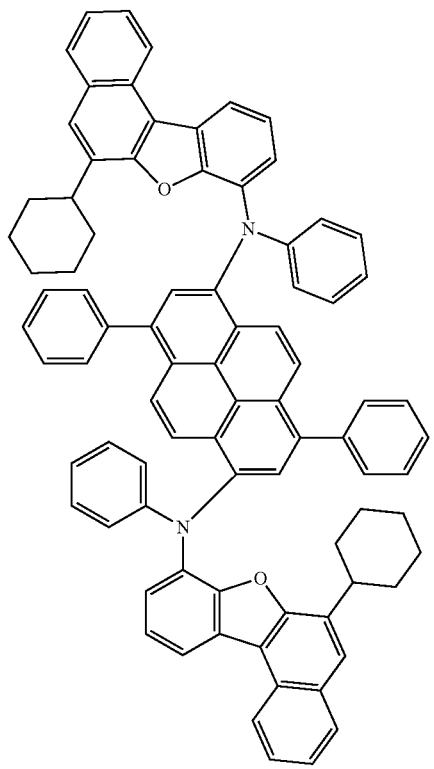
(141)
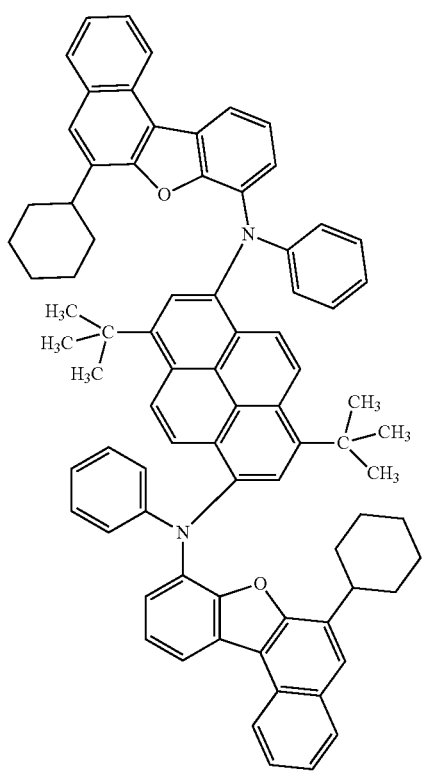

(142)

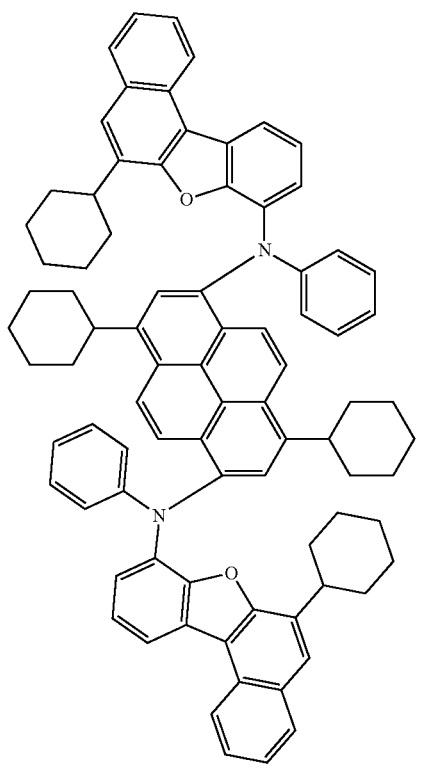

(144)

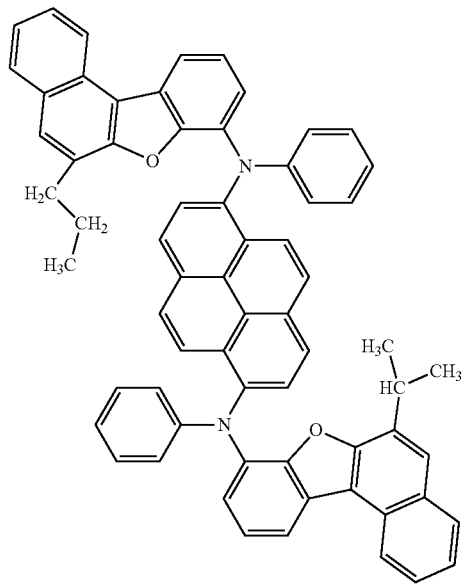

(145)

(143)

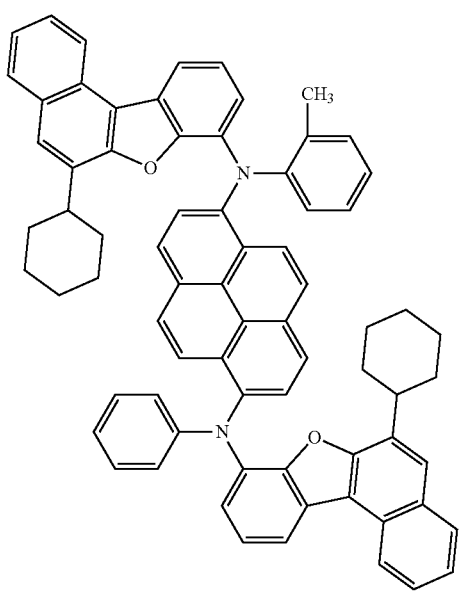

Note that the organic compounds represented by Structural Formulae (100) to (145) are examples of the organic compound represented by any of General Formulae (G1) to (G4). The organic compound of one embodiment of the present invention is not limited thereto.

Next, an example of a method for synthesizing the organic compound which is one embodiment of the present invention and is represented by General Formula (G1) will be described.

<<Method for Synthesizing Organic Compound Represented by General Formula (G1)>>

An example of a method for synthesizing the organic compound represented by General Formula (G1) will be described.

(G1)

A―(Ar¹/X¹)ₙ

(G1-1)

X¹ =

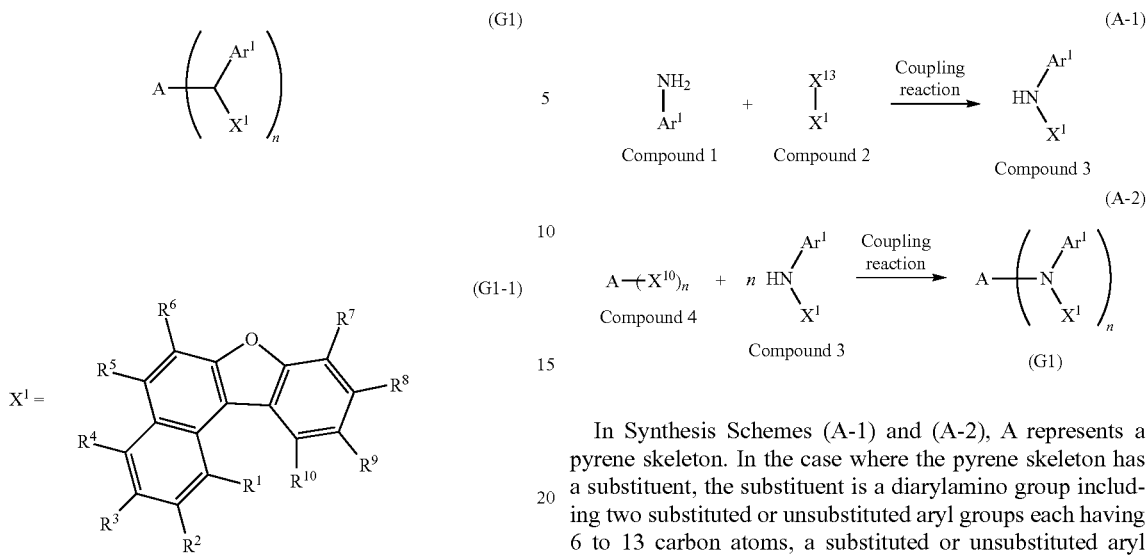

In General Formula (G1), A represents a pyrene skeleton. In the case where the pyrene skeleton has a substituent, the substituent is a diarylamino group including two substituted or unsubstituted aryl groups each having 6 to 13 carbon atoms, a substituted or unsubstituted aryl group having 6 to 13 carbon atoms, an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. The two aryl groups of the diarylamino group may be the same or different. In $X^1$ represented by General Formula (G1-1), one of $R^6$ and $R^7$ is bonded to N in General Formula (G1), and the other of $R^6$ and $R^7$ represents an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. $Ar^1$ represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms. In addition, n represents 1 to 4, and in the case where n is 2 or more, amine skeletons may be the same or different.

<Method for Synthesizing Organic Compound Represented by General Formula (G1)>

The organic compound represented by General Formula (G1) can be synthesized by a synthesis method in which any of a variety of reactions is used. For example, the organic compound can be synthesized by Synthesis Schemes (A-1) and (A-2) below. First, an arylamine (a compound 1) and a halogenated aryl (a compound 2) are coupled, whereby a benzo[b]naphtho[1,2-d]furanylamine compound (a compound 3) is obtained. Next, the benzo[b]naphtho[1,2-d]furanylamine compound (the compound 3) and a pyrene compound (a compound 4) are coupled, whereby the organic compound represented by General Formula (G1) can be obtained.

(A-1)

$NH_2$ | $Ar^1$  +  $X^{13}$ | $X^1$  →[Coupling reaction]  $Ar^1$ | HN | $X^1$

Compound 1    Compound 2           Compound 3

(A-2)

A―(X¹⁰)ₙ  +  n HN(Ar¹/X¹)  →[Coupling reaction]  A―(N(Ar¹)/X¹)ₙ

Compound 4        Compound 3                        (G1)

In Synthesis Schemes (A-1) and (A-2), A represents a pyrene skeleton. In the case where the pyrene skeleton has a substituent, the substituent is a diarylamino group including two substituted or unsubstituted aryl groups each having 6 to 13 carbon atoms, a substituted or unsubstituted aryl group having 6 to 13 carbon atoms, an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. The two aryl groups of the diarylamino group may be the same or different. In $X^1$ represented by General Formula (G1-1), one of $R^6$ and $R^7$ is bonded to N in General Formula (G1), and the other of $R^6$ and $R^7$ represents an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. $Ar^1$ represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms. In addition, n represents 1 to 4, and in the case where n is 2 or more, amine skeletons may be the same or different.

In the case where a Buchwald-Hartwig reaction using a palladium catalyst is employed in Synthesis Schemes (A-1) and (A-2), $X^{10}$ represents a halogen group or a triflate group. As the halogen, iodine, bromine, or chlorine is preferable. In the case where n is 2 or more and different amino groups are bonded to the pyrene skeleton, different halogens are preferably used as $X^{10}$ to selectively react with the amino groups. In the reaction, a palladium compound such as bis(dibenzylideneacetone)palladium(0) or palladium(II) acetate and a ligand such as tri(tert-butyl)phosphine, tri(n-hexyl)phosphine, tricyclohexylphosphine, di(1-adamantyl)-n-butylphosphine, or 2-dicyclohexylphosphino-2',6'-dimethoxy-1,1'-biphenyl can be used. In addition, an organic base such as sodium tert-butoxide, an inorganic base such as potassium carbonate, cesium carbonate, or sodium carbonate, or the like can be used. Furthermore, toluene, xylene, benzene, tetrahydrofuran, dioxane, or the like can be used as a solvent. Reagents that can be used in the reaction are not limited thereto.

The reaction employed in Synthesis Schemes (A-1) and (A-2) is not limited to the Buchwald-Hartwig reaction. A Migita-Kosugi-Stille coupling reaction using an organotin compound, a coupling reaction using a Grignard reagent, an Ullmann reaction using copper or a copper compound, or the like can be used.

Note that the benzo[b]naphtho[1,2-d]furanylamine compound (the compound 3) obtained by coupling of the arylamine (the compound 1) and the halogenated aryl (the compound 2) in Synthesis Scheme (A-1) is a compound obtained as an intermediate at the time of synthesizing the organic compound of one embodiment of the present invention and is another organic compound of one embodiment of the present invention.

Specific examples of the compound 3 shown in Synthesis Scheme (A-1) include those which are represented by Structural Formulae (201) to (227) below.

(201)

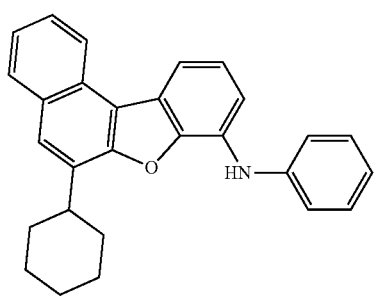

(202)

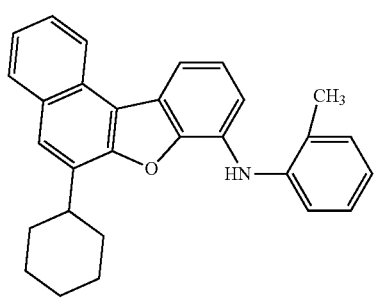

(203)

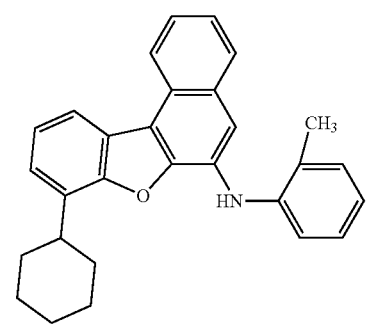

(204)

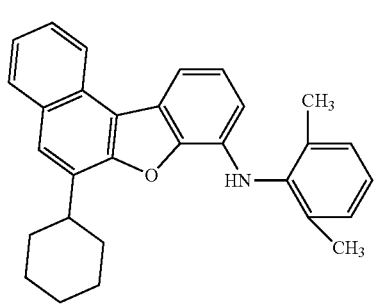

(205)

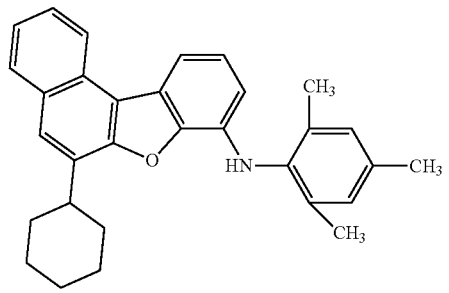

(206)

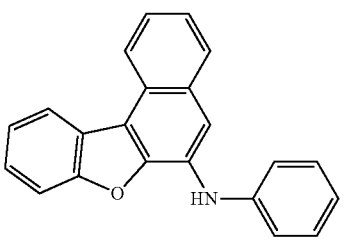

(207)

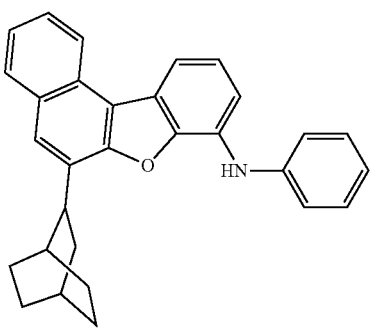

(208)

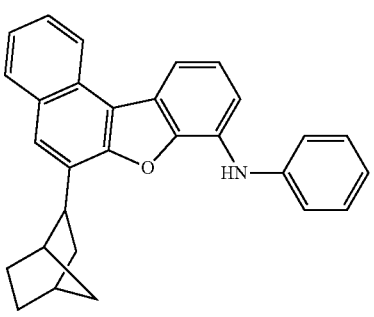

(209)

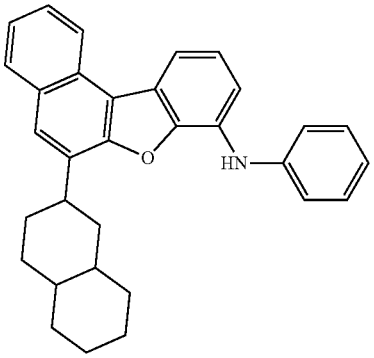

(210) 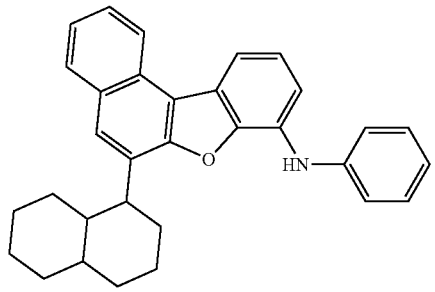
(211) 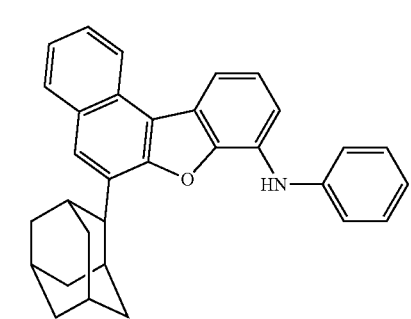
(212) 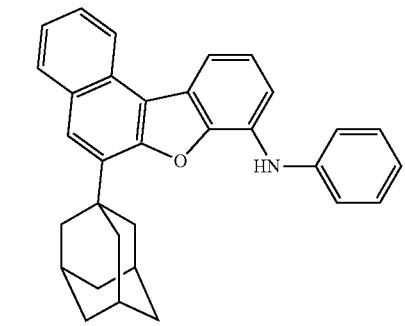
(213) 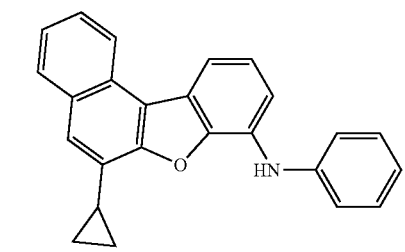
(214) 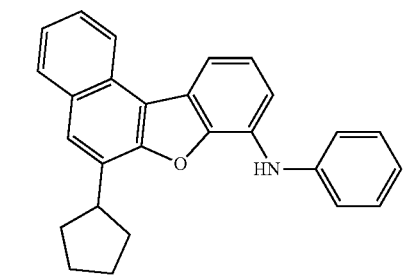
(215) 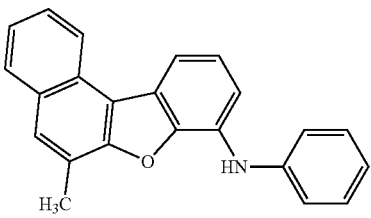
(216) 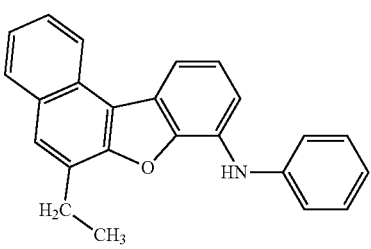
(217) 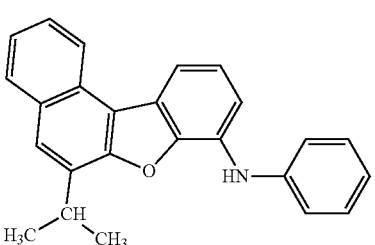
(218) 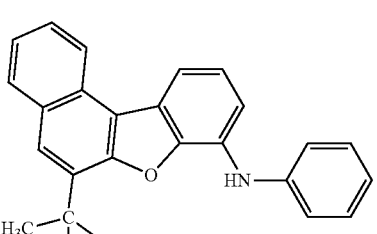
(219) 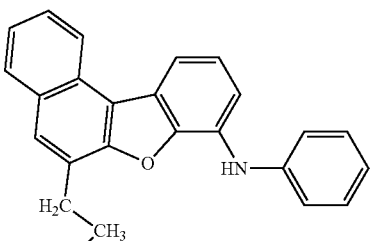
(220) 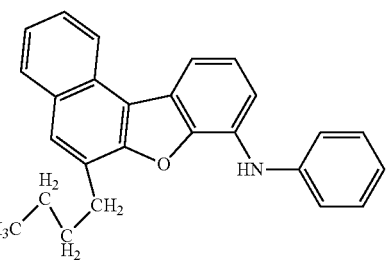

(221) 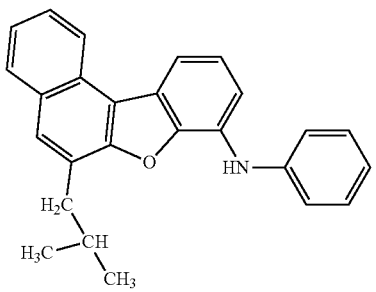

(222) 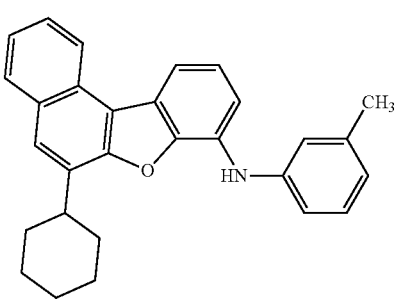

(223) 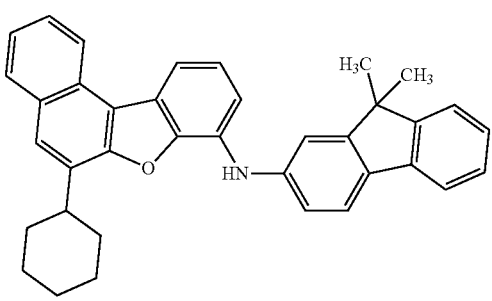

(224) 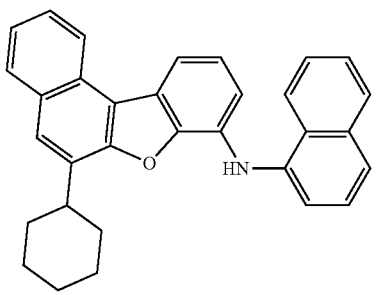

(225) 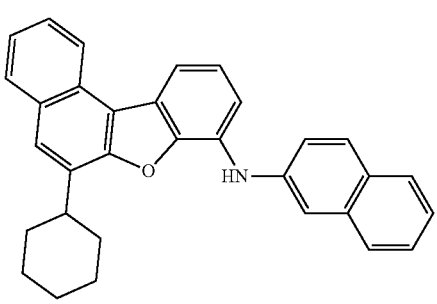

(226) 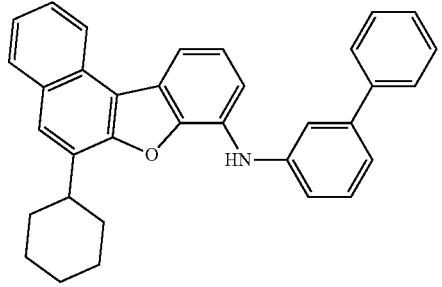

(227) 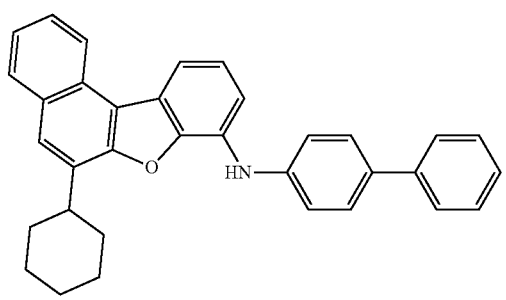

Next, an example of a method for synthesizing the organic compound which is one embodiment of the present invention and is represented by General Formula (G2) will be described.

<Method for Synthesizing Organic Compound Represented by General Formula (G2)>

An example of a method for synthesizing the organic compound represented by General Formula (G2) will be described.

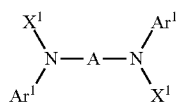
(G2)

$X^1, X^2 =$ 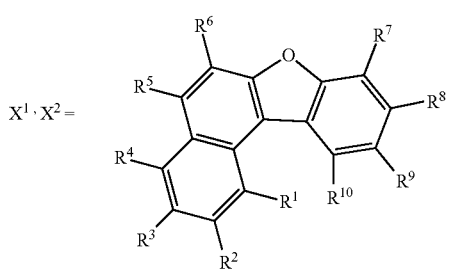
(G2-1)

In General Formula (G2), A represents a substituted or unsubstituted pyrene skeleton. $X^1$ and $X^2$ represented by General Formula (G2-1) are independent of each other. One of $R^6$ and $R^7$ is bonded to N in General Formula (G2), and the other of $R^6$ and $R^7$ represents an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. Each of $Ar^1$ and $Ar^2$ independently represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

Alternatively, in General Formula (G2), A represents a substituted or unsubstituted pyrene skeleton. $X^1$ and $X^2$ represented by General Formula (G2-1) are independent of each other. One of $R^6$ and $R^7$ is bonded to N in General Formula (G2), and the other of $R^6$ and $R^7$ represents a trialkylsilyl group having 3 to 18 carbon atoms or a substituted or unsubstituted triarylsilyl group having 18 to 30 carbon atoms. Each of $Ar^1$ and $Ar^2$ independently represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

<Method for Synthesizing Organic Compound Represented by General Formula (G2)>

The organic compound represented by General Formula (G2) can be synthesized by a synthesis method in which any of a variety of reactions is used. For example, the organic compound can be synthesized by Synthesis Schemes (B-1) and (B-2) below. First, a pyrene compound (a compound 5), an arylamine (a compound 6), and an arylamine (a compound 7) are coupled, whereby a pyrenediamine compound (a compound 8) is obtained. Next, the pyrenediamine compound (the compound 8), the halogenated aryl (the compound 2), and a halogenated aryl (a compound 9) are coupled, whereby the organic compound represented by General Formula (G2) can be obtained.

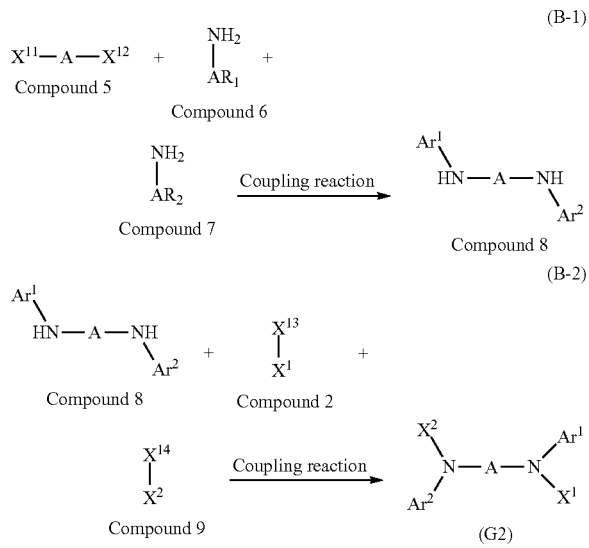

In Synthesis Schemes (B-1) and (B-2), A represents a pyrene skeleton. In the case where the pyrene skeleton has a substituent, the substituent is a diarylamino group including two substituted or unsubstituted aryl groups each having 6 to 13 carbon atoms, a substituted or unsubstituted aryl group having 6 to 13 carbon atoms, an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. The two aryl groups of the diarylamino group may be the same or different. In $X^1$ represented by General Formula (G2-1), one of $R^6$ and $R^7$ is bonded to N in General Formula (G2), and the other of $R^6$ and $R^7$ represents an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. $Ar^1$ represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

Alternatively, in Synthesis Scheme (B-2), A represents a substituted or unsubstituted pyrene skeleton. $X^1$ and $X^2$ represented by General Formula (G2-1) are independent of each other. One of $R^6$ and $R^7$ is bonded to N in General Formula (G2), and the other of $R^6$ and $R^7$ represents a trialkylsilyl group having 3 to 18 carbon atoms or a substituted or unsubstituted triarylsilyl group having 18 to 30 carbon atoms. Each of $Ar^1$ and $Ar^2$ independently represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

In the case where a Buchwald-Hartwig reaction using a palladium catalyst is employed in Synthesis Schemes (B-1) and (B-2), $X^{11}$ to $X^{14}$ represent a halogen group or a triflate group. As the halogen, iodine, bromine, or chlorine is preferable. In the reaction, a palladium compound such as bis(dibenzylideneacetone)palladium(0) or palladium(II) acetate and a ligand such as tri(tert-butyl)phosphine, tri(n-hexyl)phosphine, tricyclohexylphosphine, di(1-adamantyl)-n-butylphosphine, or 2-dicyclohexylphosphino-2',6'-dimethoxy-1,1'-biphenyl can be used. In addition, an organic base such as sodium tert-butoxide, an inorganic base such as potassium carbonate, cesium carbonate, or sodium carbonate, or the like can be used. Furthermore, toluene, xylene, benzene, tetrahydrofuran, dioxane, or the like can be used as a solvent. Reagents that can be used in the reaction are not limited thereto.

The reaction employed in Synthesis Schemes (B-1) and (B-2) is not limited to the Buchwald-Hartwig reaction. A Migita-Kosugi-Stille coupling reaction using an organotin compound, a coupling reaction using a Grignard reagent, an Ullmann reaction using copper or a copper compound, or the like can be used.

In the case where the compound 6 and the compound 7 have different structures in Synthesis Scheme (B-1), it is preferable that the compound 5 and the compound 6 be reacted first to form a coupling product and then the coupling product and the compound 7 be reacted. In the case where the compound 5 is reacted with the compound 6 and the compound 7 one by one, it is preferable that the compound 5 be a dihalogen compound and $X^{11}$ and $X^{12}$ be different halogens and selectively subjected to amination reactions one by one.

Furthermore, in the case where the compound 2 and the compound 9 have different structures in Synthesis Scheme (B-2), it is preferable that the compound 8 and the compound 2 be reacted first to form a coupling product and then the coupling product and the compound 9 be reacted.

Next, an example of a method for synthesizing an organic compound which is one embodiment of the present invention and is represented by General Formula (G2') will be described. In the organic compound represented by General Formula (G2'), $X^1$ and $X^2$ in General Formula (G2) have the same structure.

<Method for Synthesizing Organic Compound Represented by General Formula (G2')>

An example of a method for synthesizing the organic compound represented by General Formula (G2') will be described.

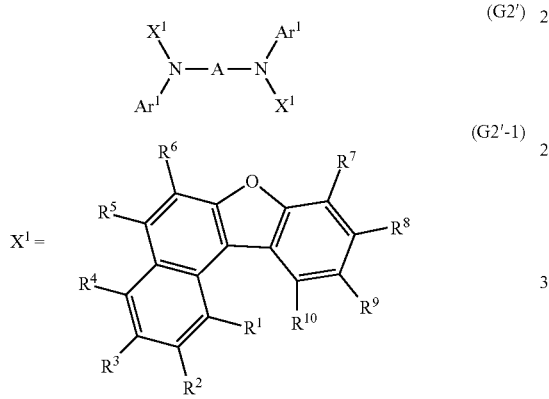

In General Formula (G2'), A represents a substituted or unsubstituted pyrene skeleton. One of $R^6$ and $R^7$ is bonded to N in General Formula (G2'), and the other of $R^6$ and $R^7$ represents an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. $Ar^1$ represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

Alternatively, in General Formula (G2'), A represents a substituted or unsubstituted pyrene skeleton. One of $R^6$ and $R^7$ is bonded to N in General Formula (G2'), and the other of $R^6$ and $R^7$ represents a trialkylsilyl group having 3 to 18 carbon atoms or a substituted or unsubstituted triarylsilyl group having 18 to 30 carbon atoms. Each of $Ar^1$ and $Ar^2$ independently represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

<Method for Synthesizing Organic Compound Represented by General Formula (G2')>

The organic compound represented by General Formula (G2') can be synthesized by a synthesis method in which any of a variety of reactions is used. For example, the organic compound can be synthesized by Synthesis Scheme (C-1) below. That is, the pyrene compound (the compound 5) and the benzo[b]naphtho[1,2-d]furanylamine compound (the compound 3) are coupled, whereby the organic compound represented by General Formula (G2') can be obtained.

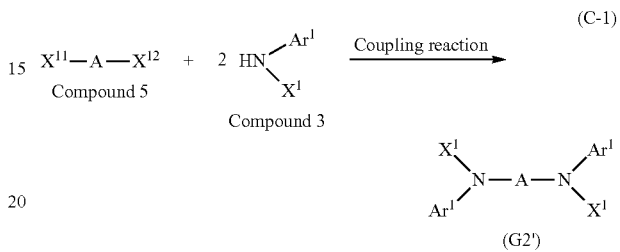

In Synthesis Scheme (C-1), A represents a pyrene skeleton. In the case where the pyrene skeleton has a substituent, the substituent is a diarylamino group including two substituted or unsubstituted aryl groups each having 6 to 13 carbon atoms, a substituted or unsubstituted aryl group having 6 to 13 carbon atoms, an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. The two aryl groups of the diarylamino group may be the same or different. In $X^1$ represented by General Formula (G2'-1), one of $R^6$ and $R^7$ is bonded to N in General Formula (G2'), and the other of $R^6$ and $R^7$ represents an alkyl group having 1 to 7 carbon atoms, a substituted or unsubstituted monocyclic saturated hydrocarbon group having 3 to 20 carbon atoms, or a substituted or unsubstituted polycyclic saturated hydrocarbon group having 7 to 10 carbon atoms. $Ar^1$ represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

Alternatively, in Synthesis Scheme (C-1), A represents a substituted or unsubstituted pyrene skeleton. One of $R^6$ and $R^7$ is bonded to N in General Formula (G2'), and the other of $R^6$ and $R^7$ represents a trialkylsilyl group having 3 to 18 carbon atoms or a substituted or unsubstituted triarylsilyl group having 18 to 30 carbon atoms. $Ar^1$ represents a substituted or unsubstituted aryl group having 6 to 13 carbon atoms. Each of $R^1$ to $R^5$ and $R^8$ to $R^{10}$ independently represents hydrogen, an alkyl group having 1 to 7 carbon atoms, a substituted or unsubstituted monocyclic saturated hydrocarbon group having 3 to 20 carbon atoms, a substituted or unsubstituted polycyclic saturated hydrocarbon group having 7 to 10 carbon atoms, or a substituted or unsubstituted aryl group having 6 to 13 carbon atoms.

In the case where a Buchwald-Hartwig reaction using a palladium catalyst is employed in Synthesis Scheme (C-1), $X^{11}$ and $X^{12}$ represent a halogen group or a triflate group. As the halogen, iodine, bromine, or chlorine is preferable. To bond the same amino groups to the pyrene skeleton, it is preferable that $X^{11}$ and $X^{12}$ be the same. In the reaction, a palladium compound such as bis(dibenzylideneacetone)palladium(0) or palladium(II) acetate and a ligand such as tri(tert-butyl)phosphine, tri(n-hexyl)phosphine, tricyclohexylphosphine, di(1-adamantyl)-n-butylphosphine, or 2-dicyclohexylphosphino-2',6'-dimethoxy-1,1'-biphenyl can be used. In addition, an organic base such as sodium tert-butoxide, an inorganic base such as potassium carbonate, cesium carbonate, or sodium carbonate, or the like can be used. Furthermore, toluene, xylene, benzene, tetrahydrofuran, dioxane, or the like can be used as a solvent. Reagents that can be used in the reaction are not limited thereto.

The reaction employed in Synthesis Scheme (C-1) is not limited to the Buchwald-Hartwig reaction. A Migita-Kosugi-Stille coupling reaction using an organotin compound, a coupling reaction using a Grignard reagent, an Ullmann reaction using copper or a copper compound, or the like can be used.

The above is the description of methods for synthesizing the organic compounds which are embodiments of the present invention and are represented by General Formulae (G1), (G2), and (G2'); however, the present invention is not limited thereto, and another synthesis method may be employed.

With the use of the organic compound of one embodiment of the present invention, a light-emitting element, a light-emitting device, an electronic device, or a lighting device with high emission efficiency can be obtained. In addition, a light-emitting element, a light-emitting device, an electronic device, or a lighting device with low power consumption can be obtained.

In this embodiment, embodiments of the present invention have been described. Other embodiments of the present invention are described in the other embodiments. Note that embodiments of the present invention are not limited thereto. In other words, since various embodiments of the invention are described in this embodiment and the other embodiments, embodiments of the present invention are not limited to particular embodiments.

The structures described in this embodiment can be combined with any of the structures described in the other embodiments as appropriate.

Embodiment 2

In this embodiment, a light-emitting element including any of the organic compounds described in Embodiment 1 is described with reference to FIGS. 1A to 1E.

<<Basic Structure of Light-Emitting Element>>

A basic structure of a light-emitting element will be described. FIG. 1A illustrates a light-emitting element including, between a pair of electrodes, an EL layer having a light-emitting layer. Specifically, an EL layer 103 is provided between a first electrode 101 and a second electrode 102.

Figure 1B:
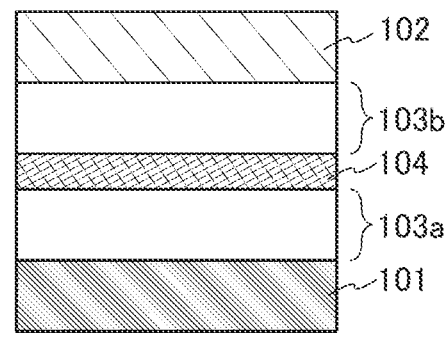

FIG. 1B illustrates a light-emitting element that has a stacked-layer structure (tandem structure) in which a plurality of EL layers (two EL layers 103a and 103b in FIG. 1B) are provided between a pair of electrodes and a charge-generation layer 104 is provided between the EL layers. With the use of such a tandem light-emitting element, a light-emitting device which can be driven at low voltage with low power consumption can be obtained.

The charge-generation layer 104 has a function of injecting electrons into one of the EL layers (103a or 103b) and injecting holes into the other of the EL layers (103b or 103a) when voltage is applied between the first electrode 101 and the second electrode 102. Thus, when voltage is applied in FIG. 1B such that the potential of the first electrode 101 is higher than that of the second electrode 102, the charge-generation layer 104 injects electrons into the EL layer 103a and injects holes into the EL layer 103b.

Note that in terms of light extraction efficiency, the charge-generation layer 104 preferably has a property of transmitting visible light (specifically, the charge-generation layer 104 has a visible light transmittance of 40% or more). The charge-generation layer 104 functions even when it has lower conductivity than the first electrode 101 or the second electrode 102.

Figure 1C:
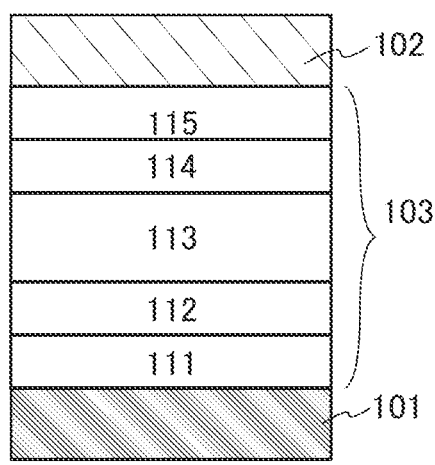

FIG. 1C illustrates a stacked-layer structure of the EL layer 103 in the light-emitting element of one embodiment of the present invention. In this case, the first electrode 101 is regarded as functioning as an anode. The EL layer 103 has a structure in which a hole-injection layer 111, a hole-transport layer 112, a light-emitting layer 113, an electron-transport layer 114, and an electron-injection layer 115 are stacked in this order over the first electrode 101. Even in the case where a plurality of EL layers are provided as in the tandem structure illustrated in FIG. 1i, the layers in each EL layer are sequentially stacked from the anode side as described above. When the first electrode 101 is a cathode and the second electrode 102 is an anode, the stacking order is reversed.

The light-emitting layer 113 included in the EL layers (103, 103a, and 103b) contains an appropriate combination of a light-emitting substance and a plurality of substances, so that fluorescence or phosphorescence of a desired emission color can be obtained. The light-emitting layer 113 may have a stacked-layer structure having different emission colors. In that case, the light-emitting substance and other substances are different between the stacked light-emitting layers. Alternatively, the plurality of EL layers (103a and 103b) in FIG. 1B may exhibit their respective emission colors. Also in that case, the light-emitting substance and other substances are different between the light-emitting layers.

In the light-emitting element of one embodiment of the present invention, for example, a micro optical resonator (microcavity) structure in which the first electrode 101 is a reflective electrode and the second electrode 102 is a transflective electrode can be employed in FIG. 1C, whereby light emission from the light-emitting layer 113 in the EL layer 103 can be resonated between the electrodes and light emission obtained through the second electrode 102 can be intensified.

Note that when the first electrode 101 of the light-emitting element is a reflective electrode having a structure in which a reflective conductive material and a light-transmitting conductive material (transparent conductive film) are stacked, optical adjustment can be performed by controlling the thickness of the transparent conductive film. Specifically, when the wavelength of light obtained from the light-emitting layer 113 is λ, the distance between the first electrode 101 and the second electrode 102 is preferably adjusted to around mλ/2 (m is a natural number).

To amplify desired light (wavelength: k) obtained from the light-emitting layer 113, the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) are preferably adjusted to around (2m'+1)λ/4 (m' is a natural number).

Here, the light-emitting region means a region where holes and electrons are recombined in the light-emitting layer 113.

By such optical adjustment, the spectrum of specific monochromatic light obtained from the light-emitting layer 113 can be narrowed and light emission with high color purity can be obtained.

In that case, the optical path length between the first electrode 101 and the second electrode 102 is, to be exact, the total thickness from a reflective region in the first electrode 101 to a reflective region in the second electrode 102. However, it is difficult to precisely determine the reflective regions in the first electrode 101 and the second electrode 102; thus, it is assumed that the above effect can be sufficiently obtained wherever the reflective regions may be set in the first electrode 101 and the second electrode 102. Furthermore, the optical path length between the first electrode 101 and the light-emitting layer emitting the desired light is, to be exact, the optical path length between the reflective region in the first electrode 101 and the light-emitting region in the light-emitting layer emitting the desired light. However, it is difficult to precisely determine the reflective region in the first electrode 101 and the light-emitting region in the light-emitting layer emitting the desired light; thus, it is assumed that the above effect can be sufficiently obtained wherever the reflective region and the light-emitting region may be set in the first electrode 101 and the light-emitting layer emitting the desired light.

The light-emitting element in FIG. 1C has a microcavity structure, so that light (monochromatic light) with different wavelengths can be extracted even if the same EL layer is used. Thus, separate coloring for obtaining a plurality of emission colors (e.g., R, G, and B) is not necessary. Therefore, high resolution can be easily achieved. Note that a combination with coloring layers (color filters) is also possible. Furthermore, emission intensity of light with a specific wavelength in the front direction can be increased, whereby power consumption can be reduced.

Figure 1D:
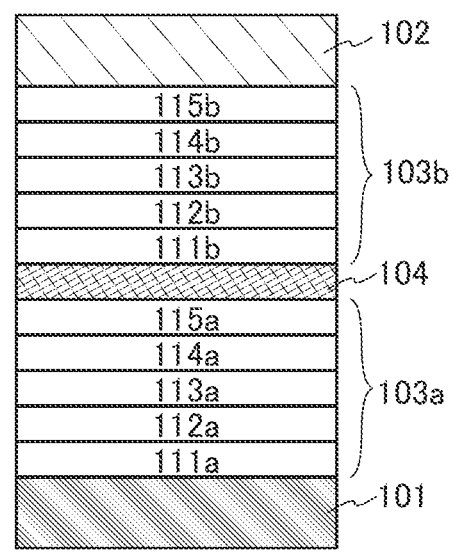
Figure 1E:
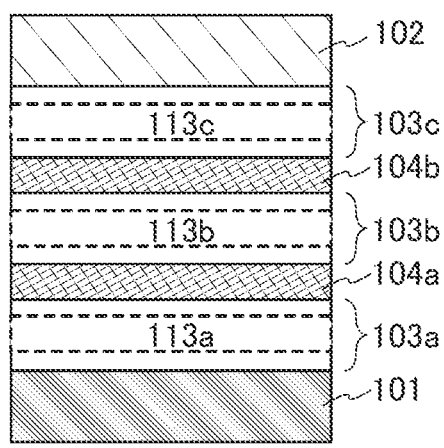

A light-emitting element illustrated in FIG. 1E is an example of the light-emitting element with the tandem structure illustrated in FIG. 1B, and includes three EL layers (103a, 103b, and 103c) stacked with charge-generation layers (104a and 104b) positioned therebetween, as illustrated in the figure. The three EL layers (103a, 103b, and 103c) include respective light-emitting layers (113a, 113b, and 113c) and the emission colors of the light-emitting layers can be selected freely. For example, the light-emitting layer 113a can be blue, the light-emitting layer 113b can be red, green, or yellow, and the light-emitting layer 113c can be blue. For another example, the light-emitting layer 113a can be red, the light-emitting layer 113b can be blue, green, or yellow, and the light-emitting layer 113c can be red.

In the light-emitting element of one embodiment of the present invention, at least one of the first electrode 101 and the second electrode 102 is a light-transmitting electrode (e.g., a transparent electrode or a transflective electrode). In the case where the light-transmitting electrode is a transparent electrode, the transparent electrode has a visible light transmittance of higher than or equal to 40%. In the case where the light-transmitting electrode is a transflective electrode, the transflective electrode has a visible light reflectance of higher than or equal to 20% and lower than or equal to 80%, and preferably higher than or equal to 40% and lower than or equal to 70%. These electrodes preferably have a resistivity of $1\times10^{-2}$ Ωcm or less.

Furthermore, when one of the first electrode 101 and the second electrode 102 is a reflective electrode in the light-emitting element of one embodiment of the present invention, the visible light reflectance of the reflective electrode is higher than or equal to 40% and lower than or equal to 100%, and preferably higher than or equal to 70% and lower than or equal to 100%. This electrode preferably has a resistivity of $1\times10^{-2}$ Ωcm or less.

<<Specific Structure and Fabrication Method of Light-Emitting Element>>

Specific structures and specific fabrication methods of light-emitting elements of embodiments of the present invention will be described with reference to FIGS. 1A to 1E. Here, a light-emitting element having the tandem structure in FIG. 1B and a microcavity structure will be described with reference to FIG. 1D. In the light-emitting element in FIG. 1D, the first electrode 101 is formed as a reflective electrode and the second electrode 102 is formed as a transflective electrode. Thus, a single-layer structure or a stacked-layer structure can be formed using one or more kinds of desired electrode materials. Note that the second electrode 102 is formed after formation of the EL layer 103b, with the use of a material selected as described above. For fabrication of these electrodes, a sputtering method or a vacuum evaporation method can be used.

<First Electrode and Second Electrode>

As materials used for the first electrode 101 and the second electrode 102, any of the following materials can be used in an appropriate combination as long as the functions of the electrodes described above can be fulfilled. For example, a metal, an alloy, an electrically conductive compound, a mixture of these, and the like can be appropriately used. Specifically, an In—Sn oxide (also referred to as ITO), an In—Si—Sn oxide (also referred to as ITSO), an In—Zn oxide, an In—W—Zn oxide, or the like can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table, which is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

In the light-emitting element in FIG. 1D, when the first electrode 101 is an anode, a hole-injection layer 111a and a hole-transport layer 112a of the EL layer 103a are sequentially stacked over the first electrode 101 by a vacuum evaporation method. After the EL layer 103a and the charge-generation layer 104 are formed, a hole-injection layer 111b and a hole-transport layer 112b of the EL layer 103b are sequentially stacked over the charge-generation layer 104 in a similar manner.

<Hole-Injection Layer and Hole-Transport Layer>

The hole-injection layers (111, 111a, and 111b) inject holes from the first electrode 101 that is an anode and the charge-generation layer (104) to the EL layers (103, 103a, and 103b) and each contain a material with a high hole-injection property.

As examples of the material with a high hole-injection property, transition metal oxides such as molybdenum oxide, vanadium oxide, ruthenium oxide, tungsten oxide, and manganese oxide can be given. Alternatively, it is possible to use any of the following materials: phthalocyanine-based compounds such as phthalocyanine (abbreviation: $H_2Pc$) and copper phthalocyanine (abbreviation: CuPc); aromatic amine compounds such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD); high molecular compounds such as poly(3,4-ethylenedioxythiophene)/poly(styrenesulfonic acid) (abbreviation: PEDOT/PSS); and the like.

Alternatively, as the material with a high hole-injection property, a composite material containing a hole-transport material and an acceptor material (an electron-accepting material) can also be used. In that case, the acceptor material extracts electrons from the hole-transport material, so that holes are generated in the hole-injection layers (111, 111a, and 111b) and the holes are injected into the light-emitting layers (113, 113a, and 113b) through the hole-transport layers (112, 112a, and 112b). Note that each of the hole-injection layers (111, 111a, and 111b) may be formed to have a single-layer structure using a composite material containing a hole-transport material and an acceptor material (electron-accepting material), or a stacked-layer structure in which a layer including a hole-transport material and a layer including an acceptor material (electron-accepting material) are stacked.

The hole-transport layers (112, 112a, and 112b) transport the holes, which are injected from the first electrode 101 and the charge-generation layer (104) by the hole-injection layers (111, 111a, and 111b), to the light-emitting layers (113, 113a, and 113b). Note that the hole-transport layers (112, 112a, and 112b) each contain a hole-transport material. It is particularly preferable that the HOMO level of the hole-transport material included in the hole-transport layers (112, 112a, and 112b) be the same as or close to that of the hole-injection layers (111, 111a, and 111b).

Examples of the acceptor material used for the hole-injection layers (111, 111a, and 111b) include an oxide of a metal belonging to any of Groups 4 to 8 of the periodic table. Specifically, molybdenum oxide, vanadium oxide, niobium oxide, tantalum oxide, chromium oxide, tungsten oxide, manganese oxide, and rhenium oxide can be given. Among these, molybdenum oxide is especially preferable since it is stable in the air, has a low hygroscopic property, and is easy to handle. Alternatively, organic acceptors such as a quinodimethane derivative, a chloranil derivative, and a hexaazatriphenylene derivative can be used. Specifically, 7,7,8,8-tetracyano-2,3,5,6-tetrafluoroquinodimethane (abbreviation: $F_4$-TCNQ), chloranil, 2,3,6,7,10,11-hexacyano-1,4,5,8,9,12-hexaazatriphenylene (abbreviation: HAT-CN), and the like can be used.

The hole-transport materials used for the hole-injection layers (111, 111a, and 111b) and the hole-transport layers (112, 112a, and 112b) are preferably substances with a hole mobility of greater than or equal to $10^{-6}$ cm$^2$/Vs. Note that other substances may be used as long as the substances have a hole-transport property higher than an electron-transport property.

Preferred hole-transport materials are π-electron rich heteroaromatic compounds (e.g., carbazole derivatives and indole derivatives) and aromatic amine compounds, examples of which include compounds having an aromatic amine skeleton, such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 3-[4-(9-phenanthryl)-phenyl]-9-phenyl-9H-carbazole (abbreviation: PCPPn), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 4,4',4''-tris(carbazol-9-yl)triphenylamine (abbreviation: TCTA), 4,4',4''-tris(N,N-diphenylamino)triphenylamine (abbreviation: TDATA), and 4,4',4''-tris[N-(3-methylphenyl)-N-phenylamino]triphenylamine (abbreviation: MTDATA); compounds having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 3,3'-bis(9-phenyl-9H-carbazole) (abbreviation: PCCP), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA); compounds having a thiophene skeleton, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

Note that the hole-transport material is not limited to the above examples and may be one of or a combination of various known materials when used for the hole-injection layers (111, 111a, and 111b) and the hole-transport layers (112, 112a, and 112b). Note that the hole-transport layers (112, 112a, and 112b) may each be formed of a plurality of layers. That is, for example, the hole-transport layers may each have a stacked-layer structure of a first hole-transport layer and a second hole-transport layer.

In the light-emitting element in FIG. 1D, the light-emitting layer 113a is formed over the hole-transport layer 112a of the EL layer 103a by a vacuum evaporation method. After the EL layer 103a and the charge-generation layer 104 are formed, the light-emitting layer 113b is formed over the hole-transport layer 112b of the EL layer 103b by a vacuum evaporation method.

<Light-Emitting Layer>

The light-emitting layers (113, 113a, 113b, and 113c) each contain a light-emitting substance. Note that as the light-emitting substance, a substance whose emission color is blue, violet, bluish violet, green, yellowish green, yellow, orange, red, or the like is appropriately used. When the plurality of light-emitting layers (113a, 113b, and 113c) are formed using different light-emitting substances, different emission colors can be exhibited (for example, complementary emission colors are combined to achieve white light emission). Furthermore, a stacked-layer structure in which one light-emitting layer contains two or more kinds of light-emitting substances may be employed.

The light-emitting layers (113, 113a, 113b, and 113c) may each contain one or more kinds of organic compounds (a host material and an assist material) in addition to a light-emitting substance (guest material). As the one or more kinds of organic compounds, one or both of the hole-transport material and the electron-transport material described in this embodiment can be used.

As the light-emitting substance that can be used for the light-emitting layers (113, 113a, 113b, and 113c), a light-emitting substance that converts singlet excitation energy into light emission in the visible light range or a light-emitting substance that converts triplet excitation energy into light emission in the visible light range can be used.

Examples of other light-emitting substances are given below.

As an example of the light-emitting substance that converts singlet excitation energy into light emission, a substance that emits fluorescence (fluorescent material) can be given. Examples of the substance that emits fluorescence include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-diphenyl-N,N'-bis[4-(9-phenyl-9H-fluoren-9-yl)phenyl]pyrene-1,6-diamine (abbreviation: 1,6FLPAPrn), N,N'-bis(dibenzofuran-2-yl)-N,N'-diphenylpyrene-1,6-diamine (abbreviation: 1,6FrAPrn), N,N'-bis(dibenzothiophen-2-yl)-N,N'-diphenylpyrene-1,6-diamine (abbreviation: 1,6ThAPrn), N,N'-(pyrene-1,6-diyl)bis[(N-phenylbenzo[b]naphtho[1,2-d]furan)-6-amine](abbreviation: 1,6BnfAPrn), N,N'-(pyrene-1,6-diyl)bis[(N-phenylbenzo[b]naphtho[1,2-d]furan)-8-amine] (abbreviation: 1,6BnfAPrn-02), and N,N'-(pyrene-1,6-diyl)bis[(6,N-diphenylbenzo[b]naphtho[1,2-d]furan)-8-amine] (abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl) triphenylamine (abbreviation: PCBAPBA), perylene, 2,5,8,11-tetra(tert-butyl)perylene (abbreviation: TBP), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), or the like.

As examples of a light-emitting substance that converts triplet excitation energy into light emission, a substance that emits phosphorescence (phosphorescent material) and a thermally activated delayed fluorescence (TADF) material that exhibits thermally activated delayed fluorescence can be given.

Examples of a phosphorescent material include an organometallic complex, a metal complex (platinum complex), and a rare earth metal complex. These substances exhibit the respective emission colors (emission peaks) and thus, any of them is appropriately selected according to need.

As examples of a phosphorescent material which emits blue or green light and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-$\kappa N^2$]phenyl-$\kappa C$}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris (1-methyl-5-phenyl-3-propyl-1H-1,2,4-triazolato)iridium (III) (abbreviation: [Ir(Prptz1-Me)$_3$]); organometallic complexes having an imidazole skeleton, such as fac-tris[1-(2,6-diisopropylphenyl)-2-phenyl-1H-imidazole]iridium (III) (abbreviation: [Ir(iPrpmi)$_3$]) and tris[3-(2,6-dimethylphenyl)-7-methylimidazo[1,2-f]phenanthridinato]iridium (III) (abbreviation: [Ir(dmpimpt-Me)$_3$]); organometallic complexes in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: [Ir(CF$_3$ppy)$_2$(pic)]), and bis[2-(4',6'-difluorophenyl)pyridinato-N,$C^{2'}$]iridium(III) acetylacetonate (abbreviation: FIr(acac)); and the like can be given.

As examples of a phosphorescent material which emits green or yellow light and whose emission spectrum has a peak wavelength at greater than or equal to 495 nm and less than or equal to 590 nm, the following substances can be given.

For example, organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato) iridium(III) (abbreviation: [Ir(tBuppm)$_2$(acac)]), (acetylacetonato)bis[6-(2-norbornyl)-4-phenylpyrimidinato]iridium (III) (abbreviation: [Ir(nbppm)$_2$(acac)]), (acetylacetonato)

bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-κN$^3$]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); organometallic complexes such as bis(2,4-diphenyl-1,3-oxazolato-N,C$^{2'}$)iridium(III) acetylacetonate (abbreviation: [Ir(dpo)$_2$(acac)]), bis{2-[4'-(perfluorophenyl)phenyl]pyridinato-N,C$^{2'}$}iridium(III) acetylacetonate (abbreviation: [Ir(p-PF-ph)$_2$(acac)]), and bis(2-phenylbenzothiazolato-N,C$^{2'}$)iridium(III) acetylacetonate (abbreviation: [Ir(bt)$_2$(acac)]); and rare earth metal complexes such as tris(acetylacetonato)(monophenanthroline)terbium(III) (abbreviation: [Tb(acac)$_3$(Phen)]) can be given.

As examples of a phosphorescent material which emits yellow or red light and whose emission spectrum has a peak wavelength at greater than or equal to 570 nm and less than or equal to 750 nm, the following substances can be given.

For example, organometallic complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato](dipivaloylmethanato)iridium(III) (abbreviation: [Ir(d1npm)$_2$(dpm)]); organometallic complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), bis{4,6-dimethyl-2-[3-(3,5-dimethylphenyl)-5-phenyl-2-pyrazinyl-κN]phenyl-κC}(2,6-dimethyl-3,5-heptanedionato-κ$^2$O,O')iridium(III) (abbreviation: [Ir(dmdppr-P)$_2$(dibm)]), bis{4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ$^2$O,O')iridium(III) (abbreviation: [Ir(dmdppr-dmCP)$_2$(dpm)]), (acetylacetonato)bis[2-methyl-3-phenylquinoxalinato-N,C$^{2'}$]iridium(III) (abbreviation: [Ir(mpq)$_2$(acac)]), (acetylacetonato)bis(2,3-diphenylquinoxalinato-N,C$^{2'}$)iridium(III) (abbreviation: [Ir(dpq)$_2$(acac)]), and (acetylacetonato)bis[2,3-bis(4-fluorophenyl)quinoxalinato]iridium(III) (abbreviation: [Ir(Fdpq)$_2$(acac)]); organometallic complexes having a pyridine skeleton, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); platinum complexes such as 2,3,7,8,12,13,17,18-octaethyl-21H,23H-porphyrin platinum(II) (abbreviation: [PtOEP]); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]) can be given.

As the organic compounds (the host material and the assist material) used in the light-emitting layers (113, 113a, 113b, and 113c), one or more kinds of substances having a larger energy gap than the light-emitting substance (the guest material) are used.

When the light-emitting substance is a fluorescent material, it is preferable to use, as the host material, an organic compound that has a high energy level in a singlet excited state and has a low energy level in a triplet excited state. For example, an anthracene derivative or a tetracene derivative is preferably used. Specific examples thereof include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), 5,12-diphenyltetracene, and 5,12-bis(biphenyl-2-yl)tetracene.

In the case where the light-emitting substance is a phosphorescent material, an organic compound having triplet excitation energy (energy difference between a ground state and a triplet excited state) which is higher than that of the light-emitting substance is preferably selected as the host material. In that case, it is possible to use a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, a phenanthroline derivative, an aromatic amine, a carbazole derivative, and the like.

More specifically, any of the following hole-transport materials and electron-transport materials can be used as the host material, for example.

Examples of the host material having a high hole-transport property include aromatic amine compounds such as N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

Carbazole derivatives such as 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1) are also given. Other examples of the carbazole derivative include 4,4'-di(N-carbazolyl)biphenyl (abbreviation: CBP), 1,3,5-tris[4-(N-carbazolyl)phenyl]benzene (abbreviation: TCPB), and 1,4-bis[4-(N-carbazolyl)phenyl]-2,3,5,6-tetraphenylbenzene.

Examples of the host material having a high hole-transport property include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris[N-(1-naphthyl)-N-phenylamino]triphenylamine (abbreviation: 1'-TNATA), 4,4',4''-tris(N,N-diphenylamino)triphenylamine (abbreviation: TDATA), 4,4',4''-tris[N-(3-methylphenyl)-N-phenylamino]triphenylamine (abbreviation: m-MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N''-triphenyl-N,N',N''-tris(9-phenylcarbazol-3-yl)benzene-1,3,5-triamine (abbreviation: PCA3B), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]-spiro-9,9'-bifluorene (abbreviation: DPA2SF), N-[4-(9H-carbazol-9-yl)phenyl]-N-(4-phenyl)phenylaniline (abbreviation: YGA1BP), and N,N'-bis[4-(carbazol-9-yl)phenyl]-N,N'-diphenyl-9,9-dimethylfluorene-2,7-diamine (abbreviation: YGA2F). Other examples are carbazole compounds, thiophene compounds, furan compounds, fluorene compounds, triphenylene compounds, phenanthrene compounds, and the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 4-{3-[3-(9-phenyl-9H-fluoren-9-yl)phenyl]phenyl}dibenzofuran (abbreviation: mmDBFFLBi-II), 4,4',4''-(benzene-1,3,5-triyl)tri(dibenzofuran) (abbreviation: DBF3P-II), 1,3,5-tri(dibenzothiophen-4-yl)-benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II).

Examples of the host material having a high electron-transport property include a metal complex having a quinoline skeleton or a benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]-quinolinato)beryllium(II) (abbreviation: BeBq2), bis(2-methyl-8-quinolinolato)(4-phenylphenolato)aluminum(III) (abbreviation: BAlq), or bis (8-quinolinolato)zinc(II) (abbreviation.: Znq). Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ) can be used. Other than such metal complexes, any of the following can be used: oxadiazole derivatives such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), and 9-[4-(5-phenyl-1,3,4-oxadiazol-2-yl)phenyl]-9H-carbazole (abbreviation: CO11); a triazole derivative such as 3-(4-biphenylyl)-4-phenyl-5-(4-tert-butylphenyl)-1,2,4-triazole (abbreviation: TAZ); a compound having an imidazole skeleton (in particular, a benzimidazole derivative) such as 2,2',2''-(1,3,5-benzenetriyl)tris(1-phenyl-1H-benzimidazole) (abbreviation: TPBI) or 2-[3-(dibenzothiophen-4-yl)phenyl]-1-phenyl-1H-benzimidazole (abbreviation: mDBTBIm-II); a compound having an oxazole skeleton (in particular, a benzoxazole derivative) such as 4,4'-bis(5-methylbenzoxazol-2-yl)stilbene (abbreviation: BzOs); a phenanthroline derivative such as bathophenanthroline (abbreviation: Bphen), bathocuproine (abbreviation: BCP), and 2,9-bis(naphthalen-2-yl)-4,7-diphenyl-1,10-phenanthroline (abbreviation: NBphen); heterocyclic compounds having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); heterocyclic compounds having a triazine skeleton such as 2-{4-[3-(N-phenyl-9H-carbazol-3-yl)-9H-carbazol-9-yl]phenyl}-4,6-diphenyl-1,3,5-triazine (abbreviation: PCCzPTzn); heterocyclic compounds having a pyridine skeleton such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can be used.

Examples of the host material include condensed polycyclic aromatic compounds such as anthracene derivatives, phenanthrene derivatives, pyrene derivatives, chrysene derivatives, and dibenzo[g,p]chrysene derivatives. Specific examples of the condensed polycyclic aromatic compound include 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation:

PCAPBA), 2PCAPA, 6,12-dimethoxy-5,11-diphenylchrysene, DBC1, 9-[4-(10-phenyl-9-anthracenyl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), and 1,3,5-tri(1-pyrenyl)benzene (abbreviation: TPB3).

In the case where a plurality of organic compounds are used for the light-emitting layers (113, 113a, 113b, and 113c), it is possible to use two compounds that form an exciplex (a first compound and a second compound) combined with an organometallic complex. In that case, although any of various organic compounds can be combined appropriately to be used, to form an exciplex efficiently, it is particularly preferable to combine a compound that easily accepts holes (a hole-transport material) and a compound that easily accepts electrons (an electron-transport material). As the hole-transport material and the electron-transport material, specifically, any of the materials described in this embodiment can be used. With the above structure, high efficiency, low voltage, and a long lifetime can be achieved at the same time.

The TADF material is a material that can up-convert a triplet excited state into a singlet excited state (i.e., reverse intersystem crossing is possible) using a little thermal energy and efficiently exhibits light emission (fluorescence) from the singlet excited state. The TADF is efficiently obtained under the condition where the difference in energy between the triplet excited level and the singlet excited level is greater than or equal to 0 eV and less than or equal to 0.2 eV, preferably greater than or equal to 0 eV and less than or equal to 0.1 eV. Note that "delayed fluorescence" exhibited by the TADF material refers to light emission having the same spectrum as normal fluorescence and an extremely long lifetime. The lifetime is $10^{-6}$ seconds or longer, preferably $10^{-3}$ seconds or longer.

Examples of the TADF material include fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: $SnF_2$(Proto IX)), a mesoporphyrin-tin fluoride complex (abbreviation: $SnF_2$(Meso IX)), a hematoporphyrin-tin fluoride complex (abbreviation: $SnF_2$(Hemato IX)), a coproporphyrin tetramethyl ester-tin fluoride complex (abbreviation: $SnF_2$(Copro III-4Me)), an octaethylporphyrin-tin fluoride complex (abbreviation: $SnF_2$(OEP)), an etioporphyrin-tin fluoride complex (abbreviation: $SnF_2$(Etio I)), and an octaethylporphyrin-platinum chloride complex (abbreviation: $PtCl_2OEP$).

Alternatively, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. Note that a substance in which the π-electron rich heteroaromatic ring is directly bonded to the π-electron deficient heteroaromatic ring is particularly preferable because both the donor property of the π-electron rich heteroaromatic ring and the acceptor property of the π-electron deficient heteroaromatic ring are increased and the energy difference between the singlet excited state and the triplet excited state becomes small.

Note that when a TADF material is used, the TADF material can be combined with another organic compound.

In the light-emitting element in FIG. 1D, the electron-transport layer 114a is formed over the light-emitting layer 113a of the EL layer 103a by a vacuum evaporation method. After the EL layer 103a and the charge-generation layer 104 are formed, the electron-transport layer 114b is formed over the light-emitting layer 113b of the EL layer 103b by a vacuum evaporation method.

<Electron-Transport Layer>

The electron-transport layers (114, 114a, and 114b) transport the electrons, which are injected from the second electrode 102 and the charge-generation layer (104) by the electron-injection layers (115, 115a, and 115b), to the light-emitting layers (113, 113a, and 113b). Note that the electron-transport layers (114, 114a, and 114b) each contain an electron-transport material. It is preferable that the electron-transport materials included in the electron-transport layers (114, 114a, and 114b) be substances with an electron mobility of higher than or equal to $1\times10^{-6}$ $cm^2/Vs$. Note that other substances may also be used as long as the substances have an electron-transport property higher than a hole-transport property.

Examples of the electron-transport material include metal complexes having a quinoline ligand, a benzoquinoline ligand, an oxazole ligand, and a thiazole ligand; an oxadiazole derivative; a triazole derivative; a phenanthroline derivative; a pyridine derivative; and a bipyridine derivative. In addition, a π-electron deficient heteroaromatic compound such as a nitrogen-containing heteroaromatic compound can also be used.

Specifically, it is possible to use metal complexes such as $Alq_3$, tris(4-methyl-8-quinolinolato)aluminum (abbreviation: $Almq_3$), bis(10-hydroxybenzo[h]quinolinato)beryllium (abbreviation: $BeBq_2$), BAlq, bis[2-(2-hydroxyphenyl)benzoxazolato]zinc(II) (abbreviation: $Zn(BOX)_2$), and bis[2-(2-hydroxyphenyl)benzothiazolato]zinc (abbreviation: $Zn(BTZ)_2$), heteroaromatic compounds such as 2-(4-biphenylyl)-5-(4-tert-butylphenyl)-1,3,4-oxadiazole (abbreviation: PBD), OXD-7, 3-(4'-tert-butylphenyl)-4-phenyl-5-(4"-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), and 4,4'-bis(5-methylbenzoxazol-2-yl)stilbene (abbreviation: BzOs), and quinoxaline derivatives and dibenzoquinoxaline derivatives such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can be used.

Each of the electron-transport layers (114, 114a, and 114b) is not limited to a single layer, but may be a stack of two or more layers each containing any of the above substances.

In the light-emitting element in FIG. 1D, the electron-injection layer 115a is formed over the electron-transport layer 114a of the EL layer 103a by a vacuum evaporation method. Subsequently, the EL layer 103a and the charge-generation layer 104 are formed, the components up to the electron-transport layer 114b of the EL layer 103b are formed, and then the electron-injection layer 115b is formed thereover by a vacuum evaporation method.

<Electron-Injection Layer>

The electron-injection layers (115, 115a, and 115b) each contain a substance having a high electron-injection property. The electron-injection layers (115, 115a, and 115b) can each be formed using an alkali metal, an alkaline earth metal, or a compound thereof, such as lithium fluoride (LiF), cesium fluoride (CsF), calcium fluoride (CaF$_2$), or lithium oxide (LiO$_x$). A rare earth metal compound like erbium fluoride (ErF$_3$) can also be used. Electride may also be used for the electron-injection layers (115, 115a, and 115b). Examples of the electride include a substance in which electrons are added at high concentration to calcium oxide-aluminum oxide. Any of the substances for forming the electron-transport layers (114, 114a, and 114b), which are given above, can also be used.

A composite material in which an organic compound and an electron donor (donor) are mixed may also be used for the electron-injection layers (115, 115a, and 115b). Such a composite material is excellent in an electron-injection property and an electron-transport property because electrons are generated in the organic compound by the electron donor. The organic compound here is preferably a material excellent in transporting the generated electrons; specifically, for example, the electron-transport materials for forming the electron-transport layers (114, 114a, and 114b) (e.g., a metal complex or a heteroaromatic compound) can be used. As the electron donor, a substance showing an electron-donating property with respect to the organic compound may be used. Preferable examples are an alkali metal, an alkaline earth metal, and a rare earth metal. Specifically, lithium, cesium, magnesium, calcium, erbium, ytterbium, and the like can be given. Furthermore, an alkali metal oxide and an alkaline earth metal oxide are preferable, and a lithium oxide, a calcium oxide, a barium oxide, and the like can be given. Alternatively, a Lewis base such as magnesium oxide can be used. Further alternatively, an organic compound such as tetrathiafulvalene (abbreviation: TTF) can be used.

In the case where light obtained from the light-emitting layer 113b is amplified, for example, the optical path length between the second electrode 102 and the light-emitting layer 113b is preferably less than one fourth of the wavelength k of light emitted from the light-emitting layer 113b. In that case, the optical path length can be adjusted by changing the thickness of the electron-transport layer 114b or the electron-injection layer 115b.

<Charge-Generation Layer>

The charge-generation layer 104 has a function of injecting electrons into the EL layer 103a and injecting holes into the EL layer 103b when a voltage is applied between the first electrode (anode) 101 and the second electrode (cathode) 102. The charge-generation layer 104 may have either a structure in which an electron acceptor (acceptor) is added to a hole-transport material or a structure in which an electron donor (donor) is added to an electron-transport material. Alternatively, both of these structures may be stacked. Note that forming the charge-generation layer 104 by using any of the above materials can suppress an increase in drive voltage caused by the stack of the EL layers.

In the case where the charge-generation layer 104 has a structure in which an electron acceptor is added to a hole-transport material, any of the materials described in this embodiment can be used as the hole-transport material. As the electron acceptor, it is possible to use 7,7,8,8-tetracyano-2,3,5,6-tetrafluoroquinodimethane (abbreviation: F$_4$-TCNQ), chloranil, and the like. In addition, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, rhenium oxide, or the like is used.

In the case where the charge-generation layer 104 has a structure in which an electron donor is added to an electron-transport material, any of the materials described in this embodiment can be used as the electron-transport material. As the electron donor, it is possible to use an alkali metal, an alkaline earth metal, a rare earth metal, metals that belong to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that the EL layer 103c in FIG. 1E has a structure similar to those of the above-described EL layers (103, 103a, and 103b). In addition, the charge-generation layers 104a and 104b each have a structure similar to that of the above-described charge-generation layer 104.

<Substrate>

The light-emitting element described in this embodiment can be formed over any of a variety of substrates. Note that the type of the substrate is not limited to a certain type. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film.

Examples of the glass substrate include a barium borosilicate glass substrate, an aluminoborosilicate glass substrate, and a soda lime glass substrate. Examples of the flexible substrate, the attachment film, and the base material film include plastics typified by polyethylene terephthalate (PET), polyethylene naphthalate (PEN), and polyether sulfone (PES); a synthetic resin such as acrylic; polypropylene; polyester; polyvinyl fluoride; polyvinyl chloride; polyamide; polyimide; aramid; epoxy; an inorganic vapor deposition film; and paper.

For fabrication of the light-emitting element in this embodiment, a vacuum process such as an evaporation method or a solution process such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers (the hole-injection layers (111, 111a, and 111b), the hole-transport layers (112, 112a, and 112b), the light-emitting layers (113, 113a, 113b, and 113c), the electron-transport layers (114, 114a, and 114b), the electron-injection layers (115, 115a, and 115b)) included in the EL layers and the charge-generation layers (104, 104a, and 104b) of the light-emitting element can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, or micro-contact printing), or the like.

Note that materials that can be used for the functional layers (the hole-injection layers (111, 111a, and 111b), the hole-transport layers (112, 112a, and 112b), the light-emitting layers (113, 113a, 113b, and 113c), the electron-transport layers (114, 114a, and 114b), and the electron-injection layers (115, 115a, and 115b)) that are included in the EL layers (103, 103a, and 103b) and the charge-generation layers (104, 104a, and 104b) in the light-emitting element described in this embodiment are not limited to the above materials, and other materials can be used in combination as long as the functions of the layers are fulfilled. For example, a high molecular compound (e.g., an oligomer, a dendrimer, or a polymer), a middle molecular compound (a compound between a low molecular compound and a high molecular compound with a molecular weight of 400 to 4000), an inorganic compound (e.g., a quantum dot material), or the like can be used. The quantum dot may be a colloidal quantum dot, an alloyed quantum dot, a core-shell quantum dot, a core quantum dot, or the like.

The structures described in this embodiment can be combined with any of the structures described in the other embodiments as appropriate.

Embodiment 3

Figure 2A:
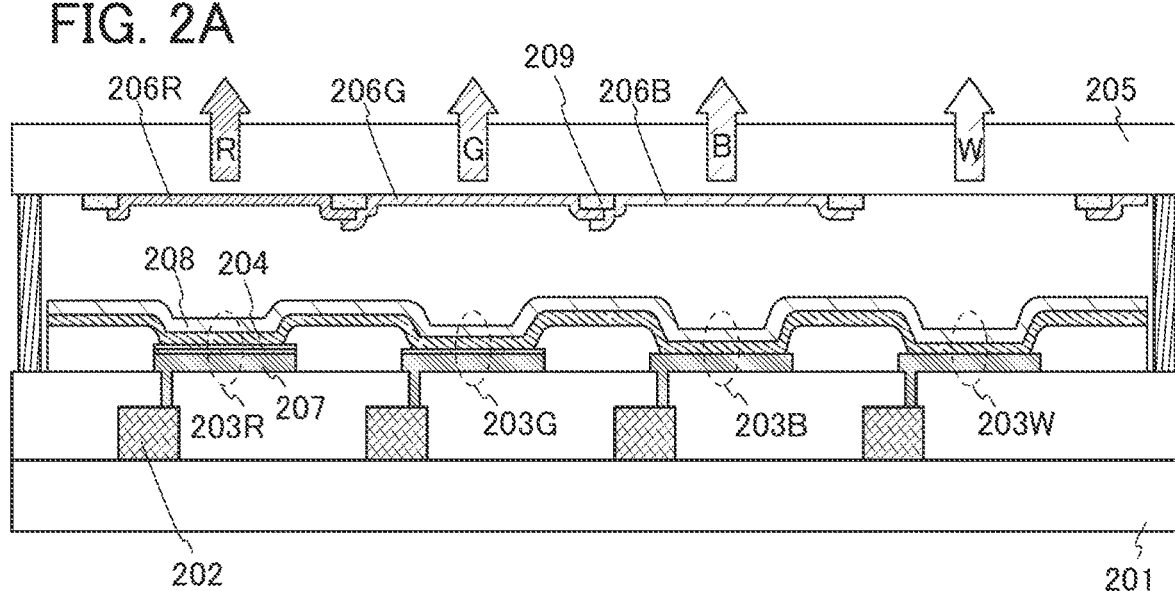
FIGS. 2A to 2C illustrate light-emitting devices.

In this embodiment, a light-emitting device of one embodiment of the present invention is described. Note that a light-emitting device illustrated in FIG. 2A is an active-matrix light-emitting device in which transistors (FETs) 202 are electrically connected to light-emitting elements (203R, 203G, 203B, and 203W) over a first substrate 201. The light-emitting elements (203R, 203G, 203B, and 203W) include a common EL layer 204 and each have a microcavity structure in which the optical path length between electrodes is adjusted depending on the emission color of the light-emitting element. The light-emitting device is a top-emission light-emitting device in which light is emitted from the EL layer 204 through color filters (206R, 206G, and 206B) formed on a second substrate 205.

The light-emitting device illustrated in FIG. 2A is fabricated such that a first electrode 207 functions as a reflective electrode and a second electrode 208 functions as a transflective electrode. Note that description in any of the other embodiments can be referred to as appropriate for electrode materials for the first electrode 207 and the second electrode 208.

Figure 2B:
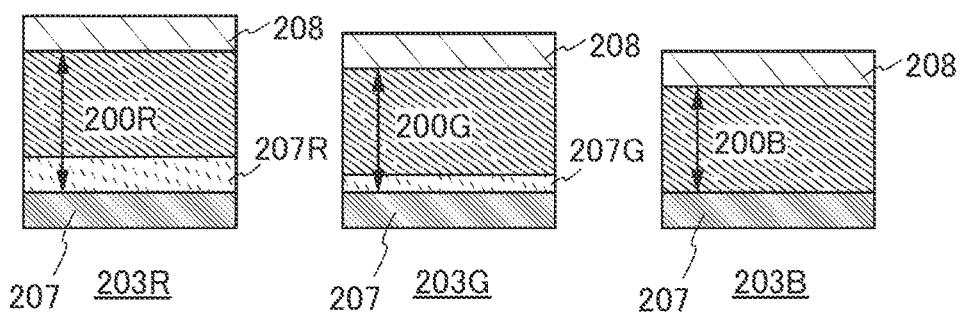

In the case where the light-emitting element 203R functions as a red light-emitting element, the light-emitting element 203G functions as a green light-emitting element, the light-emitting element 203B functions as a blue light-emitting element, and the light-emitting element 203W functions as a white light-emitting element in FIG. 2A, for example, a gap between the first electrode 207 and the second electrode 208 in the light-emitting element 203R is adjusted to have an optical path length 200R, a gap between the first electrode 207 and the second electrode 208 in the light-emitting element 203G is adjusted to have an optical path length 200G, and a gap between the first electrode 207 and the second electrode 208 in the light-emitting element 203B is adjusted to have an optical path length 200B as illustrated in FIG. 2B. Note that optical adjustment can be performed in such a manner that a conductive layer 210R is stacked over the first electrode 207 in the light-emitting element 203R and a conductive layer 210G is stacked over the first electrode 207 in the light-emitting element 203G as illustrated in FIG. 2B.

The second substrate 205 is provided with the color filters (206R, 206G, and 206B). Note that the color filters each transmit visible light in a specific wavelength range and blocks visible light in a specific wavelength range. Thus, as illustrated in FIG. 2A, the color filter 206R that transmits only light in the red wavelength range is provided in a position overlapping with the light-emitting element 203R, whereby red light emission can be obtained from the light-emitting element 203R. Furthermore, the color filter 206G that transmits only light in the green wavelength range is provided in a position overlapping with the light-emitting element 203G, whereby green light emission can be obtained from the light-emitting element 203G. Moreover, the color filter 206B that transmits only light in the blue wavelength range is provided in a position overlapping with the light-emitting element 203B, whereby blue light emission can be obtained from the light-emitting element 203B. Note that the light-emitting element 203W can emit white light without a color filter. Note that a black layer (black matrix) 209 may be provided at an end portion of each color filter. The color filters (206R, 206G, and 206B) and the black layer 209 may be covered with an overcoat layer formed using a transparent material.

Figure 2C:
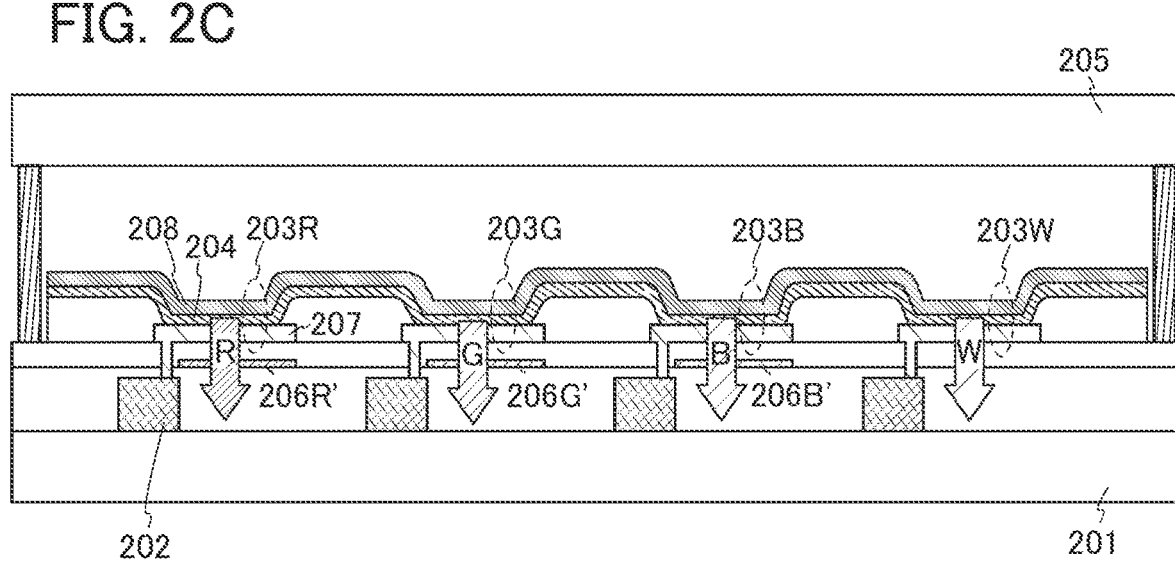

Although the light-emitting device in FIG. 2A has a structure in which light is extracted from the second substrate 205 side (top emission structure), a structure in which light is extracted from the first substrate 201 side where the FETs 202 are formed (bottom emission structure) may be employed as illustrated in FIG. 2C. In the case of a bottom-emission light-emitting device, the first electrode 207 is formed as a transflective electrode and the second electrode 208 is formed as a reflective electrode. As the first substrate 201, a substrate having at least a light-transmitting property is used. As illustrated in FIG. 2C, color filters (206R', 206G', and 206B') are provided so as to be closer to the first substrate 201 than the light-emitting elements (203R, 203G, and 203B) are.

In FIG. 2A, the light-emitting elements are the red light-emitting element, the green light-emitting element, the blue light-emitting element, and the white light-emitting element; however, the light-emitting elements of one embodiment of the present invention are not limited to the above, and a yellow light-emitting element or an orange light-emitting element may be used. Note that description in any of the other embodiments can be referred to as appropriate for materials that are used for the EL layers (a light-emitting layer, a hole-injection layer, a hole-transport layer, an electron-transport layer, an electron-injection layer, a charge-generation layer, and the like) to fabricate each of the light-emitting elements. In that case, a color filter needs to be appropriately selected depending on the emission color of the light-emitting element.

With the above structure, a light-emitting device including light-emitting elements that exhibit a plurality of emission colors can be fabricated.

Note that the structures described in this embodiment can be combined with any of the structures described in the other embodiments as appropriate.

Embodiment 4

In this embodiment, a light-emitting device of one embodiment of the present invention is described.

The use of the element structure of the light-emitting element of one embodiment of the present invention allows fabrication of an active-matrix light-emitting device or a passive-matrix light-emitting device. Note that an active-matrix light-emitting device has a structure including a combination of a light-emitting element and a transistor (FET). Thus, each of a passive-matrix light-emitting device and an active-matrix light-emitting device is one embodiment of the present invention. Note that any of the light-emitting elements described in other embodiments can be used in the light-emitting device described in this embodiment.

In this embodiment, an active-matrix light-emitting device will be described with reference to FIGS. 3A and 3B.

Figure 3A:
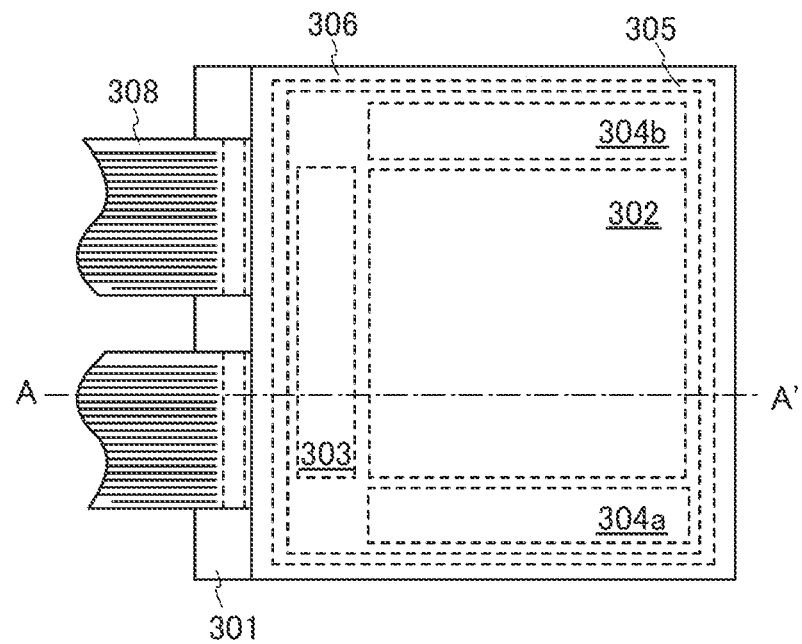
FIGS. 3A and 3B illustrate a light-emitting device.
Figure 3B:
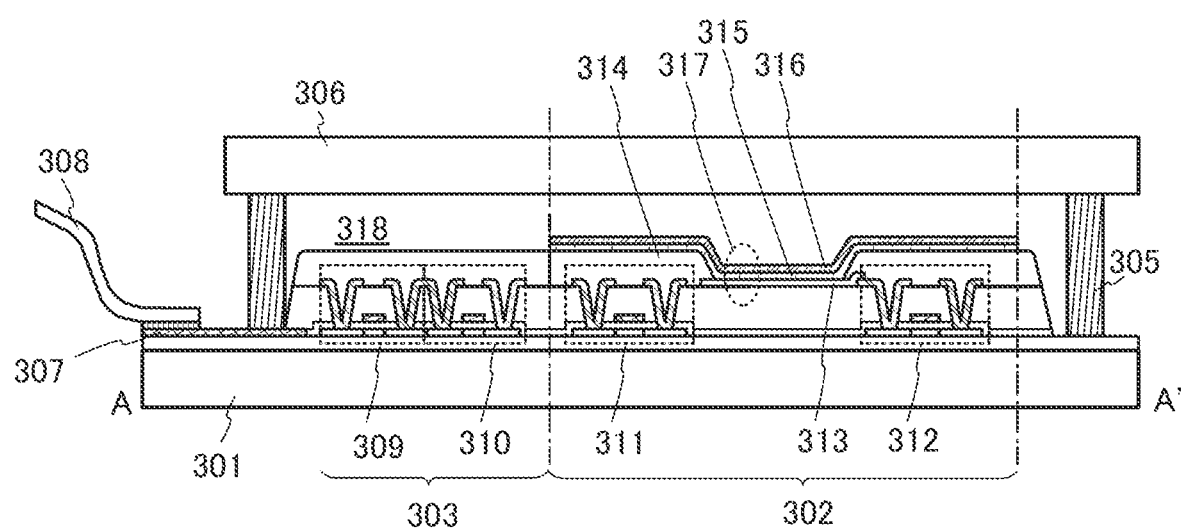

FIG. 3A is a top view illustrating the light-emitting device, and FIG. 3B is a cross-sectional view taken along chain line A-A' in FIG. 3A. The active-matrix light-emitting device includes a pixel portion 302, a driver circuit portion (source line driver circuit) 303, and driver circuit portions (gate line driver circuits) (304a and 304b) that are provided over a first substrate 301. The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is connected to an FPC 308 that is an external input terminal. Note that the FPC 308 transmits a signal (e.g., a video signal, a clock signal, a start signal, or a reset signal) or a potential from the outside to the driver circuit portions (303, 304a, and 304b). The FPC 308 may be provided with a printed wiring board (PWB). Note that the light-emitting device provided with an FPC or a PWB is included in the category of a light-emitting device.

FIG. 3B illustrates a cross-sectional structure of the light-emitting device.

The pixel portion 302 includes a plurality of pixels each of which includes an FET (switching FET) 311, an FET (current control FET) 312, and a first electrode 313 electrically connected to the FET 312. Note that the number of FETs included in each pixel is not particularly limited and can be set appropriately.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. A semiconductor having crystallinity is preferably used, in which case deterioration of the transistor characteristics can be suppressed.

For the semiconductor, a Group 14 element, a compound semiconductor, an oxide semiconductor, an organic semiconductor, or the like can be used, for example. As a typical example, a semiconductor containing silicon, a semiconductor containing gallium arsenide, or an oxide semiconductor containing indium can be used.

The driver circuit portion 303 includes the FET 309 and the FET 310. The FET 309 and the FET 310 may be formed with a circuit including transistors having the same conductivity type (either n-channel transistors or p-channel transistors) or a CMOS circuit including an n-channel transistor and a p-channel transistor. Furthermore, a driver circuit may be provided outside.

An end portion of the first electrode 313 is covered with an insulator 314. The insulator 314 can be formed using an organic compound such as a negative photosensitive resin or a positive photosensitive resin (acrylic resin), or an inorganic compound such as silicon oxide, silicon oxynitride, or silicon nitride. The insulator 314 preferably has a curved surface with curvature at an upper end portion or a lower end portion thereof. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the components of a light-emitting element 317 described in this embodiment. Although not illustrated, the second electrode 316 is electrically connected to the FPC 308 that is an external input terminal.

Although the cross-sectional view in FIG. 3B illustrates only one light-emitting element 317, a plurality of light-emitting elements are arranged in a matrix in the pixel portion 302. Light-emitting elements that emit light of three kinds of colors (R, G, and B) are selectively formed in the pixel portion 302, whereby a light-emitting device capable of displaying a full-color image can be obtained. In addition to the light-emitting elements that emit light of three kinds of colors (R, G, and B), for example, light-emitting elements that emit light of white (W), yellow (Y), magenta (M), cyan (C), and the like may be formed. For example, the light-emitting elements that emit light of some of the above colors are used in combination with the light-emitting elements that emit light of three kinds of colors (R, G, and B), whereby effects such as an improvement in color purity and a reduction in power consumption can be achieved. Alternatively, a light-emitting device which is capable of displaying a full-color image may be fabricated by a combination with color filters. As color filters, red (R), green (G), blue (B), cyan (C), magenta (M), and yellow (Y) color filters and the like can be used.

When the second substrate 306 and the first substrate 301 are bonded to each other with the sealant 305, the FETs (309, 310, 311, and 312) and the light-emitting element 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy-based resin, glass frit, or the like can be used for the sealant 305. It is preferable to use a material that is permeable to as little moisture and oxygen as possible for the sealant 305. As the second substrate 306, a substrate that can be used as the first substrate 301 can be similarly used. Thus, any of the various substrates described in the other embodiments can be appropriately used. As the substrate, a glass substrate, a quartz substrate, or a plastic substrate made of fiber-reinforced plastic (FRP), polyvinyl fluoride (PVF), polyester, acrylic, or the like can be used. In the case where glass frit is used for the sealant, the first substrate 301 and the second substrate 306 are preferably glass substrates in terms of adhesion.

Accordingly, the active-matrix light-emitting device can be obtained.

In the case where the active-matrix light-emitting device is provided over a flexible substrate, the FETs and the light-emitting element may be directly formed over the flexible substrate; alternatively, the FETs and the light-emitting element may be formed over a substrate provided with a separation layer and then separated at the separation layer by application of heat, force, laser, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. With the use of any of these substrates, an increase in durability, an increase in heat resistance, a reduction in weight, and a reduction in thickness can be achieved.

Note that the structures described in this embodiment can be combined with any of the structures described in the other embodiments as appropriate.

Embodiment 5

In this embodiment, examples of a variety of electronic devices and an automobile manufactured using the light-emitting device of one embodiment of the present invention or a display device including the light-emitting element of one embodiment of the present invention are described.

Electronic devices illustrated in FIGS. 4A to 4E can include a housing 7000, a display portion 7001, a speaker 7003, an LED lamp 7004, operation keys 7005 (including a power switch or an operation switch), a connection terminal 7006, a sensor 7007 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 7008, and the like.

Figure 4A:
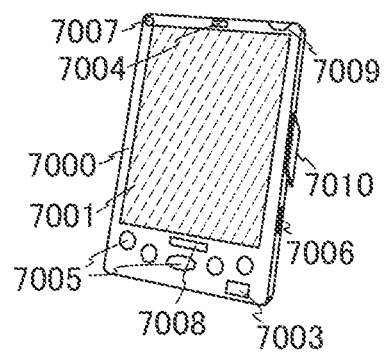
FIGS. 4A to 4G illustrate electronic devices.

FIG. 4A illustrates a mobile computer that can include a switch 7009, an infrared port 7010, and the like in addition to the above components.

Figure 4B:
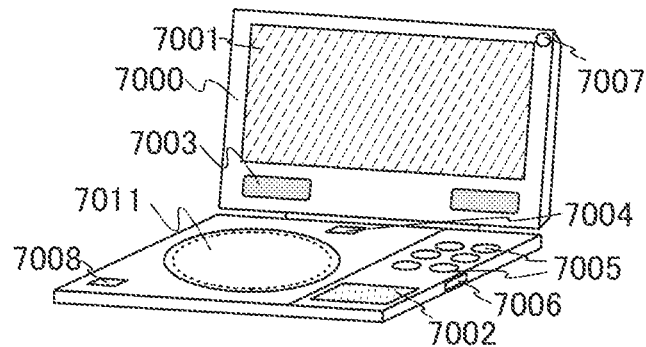

FIG. 4B illustrates a portable image reproducing device (e.g., a DVD player) that is provided with a recording medium and can include a second display portion 7002, a recording medium reading portion 7011, and the like in addition to the above components.

Figure 4C:
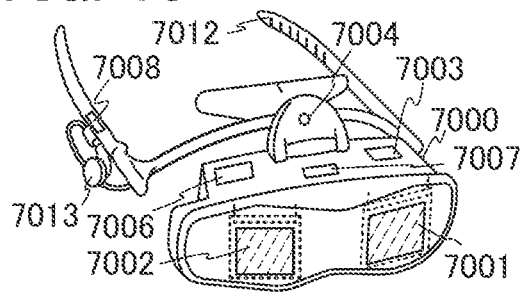

FIG. 4C illustrates a goggle-type display that can include the second display portion 7002, a support 7012, an earphone 7013, and the like in addition to the above components.

Figure 4D:
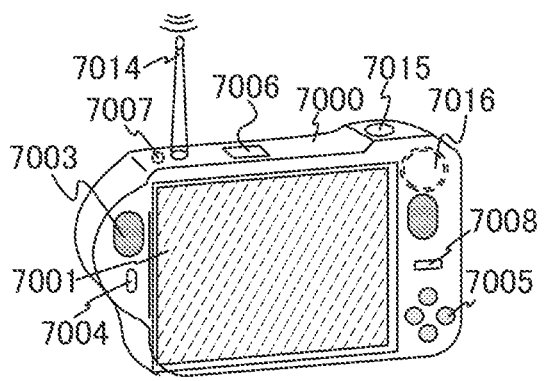

FIG. 4D illustrates a digital camera that has a television reception function and can include an antenna 7014, a shutter button 7015, an image receiving portion 7016, and the like in addition to the above components.

Figure 4E:
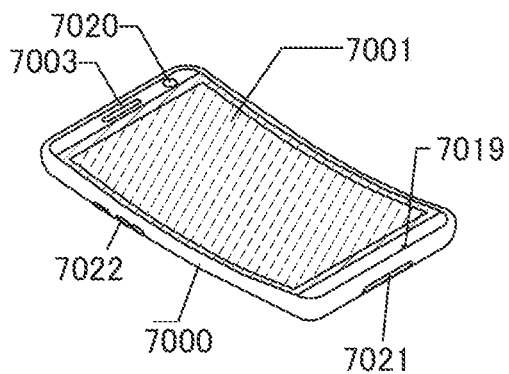

FIG. 4E illustrates a cellular phone (including a smartphone) and can include the display portion 7001, a microphone 7019, the speaker 7003, a camera 7020, an external connection portion 7021, an operation button 7022, and the like in the housing 7000.

Figure 4F:
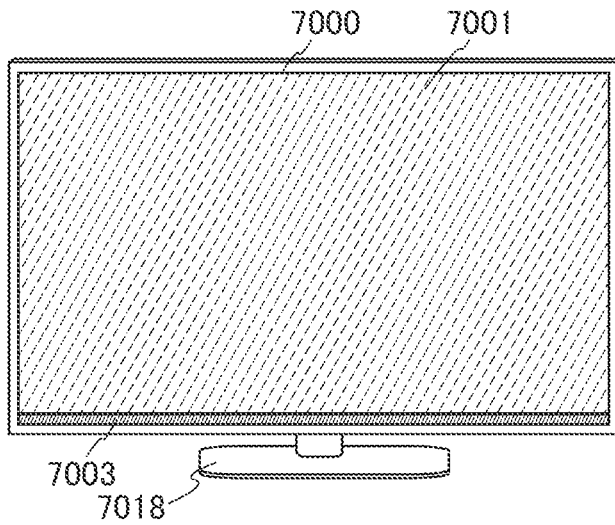

FIG. 4F illustrates a large-size television set (also referred to as TV or a television receiver) and can include the housing 7000, the display portion 7001, the speaker 7003, and the like. In addition, here, the housing 7000 is supported by a stand 7018.

The electronic devices illustrated in FIGS. 4A to 4F can have a variety of functions, such as a function of displaying a variety of data (a still image, a moving image, a text image, and the like) on the display portion, a touch panel function, a function of displaying a calendar, date, time, and the like, a function of controlling a process with a variety of types of software (programs), a wireless communication function, a function of connecting to a variety of computer networks with a wireless communication function, a function of transmitting and receiving a variety of data with a wireless communication function, a function of reading a program or data stored in a recording medium and displaying the program or data on the display portion, and the like. Furthermore, the electronic device including a plurality of display portions can have a function of displaying image data mainly on one display portion while displaying text data on another display portion, a function of displaying a three-dimensional image by displaying images on a plurality of display portions with a parallax taken into account, or the like. Furthermore, the electronic device including an image receiving portion can have a function of taking a still image, a function of taking a moving image, a function of automatically or manually correcting a taken image, a function of storing a taken image in a recording medium (an external recording medium or a recording medium incorporated in the camera), a function of displaying a taken image on the display portion, or the like. Note that functions that can be provided for the electronic devices illustrated in FIGS. 4A to 4F are not limited to those described above, and the electronic devices can have a variety of functions.

Figure 4G:
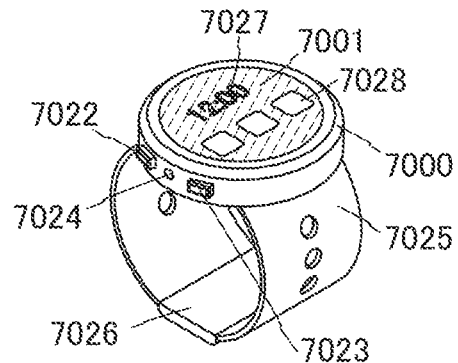

FIG. 4G illustrates a smart watch, which includes the housing 7000, the display portion 7001, operation buttons 7022 and 7023, a connection terminal 7024, a band 7025, a clasp 7026, and the like.

The display portion 7001 mounted in the housing 7000 serving as a bezel includes a non-rectangular display region. The display portion 7001 can display an icon 7027 indicating time, another icon 7028, and the like. The display portion 7001 may be a touch panel (an input/output device) including a touch sensor (an input device).

The smart watch illustrated in FIG. 4G can have a variety of functions, such as a function of displaying a variety of information (e.g., a still image, a moving image, and a text image) on the display portion, a touch panel function, a function of displaying a calendar, date, time, and the like, a function of controlling processing with a variety of types of software (programs), a wireless communication function, a function of connecting to a variety of computer networks with a wireless communication function, a function of transmitting and receiving a variety of data with a wireless communication function, a function of reading a program or data stored in a recording medium and displaying the program or data on the display portion, and the like.

The housing 7000 can include a speaker, a sensor (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like.

Note that the light-emitting device of one embodiment of the present invention or the display device including the light-emitting element of one embodiment of the present invention can be used in the display portion of each electronic device described in this embodiment, enabling display with high color purity.

Figure 5A:
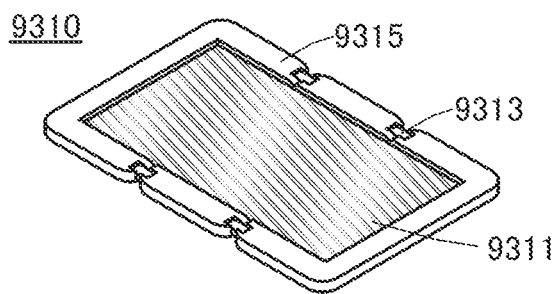
FIGS. 5A to 5C illustrate an electronic device.
Figure 5B:
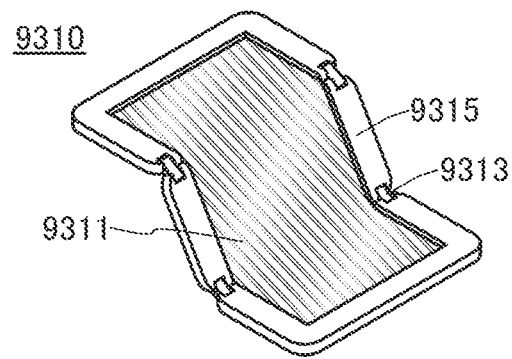
Figure 5C:
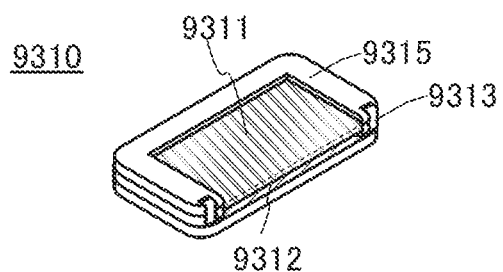

Another electronic device including the light-emitting device is a foldable portable information terminal illustrated in FIGS. 5A to 5C. FIG. 5A illustrates a portable information terminal 9310 which is opened. FIG. 5B illustrates the portable information terminal 9310 which is being opened or being folded. FIG. 5C illustrates the portable information terminal 9310 which is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (an input/output device) including a touch sensor (an input device). By bending the display portion 9311 at a connection portion between two housings 9315 with the use of the hinges 9313, the portable information terminal 9310 can be reversibly changed in shape from an opened state to a folded state. The light-emitting device of one embodiment of the present invention can be used for the display portion 9311. In addition, display with high color purity can be performed. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of application and the like can be smoothly performed.

Figure 6A:
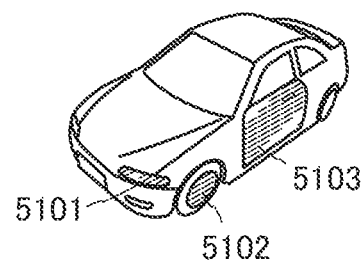
FIGS. 6A and 6B illustrate an automobile.
Figure 6B:
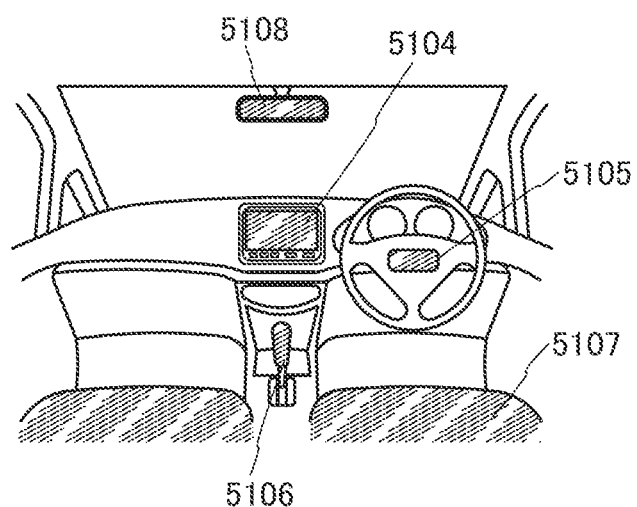

FIGS. 6A and 6B illustrate an automobile including the light-emitting device. The light-emitting device can be incorporated in the automobile, and specifically, can be included in lights 5101 (including lights of the rear part of the car), a wheel cover 5102, a part or whole of a door 5103, or the like on the outer side of the automobile which is illustrated in FIG. 6A. The light-emitting device can also be included in a display portion 5104, a steering wheel 5105, a gear lever 5106, a seat 5107, an inner rearview mirror 5108, or the like on the inner side of the automobile which is illustrated in FIG. 6B, or in a part of a glass window.

As described above, the electronic devices and automobiles can be obtained using the light-emitting device or the display device of one embodiment of the present invention. In that case, display with high color purity can be performed. Note that the light-emitting device or the display device can be used for electronic devices and automobiles in a variety of fields without being limited to those described in this embodiment.

Note that the structures described in this embodiment can be combined with any of the structures described in the other embodiments as appropriate.

Embodiment 6

In this embodiment, a structure of a lighting device fabricated using the light-emitting device of one embodiment of the present invention or the light-emitting element which is a part of the light-emitting device is described with reference to FIGS. 7A to 7D.

Figure 7A:
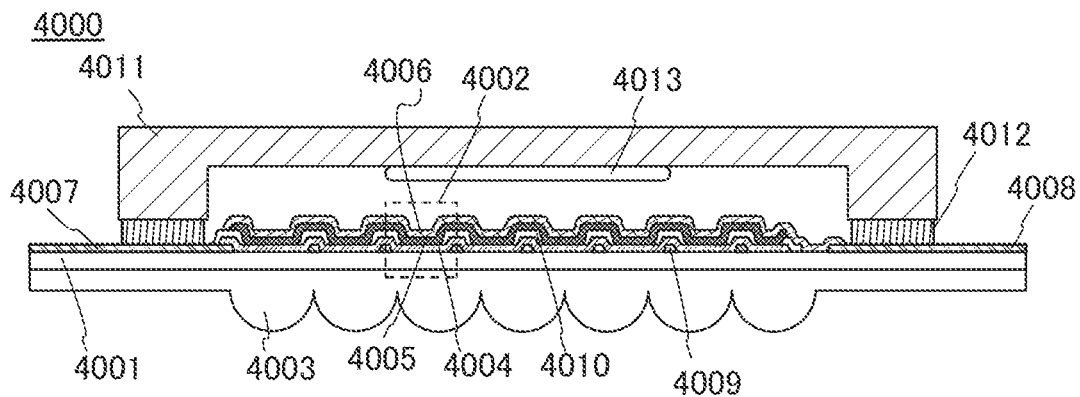
FIGS. 7A to 7D illustrate lighting devices.
Figure 7B:
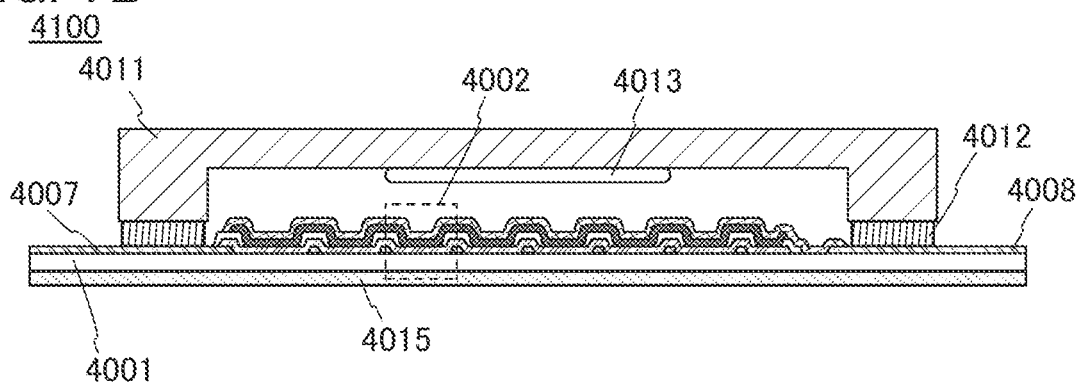
Figure 7C:
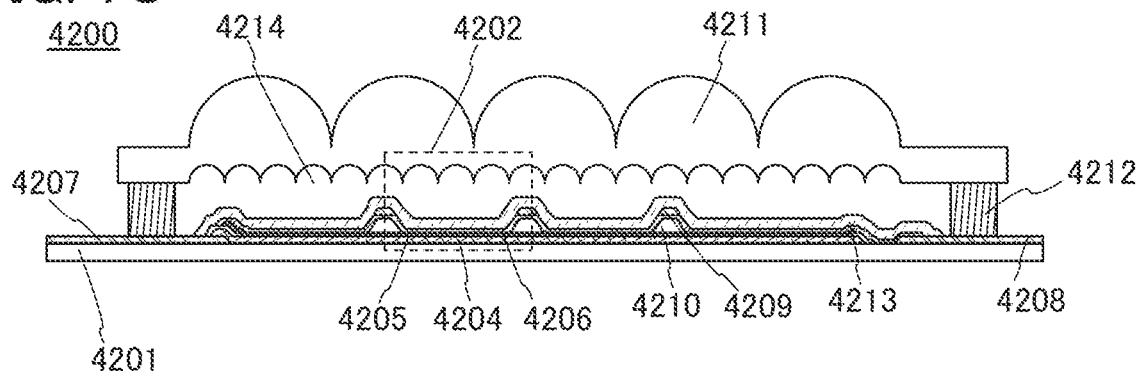
Figure 7D:
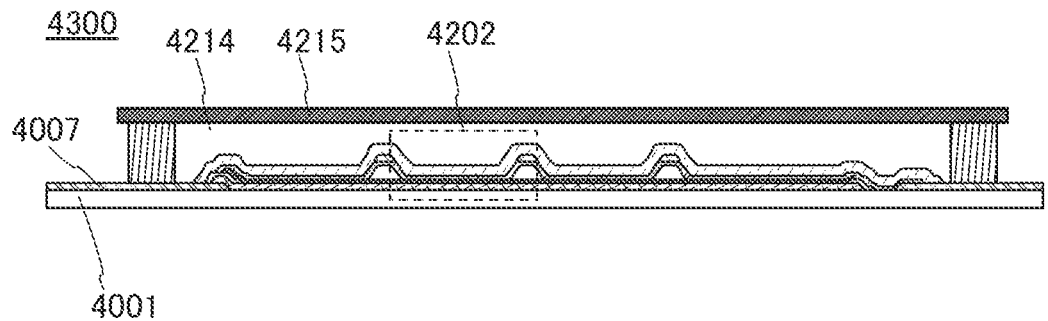

FIGS. 7A to 7D are examples of cross-sectional views of lighting devices. FIGS. 7A and 7B illustrate bottom-emission lighting devices in which light is extracted from the substrate side, and FIGS. 7C and 7D illustrate top-emission lighting devices in which light is extracted from the sealing substrate side.

A lighting device 4000 illustrated in FIG. 7A includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting element 4002. The substrate 4003 has the unevenness illustrated in FIG. 7A, whereby the extraction efficiency of light emitted from the light-emitting element 4002 can be increased.

Instead of the substrate 4003, a diffusion plate 4015 may be provided on the outside of the substrate 4001 as in a lighting device 4100 illustrated in FIG. 7B.

A lighting device 4200 illustrated in FIG. 7C includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting element 4202. The sealing substrate 4211 has the unevenness illustrated in FIG. 7C, whereby the extraction efficiency of light emitted from the light-emitting element 4202 can be increased.

Instead of the sealing substrate 4211, a diffusion plate 4215 may be provided over the light-emitting element 4202 as in a lighting device 4300 illustrated in FIG. 7D.

Note that with the use of the light-emitting device of one embodiment of the present invention or the light-emitting element which is a part of the light-emitting device as described in this embodiment, a lighting device having desired chromaticity can be provided.

Note that the structures described in this embodiment can be combined with any of the structures described in the other embodiments as appropriate.

Embodiment 7

Figure 8:
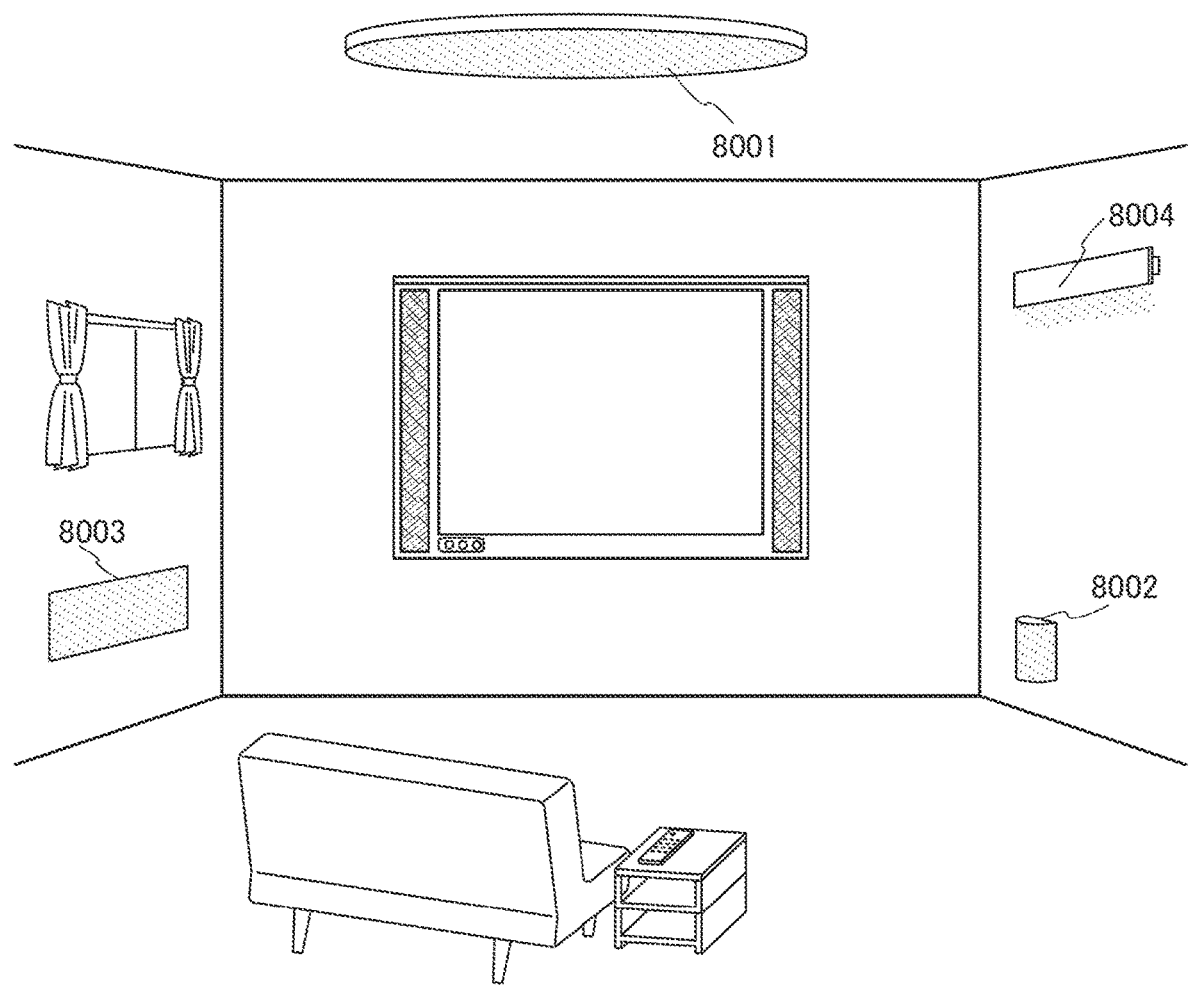
FIG. 8 illustrates lighting devices.

In this embodiment, application examples of lighting devices fabricated using the light-emitting device of one embodiment of the present invention or the light-emitting element which is a part of the light-emitting device will be described with reference to FIG. 8.

A ceiling light 8001 can be used as an indoor lighting device. Examples of the ceiling light 8001 include a direct-mount light and an embedded light. Such a lighting device is fabricated using the light-emitting device and a housing or a cover in combination. Besides, application to a cord pendant light (light that is suspended from a ceiling by a cord) is also possible.

Afoot light 8002 lights a floor so that safety on the floor can be improved. For example, it can be effectively used in a bedroom, on a staircase, or on a passage. In that case, the size or shape of the foot light can be changed depending on the area or structure of a room. The foot light 8002 can be a stationary lighting device fabricated using the light-emitting device and a support base in combination.

A sheet-like lighting 8003 is a thin sheet-like lighting device. The sheet-like lighting, which is attached to a wall when used, is space-saving and thus can be used for a wide variety of uses. Furthermore, the area of the sheet-like lighting can be increased. The sheet-like lighting can also be used on a wall or housing having a curved surface.

In addition, a lighting device 8004 in which the direction of light from a light source is controlled to be only a desired direction can be used.

Besides the above examples, when the light-emitting device of one embodiment of the present invention or the light-emitting element which is a part of the light-emitting device is used as part of furniture in a room, a lighting device that functions as the furniture can be obtained.

As described above, a variety of lighting devices that include the light-emitting device can be obtained. Note that these lighting devices are also embodiments of the present invention.

The structures described in this embodiment can be combined with any of the structures described in the other embodiments as appropriate.

Example 1

Synthesis Example 1

In this example, a method for synthesizing N,N'-(pyrene-1,6-diyl)bis(N-phenyl-6-cyclohexylbenzo[b]naphtho[1,2-d]furan-8-amine) (abbreviation: 1,6chBnfAPrn), which is the organic compound of one embodiment of the present invention and which is represented by Structural Formula (100) in Embodiment 1, is described. The structure of 1,6chBnfAPrn is shown below.

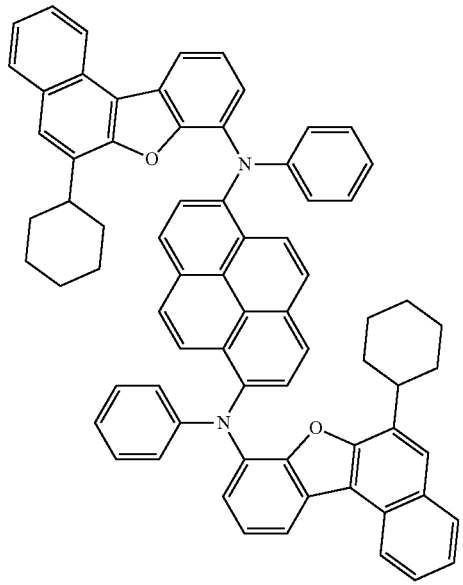

(100)

1,6chBnfAPrn

Step 1: Synthesis of 3-cyclohexyl-2-methoxynaphthalene

Into a 1 L three-neck flask were put 8.9 g (37 mmol) of 2-bromo-3-methoxynaphthalene and 0.53 g (1.1 mmol) of 2-dicyclohexylphosphino-2',4',6'-triisopropylbiphenyl (abbreviation: XPhos), and the air in the flask was replaced with nitrogen. Then, 94 mL of tetrahydrofuran (abbreviation: TIF) was added, and the resulting mixture was degassed under reduced pressure and then stirred at 70° C. To this mixture was added 0.51 g (0.56 mmol) of tris(dibenzylideneacetone)dipalladium(0) (abbreviation: $Pd_2(dba)_3$), and 100 mL of cyclohexylmagnesium bromide (a 1.0 mol/L tetrahydrofuran solution, 0.10 mol) was dropped into the mixture; then, the resulting mixture was stirred for 6 hours at 70° C. under a nitrogen stream.

After the stirring, this mixture was dropped into 0° C. hydrochloric acid (1 mol/L), and an aqueous layer of the resulting mixture was subjected to extraction using toluene. The obtained solution of the extract and an organic layer were combined, and the mixture was washed with water and saturated brine. Then, the mixture was dried with magnesium sulfate. The mixture was separated by gravity filtration, and the obtained filtrate was concentrated to give a yellow oily substance.

The obtained oily substance was purified by silica gel column chromatography (a developing solvent was a mixed solvent of toluene:hexane=9:1) to give 6.5 g of a target white solid in a yield of 73%. A synthesis scheme of Step 1 is shown in (a-1).

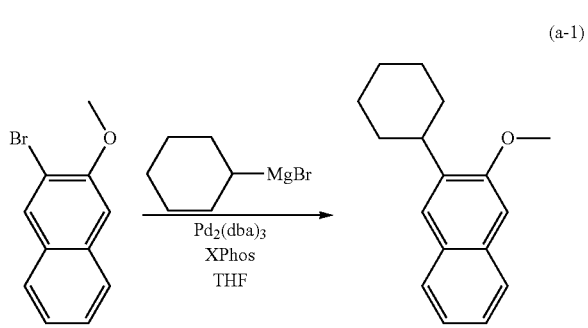

(a-1)

Step 2: Synthesis of 3-cyclohexyl-2-naphthol

Into a 500 mL three-neck flask was put 6.5 g (27 mmol) of 3-cyclohexyl-2-methoxynaphthalene, and the air in the flask was replaced with nitrogen. Then, 140 mL of dichloromethane was added, and the resulting solution was stirred at 0° C. Into the solution, 55 mL of boron tribromide (a 1.0 mol/L dichloromethane solution, 55 mmol) was dropped; then, the resulting solution was stirred for 15 hours while the temperature was returned to room temperature.

After the stirring, this mixture was dropped into a 0° C. saturated aqueous solution of sodium hydrogencarbonate, and an aqueous layer of the resulting mixture was subjected to extraction using dichloromethane. The obtained solution of the extract and an organic layer were combined, and the mixture was washed with water and saturated brine. Then, the mixture was dried with magnesium sulfate. The mixture was separated by gravity filtration, and the obtained filtrate was concentrated to give 5.9 g of a target yellowish white solid in a yield of 96%. A synthesis scheme of Step 2 is shown in (a-2).

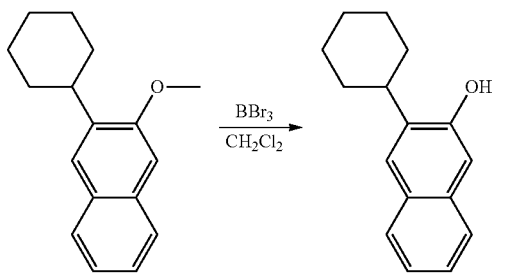

(a-2)

Results of nuclear magnetic resonance (H NMR) spectroscopy analysis of the yellowish white solid obtained in Step 2 are shown below. The results reveal that 3-cyclohexyl-2-naphthol was obtained.

$^1$H NMR (CDCl$_3$, 300 MHz): σ=7.74 (d, J=8.3 Hz, 1H), 7.63-7.61 (m, 2H), 7.39-7.26 (m, 2H), 7.07 (s, 1H), 4.93 (s, 1H), 2.99-2.91 (m, 1H), 1.99-1.78 (m, 5H), 1.54-1.25 (m, 5H).

Step 3: Synthesis of 6-cyclohexylbenzo[b]naphtho [1,2-d]furan

Into a 500 mL three-neck flask were put 5.9 g (26 mmol) of 3-cyclohexyl-2-naphthol, 9.2 g (52 mmol) of 2-bromofluorobenzene, and 17 g (52 mmol) of cesium carbonate, and the air in the flask was replaced with nitrogen. Then, 130 mL of N-methyl-2-pyrrolidone (abbreviation: NMP) was added and the resulting solution was degassed under reduced pressure and then stirred for 6.5 hours at 180° C. under a nitrogen stream.

After the stirring, 10 g (31 mmol) of cesium carbonate and 0.7 g (2.7 mmol) of triphenylphosphine were added to this mixture. The resulting mixture was degassed by being stirred under reduced pressure. To this mixture was added 0.30 g (1.3 mmol) of palladium(II) acetate, and the resulting mixture was stirred for 6 hours at 180° C. under a nitrogen stream.

After the stirring, water was added to this mixture, and an aqueous layer was subjected to extraction using ethyl acetate. The obtained solution of the extract and an organic layer were combined, and the mixture was washed with water and saturated brine. Then, the mixture was dried with magnesium sulfate. The mixture was separated by gravity filtration, and the obtained filtrate was concentrated to give a brown oily substance. The obtained oily substance was purified by silica gel column chromatography (a developing solvent: hexane) to give 7.0 g of a target white solid in a yield of 89%. A synthesis scheme of Step 3 is shown in (a-3).

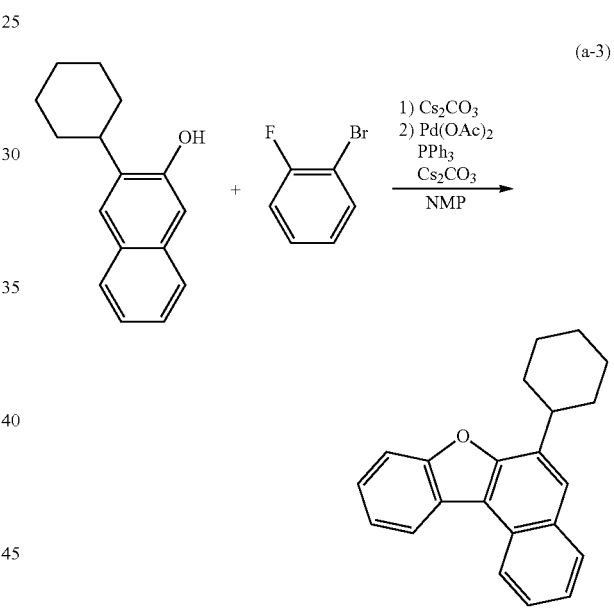

(a-3)

Results of nuclear magnetic resonance ($^1$H NMR) spectroscopy analysis of the white solid obtained in Step 3 are shown below. The results reveal that 6-cyclohexylbenzo[b] naphtho[1,2-d]furan was obtained.

$^1$H NMR (CDCl$_3$, 300 MHz): σ=8.60 (d, J=8.3 Hz, 1H), 8.41-8.38 (m, 1H), 7.99 (d, J=7.8 Hz, 1H), 7.74-7.71 (m, 2H), 7.68-7.63 (m, 1H), 7.54-7.46 (m, 3H), 3.38-3.28 (m, 1H), 2.17-1.38 (m, 10H).

Step 4: Synthesis of 6-cyclohexyl-8-iodobenzo[b] naphtho[1,2-d]furan

Into a 300 mL three-neck flask was put 3.1 g (10 mmol) of 6-cyclohexylbenzo[b]naphtho[1,2-d]furan, and the air in the flask was replaced with nitrogen. Then, 75 mL of tetrahydrofuran was added, and the mixture was stirred at −80° C. Into this solution was dropped 7.2 mL (12 mmol) of n-butyllithium (a 1.6 mol/L n-hexane solution), the temperature was returned to room temperature, and the mixture was stirred for 2 hours under a nitrogen stream. After the stirring, the temperature of the resulting mixture was reduced to −80° C.; then, a solution of 5.3 g (21 mmol) of iodine in 20 mL of tetrahydrofuran was added to the mixture, and stirring was performed for 15 hours while the temperature was gradually returned to room temperature.

After the stirring, an aqueous solution of sodium thiosulfate was added to this mixture, and an aqueous layer was subjected to extraction using ethyl acetate. The obtained solution of the extract and an organic layer were combined, and the mixture was washed with water and saturated brine. Then, the mixture was dried with magnesium sulfate. The mixture was separated by gravity filtration, and the obtained filtrate was concentrated to give a brown oily substance.

The obtained compound was purified by silica gel column chromatography (a developing solvent: hexane) to give 3.6 g of a target white solid. A synthesis scheme of Step 4 is shown in (a-4).

mixture was added 20 mL of toluene, and the resulting mixture was degassed under reduced pressure. To this mixture were added 0.30 mL (0.35 mmol) of tri(tert-butyl) phosphine (a 10 wt % hexane solution) and 40 mg (70 μmol) of bis(dibenzylideneacetone)palladium(0) and then, stirring was performed for 7 hours at 80° C. under a nitrogen stream.

After the stirring, 300 mL of toluene was added to the resulting mixture and then, suction filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina to give a filtrate. The obtained filtrate was concentrated to give a brown solid.

This solid was purified by silica gel column chromatography (a developing solvent was a mixed solvent of hexane:toluene=4:1) to give 1.2 g of a target white solid in a yield of 82%. In addition, 0.20 g of 6-cyclohexylbenzo[b]naphtho[1,2-d]furan was collected. A synthesis scheme of Step 5 is shown in (a-5).

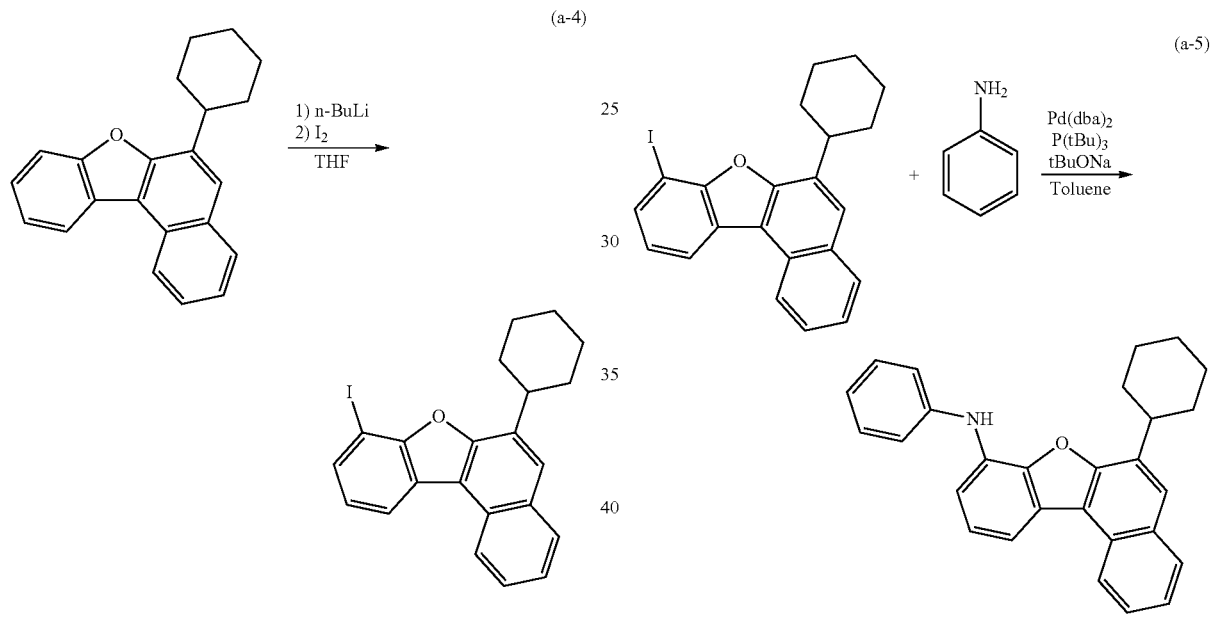

Results of nuclear magnetic resonance (1H NMR) spectroscopy analysis of the white solid obtained in Step 4 are shown below. The results reveal that 6-cyclohexyl-8-iodobenzo[b]naphtho[1,2-d]furan was obtained.

$^1$H NMR (CDCl$_3$, 300 MHz): σ=8.54 (d, J=8.3 Hz, 1H), 8.36-8.33 (m, 1H), 7.99 (d, J=7.8 Hz, 1H), 7.86-7.83 (m, 1H), 7.76 (s, 1H), 7.69-7.61 (m, 1H), 7.56-7.50 (m, 1H), 7.25 (t, J=7.8 Hz, 1H), 3.37-3.28 (m, 1H), 2.18-1.38 (m, 10H).

By $^1$H NMR analysis, the obtained 6-cyclohexyl-8-iodobenzo[b]naphtho[1,2-d]furan was found to contain 18% 6-cyclohexylbenzo[b]naphtho[1,2-d]furan, the raw material, according to the NMR ratio.

Step 5: Synthesis of N-phenyl-6-cyclohexylbenzo[b]naphtho[1,2-d]furan-8-amine

Figure 9A:
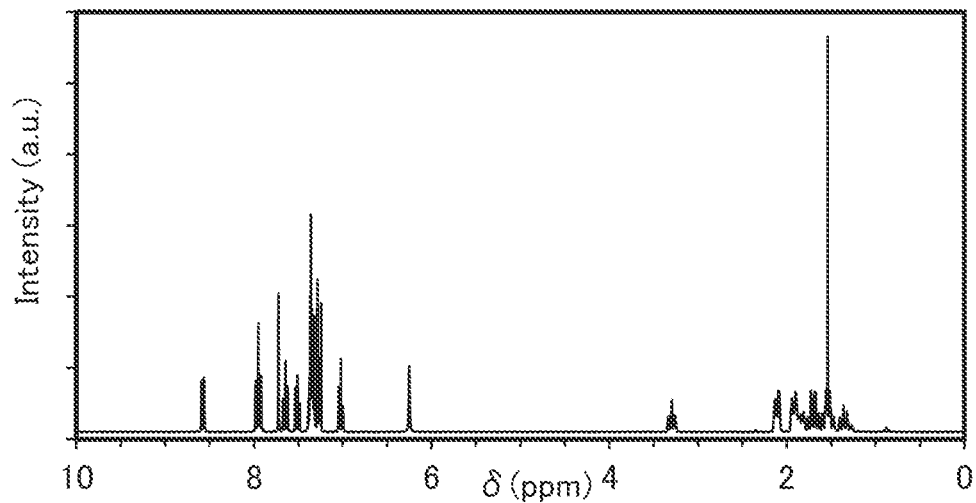
FIGS. 9A to 9C show $^1$H-NMR charts of N-phenyl-6-cyclohexylbenzo[b]naphtho[1,2-d]furan-8-amine.
Figure 9B:
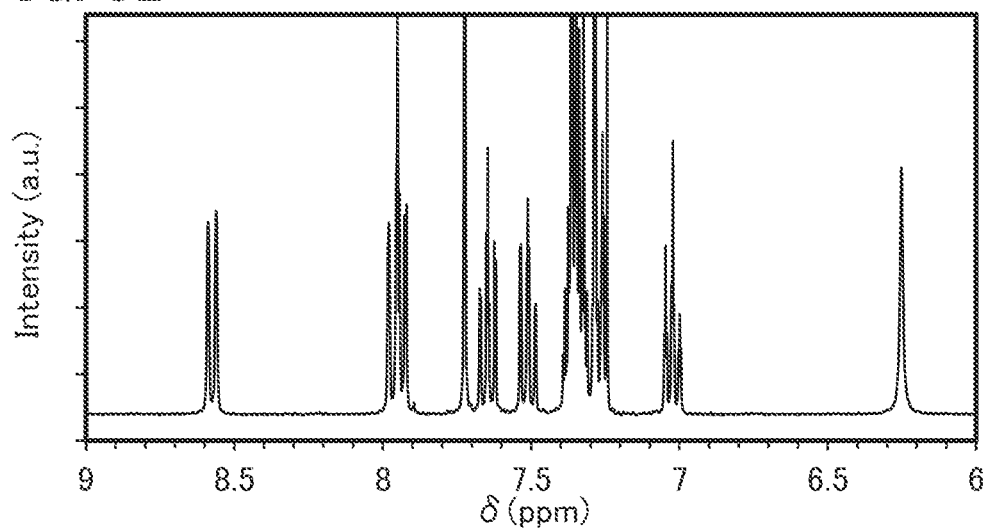
Figure 9C:
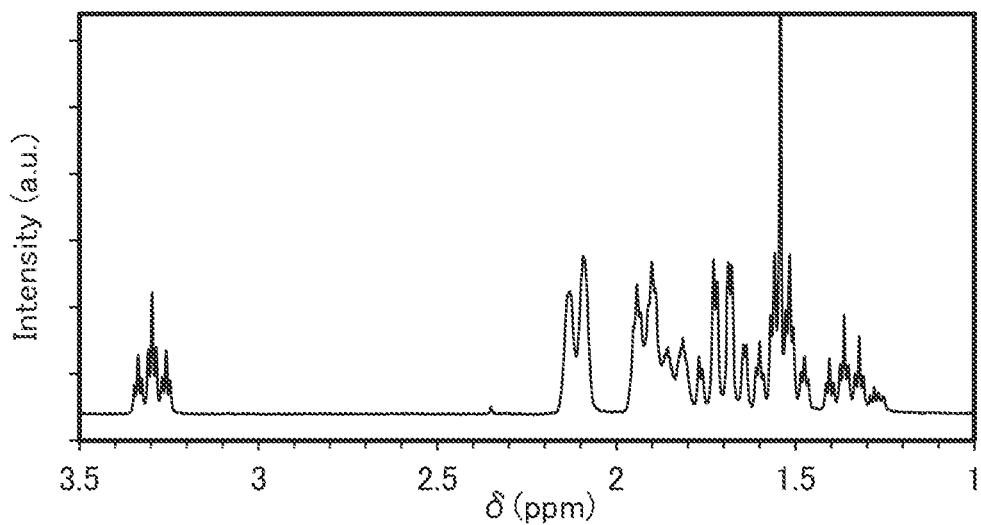

Into a 100 mL three-neck flask were put 1.7 g (3.9 mmol) of 6-cyclohexyl-8-iodobenzo[b]naphtho[1,2-d]furan (which contained 18% 6-cyclohexylbenzo[b]naphtho[1,2-d]furan according to the NMR ratio) obtained in Step 4, 0.44 g (4.7 mmol) of aniline, and 1.1 g (12 mmol) of sodium t-butoxide, and the air in the flask was replaced with nitrogen. To this Results of nuclear magnetic resonance ($^1$H NMR) spectroscopy analysis of the white solid obtained in Step 5 are shown below. In addition, $^1$H NMR charts are shown in FIGS. 9A to 9C. Note that FIG. 9B is an enlarged chart showing the range of 6.0 ppm to 9.0 ppm in FIG. 9A. FIG. 9C is an enlarged chart showing the range of 1.0 ppm to 3.5 ppm in FIG. 9A. The results reveal that N-phenyl-6-cyclohexylbenzo[b]naphtho[1,2-d]furan-8-amine was obtained.

$^1$H NMR (CDCl$_3$, 300 MHz): σ=8.59 (d, J=8.3 Hz, 1H), 7.98-7.92 (m, 2H), 7.72 (s, 1H), 7.67-7.62 (m, 1H), 7.54-7.48 (m, 1H), 7.39-7.25 (m, 6H), 7.05-6.99 (m, 1H), 6.25 (s, 1H), 3.35-3.25 (m, 1H), 2.13-1.31 (m, 10H).

Step 6: Synthesis of 1,6chBnfAPrn

Into a 200 mL three-neck flask were put 0.79 g (2.2 mmol) of 1,6-dibromopyrene, 1.7 g (4.4 mmol) of N-phenyl-6-cyclohexylbenzo[b]naphtho[1,2-d]furan-8-amine, 0.84 g (8.7 mmol) of sodium t-butoxide, and 60 mg (0.15 mmol) of 2-dicyclohexylphosphino-2',6'-dimethoxy-1,1'-biphenyl (abbreviation: SPhos), and the air in the flask was replaced with nitrogen. To this mixture was added 22 mL of xylene, and the resulting mixture was degassed under reduced pressure; then, 40 mg (70 μmol) of bis(dibenzylideneacetone)palladium(0) was added to the mixture and the resulting mixture was stirred for 7 hours at 140° C. under a nitrogen stream.

After the stirring, 500 mL of toluene was added and heating was performed; then, hot filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina. A yellow solid obtained by concentration of the resulting filtrate was purified by silica gel column chromatography (a developing solvent was a mixed solvent of hexane and toluene, and the ratio of hexane to toluene was changed from 9:1 to 7:3 to form a gradient) to give a target yellow solid. The obtained yellow solid was recrystallized with toluene to give 1.2 g of a target yellow solid in a yield of 56%.

By a train sublimation method, 1.2 g of the obtained yellow solid was purified by sublimation. In the purification by sublimation, the yellow solid was heated at 320° C. under a pressure of $2.0 \times 10^{-2}$ Pa for 6 hours. After the purification by sublimation, 0.92 g of a target yellow solid was obtained at a collection rate of 76%. A synthesis scheme of Step 6 is shown in (a-6).

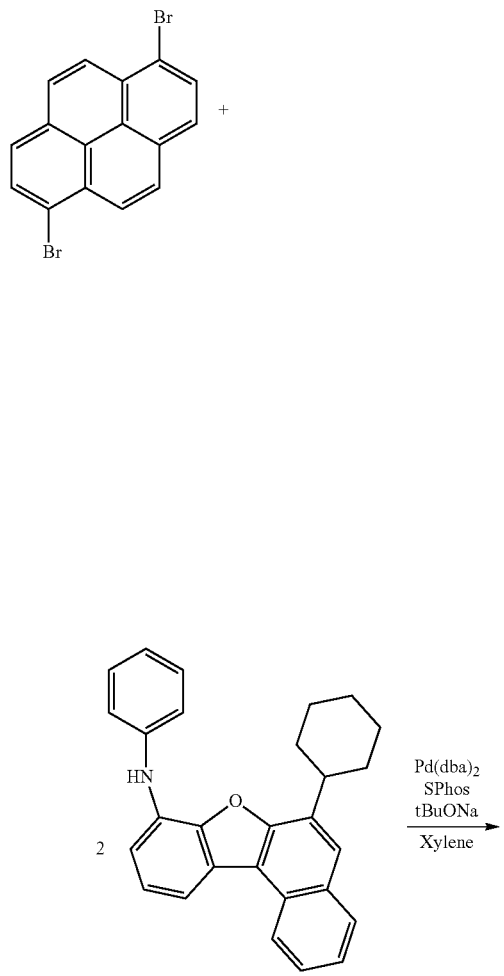

(a-6)

-continued

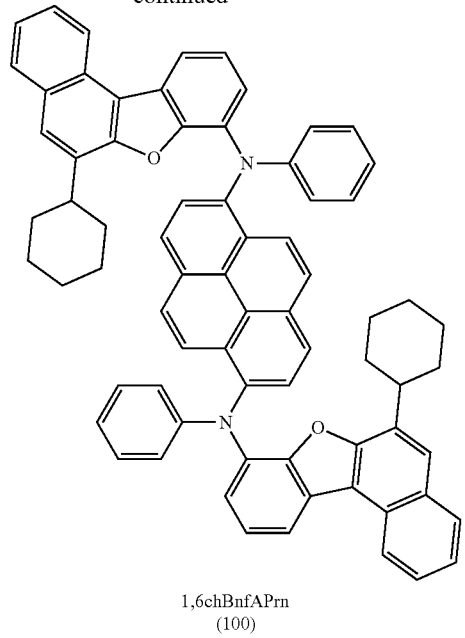

1,6chBnfAPrn
(100)

Figure 10A:
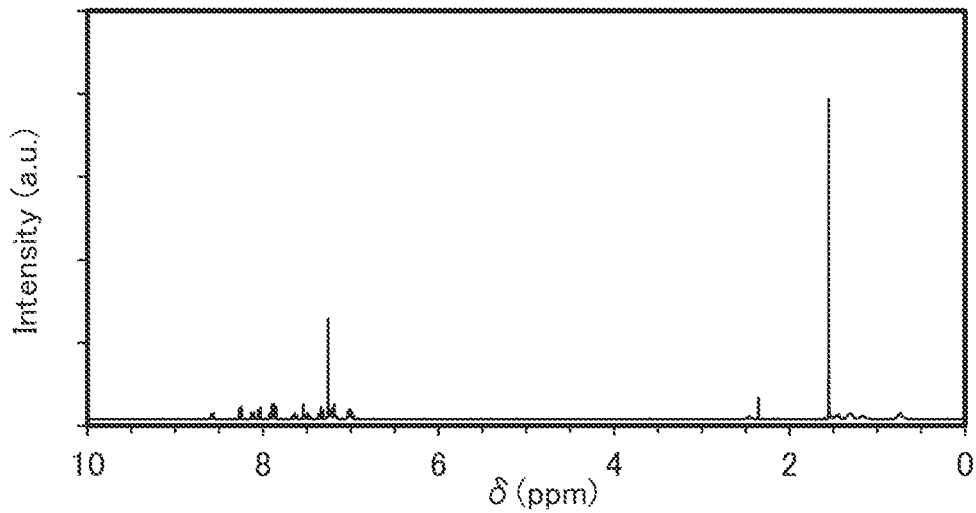
FIGS. 10A to 10C show $^1$H-NMR charts of an organic compound represented by Structural Formula (100).
Figure 10B:
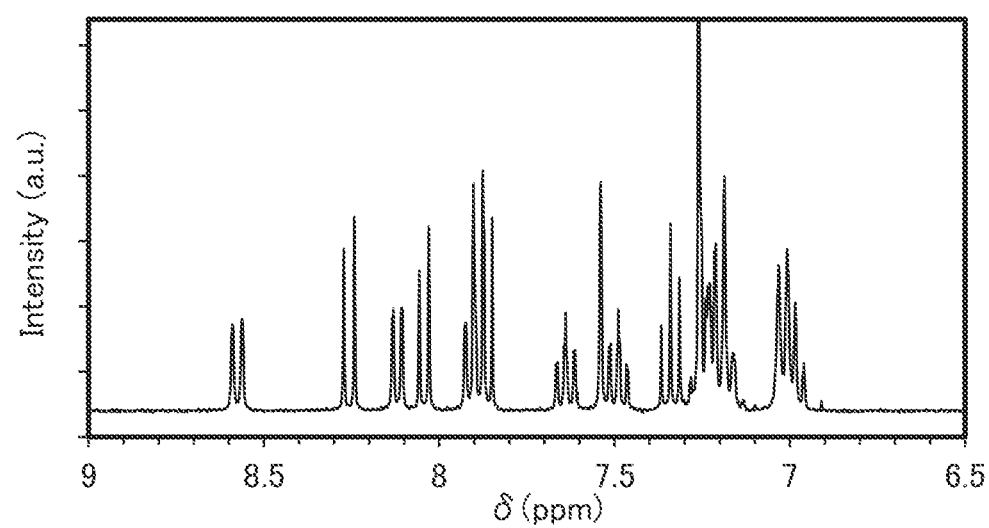
Figure 10C:
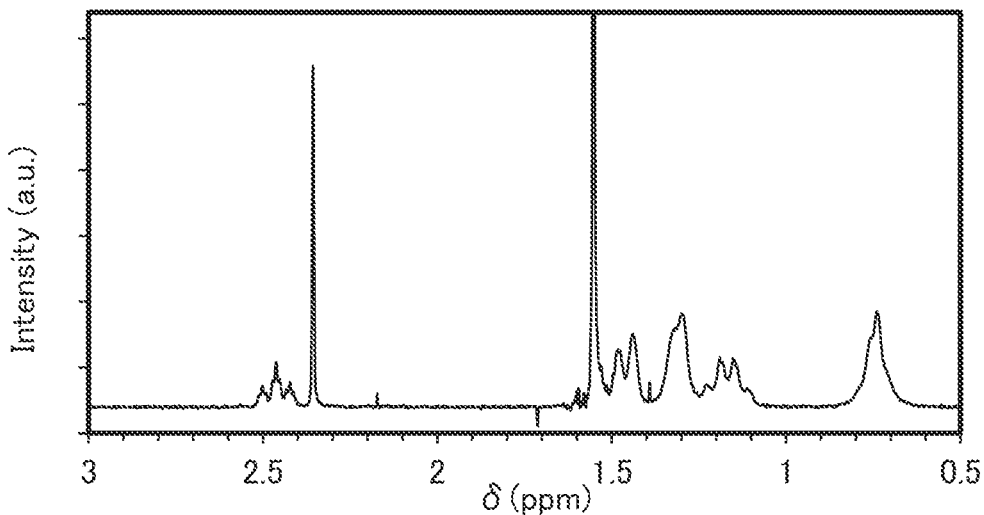

Results of nuclear magnetic resonance (H NMR) spectroscopy analysis of the yellow solid obtained in Step 6 are shown below. In addition, $^1$H NMR charts are shown in FIGS. 10A to 10C. Note that FIG. 10B is an enlarged chart showing the range of 6.5 ppm to 9.0 ppm in FIG. 10A. FIG. 10C is an enlarged chart showing the range of 0.5 ppm to 3.0 ppm in FIG. 10A. The results reveal that 1,6chBnfAPrn (Structural Formula (100)) was obtained.

$^1$H NMR (CDCl$_3$, 300 MHz): σ=8.59 (d, J=8.3 Hz, 2H), 8.27 (d, J=8.8 Hz, 2H), 8.13-8.10 (m, 2H), 8.06 (d, J=8.1 Hz, 2H), 7.92-7.85 (m, 6H), 7.67-7.61 (m, 2H), 7.54-7.47 (m, 4H), 7.37 (t, J=7.8 Hz, 2H), 7.24-7.16 (m, 6H), 7.03-6.96 (m, 6H), 2.51-2.41 (m, 2H), 1.48-0.74 (m, 20H).

Next, ultraviolet-visible absorption spectra (hereinafter simply referred to as "absorption spectra") and emission spectra of a toluene solution and a solid thin film of 1,6chBnfAPrn were measured. The solid thin film was formed over a quartz substrate by a vacuum evaporation method. The absorption spectra were measured using UV-visible spectrophotometers (solution: V-550 manufactured by JASCO Corporation, thin film: U-4100 manufactured by Hitachi High-Technologies Corporation). Note that the absorption spectrum of the solution was calculated by subtraction of the measured absorption spectrum of only toluene in a quartz cell, and the absorption spectrum of the thin film was calculated using an absorbance (−log$_{10}$[% T/(100−% R)]) obtained from a transmittance and a reflectance of the substrate and the thin film. Note that % T represents transmittance and % R represents reflectance. The emission spectra were measured using a fluorescence spectrophotometer (FS920 manufactured by Hamamatsu Photonics K.K.).

Figure 11A:
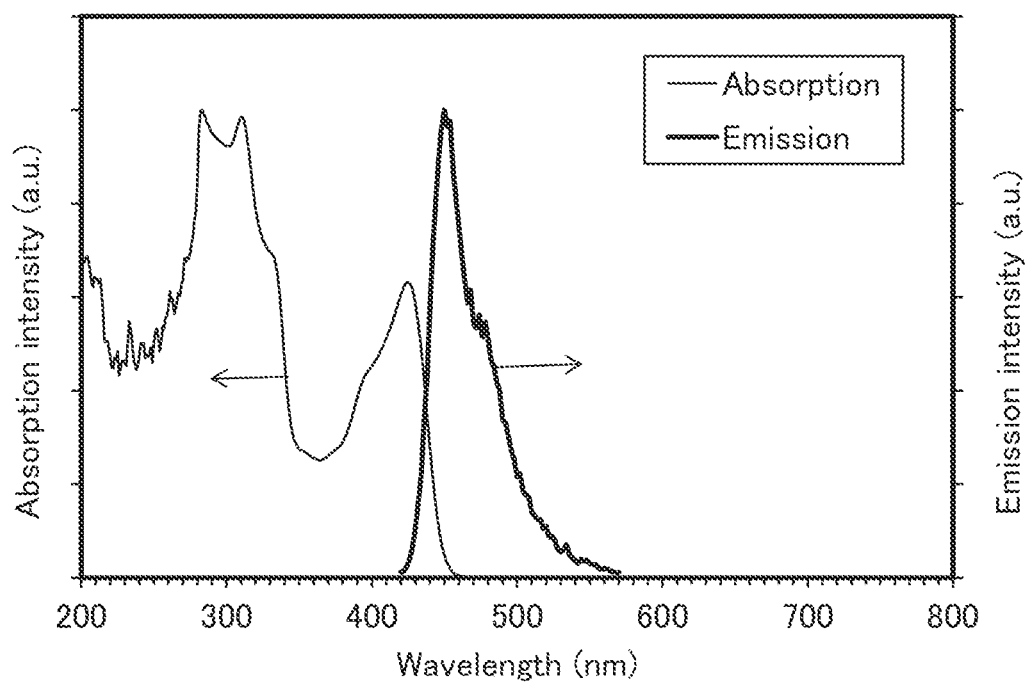
FIGS. 11A and 11B each show an ultraviolet-visible absorption spectrum and an emission spectrum of the organic compound represented by Structural Formula (100).
Figure 11B:
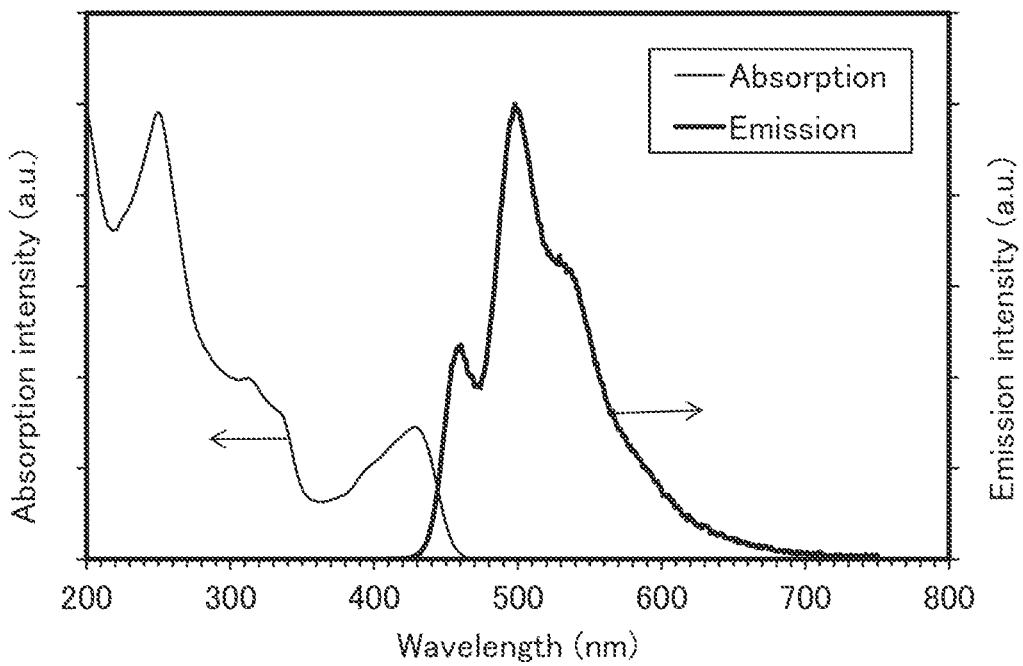

FIG. 11A shows the obtained absorption and emission spectra of the toluene solution. The horizontal axis represents wavelength and the vertical axes represent absorption intensity and emission intensity. FIG. 11B shows the obtained absorption and emission spectra of the solid thin film. The horizontal axis represents wavelength and the vertical axes represent absorption intensity and emission intensity.

As shown by the results in FIG. 11A, the toluene solution of 1,6chBnfAPrn exhibited an absorption peak at around 425 nm and an emission wavelength peak at 450 nm (excitation wavelength: 415 nm). Furthermore, as shown by the results in FIG. 11B, the solid thin film of 1,6chBnfAPrn exhibited an absorption peak at around 425 nm and emission wavelength peaks at around 498 nm and 460 nm (excitation wavelength: 400 nm).

Furthermore, differential scanning calorimetry (DSC) measurement was performed on 1,6chBnfAPrn by Pyris1DSC manufactured by PerkinElmer, Inc. In the differential scanning calorimetry measurement, the temperature was raised from −10° C. to 370° C. at a temperature rising rate of 50° C./min, kept for 1 minute, lowered to −10° C. at a temperature decreasing rate of 100° C./min, raised from −10° C. to 370° C. at a temperature rising rate of 10° C./min, kept for 1 minute, and then lowered to −10° C. at a temperature decreasing rate of 10° C./min. No peak was observed in the DSC measurement results during the second temperature rise; from the DSC measurement results during the first temperature rise, the melting point of 1,6chBnfAPrn was found to be 354° C.

Thermogravimetry-differential thermal analysis (TG-DTA) was performed on 1,6chBnfAPrn. The measurement was performed using a high vacuum differential type differential thermal balance (TG-DTA2410SA, manufactured by Bruker AXS K.K.). The measurement was performed at 10 Pa at a temperature rising rate of 10° C./min under a nitrogen stream (a flow rate of 3.5 mL/min). The thermogravimetry-differential thermal analysis showed that the temperature (decomposition temperature) at which the weight measured by thermogravimetry becomes −5% of the weight at the start of the measurement is 338° C., which means sublimation at a relatively low temperature (350° C.).

Example 2

Synthesis Example 2

In this example, a method for synthesizing N,N'-(pyrene-1,6-diyl)bis[N-(2-methylphenyl)-6-cyclohexylbenzo[b]naphtho[1,2-d]furan-8-amine] (abbreviation: 1,6oMechBnfAPrn), which is the organic compound of one embodiment of the present invention and which is represented by Structural Formula (101) in Embodiment 1, is described. The structure of 1,6oMechBnfAPrn is shown below.

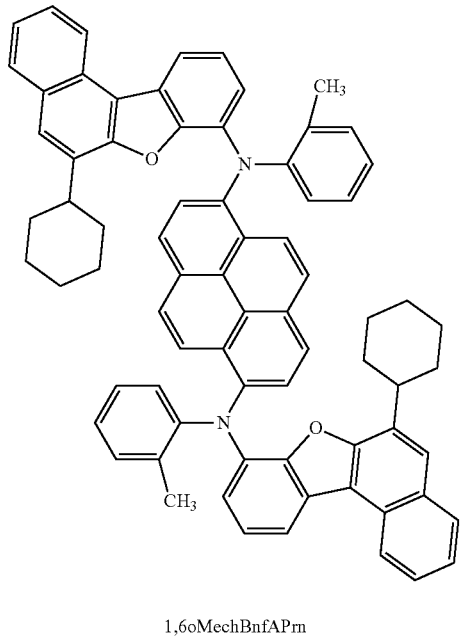

(101)

1,6oMechBnfAPrn

The method for synthesizing 1,6oMechBnfAPrn described in this example and the method for synthesizing 1,6chBnfAPrn described in Example 1 share Steps 1 to 4 (synthesis of 6-cyclohexyl-8-iodobenzo[b]naphtho[1,2-d]furan). Example 1 can be referred to for the common Steps 1 to 4; the subsequent Steps 7 and 8 are described in this example.

Step 7: Synthesis of N-(2-methylphenyl)-6-cyclohexylbenzo[b]naphtho[1,2-d]furan-8-amine Into a 100 mL three-neck flask were put 1.1 g (2.6 mmol) of 6-cyclohexyl-8-iodobenzo[b]naphtho[1,2-d]furan, 0.33 g (3.1 mmol) of o-toluidine, and 0.74 g (7.7 mmol) of sodium t-butoxide, and the air in the flask was replaced with nitrogen. To this mixture was added 13 mL of toluene, and the resulting mixture was degassed under reduced pressure. To this mixture were added 0.30 mL (0.35 mmol) of tri(tert-butyl)phosphine (a 10 wt % hexane solution) and 40 mg (70 μmol) of bis(dibenzylideneacetone)palladium(0) and then, stirring was performed for 4 hours at 80° C. under a nitrogen stream.

After the stirring, 300 mL of toluene was added to the resulting mixture and then, suction filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina to give a filtrate. The obtained filtrate was concentrated to give a brown solid.

This solid was purified by silica gel column chromatography (a developing solvent was a mixed solvent of hexane:toluene=4:1) to give 0.64 g of a target white solid in a yield of 61%. A synthesis scheme of Step 7 is shown in (a-7).

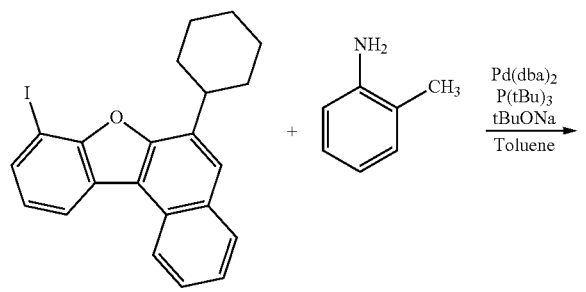

(a-7)

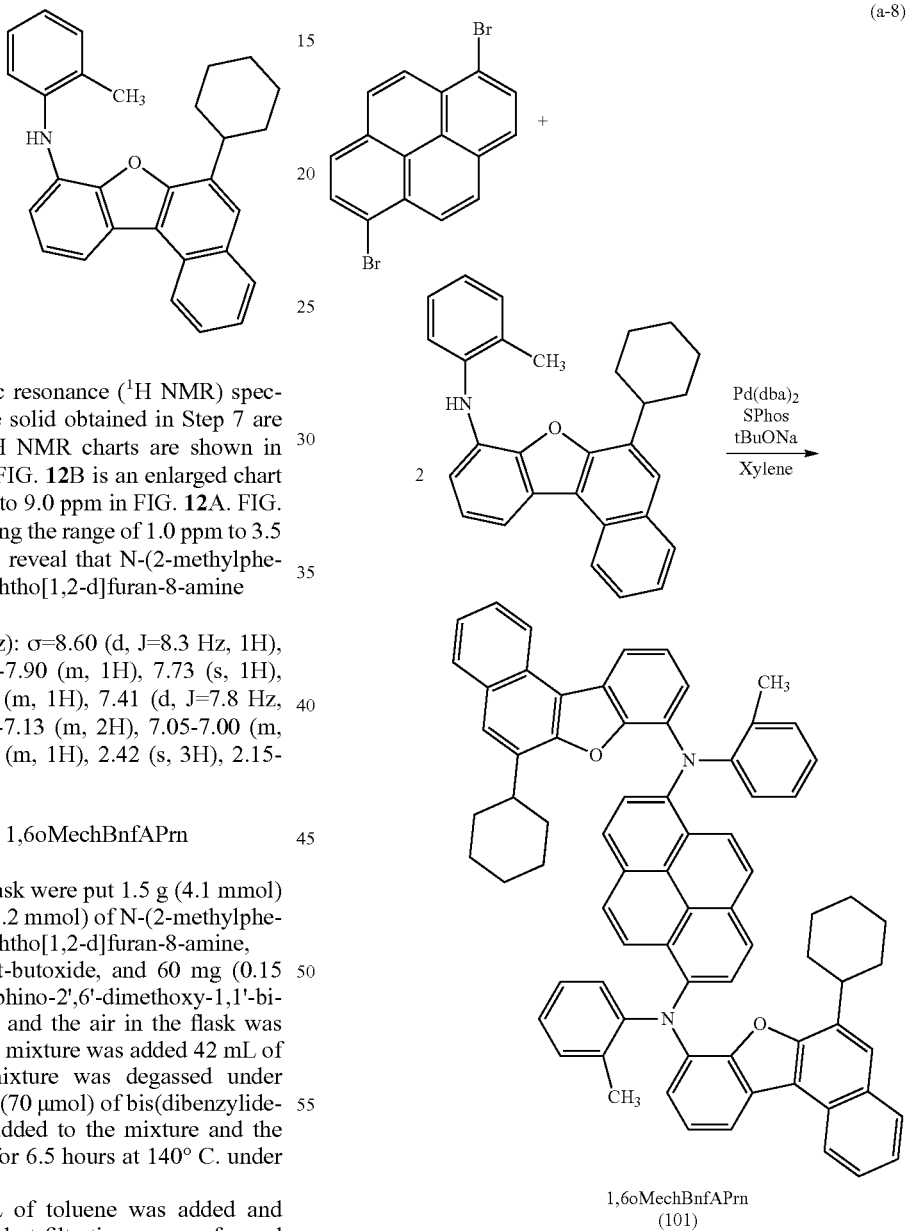

Figure 12A:
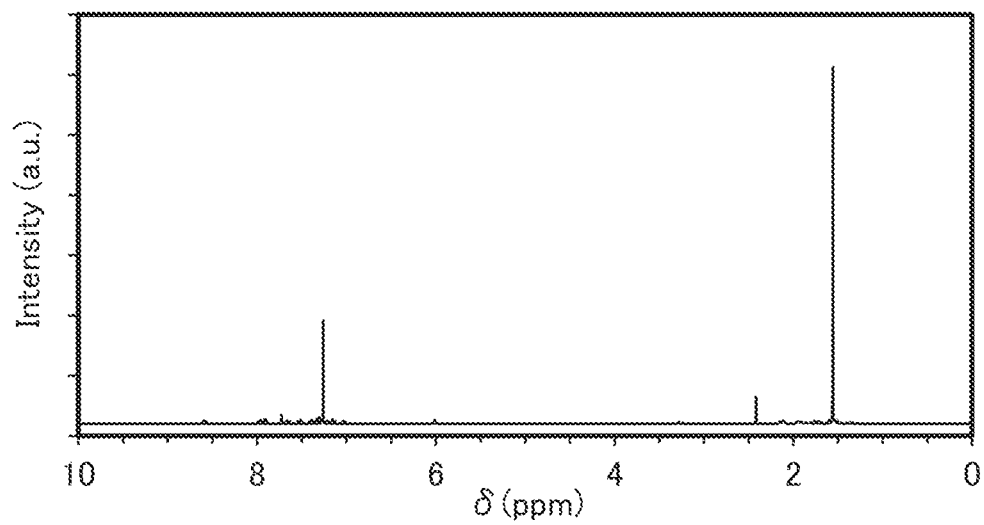
FIGS. 12A to 12C show $^1$H-NMR charts of N-(2-methylphenyl)-6-cyclohexylbenzo[b]naphtho[1,2-d]furan-8-amine.
Figure 12B:
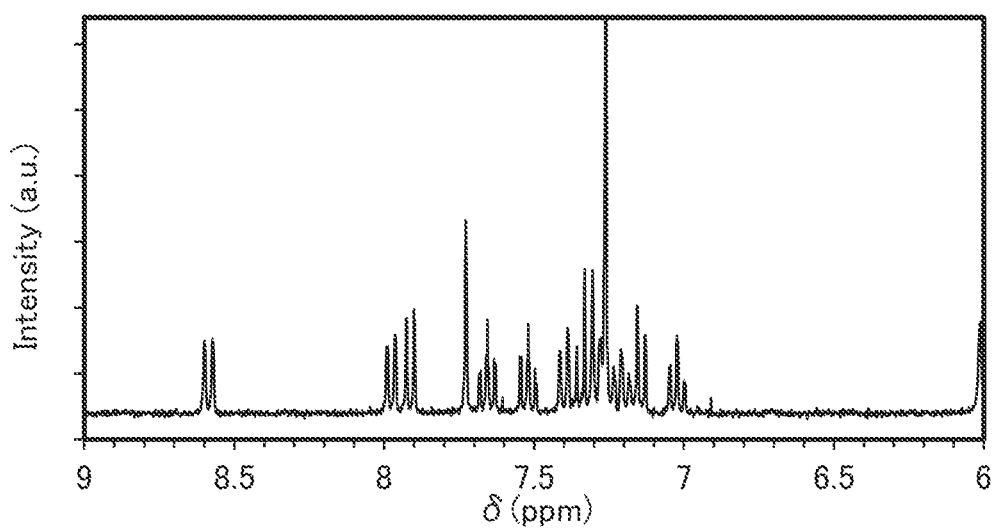
Figure 12C:
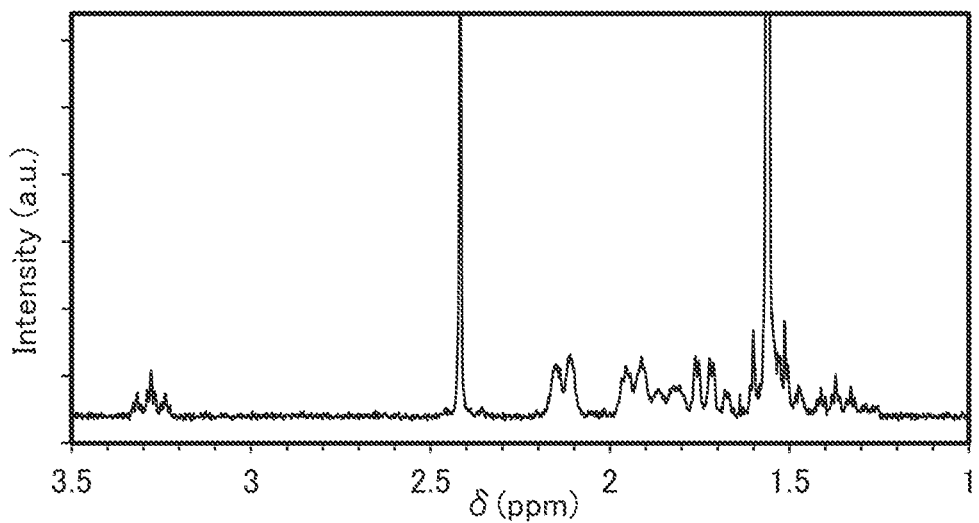

Results of nuclear magnetic resonance (¹H NMR) spectroscopy analysis of the white solid obtained in Step 7 are shown below. In addition, ¹H NMR charts are shown in FIGS. 12A to 12C. Note that FIG. 12B is an enlarged chart showing the range of 6.0 ppm to 9.0 ppm in FIG. 12A. FIG. 12C is an enlarged chart showing the range of 1.0 ppm to 3.5 ppm in FIG. 12A. The results reveal that N-(2-methylphenyl)-6-cyclohexylbenzo[b]naphtho[1,2-d]furan-8-amine was obtained.

¹H NMR (CDCl$_3$, 300 MHz): σ=8.60 (d, J=8.3 Hz, 1H), 7.99 (d, J=7.8 Hz, 1H), 7.92-7.90 (m, 1H), 7.73 (s, 1H), 7.68-7.62 (m, 1H), 7.55-7.50 (m, 1H), 7.41 (d, J=7.8 Hz, 1H), 7.36-7.28 (m, 2H), 7.23-7.13 (m, 2H), 7.05-7.00 (m, 1H), 6.01 (bs, 1H), 3.31-3.24 (m, 1H), 2.42 (s, 3H), 2.15-1.33 (m, 10H).

Step 8: Synthesis of 1,6oMechBnfAPrn

Into a 200 mL three-neck flask were put 1.5 g (4.1 mmol) of 1,6-dibromopyrene, 3.3 g (8.2 mmol) of N-(2-methylphenyl)-6-cyclohexylbenzo[b]naphtho[1,2-d]furan-8-amine, 1.6 g (16 mmol) of sodium t-butoxide, and 60 mg (0.15 mmol) of 2-dicyclohexylphosphino-2',6'-dimethoxy-1,1'-biphenyl (abbreviation: SPhos), and the air in the flask was replaced with nitrogen. To this mixture was added 42 mL of xylene, and the resulting mixture was degassed under reduced pressure; then, 40 mg (70 μmol) of bis(dibenzylideneacetone)palladium(0) was added to the mixture and the resulting mixture was stirred for 6.5 hours at 140° C. under a nitrogen stream.

After the stirring, 500 mL of toluene was added and heating was performed; then, hot filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina. A yellow solid obtained by concentration of the resulting filtrate was purified by silica gel column chromatography (a developing solvent was a mixed solvent of hexane and toluene, and the ratio of hexane to toluene was changed from 9:1 to 7:3 to form a gradient) to give a target yellow solid. The obtained yellow solid was recrystallized with toluene to give 1.0 g of a target yellow solid in a yield of 24%.

By a train sublimation method, 1.0 g of the obtained yellow solid was purified by sublimation. In the purification by sublimation, the yellow solid was heated at 315° C. under a pressure of 2.0×10⁻² Pa for 6 hours. After the purification by sublimation, 0.92 g of a target yellow solid was obtained at a collection rate of 92%. A synthesis scheme of Step 8 is shown in (a-8).

(a-8)

Figure 13A:
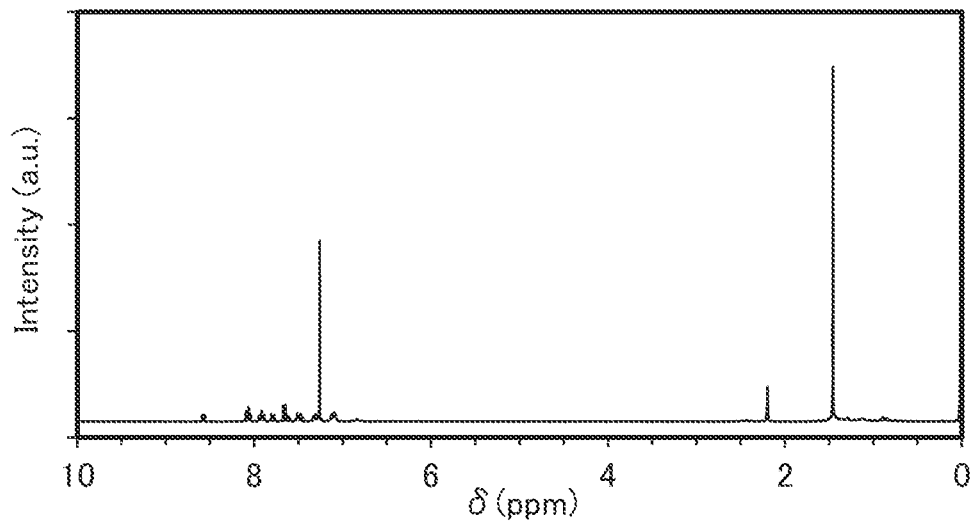
FIGS. 13A to 13C show $^1$H-NMR charts of an organic compound represented by Structural Formula (101).
Figure 13B:
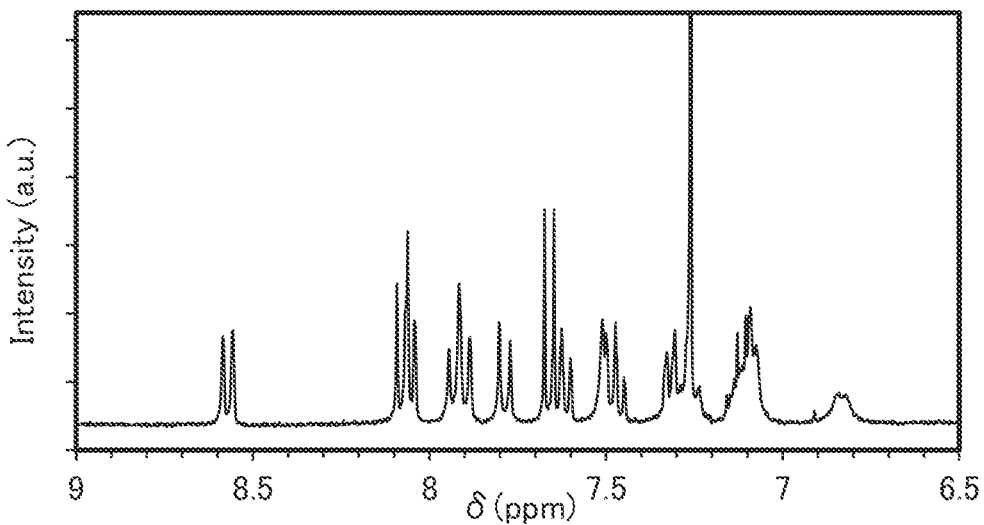
Figure 13C:
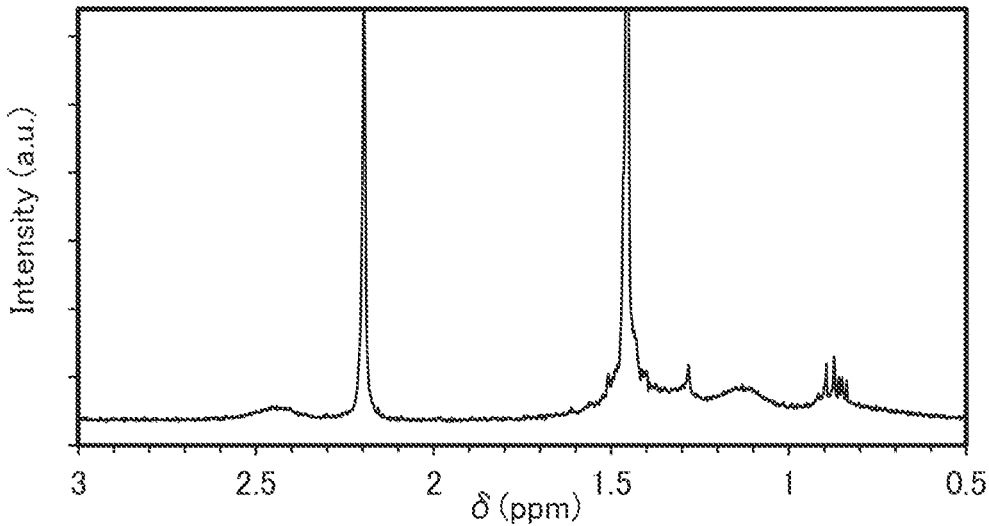

Results of nuclear magnetic resonance (H NMR) spectroscopy analysis of the yellow solid obtained in Step 8 are shown below. In addition, ¹H NMR charts are shown in FIGS. 13A to 13C. Note that FIG. 13B is an enlarged chart showing the range of 6.5 ppm to 9.0 ppm in FIG. 13A. FIG. 13C is an enlarged chart showing the range of 0.5 ppm to 3.0 ppm in FIG. 13A. The results reveal that 1,6oMechBnfAPrn (Structural Formula (101)) was obtained.

¹H NMR (CDCl₃, 60° C., 300 MHz): σ=8.58 (d, J=8.3 Hz, 2H), 8.09-8.04 (m, 4H), 7.95-7.89 (m, 4H), 7.80 (d, J=9.3 Hz, 2H), 7.67-7.60 (m, 4H), 7.51-7.45 (m, 4H), 7.32-7.24 (m, 4H), 7.16-7.07 (m, 6H), 6.85-6.82 (m, 2H), 2.46-2.40 (m, 2H), 2.20 (s, 6H), 1.51-0.84 (m, 20H).

Next, absorption spectra and emission spectra of a toluene solution and a solid thin film of 1,6oMechBnfAPrn were measured. The solid thin film was formed over a quartz substrate by a vacuum evaporation method. The absorption spectra were measured using UV-visible spectrophotometers (solution: V-550 manufactured by JASCO Corporation, thin film: U-4100 manufactured by Hitachi High-Technologies Corporation). Note that the absorption spectrum of the solution was calculated by subtraction of the measured absorption spectrum of only toluene in a quartz cell, and the absorption spectrum of the thin film was calculated using an absorbance ($-\log_{10}$[% T/(100−% R)]) obtained from a transmittance and a reflectance of the substrate and the thin film. Note that % T represents transmittance and % R represents reflectance. The emission spectra were measured using a fluorescence spectrophotometer (FS920 manufactured by Hamamatsu Photonics K.K.).

Figure 14A:
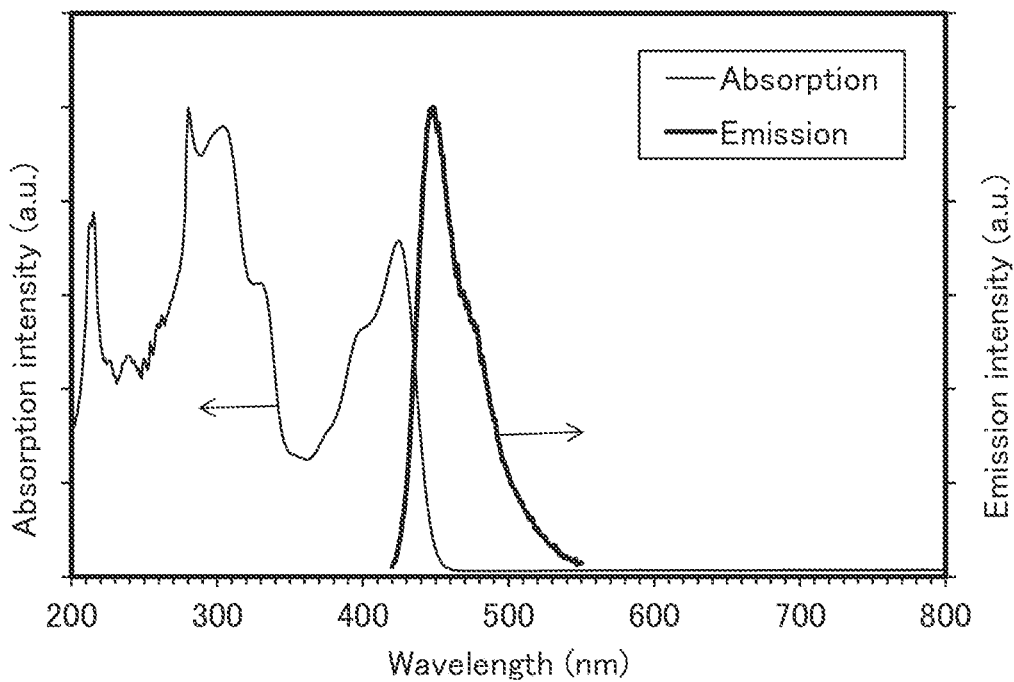
FIGS. 14A and 14B each show an ultraviolet-visible absorption spectrum and an emission spectrum of the organic compound represented by Structural Formula (101).
Figure 14B:
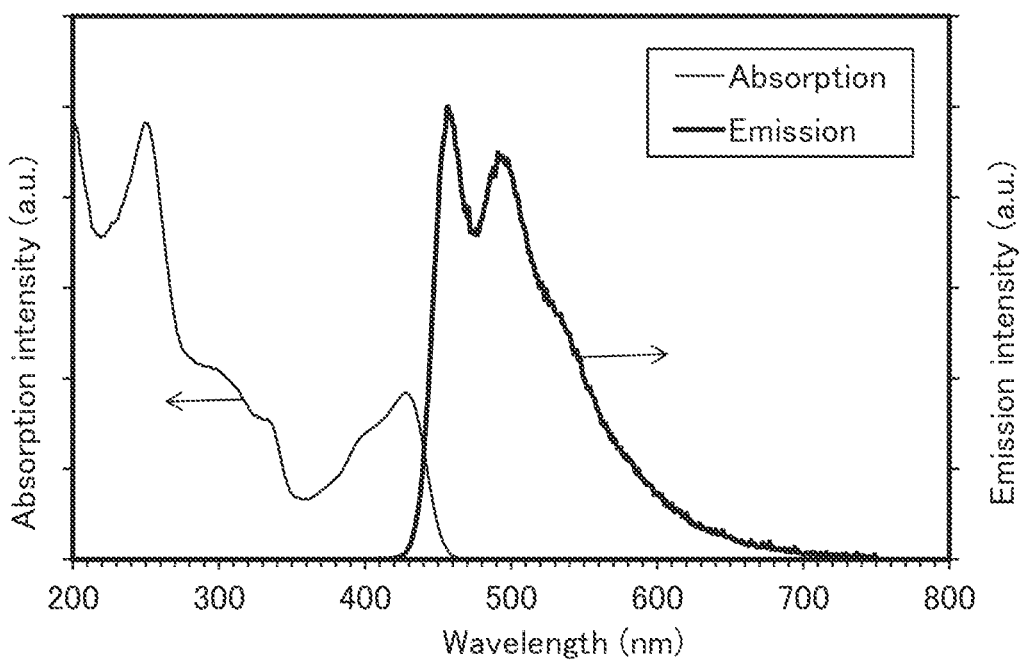

FIG. 14A shows the obtained absorption and emission spectra of the toluene solution. The horizontal axis represents wavelength and the vertical axes represent absorption intensity and emission intensity. FIG. 14B shows the obtained absorption and emission spectra of the solid thin film. The horizontal axis represents wavelength and the vertical axes represent absorption intensity and emission intensity.

As shown by the results in FIG. 14A, the toluene solution of 1,6oMechBnfAPrn exhibited an absorption peak at around 424 nm and an emission wavelength peak at 448 nm (excitation wavelength: 415 nm). Furthermore, as shown by the results in FIG. 14B, the solid thin film of 1,6oMechBnfAPrn exhibited an absorption peak at around 428 nm and emission wavelength peaks at around 493 nm and 457 nm (excitation wavelength: 400 nm).

Example 3

Synthesis Example 3

In this example, a method for synthesizing N,N'-(pyrene-1,6-diyl)bis(N-phenyl-6-isopropylbenzo[b]naphtho[1,2-d]furan-8-amine) (abbreviation: 1,6iPrBnfAPrn), which is the organic compound of one embodiment of the present invention and which is represented by Structural Formula (116) in Embodiment 1, and N,N'-(pyrene-1,6-diyl)bis(N-phenyl-6-normalpropylbenzo[b]naphtho[1,2-d]furan-8-amine) (abbreviation: 1,6nPrBnfAPrn) represented by Structural Formula (118) is described. The structures of 1,6iPrBnfAPrn and 1,6nPrBnfAPrn are shown below.

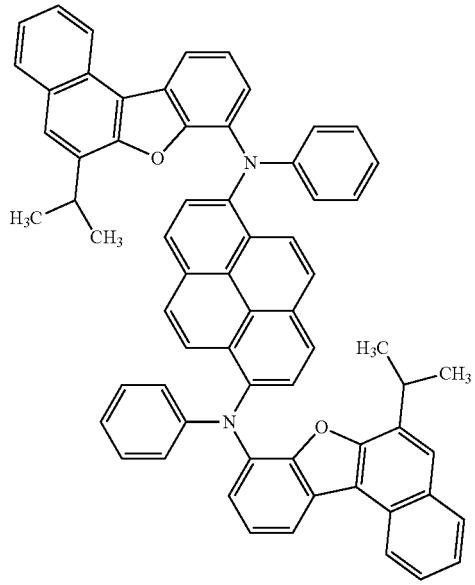

1,6iPrBnfAPrn

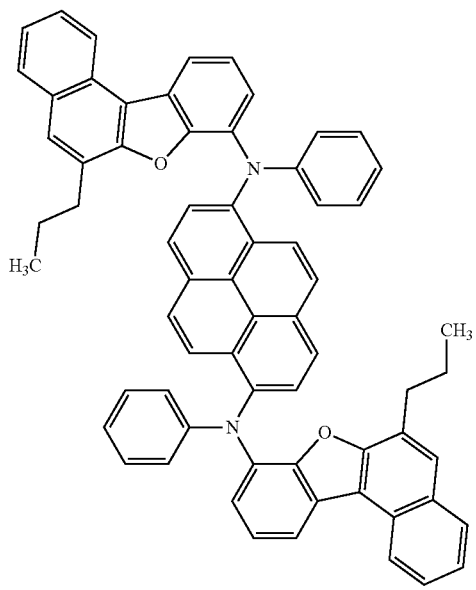

1,6nPrBnfAPrn

Step 1: Synthesis of 3-isopropyl-2-methoxynaphthalene

Into a 1 L three-neck flask were put 3.5 g (15 mmol) of 2-bromo-3-methoxynaphthalene and 0.21 g (0.44 mmol) of 2-dicyclohexylphosphino-2',4',6'-triisopropylbiphenyl (abbreviation: XPhos), and the air in the flask was replaced with nitrogen. Then, 60 mL of tetrahydrofuran (abbreviation: TIF) was added, and the resulting mixture was degassed under reduced pressure and then stirred at 70° C. To this mixture was added 0.20 g (0.22 mmol) of tris(dibenzylideneacetone)dipalladium(0) (abbreviation: Pd₂(dba)₃), and 22 mL of cyclohexylmagnesium bromide (a 2.0 mol/L tetrahydrofuran solution, 44 mmol) was dropped into the mixture; then, this mixture was stirred for 6 hours at 70° C. under a nitrogen stream.

After the stirring, this mixture was dropped into 0° C. hydrochloric acid (1 mol/L), and an aqueous layer of the resulting mixture was subjected to extraction using toluene. The obtained solution of the extract and an organic layer were combined, and the mixture was washed with water and saturated brine. Then, the mixture was dried with magnesium sulfate. The mixture was separated by gravity filtration, and the obtained filtrate was concentrated to give a yellow oily substance.

The obtained oily substance was purified by silica gel column chromatography (a developing solvent: hexane) to give 2.5 g of a white solid in a yield of 75%. A synthesis scheme of Step 1 is shown in (b-1).

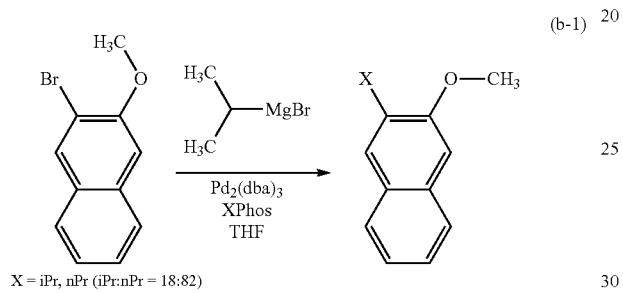

X = iPr, nPr (iPr:nPr = 18:82)

The white solid obtained in Step 1 was analyzed by nuclear magnetic resonance (H NMR) spectroscopy. The results revealed that a mixture of 3-isopropyl-2-methoxynaphthalene and 3-normalpropyl-2-methoxynaphthalene was obtained.

The above $^1$H NMR analysis showed that 3-isopropyl-2-methoxynaphthalene and 3-normalpropyl-2-methoxynaphthalene were generated in a ratio of 18:82.

Step 2: Synthesis of 3-isopropyl-2-naphthol and 3-normalpropyl-2-naphthol

Into a 300 mL three-neck flask were put 2.5 g (13 mmol) of a mixture of 3-isopropyl-2-methoxynaphthalene and 3-normalpropyl-2-methoxynaphthalene, and the air in the flask was replaced with nitrogen. Then, 65 mL of dichloromethane was added, and the resulting solution was stirred at 0° C. Into the solution, 26 mL of boron tribromide (a 1.0 mol/L dichloromethane solution, 26 mmol) was dropped; then, the resulting solution was stirred for 15 hours while the temperature was returned to room temperature.

After the stirring, this mixture was dropped into a 0° C. saturated aqueous solution of sodium hydrogencarbonate, and an aqueous layer of the resulting mixture was subjected to extraction using dichloromethane. The obtained solution of the extract and an organic layer were combined, and the mixture was washed with water and saturated brine. Then, the mixture was dried with magnesium sulfate. The mixture was separated by gravity filtration, and the obtained filtrate was concentrated to give 2.3 g of a target yellowish white solid in a yield of 98%. A synthesis scheme of Step 2 is shown in (b-2).

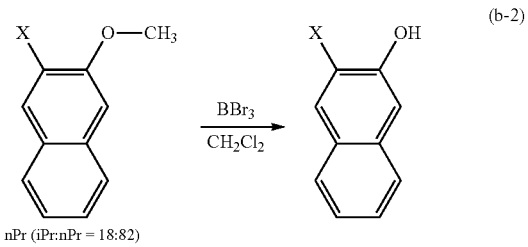

X = iPr, nPr (iPr:nPr = 18:82)

The yellowish white solid obtained in Step 2 was analyzed by nuclear magnetic resonance ($^1$H NMR) spectroscopy. The results revealed that a naphthol compound was obtained.

Step 3: Synthesis of 6-isopropylbenzo[b]naphtho[1, 2-d]furan and 6-normalpropylbenzo[b]naphtho[1,2-d]furan Into a 200 mL three-neck flask were put 2.3 g (12 mmol) of a mixture of 3-isopropyl-2-naphthol and 3-normalpropyl-2-naphthol, 4.3 g (25 mmol) of 2-bromofluorobenzene, and 8.0 g (25 mmol) of cesium carbonate, and the air in the flask was replaced with nitrogen. Then, 62 mL of N-methyl-2-pyrrolidone (abbreviation: NMP) was added and the resulting solution was degassed under reduced pressure and then stirred for 7 hours at 180° C. under a nitrogen stream.

After the stirring, 7.2 g (22 mmol) of cesium carbonate and 0.30 g (1.1 mmol) of triphenylphosphine were added to this mixture. The resulting mixture was degassed by being stirred under reduced pressure. To this mixture was added 0.13 g (0.58 mmol) of palladium(II) acetate, and the resulting mixture was stirred for 7 hours at 180° C. under a nitrogen stream.

After the stirring, water was added to this mixture, and an aqueous layer was subjected to extraction using ethyl acetate. The obtained solution of the extract and an organic layer were combined, and the mixture was washed with water and saturated brine. Then, the mixture was dried with magnesium sulfate. The mixture was separated by gravity filtration, and the obtained filtrate was concentrated to give a brown oily substance. The obtained oily substance was purified by silica gel column chromatography (a developing solvent: hexane) to give 2.7 g of a target white solid in a yield of 84%. A synthesis scheme of Step 3 is shown in (b-3).

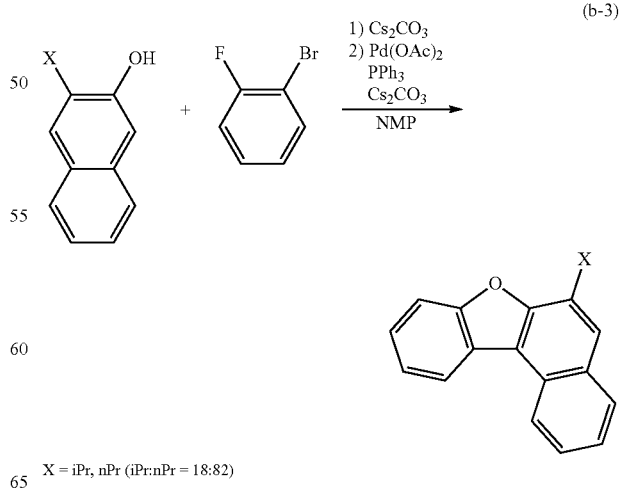

X = iPr, nPr (iPr:nPr = 18:82)

The white solid obtained in Step 3 was analyzed by nuclear magnetic resonance (H NMR) spectroscopy. The results revealed that a benzo[b]naphtho[1,2-d]furan compound was obtained.

Step 4: Synthesis of 6-isopropyl-8-iodobenzo[b]naphtho[1,2-d]furan and 6-normalpropyl-8-iodobenzo[b]naphtho[1,2-d]furan Into a 300 mL three-neck flask was put 2.7 g (10 mmol) of a mixture of 6-isopropylbenzo[b]naphtho[1,2-d]furan and 6-normalpropylbenzo[b]naphtho[1,2-d]furan, and the air in the flask was replaced with nitrogen. Then, 75 mL of tetrahydrofuran was added, and the mixture was stirred at −80° C. Into this solution was dropped 7.2 mL (12 mmol) of n-butyllithium (a 1.6 mol/L n-hexane solution), the temperature was returned to room temperature, and the mixture was stirred for 2 hours under a nitrogen stream. After the stirring, the temperature of the resulting mixture was reduced to −80° C.; then, a solution of 5.3 g (21 mmol) of iodine in 20 mL of tetrahydrofuran was added to the mixture, and stirring was performed for 15 hours while the temperature was gradually returned to room temperature.

After the stirring, an aqueous solution of sodium thiosulfate was added to this mixture, and an aqueous layer was subjected to extraction using ethyl acetate. The obtained solution of the extract and an organic layer were combined, and the mixture was washed with water and saturated brine. Then, the mixture was dried with magnesium sulfate. The mixture was separated by gravity filtration, and the obtained filtrate was concentrated to give a brown oily substance.

The obtained compound was purified by silica gel column chromatography (a developing solvent: hexane) to give 3.2 g of a target white solid. A synthesis scheme of Step 4 is shown in (b-4).

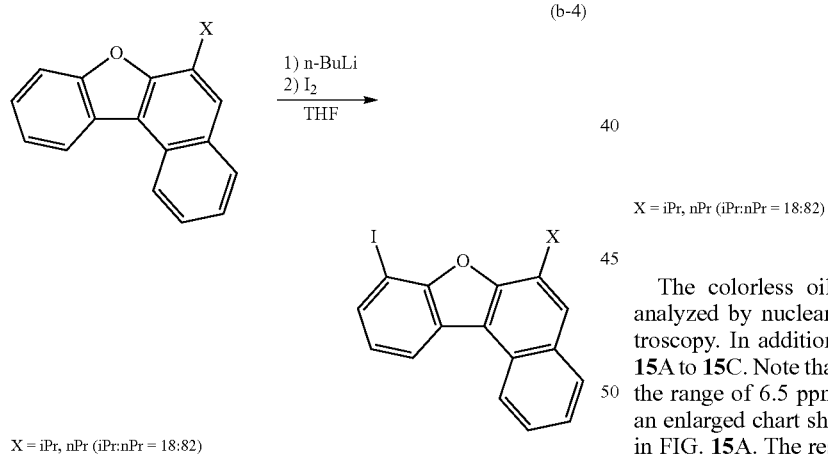

X = iPr, nPr (iPr:nPr = 18:82)

The white solid obtained in Step 4 was analyzed by nuclear magnetic resonance (H NMR) spectroscopy. The results revealed that an 8-iodobenzo[b]naphtho[1,2-d]furan compound was obtained.

The ¹H NMR analysis revealed that a mixture of a target iodide and a raw material was obtained. The NMR ratio of the iodide to the raw material was 87:13.

Step 5: Synthesis of N-phenyl-6-isopropylbenzo[b]naphtho[1,2-d]furan-8-amine and N-phenyl-6-normalpropylbenzo[b]naphtho[1,2-d]furan-8-amine Into a 100 mL three-neck flask were put 1.6 g (4.1 mmol) of a mixture of 6-isopropyl-8-iodobenzo[b]naphtho[1,2-d]furan and 6-normalpropyl-8-iodobenzo[b]naphtho[1,2-d]furan, 0.47 g (5.1 mmol) of aniline, and 1.2 g (13 mmol) of sodium t-butoxide, and the air in the flask was replaced with nitrogen. To this mixture was added 21 mL of toluene, and the resulting mixture was degassed under reduced pressure. To this mixture were added 0.30 mL (0.35 mmol) of tri(tert-butyl)phosphine (a 10 wt % hexane solution) and 40 mg (70 μmol) of bis(dibenzylideneacetone)palladium(0) and then, stirring was performed for 5.5 hours at 80° C. under a nitrogen stream.

After the stirring, 300 mL of toluene was added to the resulting mixture and then, suction filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina to give a filtrate. The obtained filtrate was concentrated to give a brown oily substance.

This oily substance was purified by silica gel column chromatography (a developing solvent was a mixed solvent of hexane:toluene=4:1) to give 1.1 g of a target colorless oily substance in a yield of 78%. A synthesis scheme of Step 5 is shown in (b-5).

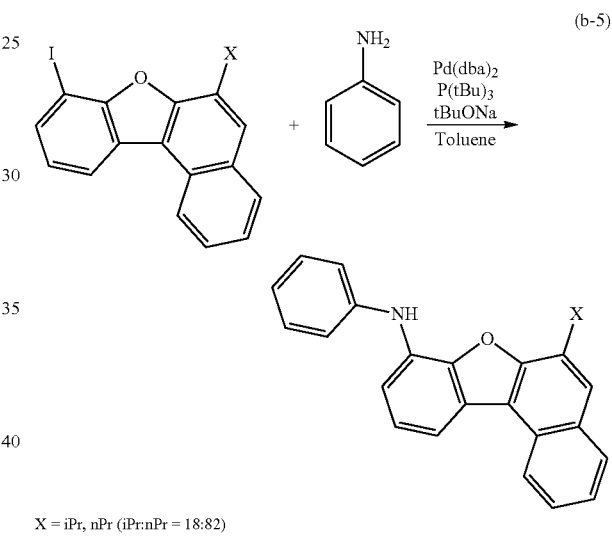

X = iPr, nPr (iPr:nPr = 18:82)

Figure 15A:
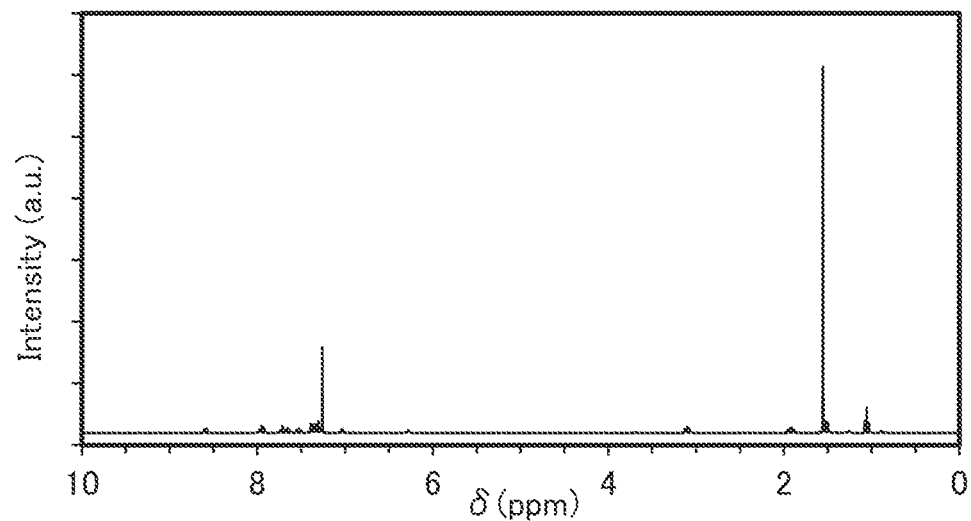
FIGS. 15A to 15C show $^1$H-NMR charts of N-phenyl-6-isopropylbenzo[b]naphtho[1,2-d]furan-8-amine.
Figure 15B:
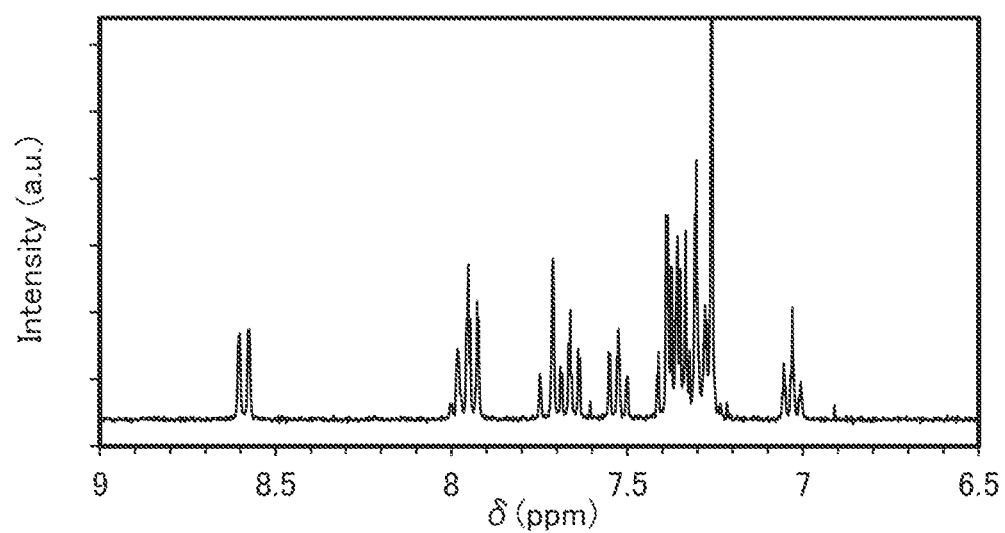
Figure 15C:
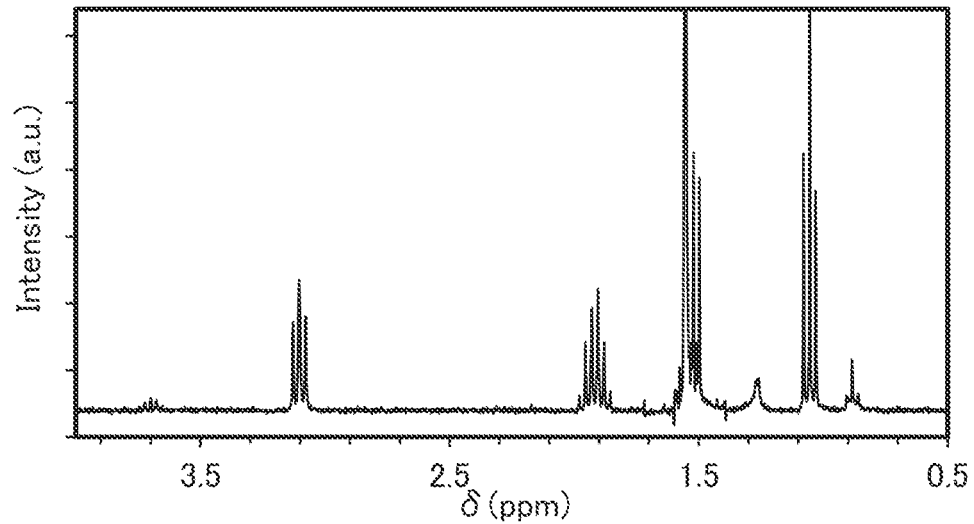

The colorless oily substance obtained in Step 5 was analyzed by nuclear magnetic resonance (¹H NMR) spectroscopy. In addition, ¹H NMR charts are shown in FIGS. 15A to 15C. Note that FIG. 15B is an enlarged chart showing the range of 6.5 ppm to 9.0 ppm in FIG. 15A. FIG. 15C is an enlarged chart showing the range of 0.5 ppm to 4.0 ppm in FIG. 15A. The results reveal that a mixture of N-phenyl-6-isopropylbenzo[b]naphtho[1,2-d]furan-8-amine and N-phenyl-6-normalpropylbenzo[b]naphtho[1,2-d]furan-8-amine was obtained.

¹H NMR (CDCl₃, 300 MHz): σ=8.60-8.58 (m, 1H), 8.00-7.92 (m, 2H), 7.75-7.63 (m, 2H), 7.55-7.50 (m, 1H), 7.42-7.27 (m, 6H), 7.65-7.01 (m, 1H), 3.72-3.68 (m, 1H (iPr)), 3.13 (t, J=7.6 Hz, 2H (nPr)), 1.93 (sext, J=7.4 Hz, 2H (nPr)), 1.52 (d, J=6.8 Hz, 6H (iPr)), 1.08 (t, J=7.6 Hz, 3H (nPr)).

Step 6: Synthesis of 1,6iPrBnfAPrn and 1,6nPrBnfAPrn

Into a 100 mL three-neck flask were put 0.36 g (1.0 mmol) of 1,6-dibromopyrene, 0.71 g (2.0 mmol) of a mixture of N-phenyl-6-isopropylbenzo[b]naphtho[1,2-d]furan-8-amine and N-phenyl-6-normalpropylbenzo[b]naphtho[1,2-d]furan-8-amine, 0.40 g (4.2 mmol) of sodium t-butoxide, and 60 mg (0.15 mmol) of 2-dicyclohexylphosphino-2',6'-dimethoxy-1,1'-biphenyl (abbreviation: SPhos), and the air in the flask was replaced with nitrogen. To this mixture was added 10 mL of xylene, and the resulting mixture was degassed under reduced pressure; then, 40 mg (70 μmol) of bis(dibenzylideneacetone)palladium(0) was added to the mixture and the resulting mixture was stirred for 6.5 hours at 140° C. under a nitrogen stream.

After the stirring, 500 mL of toluene was added and heating was performed; then, hot filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina. A yellow solid obtained by concentration of the resulting filtrate was recrystallized with toluene to give 0.43 g of a target yellow solid in a yield of 48%.

By a train sublimation method, 1.2 g of the obtained yellow solid was purified by sublimation. In the purification by sublimation, the yellow solid was heated at 327° C. under a pressure of $2.0 \times 10^{-2}$ Pa for 4 hours. After the purification by sublimation, 0.32 g of a target yellow solid was obtained at a collection rate of 75%. A synthesis scheme of Step 6 is shown in (b-6).

(b-6)

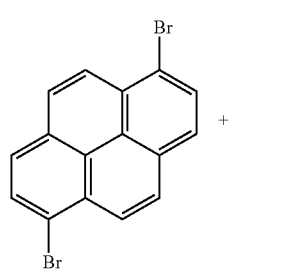

+

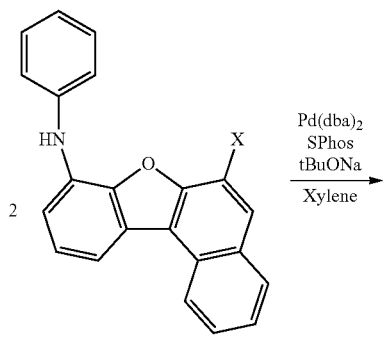

X = iPr, nPr (iPr:nPr = 18:82)

Pd(dba)₂
SPhos
tBuONa
―――――→
Xylene

-continued

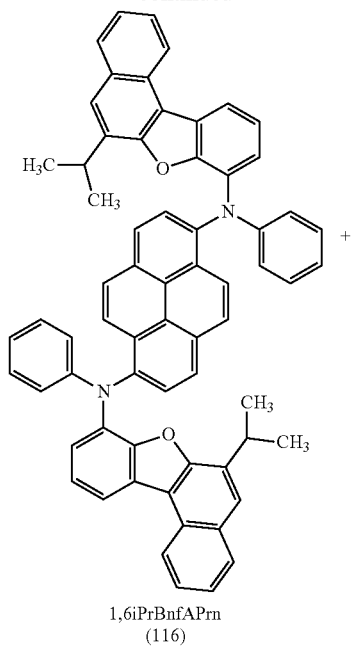

1,6iPrBnfAPrn
(116)

+

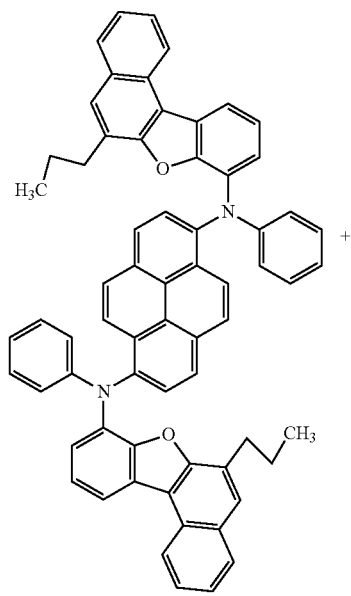

1,6nPrBnfAPrn
(118)

-continued

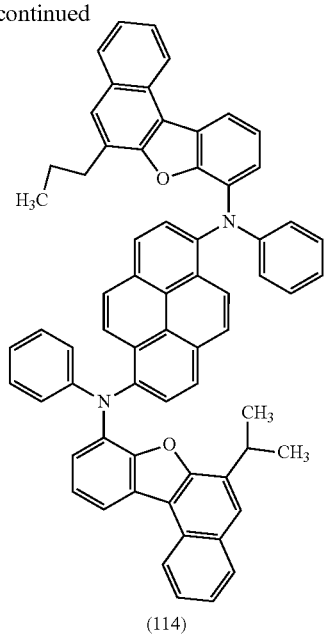

(114)

(116):(118) = 18:82

The yellow solid obtained in Step 6 was analyzed by nuclear magnetic resonance (H NMR) spectroscopy. In addition, ¹H NMR charts are shown in FIGS. 16A to 16C.

Figure 16A:
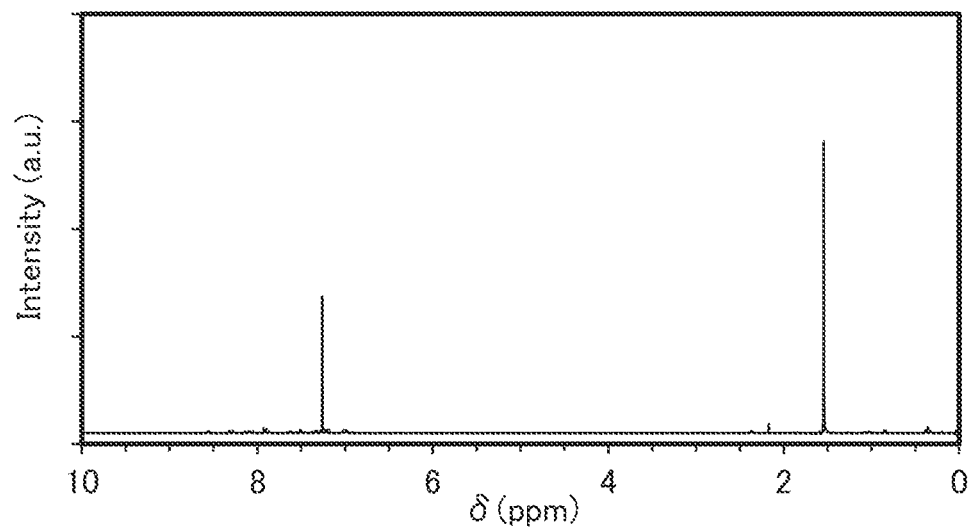
FIGS. 16A to 16C show $^1$H-NMR charts of an organic compound represented by Structural Formula (116).
Figure 16B:
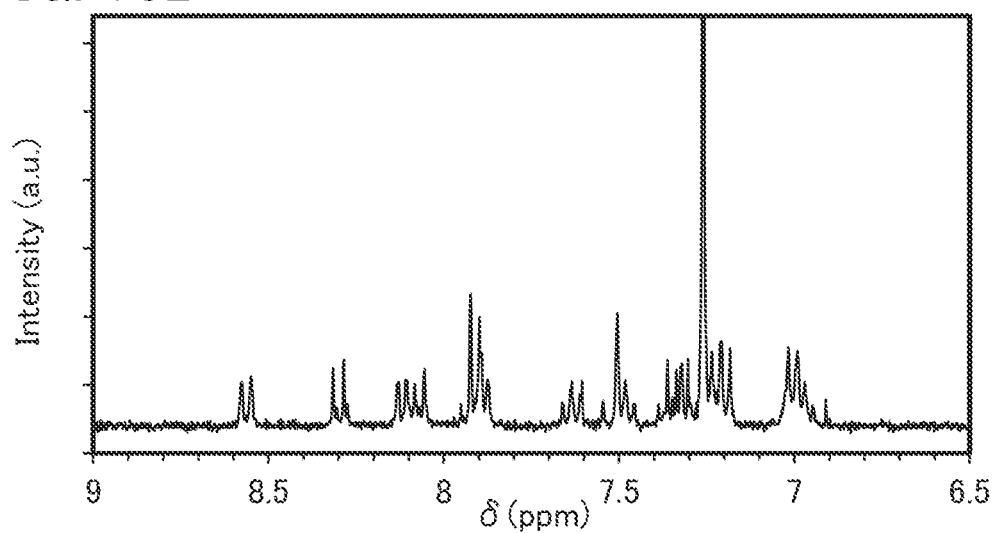
Figure 16C:
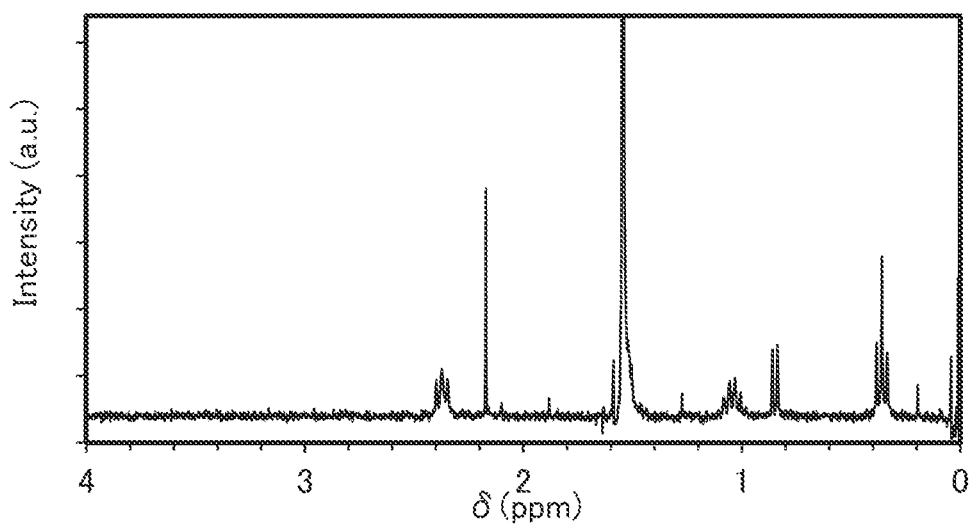

Note that FIG. 16B is an enlarged chart showing the range of 6.5 ppm to 9.0 ppm in FIG. 16A. FIG. 16C is an enlarged chart showing the range of 0 ppm to 4.0 ppm in FIG. 16A. The results revealed that 1,6iPrBnfAPrn (Structural Formula (116)) and 1,6nPrBnfAPrn (Structural Formula (118)) were obtained. A compound represented by Structural Formula (144) was probably generated as well.

Example 4

Figure 17:
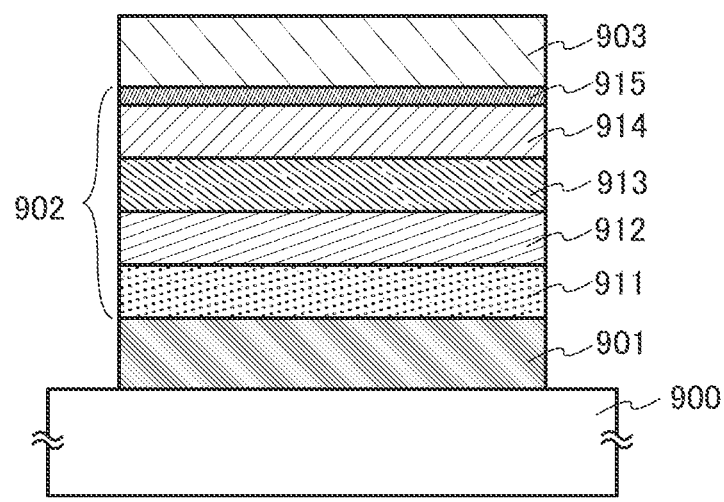
FIG. 17 illustrates a light-emitting element.
Figure 18:
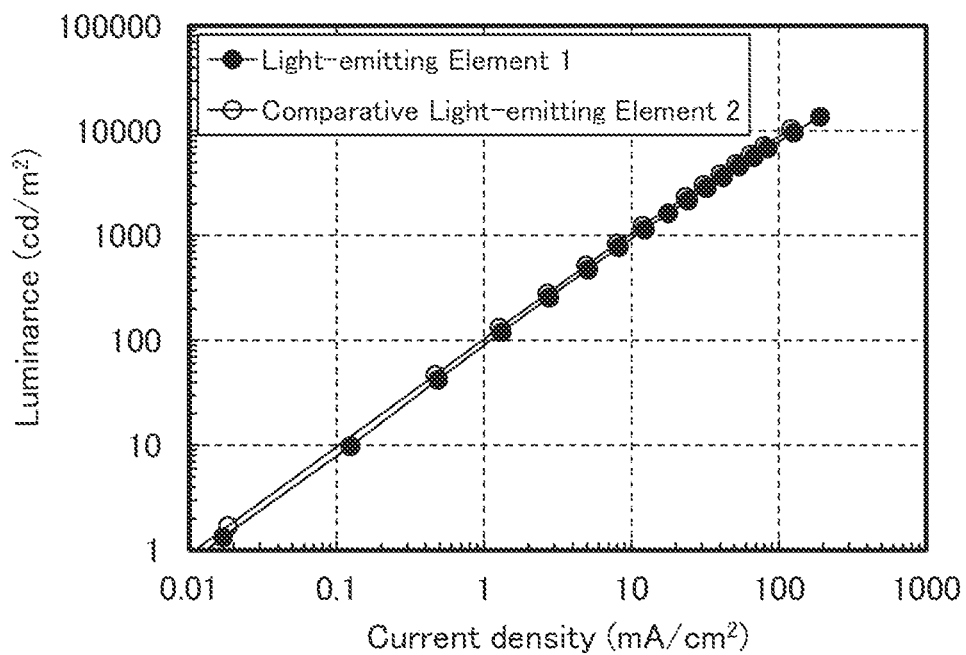
FIG. 18 shows current density-luminance characteristics of a light-emitting element 1 and a comparative light-emitting element 2.
Figure 19:
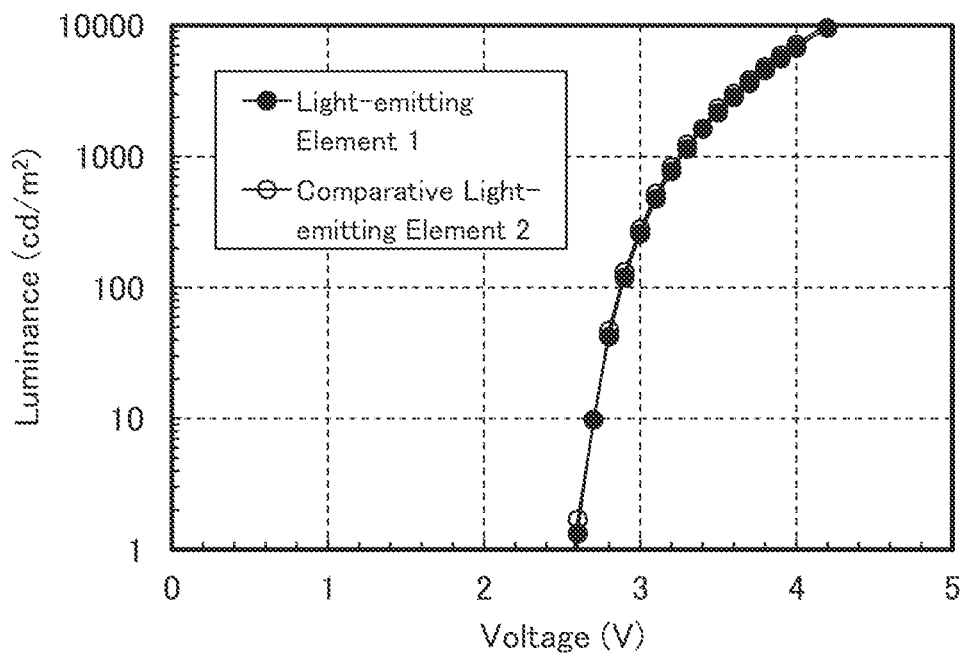
FIG. 19 shows voltage-luminance characteristics of the light-emitting element 1 and the comparative light-emitting element 2.
Figure 20:
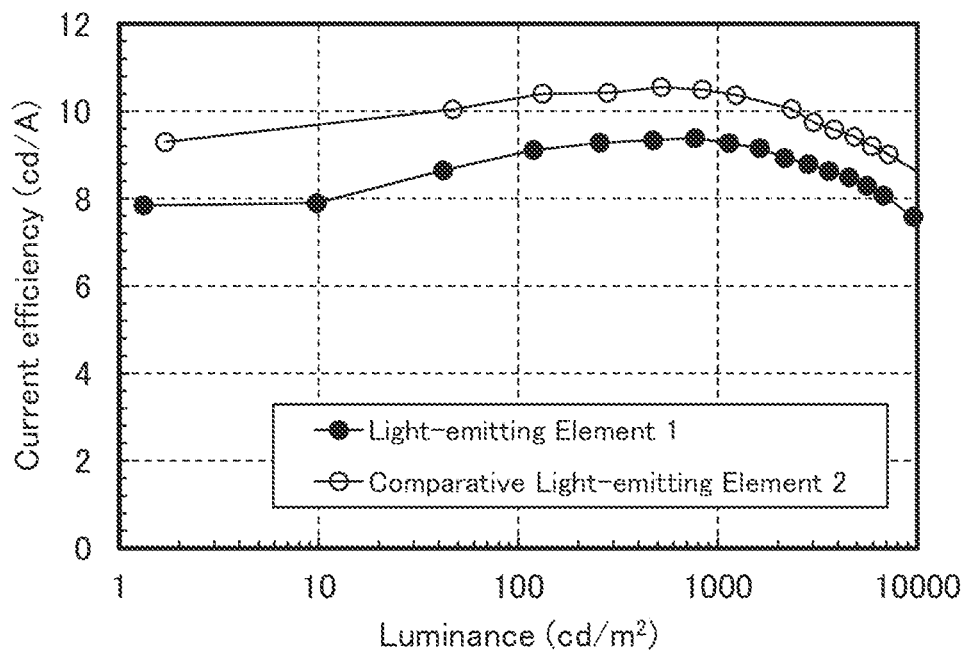
FIG. 20 shows luminance-current efficiency characteristics of the light-emitting element 1 and the comparative light-emitting element 2.
Figure 21:
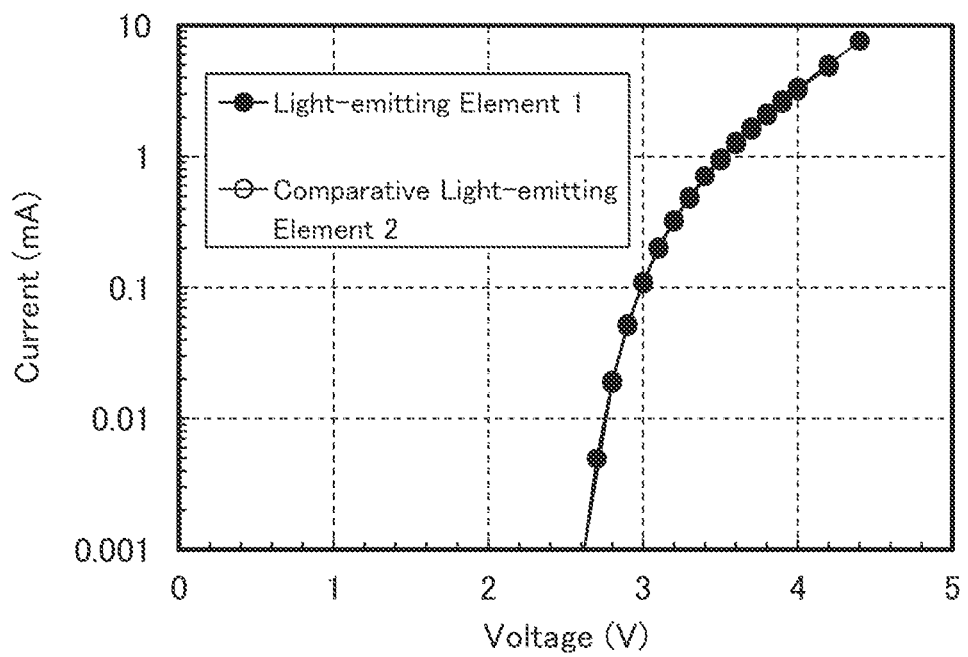
FIG. 21 shows voltage-current characteristics of the light-emitting element 1 and the comparative light-emitting element 2.

In this example, element structures, fabrication methods, and properties of a light-emitting element 1 (a light-emitting element of one embodiment of the present invention) in which 1,6chBnfAPrn (Structural Formula (100)) described in Example 1 is used in a light-emitting layer and a comparative light-emitting element 2 in which a comparative organic compound 1,6BnfAPrn-03 (Structural Formula (200)) is used in a light-emitting layer will be described. Note that FIG. 17 illustrates the element structure of the light-emitting elements used in this example, and Table 1 shows specific structures. Chemical formulae of materials used in this example are shown below.

TABLE 1

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 1 | ITSO (70 nm) | PCPPn:MoOx (4:2, 10 nm) | PCPPn (25 nm) | * | 2mDBTBPDBq-II (15 nm) | NBphen (10 nm) | LiF (1 nm) | Al (200 nm) |
| Comparative light-emitting element 2 | ITSO (70 nm) | PCPPn:MoOx (4:2, 10 nm) | PCPPn (25 nm) | ** | 2mDBTBPDBq-II (15 nm) | NBphen (10 nm) | LiF (1 nm) | Al (200 nm) |

*cgDBCzPA:1,6chBnfAPrn (1:0.03, 25 nm)
**cgDBCzPA:1,6BnfAPrn-03 (1:0.03, 25 nm)

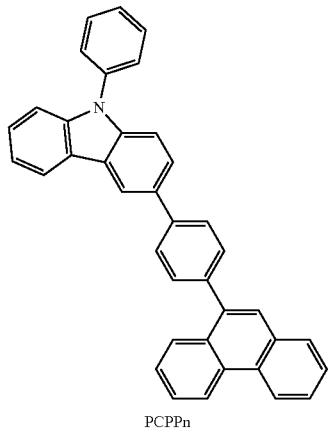 [SMILES: c1ccc(-n2c3ccccc3c3cc(-c4ccc(-c5cc6ccccc6c6ccccc56)cc4)ccc32)cc1]

PCPPn

TABLE 1-continued

| First electrode | Hole-injection layer | Hole-transport layer | Light-emitting layer | Electron-transport layer | Electron-injection layer | Second electrode |
| --- | --- | --- | --- | --- | --- | --- | cgDBCzPA 1,6chBnfAPrn
(100)

1,6BnfAPrn-03
(200)

TABLE 1-continued

| First electrode | Hole-injection layer | Hole-transport layer | Light-emitting layer | Electron-transport layer | Electron-injection layer | Second electrode |
|---|---|---|---|---|---|---|

2mDBTBPDBq-II

NBphen

<<Fabrication of Light-Emitting Elements>>

In each of the light-emitting elements described in this example, as illustrated in FIG. 17, a hole-injection layer 911, a hole-transport layer 912, a light-emitting layer 913, an electron-transport layer 914, and an electron-injection layer 915 were stacked in this order over a first electrode 901 formed over a substrate 900, and a second electrode 903 was stacked over the electron-injection layer 915.

First, the first electrode 901 was formed over the substrate 900. The electrode area was set to 4 mm$^2$ (2 mm×2 mm). A glass substrate was used as the substrate 900. The first electrode 901 was formed to a thickness of 70 nm using indium tin oxide containing silicon oxide (ITSO) by a sputtering method.

As pretreatment, a surface of the substrate was washed with water, baking was performed at 200° C. for 1 hour, and then UV ozone treatment was performed for 370 seconds. After that, the substrate was transferred into a vacuum evaporation apparatus where the pressure had been reduced to approximately 10$^{-4}$ Pa, and was subjected to vacuum baking at 170° C. for 60 minutes in a heating chamber of the vacuum evaporation apparatus, and then the substrate was cooled down for approximately 30 minutes.

Next, the hole-injection layer 911 was formed over the first electrode 901. After the pressure in the vacuum evaporation apparatus was reduced to 10$^{-4}$ Pa, the hole-injection layer 911 was formed by co-evaporation to have a mass ratio of 3-[4-(9-phenanthryl)-phenyl]-9-phenyl-9H-carbazole (abbreviation: PCPPn) to molybdenum oxide of 4:2 and a thickness of 10 nm.

Then, the hole-transport layer 912 was formed over the hole-injection layer 911. The hole-transport layer 912 was formed to a thickness of 25 nm by evaporation of PCPPn.

Next, the light-emitting layer 913 was formed over the hole-transport layer 912.

The light-emitting layer 913 in the light-emitting element 1 was formed by co-evaporation using 7-[4-(10-phenyl-9-anthryl)phenyl]-7H-dibenzo[c,g]carbazole (abbreviation: cgDBCzPA) as a host material and using N,N'-(pyrene-1,6-diyl)bis(N-phenyl-6-cyclohexylbenzo[b]naphtho[1,2-d]furan-8-amine) (abbreviation: 1,6chBnfAPrn) as a guest material to have a weight ratio of cgDBCzPA to 1,6chBnfAPrn of 1:0.03. The thickness was set to 25 nm.

The light-emitting layer 913 in the comparative light-emitting element 2 was formed by co-evaporation using cgDBCzPA as a host material and using N,N'-(pyrene-1,6-diyl)bis[(6,N-diphenylbenzo[b]naphtho[1,2-d]furan)-8-amine] (abbreviation: 1,6BnfAPrn-03) as a guest material to have a weight ratio of cgDBCzPA to 1,6BnfAPrn-03 of 1:0.03. The thickness was set to 25 nm.

Next, the electron-transport layer 914 was formed over the light-emitting layer 913. The electron-transport layer 914 was formed in the following manner: 2-[3'-(dibenzothiophen-4-yl)biphenyl-3-yl]dibenzo[f,h]quinoxaline (abbreviation: 2mDBTBPDBq-II) and 2,9-bis(naphthalen-2-yl)-4,7-diphenyl-1,10-phenanthroline (abbreviation: NBphen) were sequentially deposited by evaporation to thicknesses of 15 nm and 10 nm, respectively.

Then, the electron-injection layer 915 was formed over the electron-transport layer 914. The electron-injection layer 915 was formed to a thickness of 1 nm by evaporation of lithium fluoride (LiF).

After that, the second electrode 903 was formed over the electron-injection layer 915. The second electrode 903 was formed using aluminum to a thickness of 200 nm by an evaporation method. In this example, the second electrode 903 functioned as a cathode.

Through the above steps, the light-emitting elements in each of which the EL layer was provided between a pair of electrodes were each fabricated over the substrate 900. The hole-injection layer 911, the hole-transport layer 912, the light-emitting layer 913, the electron-transport layer 914, and the electron-injection layer 915 described above were functional layers forming the EL layer in one embodiment of the present invention. Furthermore, in all the evaporation steps in the above fabrication method, evaporation was performed by a resistance-heating method.

Each of the light-emitting elements fabricated as described above was sealed using another substrate (not illustrated) in the following manner. In a glove box containing a nitrogen atmosphere, a sealant was applied so as to surround the light-emitting element formed over the substrate 900, the substrate (not illustrated) provided with a desiccant was made to overlap with a desired position over the substrate 900, and then irradiation with 365 nm ultraviolet light at 6 J/cm$^2$ was performed.

<<Operation Characteristics of Light-Emitting Elements>>

Operation characteristics of the fabricated light-emitting element 1 and comparative light-emitting element 2 were measured. The measurement was performed at room temperature (in an atmosphere kept at 25° C.). FIGS. 18 to 21 show the operation characteristics of the fabricated light-emitting element 1 and comparative light-emitting element 2.

Table 2 shows initial values of main characteristics of the light-emitting element 1 and comparative light-emitting element 2 at a luminance of approximately 1000 cd/m$^2$.

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 1 | 3.3 | 0.49 | 12 | (0.14, 0.09) | 1100 | 9.3 | 8.8 | 11 |
| Comparative light-emitting element 2 | 3.2 | 0.32 | 8.0 | (0.14, 0.11) | 840 | 10 | 10 | 11 |

The above results revealed that the light-emitting elements fabricated in this example had a high current efficiency and a high external quantum efficiency, and especially the light-emitting element 1 had favorable chromaticity.

Figure 22:
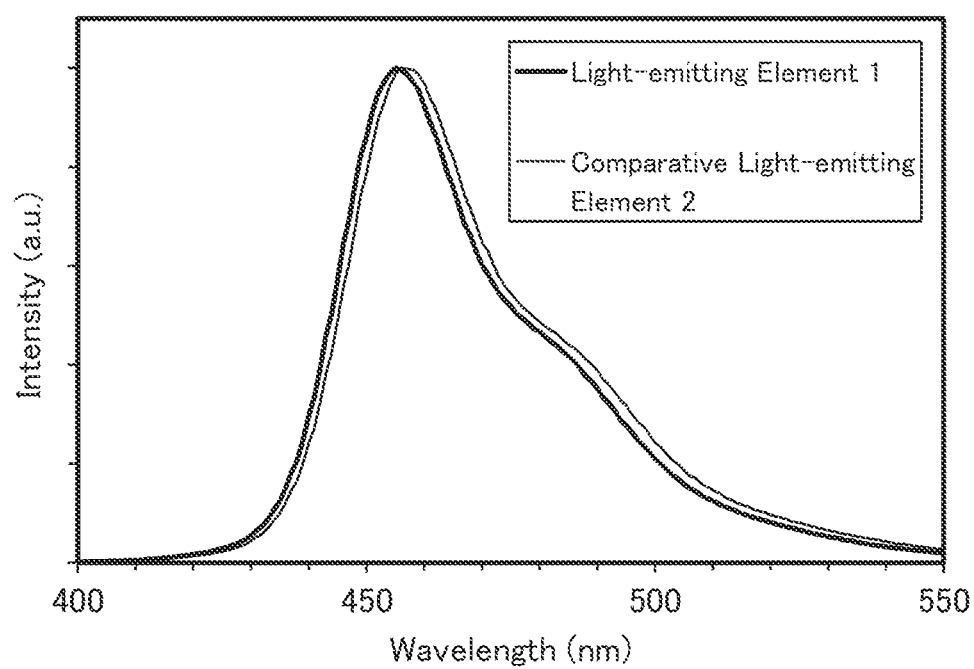
FIG. 22 shows emission spectra of the light-emitting element 1 and the comparative light-emitting element 2.

FIG. 22 shows emission spectra when current at a current density of 12.5 mA/cm$^2$ was applied to the light-emitting element 1 and comparative light-emitting element 2. As shown in FIG. 22, the emission spectra of the light-emitting element 1 and comparative light-emitting element 2 have peaks at around 456 nm, which suggests that the peaks were derived from light emission of 1,6BnfAPrn-03 and 1,6chBnfAPrn contained in the light-emitting layers 913 of the light-emitting elements. At the same time, comparison of the spectrum shapes shows that the spectrum of the light-emitting element 1 has fewer spectral components on the long wavelength side than the spectrum of the comparative light-emitting element 2. This led to the favorable blue chromaticity of the light-emitting element 1.

Figure 23:
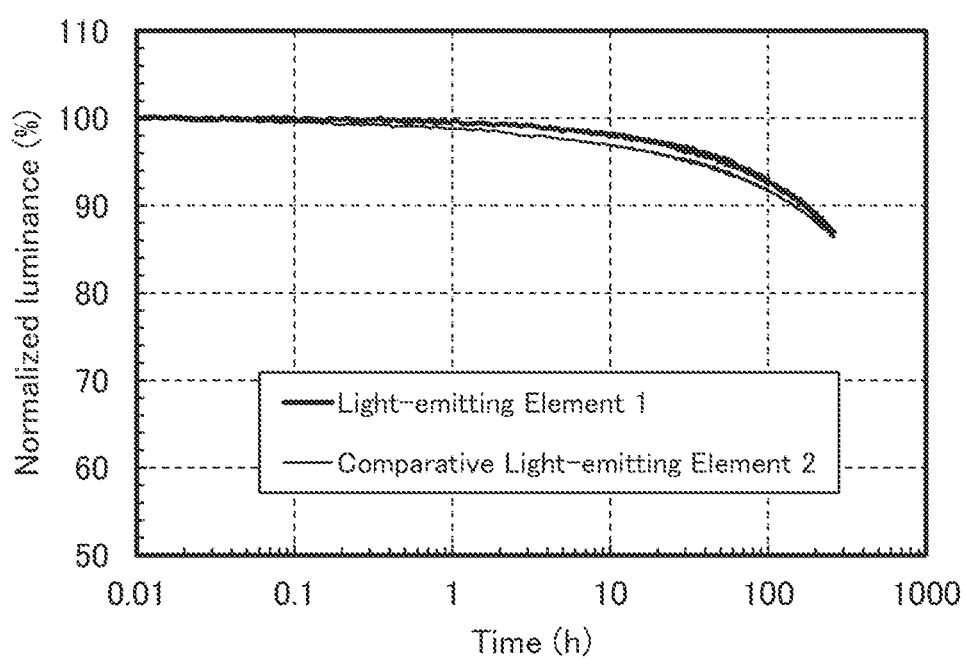
FIG. 23 shows reliability of the light-emitting element 1 and the comparative light-emitting element 2.

Next, reliability tests were performed on the light-emitting element 1 and the comparative light-emitting element 2. Results of the reliability tests are shown in FIG. 23. In FIG. 23, the vertical axis represents normalized luminance (%) with an initial luminance of 100% and the horizontal axis represents driving time (h) of the element. As the reliability tests, driving tests at a constant current of 2 mA were performed.

The results of the reliability tests showed that the light-emitting element 1 of one embodiment of the present invention had higher reliability than the comparative light-emitting element 2. Specifically, when the time (LT$_{95}$) it took for the luminance to decay to 95% of the initial luminance was compared, the LT$_{95}$ of the light-emitting element 1 was 52 hours and that of the comparative light-emitting element 2 was 33 hours, meaning that the lifetime of the light-emitting element 1 was approximately 1.6 times as long as that of the comparative light-emitting element 2. The above suggests that the use of 1,6chBnfAPrn (Structural Formula (100)), which is the organic compound of one embodiment of the present invention, is effective in increasing the lifetime of a light-emitting element.

Example 5

Synthesis Example 4

In this example, a method for synthesizing N,N'-(pyrene-1,6-diyl)bis(N-phenyl-6-normalpropylbenzo[b]naphtho[1,2-d]furan-8-amine) (abbreviation: 1,6nPrBnfAPrn), which is the organic compound of one embodiment of the present invention and which is represented by Structural Formula (118) in Embodiment 1, is described. The structure of 1,6nPrBnfAPrn is shown below.

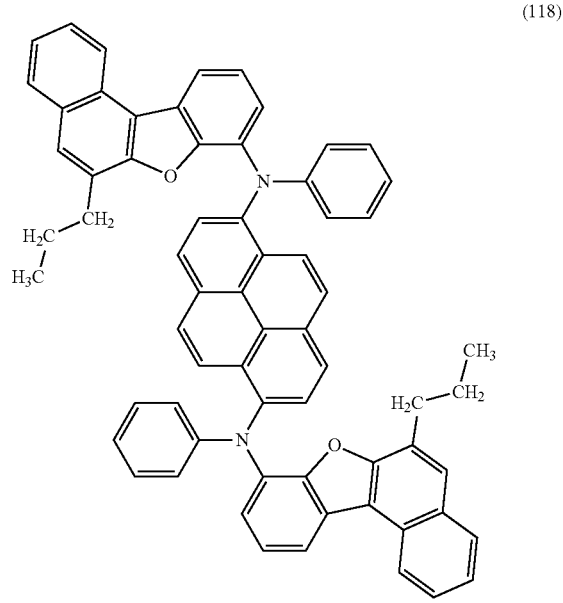

(118)

1,6nPrBnfAPrn

Step 1: Synthesis of 6-normalpropylbenzo[b]naphtho[1,2-d]furan

Into a 200 mL three-neck flask were put 1.0 g (5.4 mmol) of 3-normalpropyl-2-naphthol, 1.8 g (10 mmol) of 2-bromofluorobenzene, and 3.5 g (11 mmol) of cesium carbonate, and the air in the flask was replaced with nitrogen. Then, 30 mL of N-methyl-2-pyrrolidone (abbreviation: NMP) was added and the resulting solution was degassed under reduced pressure and then stirred for 6.5 hours at 170° C. under a nitrogen stream. After the stirring, 3.5 g (11 mmol) of cesium carbonate and 0.28 g (1.1 mmol) of triphenylphosphine were added to this mixture. The resulting mixture was degassed by being stirred under reduced pressure. To this mixture was added 0.12 g (0.54 mmol) of palladium(II) acetate, and the resulting mixture was stirred for 11 hours at 170° C. under a nitrogen stream.

After the stirring, water was added to this mixture, and an aqueous layer was subjected to extraction using ethyl acetate. The obtained solution of the extract and an organic layer were combined, and the mixture was washed with water and saturated brine. Then, the mixture was dried with magnesium sulfate. The mixture was separated by gravity filtration, and the obtained filtrate was concentrated to give a brown oily substance. The obtained oily substance was purified by silica gel column chromatography (a developing solvent: hexane) to give 1.1 g of a target white solid in a yield of 75%. A synthesis scheme of Step 1 is shown in (c-1).

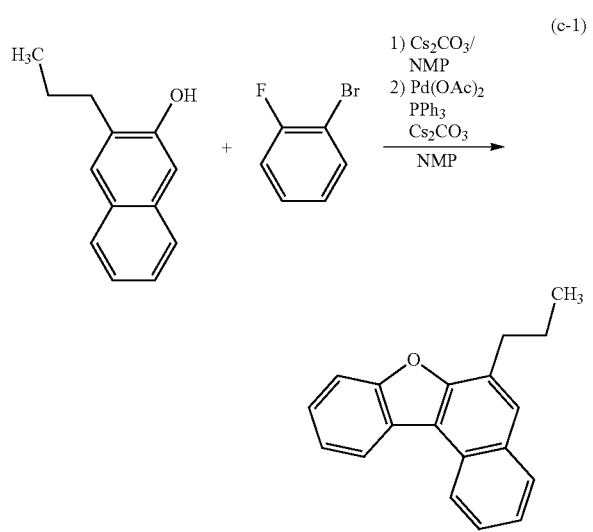

Results of nuclear magnetic resonance (1H NMR) spectroscopy measurement of the white solid obtained in Step 1 are shown below.

$^1$H NMR (CDCl$_3$, 300 MHz): σ=8.61 (d, J=8.3 Hz, 1H), 8.42-8.39 (m, 1H), 7.99 (d, J=8.3 Hz, 1H), 7.73-7.63 (m, 3H), 7.55-7.46 (m, 3H), 3.13 (t, J=6.8 Hz, 2H), 1.99-1.87 (m, J=7.8 Hz, 2H), 1.09 (t, J=7.3 Hz, 3H).

Step 2: Synthesis of 6-normalpropyl-8-iodobenzo[b]naphtho[1,2-d]furan

Into a 200 mL three-neck flask was put 0.7 g (2.8 mmol) of 6-normalpropylbenzo[b]naphtho[1,2-d]furan, and the air in the flask was replaced with nitrogen. Then, 15 mL of tetrahydrofuran was added, and the mixture was stirred at −80° C. Into this solution was dropped 3.0 mL (4.7 mmol) of n-butyllithium (a 1.6 mol/L n-hexane solution), the temperature was returned to room temperature, and the mixture was stirred for 2 hours under a nitrogen stream. After the stirring, the temperature of the resulting mixture was reduced to −80° C.; then, a solution of 1.5 g (5.9 mmol) of iodine in 6 mL of tetrahydrofuran was added to the mixture, and stirring was performed for 15 hours while the temperature was gradually returned to room temperature.

After the stirring, an aqueous solution of sodium thiosulfate was added to this mixture, and an aqueous layer was subjected to extraction using ethyl acetate. The obtained solution of the extract and an organic layer were combined, and the mixture was washed with water and saturated brine. Then, the mixture was dried with magnesium sulfate. The mixture was separated by gravity filtration, and the obtained filtrate was concentrated to give a brown oily substance.

The obtained compound was purified by silica gel column chromatography (a developing solvent: hexane) to give 0.7 g of a target white solid in a yield of 65%. A synthesis scheme of Step 2 is shown in (c-2).

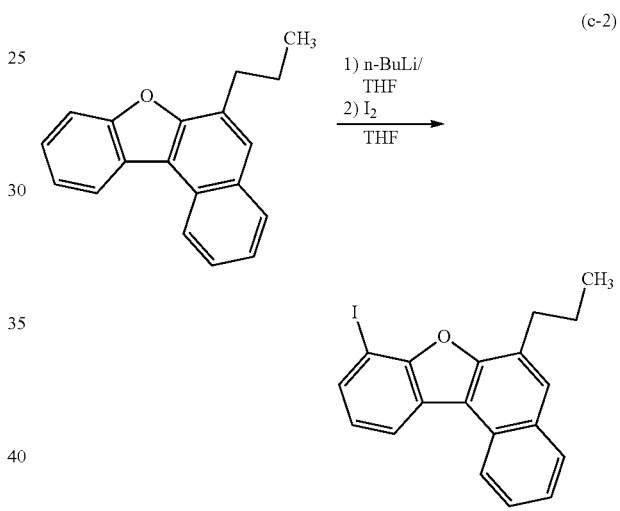

Results of $^1$H NMR measurement of the white solid obtained in Step 2 are shown below.

$^1$H NMR (CDCl$_3$, 300 MHz): σ=8.55 (d, J=8.3 Hz, 1H), 8.36-8.33 (m, 1H), 7.99 (d, J=8.3 Hz, 1H), 7.86-7.83 (m, 1H), 7.74 (s, 1H), 7.69-7.64 (m, 1H), 7.56-7.51 (m, 1H), 7.25 (t, J=7.8 Hz, 1H), 3.17 (t, J=6.8 Hz, 2H), 2.03-1.91 (m, J=7.8 Hz, 2H), 1.10 (t, J=7.3 Hz, 3H).

Step 3: Synthesis of N-phenyl-6-normalpropylbenzo[b]naphtho[1,2-d]furan-8-amine

Into a 200 mL three-neck flask were put 0.70 g (1.8 mmol) of 6-normalpropyl-8-iodobenzo[b]naphtho[1,2-d]furan, 0.20 g (2.2 mmol) of aniline, and 0.40 g (4.2 mmol) of sodium t-butoxide, and the air in the flask was replaced with nitrogen. To this mixture was added 10 mL of toluene, and the resulting mixture was degassed under reduced pressure. To this mixture were added 0.30 mL (0.35 mmol) of tri(tert-butyl)phosphine (a 10 wt % hexane solution) and 40 mg (70 µmol) of bis(dibenzylideneacetone)palladium(0) and then, stirring was performed for 3 hours at 110° C. under a nitrogen stream.

After the stirring, 300 mL of toluene was added to the resulting mixture and then, suction filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina to give a filtrate. The obtained filtrate was concentrated to give a brown solid.

This solid was purified by silica gel column chromatography (a developing solvent was a mixed solvent of hexane:toluene=4:1) to give 0.31 g of a target white solid in a yield of 50%. A synthesis scheme of Step 3 is shown in (c-3).

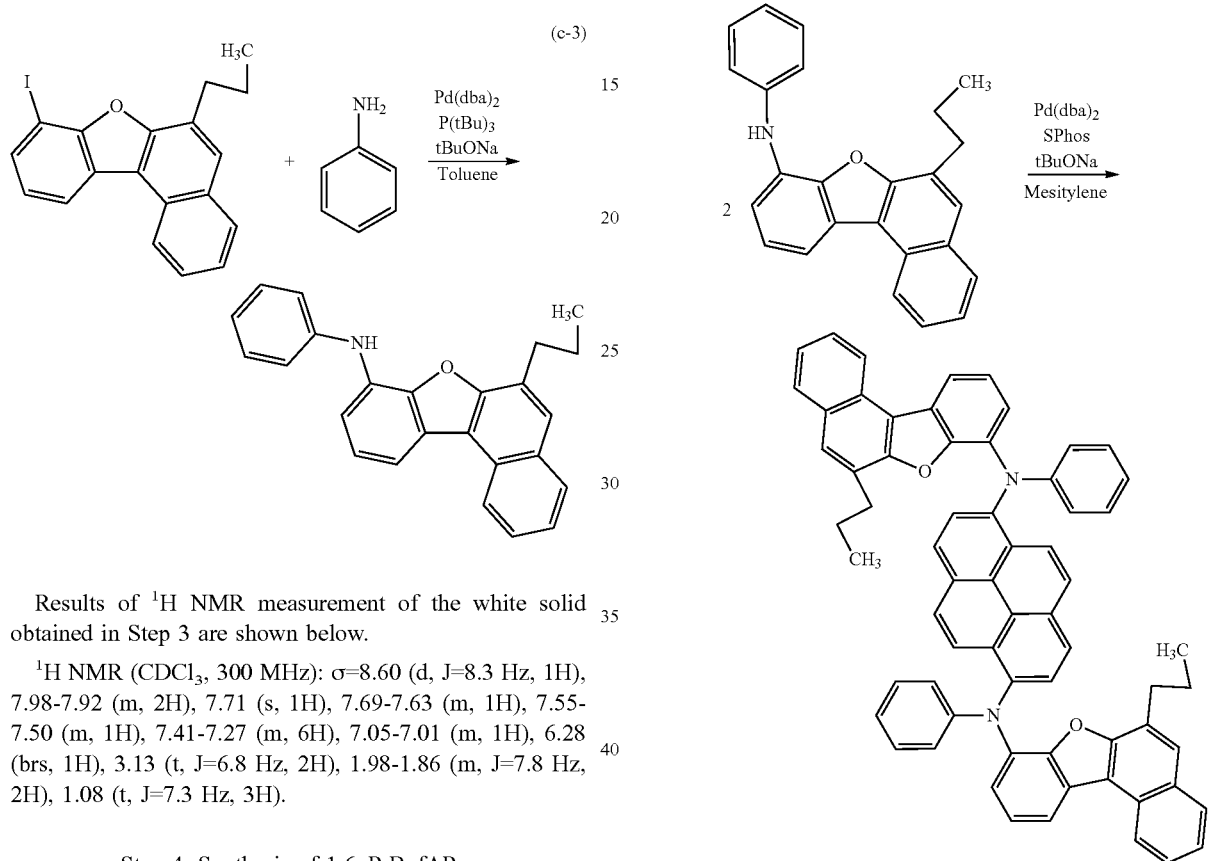

Results of ¹H NMR measurement of the white solid obtained in Step 3 are shown below.

¹H NMR (CDCl₃, 300 MHz): σ=8.60 (d, J=8.3 Hz, 1H), 7.98-7.92 (m, 2H), 7.71 (s, 1H), 7.69-7.63 (m, 1H), 7.55-7.50 (m, 1H), 7.41-7.27 (m, 6H), 7.05-7.01 (m, 1H), 6.28 (brs, 1H), 3.13 (t, J=6.8 Hz, 2H), 1.98-1.86 (m, J=7.8 Hz, 2H), 1.08 (t, J=7.3 Hz, 3H).

Step 4: Synthesis of 1,6nPrBnfAPrn

Into a 50 mL three-neck flask were put 0.16 g (0.44 mmol) of 1,6-dibromopyrene, 0.31 g (0.88 mmol) of N-phenyl-6-normalpropylbenzo[b]naphtho[1,2-d]furan-8-amine, 0.17 g (1.8 mmol) of sodium t-butoxide, and 60 mg (0.15 mmol) of 2-dicyclohexylphosphino-2',6'-dimethoxy-1,1'-biphenyl (abbreviation: SPhos), and the air in the flask was replaced with nitrogen. To this mixture was added 5 mL of mesitylene, and the resulting mixture was degassed under reduced pressure; then, 40 mg (70 μmol) of bis(dibenzylideneacetone)palladium(0) was added to the mixture and the resulting mixture was stirred for 6 hours at 170° C. under a nitrogen stream.

After the stirring, 30 mL of toluene was added, heating was performed, and the resulting mixture was purified by silica gel column chromatography (a developing solvent: toluene) to give a target yellow solid. The obtained yellow solid was recrystallized with toluene to give 0.23 g of a target yellow solid in a yield of 58%. A synthesis scheme of Step 4 is shown in (c-4).

By a train sublimation method, 0.23 g of the obtained yellow solid was purified by sublimation. In the purification by sublimation, the yellow solid was heated at 300° C. under a pressure of 3.3 Pa for 15 hours. After the purification by sublimation, 0.19 g of a target yellow solid was obtained at a collection rate of 83%.

Figure 24A:
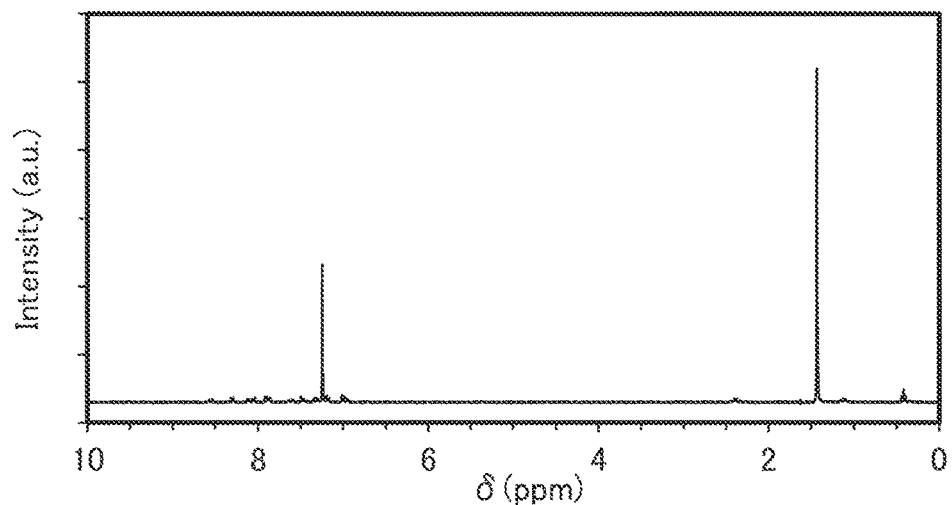
FIGS. 24A to 24C show $^1$H-NMR charts of an organic compound represented by Structural Formula (118).
Figure 24B:
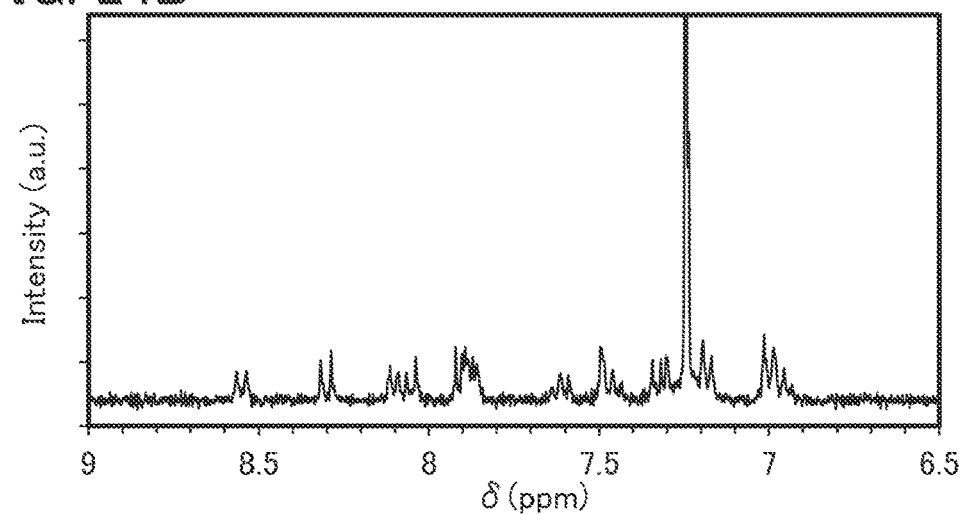
Figure 24C:
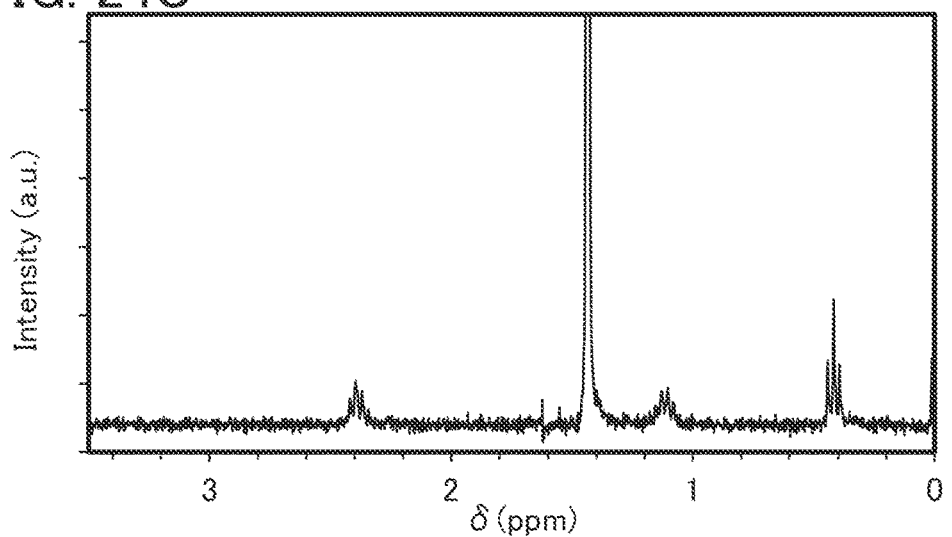

Results of ¹H NMR measurement of the yellow solid obtained in Step 4 are shown below. Furthermore, ¹H NMR charts are shown in FIGS. 24A to 24C. Note that FIG. 24B is an enlarged chart showing the range of 6.5 ppm to 9.0 ppm in FIG. 24A. FIG. 24C is an enlarged chart showing the range of 0 ppm to 3.5 ppm in FIG. 24A. The results reveal that 1,6nPrBnfAPrn (Structural Formula (118)) was obtained.

¹H NMR (CDCl₃, 300 MHz): σ=8.57 (d, J=8.8 Hz, 2H), 8.32 (d, J=9.3 Hz, 2H), 8.12-8.04 (m, 4H), 7.92-7.85 (m, 6H), 7.64-7.59 (m, 2H), 7.50-7.45 (m, 4H), 7.34-7.30 (m, 4H), 7.23-7.17 (m, 4H), 7.01-6.95 (m, 6H), 2.42-2.37 (m, 4H), 1.16-1.08 (m, 4H), 0.44 (t, J=7.3 Hz, 6H).

Results of measurement of absorption spectra and emission spectra of a toluene solution and a solid thin film of 1,6nPrBnfAPrn are described below. The measurement method was similar to that described in Example 1.

Figure 25A:
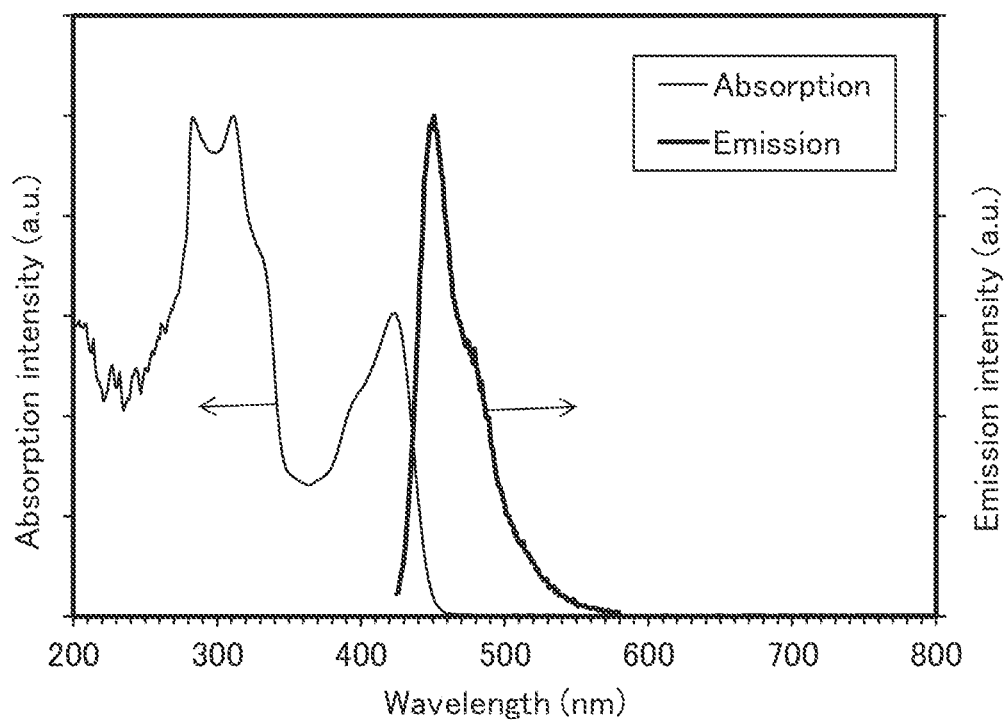
FIGS. 25A and 25B each show an ultraviolet-visible absorption spectrum and an emission spectrum of the organic compound represented by Structural Formula (118).
Figure 25B:
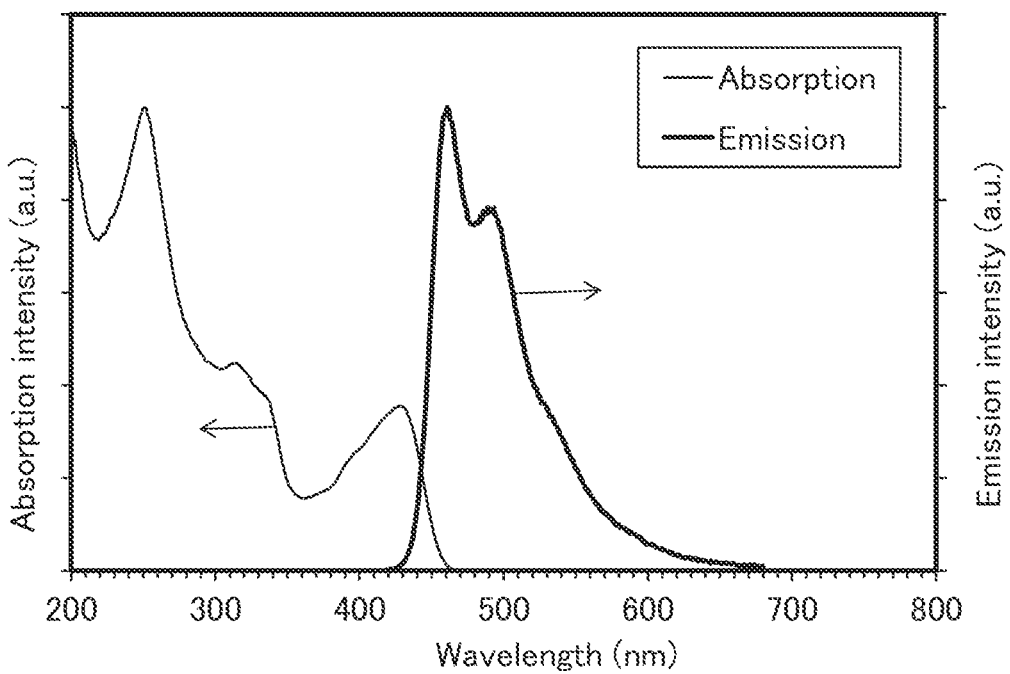

FIG. 25A shows the obtained absorption and emission spectra of the toluene solution. The horizontal axis represents wavelength and the vertical axes represent absorption intensity and emission intensity. FIG. 25B shows the obtained absorption and emission spectra of the solid thin film. The horizontal axis represents wavelength and the vertical axes represent absorption intensity and emission intensity.

As shown by the results in FIG. 25A, the toluene solution of 1,6nPrBnfAPrn exhibited an absorption peak at around 423 nm and an emission wavelength peak at 451 nm (excitation wavelength: 408 nm). Furthermore, as shown by the results in FIG. 25B, the solid thin film of 1,6nPrBnfAPrn exhibited an absorption peak at around 428 nm and emission wavelength peaks at around 461 nm and 489 nm (excitation wavelength: 410 nm).

Example 6

Synthesis Example 5

In this example, a method for synthesizing N,N'-(pyrene-1,6-diyl)bis(N-phenyl-6-tert-butylbenzo[b]naphtho[1,2-d]furan-8-amine) (abbreviation: 1,6tBuBnfAPrn), which is the organic compound of one embodiment of the present invention and which is represented by Structural Formula (117) in Embodiment 1, is described. The structure of 1,6tBuBnfAPrn is shown below.

(117)

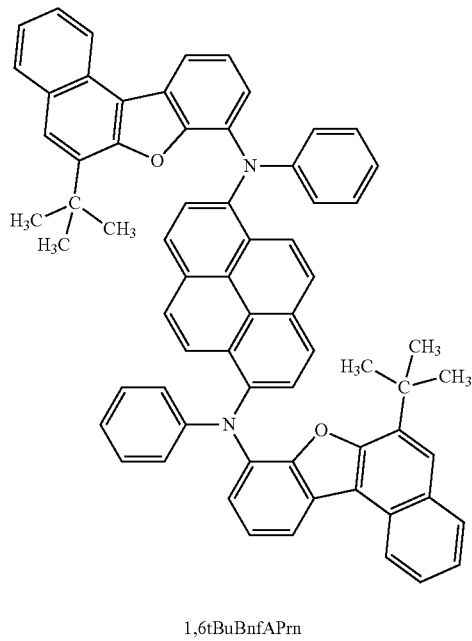

1,6tBuBnfAPrn

Step 1: Synthesis of 6-tert-butylbenzo[b]naphtho[1,2-d]furan

Into a 200 mL three-neck flask were put 1.0 g (5.0 mmol) of 3-tert-butyl-2-naphthol, 1.8 g (10 mmol) of 2-bromofluorobenzene, and 3.4 g (10 mmol) of cesium carbonate, and the air in the flask was replaced with nitrogen. Then, 30 mL of N-methyl-2-pyrrolidone (abbreviation: NMP) was added and the resulting mixture was degassed under reduced pressure and then stirred for 6.5 hours at 170° C. under a nitrogen stream. After the stirring, 3.4 g (10 mmol) of cesium carbonate and 0.14 g (0.53 mmol) of triphenylphosphine were added to this mixture. The resulting mixture was degassed by being stirred under reduced pressure. To this mixture was added 60 mg (0.27 mmol) of palladium(II) acetate, and the resulting mixture was stirred for 4.5 hours at 170° C. under a nitrogen stream.

After the stirring, water was added to this mixture, and an aqueous layer was subjected to extraction using ethyl acetate. The obtained solution of the extract and an organic layer were combined, and the mixture was washed with water and saturated brine. Then, the mixture was dried with magnesium sulfate. The mixture was separated by gravity filtration, and the obtained filtrate was concentrated to give a brown oily substance. The obtained oily substance was purified by silica gel column chromatography (a developing solvent: hexane) to give 1.2 g of a target white solid in a yield of 90%. A synthesis scheme of Step 1 is shown in (d-1).

(d-1)

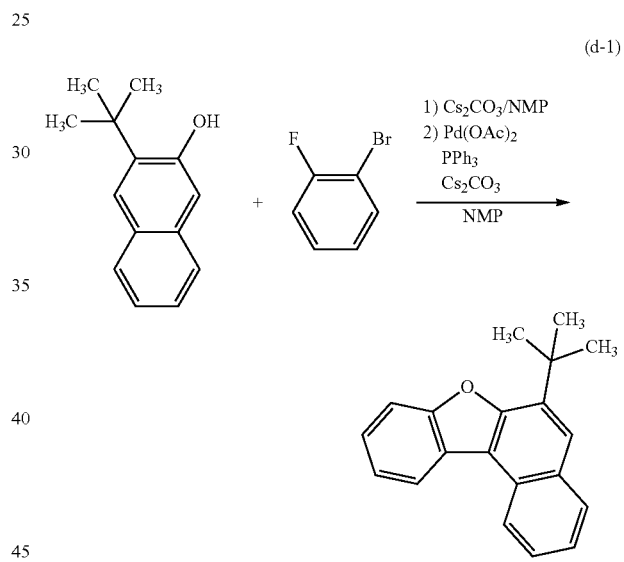

Results of $^1$H NMR measurement of the white solid obtained in Step 1 are shown below.

$^1$H NMR (CDCl$_3$, 300 MHz): σ=8.62 (d, J=8.3 Hz, 1H), 8.43-8.40 (m, 1H), 8.01-7.98 (m, 1H), 7.79 (s, 1H), 7.75-7.64 (m, 2H), 7.55-7.46 (m, 3H), 1.66 (s, 9H).

Step 2: Synthesis of 6-tert-butyl-8-iodobenzo[b]naphtho[1,2-d]furan

Into a 200 mL three-neck flask was put 1.2 g (4.5 mmol) of 6-tert-butylbenzo[b]naphtho[1,2-d]furan, and the air in the flask was replaced with nitrogen. Then, 35 mL of tetrahydrofuran was added, and the mixture was stirred at −80° C. Into this solution was dropped 4.0 mL (6.2 mmol) of n-butyllithium (a 1.6 mol/L n-hexane solution), the temperature was returned to room temperature, and the mixture was stirred for 2 hours under a nitrogen stream. After the stirring, the temperature of the resulting mixture was reduced to −80° C.; then, a solution of 2.3 g (9.0 mmol) of iodine in 15 mL of tetrahydrofuran was added to the mixture, and stirring was performed for 15 hours while the temperature was gradually returned to room temperature.

After the stirring, an aqueous solution of sodium thiosulfate was added to this mixture, and an aqueous layer was subjected to extraction using ethyl acetate. The obtained solution of the extract and an organic layer were combined, and the mixture was washed with water and saturated brine. Then, the mixture was dried with magnesium sulfate. The mixture was separated by gravity filtration, and the obtained filtrate was concentrated to give a brown oily substance.

The obtained compound was purified by silica gel column chromatography (a developing solvent: hexane) to give 1.2 g of a target white solid with an NMR purity of 45% in a yield of 35%. A synthesis scheme of Step 2 is shown in (d-2).

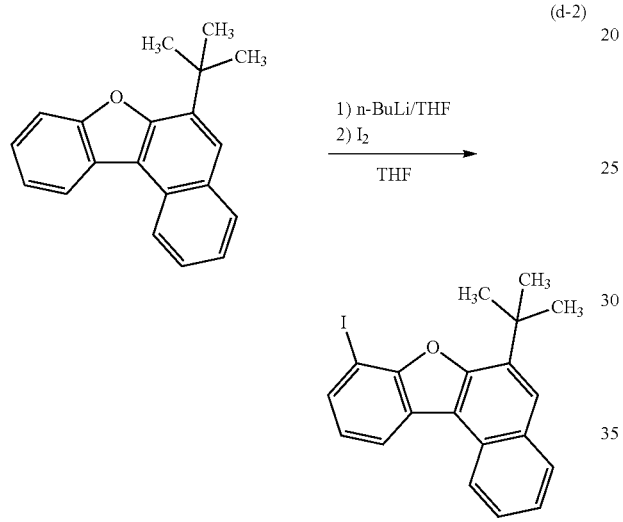

(d-2)

Results of $^1$H NMR measurement of the white solid obtained in Step 2 are shown below.

$^1$H NMR (CDCl$_3$, 300 MHz): σ=8.55 (d, J=8.3 Hz, 1H), 8.37-8.34 (m, 1H), 8.01-7.98 (m, 1H), 7.86-7.78 (m, 2H), 7.70-7.64 (m, 1H), 7.56-7.51 (m, 1H), 7.25-7.20 (m, 1H), 1.70 (s, 9H).

Step 3: Synthesis of N-phenyl-6-tert-butylbenzo[b]naphtho[1,2-d]furan-8-amine

Into a 200 mL three-neck flask were put 1.2 g (2.9 mmol) of 6-tert-butyl-8-iodobenzo[b]naphtho[1,2-d]furan, 0.33 g (3.5 mmol) of aniline, and 0.68 g (7.1 mmol) of sodium t-butoxide, and the air in the flask was replaced with nitrogen. To this mixture was added 15 mL of toluene, and the resulting mixture was degassed under reduced pressure. To this mixture were added 0.30 mL (0.35 mmol) of tri(tert-butyl)phosphine (a 10 wt % hexane solution) and 40 mg (70 μmol) of bis(dibenzylideneacetone)palladium(0) and then, stirring was performed for 3 hours at 90° C. under a nitrogen stream.

After the stirring, 300 mL of toluene was added to the resulting mixture and then, suction filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina to give a filtrate. The obtained filtrate was concentrated to give a brown solid.

This solid was purified by silica gel column chromatography (a developing solvent was a mixed solvent of hexane: toluene=4:1) to give 0.48 g of a target white solid in a yield of 82%. A synthesis scheme of Step 3 is shown in (d-3).

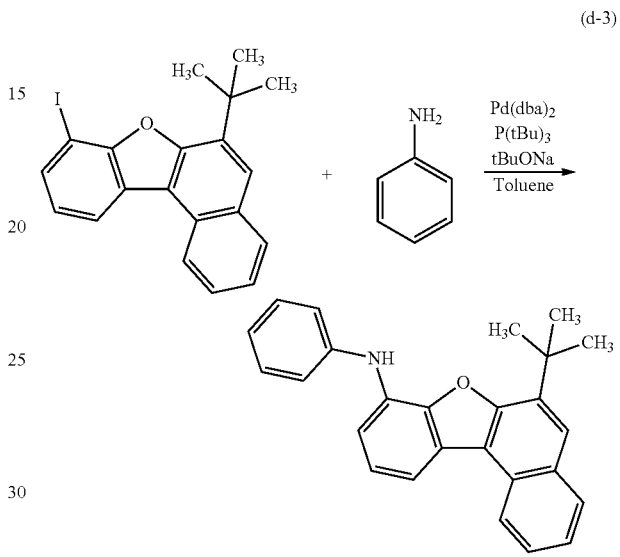

(d-3)

Results of $^1$H NMR measurement of the white solid obtained in Step 3 are shown below.

$^1$H NMR (CDCl$_3$, 300 MHz): σ=8.61 (d, J=8.3 Hz, 1H), 8.01-7.95 (m, 2H), 7.78 (s, 1H), 7.70-7.64 (m, 1H), 7.56-7.50 (m, 1H), 7.41-7.28 (m, 6H), 7.06-7.00 (m, 1H), 6.19 (brs, 1H), 3.13 (s, 9H).

Step 4: Synthesis of 1,6tBuBnfAPrn

Into a 200 mL three-neck flask were put 0.23 g (0.64 mmol) of 1,6-dibromopyrene, 0.48 g (1.3 mmol) of N-phenyl-6-tert-butylbenzo[b]naphtho[1,2-d]furan-8-amine, 0.25 g (2.6 mmol) of sodium t-butoxide, and 60 mg (0.15 mmol) of 2-dicyclohexylphosphino-2',6'-dimethoxy-1,1'-biphenyl (abbreviation: SPhos), and the air in the flask was replaced with nitrogen. To this mixture was added 10 mL of mesitylene, and the resulting mixture was degassed under reduced pressure; then, 40 mg (70 μmol) of bis(dibenzylideneacetone)palladium(0) was added to the mixture and the resulting mixture was stirred for 7 hours at 170° C. under a nitrogen stream.

After the stirring, 30 mL of toluene was added, heating was performed, and the resulting mixture was purified by silica gel column chromatography (a developing solvent was a mixed solvent of hexane and toluene, and the ratio of hexane to toluene was changed from 9:1 to 7:3 to form a gradient) to give a target yellow solid. The obtained yellow solid was recrystallized with toluene to give 0.24 g of a target yellow solid in a yield of 40%. A synthesis scheme of Step 4 is shown in (d-4).

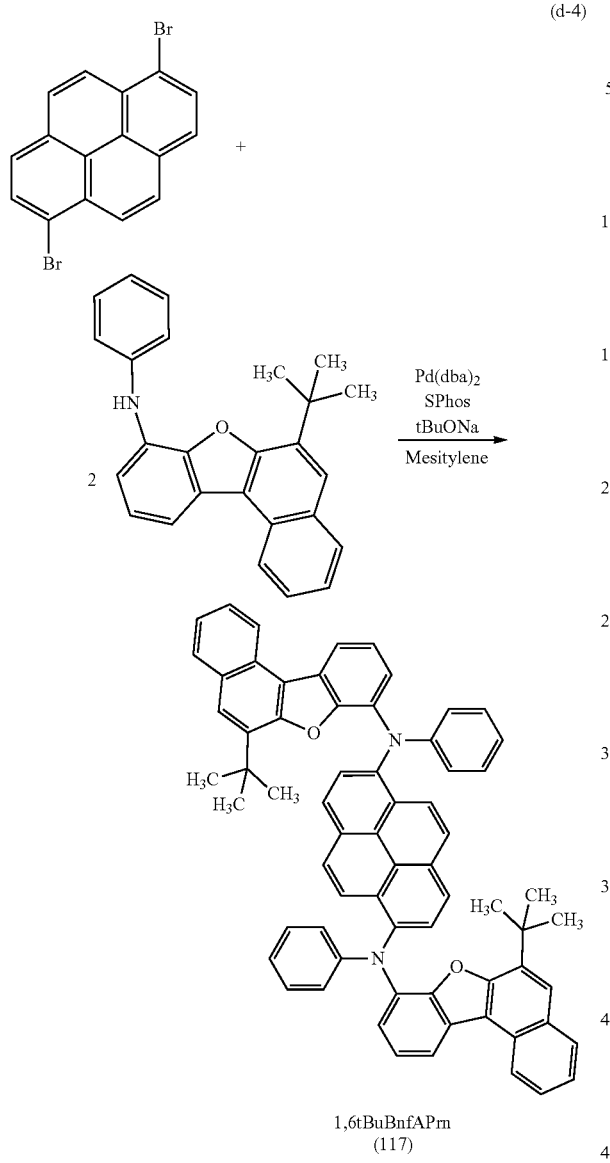

1,6tBuBnfAPrn
(117)

By a train sublimation method, 0.21 g of the obtained yellow solid was purified by sublimation. In the purification by sublimation, the yellow solid was heated at 330° C. under a pressure of 1.8×10⁻² Pa for 8 hours. After the purification by sublimation, 0.17 g of a target yellow solid was obtained at a collection rate of 81%.

Figure 26A:
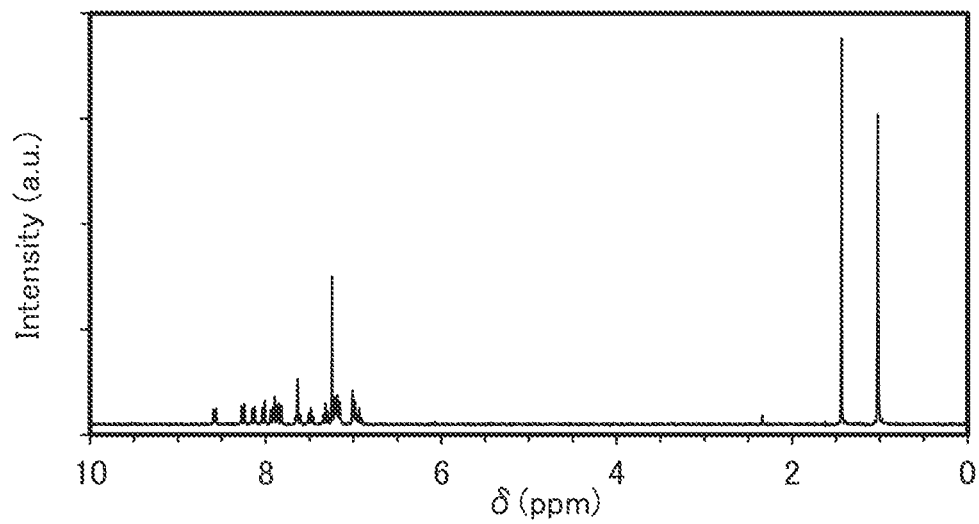
FIGS. 26A to 26C show $^1$H-NMR charts of an organic compound represented by Structural Formula (117).
Figure 26B:
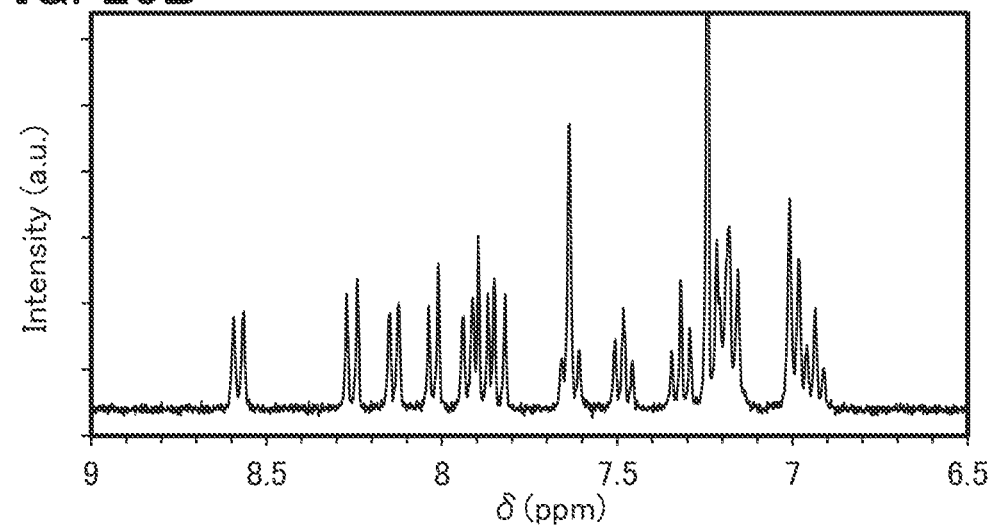
Figure 26C:
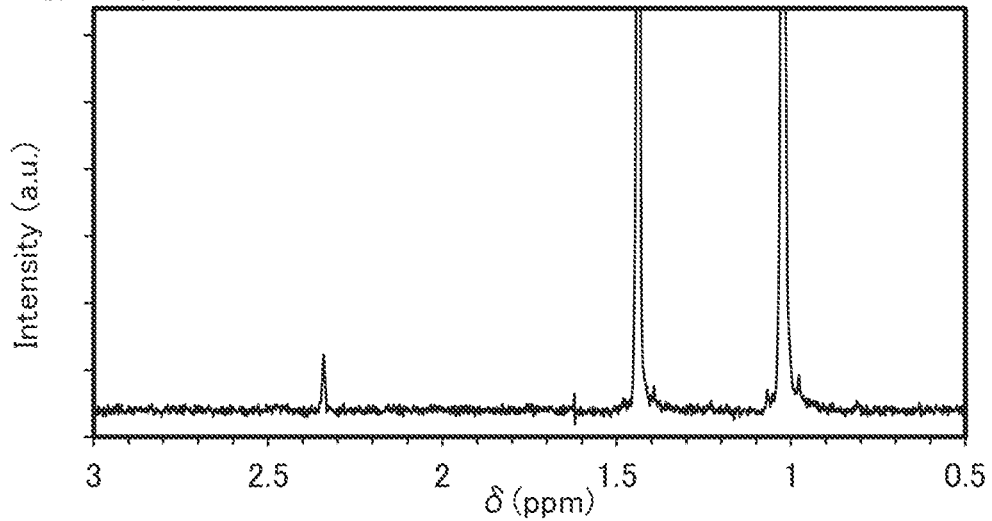

Results of ¹H NMR measurement of the yellow solid obtained in Step 4 are shown below. Furthermore, ¹H NMR charts are shown in FIGS. 26A to 26C. Note that FIG. 26B is an enlarged chart showing the range of 6.5 ppm to 9.0 ppm in FIG. 26A. FIG. 26C is an enlarged chart showing the range of 0.5 ppm to 3.0 ppm in FIG. 26A. The results reveal that 1,6tBuBnfAPrn (Structural Formula (117)) was obtained.

¹H NMR (CDCl₃, 300 MHz): σ=8.59 (d, J=8.8 Hz, 2H), 8.27 (d, J=9.3 Hz, 2H), 8.15 (d, J=7.8 Hz, 2H), 8.04 (d, J=8.3 Hz, 2H), 7.94-7.82 (m, 6H), 7.66-7.61 (m, 4H), 7.51-7.46 (m, 2H), 7.35-7.29 (m, 2H), 7.22-7.16 (m, 6H), 7.01-6.91 (m, 6H), 1.02 (s, 18H).

Results of measurement of absorption spectra and emission spectra of a toluene solution and a solid thin film of 1,6tBuBnfAPrn are described below. The measurement method was similar to that described in Example 1.

Figure 27A:
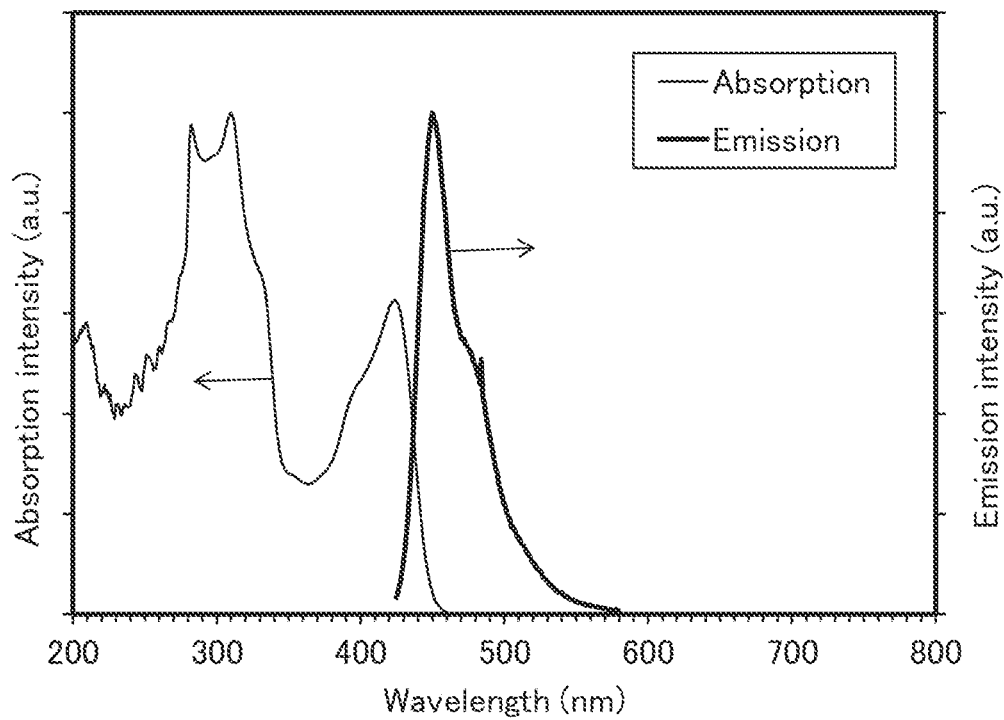
FIGS. 27A and 27B each show an ultraviolet-visible absorption spectrum and an emission spectrum of the organic compound represented by Structural Formula (117).
Figure 27B:
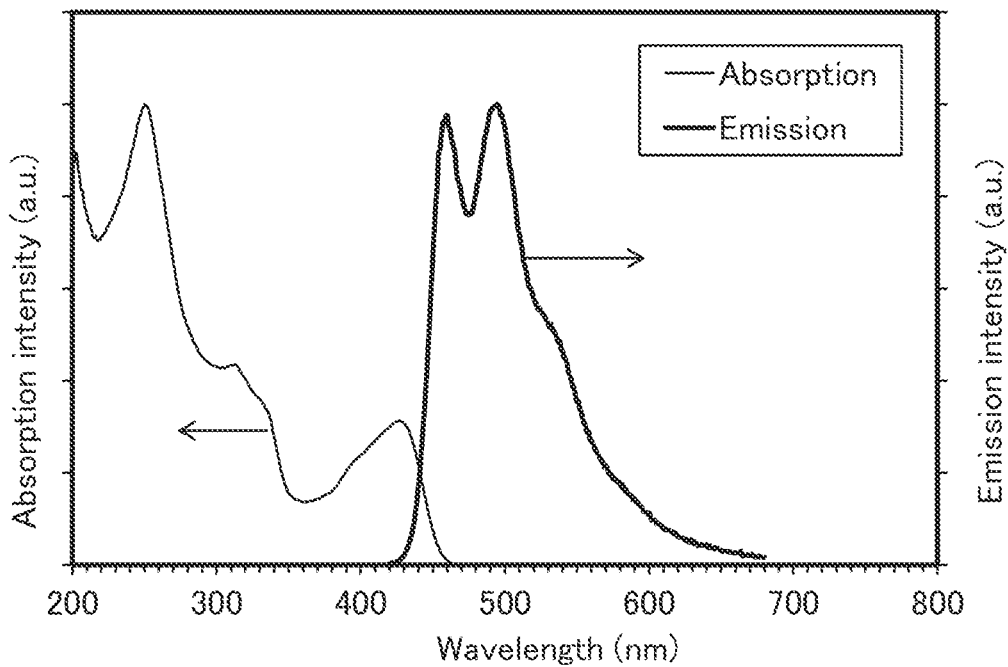

FIG. 27A shows the obtained absorption and emission spectra of the toluene solution. The horizontal axis represents wavelength and the vertical axes represent absorption intensity and emission intensity. FIG. 27B shows the obtained absorption and emission spectra of the solid thin film. The horizontal axis represents wavelength and the vertical axes represent absorption intensity and emission intensity.

As shown by the results in FIG. 27A, the toluene solution of 1,6tBuBnfAPrn exhibited an absorption peak at around 424 nm and an emission wavelength peak at 450 nm (excitation wavelength: 410 nm). Furthermore, as shown by the results in FIG. 27B, the solid thin film of 1,6tBuBnfAPrn exhibited an absorption peak at around 426 nm and emission wavelength peaks at around 460 nm and 495 nm (excitation wavelength: 410 nm).

Example 7

Synthesis Example 6

In this example, a method for synthesizing N,N'-bis(pyrene-1,6-diyl)bis(N-phenyl-6-trimethylsilylbenzo[b]naphtho[1,2-d]furan-8-amine) (abbreviation: 1,6TMSBnfAPrn), which is the organic compound of one embodiment of the present invention and which is represented by Structural Formula (145) in Embodiment 1, is described. The structure of 1,6TMSBnfAPrn is shown below.

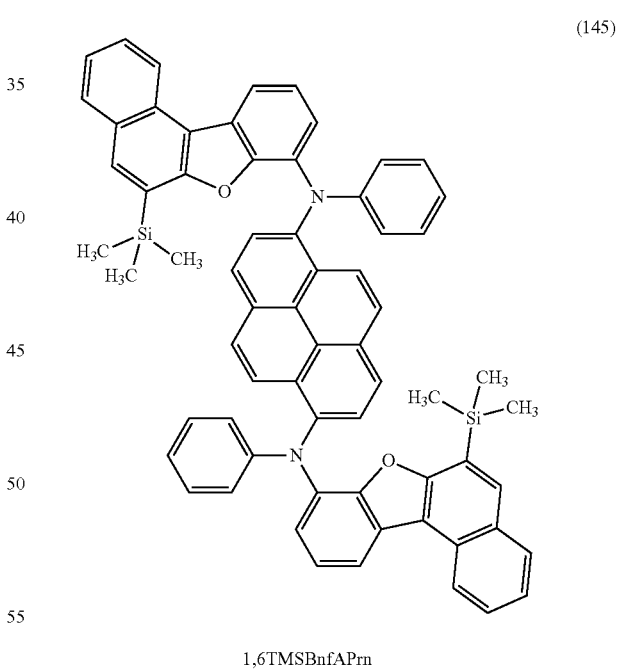

1,6TMSBnfAPrn

Step 1: Synthesis of 8-chloro-6-trimethylsilylbenzo[b]naphtho[1,2-d]furan

Into a 100 mL three-neck flask was put 1.1 g (4.4 mmol) of 8-chlorobenzo[b]naphtho[1,2-d]furan, and the air in the flask was replaced with nitrogen. Then, 20 mL of tetrahydrofuran was added, and the mixture was stirred at −80° C. Into this solution was dropped 4.0 mL (6.2 mmol) of n-butyllithium (a 1.6 mol/L n-hexane solution), the temperature was returned to room temperature, and the mixture was stirred for 2 hours under a nitrogen stream. After the stirring, the temperature of the resulting mixture was reduced to −80° C.; then, a solution of 1.1 mL (8.7 mmol) of chlorotrimethylsilane in 10 mL of tetrahydrofuran was added to the mixture, and stirring was performed for 15 hours while the temperature was gradually returned to room temperature.

After the stirring, an aqueous solution of sodium hydrogencarbonate was added to this mixture, and an aqueous layer was subjected to extraction using toluene. The obtained solution of the extract and an organic layer were combined, and the mixture was washed with water and saturated brine. Then, the mixture was dried with magnesium sulfate. The mixture was separated by gravity filtration, and the obtained filtrate was concentrated to give a brown oily substance.

The obtained compound was purified by silica gel column chromatography (a developing solvent: hexane) to give 0.67 g of a target white solid in a yield of 47%. A synthesis scheme of Step 1 is shown in (e-1).

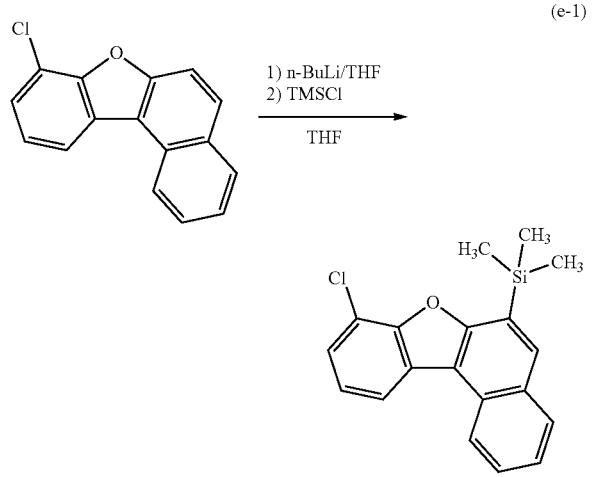

(e-1)

Results of $^1$H NMR measurement of the white solid obtained in Step 1 are shown below.

$^1$H NMR (CDCl$_3$, 300 MHz): σ=8.57 (d, J=8.3 Hz, 1H), 8.29-8.26 (m, 1H), 8.05-8.02 (m, 2H), 7.75-7.69 (m, 1H), 7.58-7.44 (m, 2H), 7.41 (t, J=7.8 Hz, 1H), 0.55 (s, 9H).

Step 2: Synthesis of N-phenyl-6-trimethylsilylbenzo[b]naphtho[1,2-d]furan-8-amine Into a 200 mL three-neck flask were put 0.65 g (2.0 mmol) of 8-chloro-6-trimethylsilylbenzo[b]naphtho[1,2-d]furan, 0.23 g (2.5 mmol) of aniline, and 0.50 g (5.2 mmol) of sodium t-butoxide, and the air in the flask was replaced with nitrogen. To this mixture was added 15 mL of toluene, and the resulting mixture was degassed under reduced pressure. To this mixture were added 0.30 mL (0.35 mmol) of tri-tert-butyl phosphine (a 10 wt % hexane solution), 0.52 g (1.5 mmol) of n-butyl-diadamantylphosphine, and 0.16 g (0.28 mmol) of bis(dibenzylideneacetone)palladium(0) and then, stirring was performed for 18 hours at 120° C. under a nitrogen stream.

After the stirring, 300 mL of toluene was added to the resulting mixture and then, suction filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina to give a filtrate. The obtained filtrate was concentrated to give a brown oily substance.

This oily substance was purified by silica gel column chromatography (a developing solvent was a mixed solvent of hexane:toluene=4:1) to give 0.45 g of a target white solid in a yield of 59%. A synthesis scheme of Step 2 is shown in (e-2).

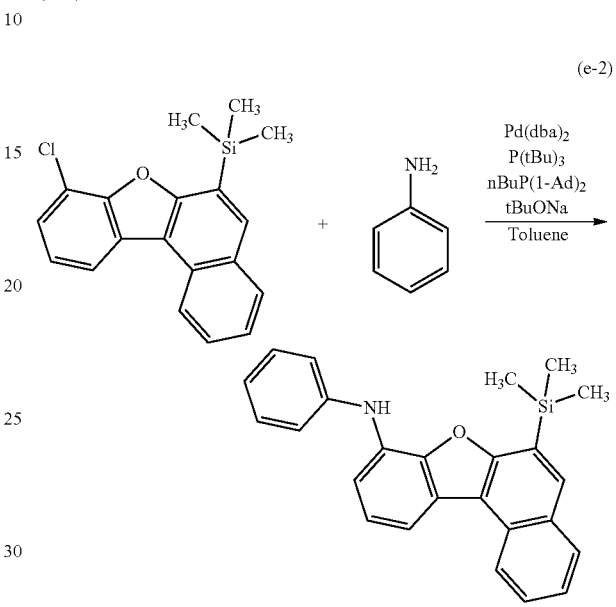

(e-2)

Results of $^1$H NMR measurement of the white solid obtained in Step 2 are shown below.

$^1$H NMR (CDCl$_3$, 300 MHz): σ=8.62 (d, J=8.3 Hz, 1H), 8.04-7.94 (m, 3H), 7.74-7.69 (m, 1H), 7.57-7.51 (m, 1H), 7.40-7.32 (m, 4H), 7.27-7.23 (m, 2H), 7.05-6.99 (m, 1H), 6.14 (brs, 1H), 0.49 (s, 9H).

Step 3: Synthesis of 1,6TMSBnfAPrn

Into a 200 mL three-neck flask were put 0.21 g (0.58 mmol) of 1,6-dibromopyrene, 0.45 g (0.88 mmol) of N-phenyl-6-trimethylsilylbenzo[b]naphtho[1,2-d]furan-8-amine, 0.23 g (1.8 mmol) of sodium t-butoxide, and 60 mg (0.15 mmol) of 2-dicyclohexylphosphino-2',6'-dimethoxy-1,1'-biphenyl (abbreviation: SPhos), and the air in the flask was replaced with nitrogen. To this mixture was added 5 mL of mesitylene, and the resulting mixture was degassed under reduced pressure; then, 40 mg (70 µmol) of bis(dibenzylideneacetone)palladium(0) was added to the mixture and the resulting mixture was stirred for 4 hours at 170° C. under a nitrogen stream.

After the stirring, 500 mL of toluene was added and heating was performed; then, hot filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina. A yellow solid obtained by concentration of the resulting filtrate was purified by silica gel column chromatography (a developing solvent was a mixed solvent of hexane and toluene, and the ratio of hexane to toluene was changed from 9:1 to 7:3 to form a gradient) to give a target yellow solid. The obtained yellow solid was recrystallized with toluene to give 0.30 g of a target yellow solid in a yield of 54%.

By a train sublimation method, 0.30 g of the obtained yellow solid was purified by sublimation. In the purification by sublimation, the yellow solid was heated at 340° C. under a pressure of $2.0 \times 10^{-2}$ Pa for 8 hours. After the purification by sublimation, 0.22 g of a target yellow solid was obtained at a collection rate of 74%. A synthesis scheme of Step 3 is shown in (e-3).

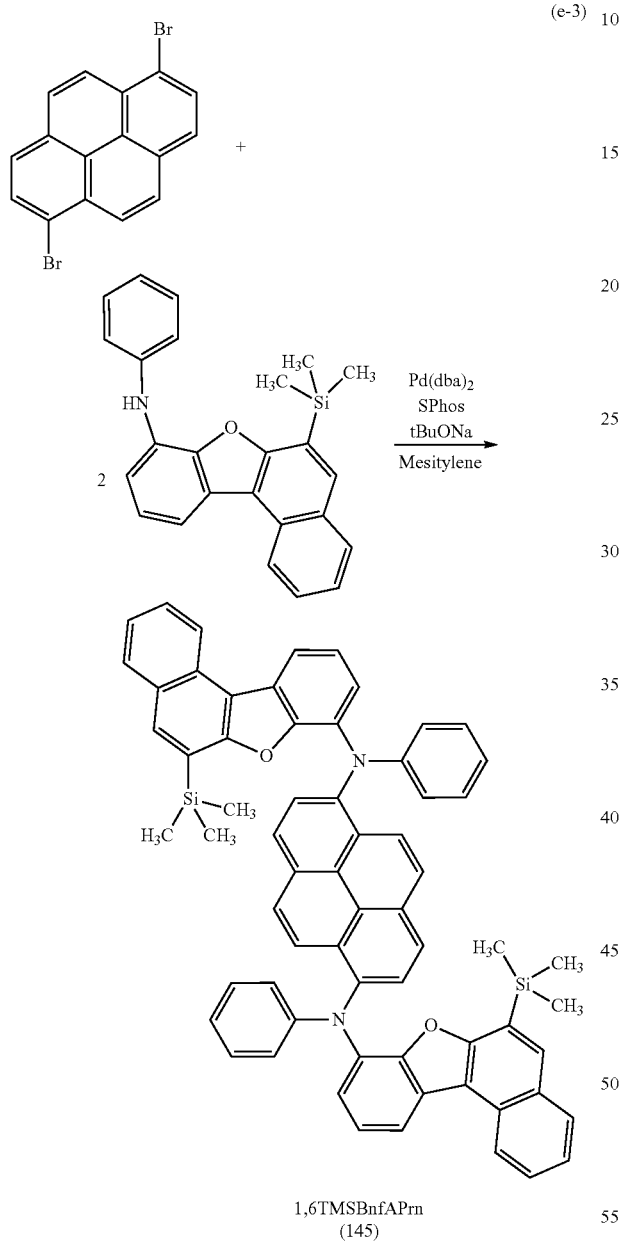

1,6TMSBnfAPrn
(145)

Figure 28A:
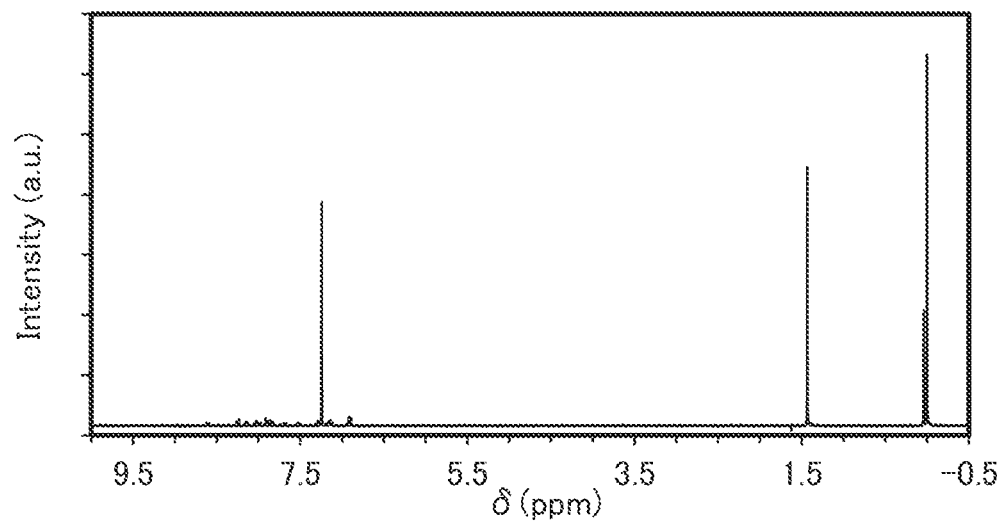
FIGS. 28A to 28C show $^1$H-NMR charts of an organic compound represented by Structural Formula (145).
Figure 28B:
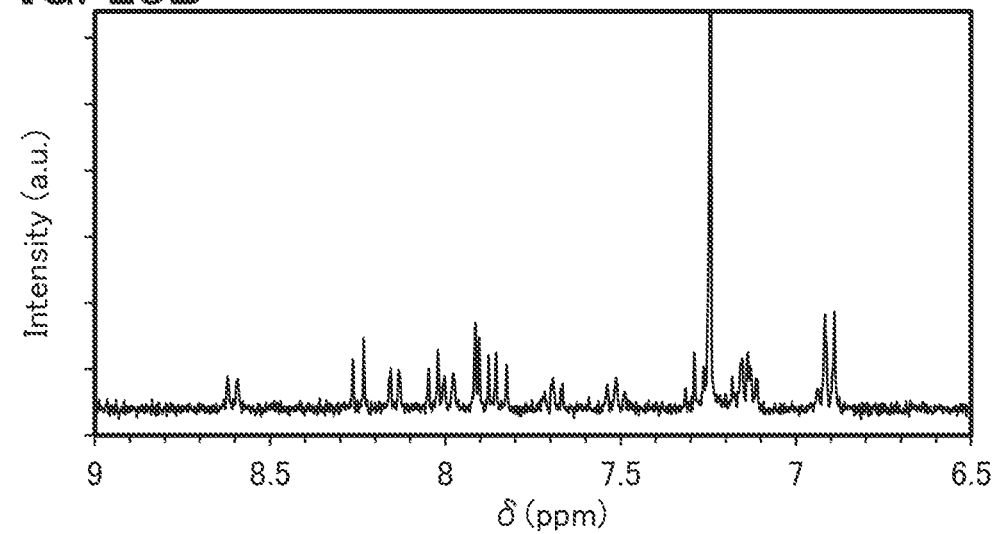
Figure 28C:
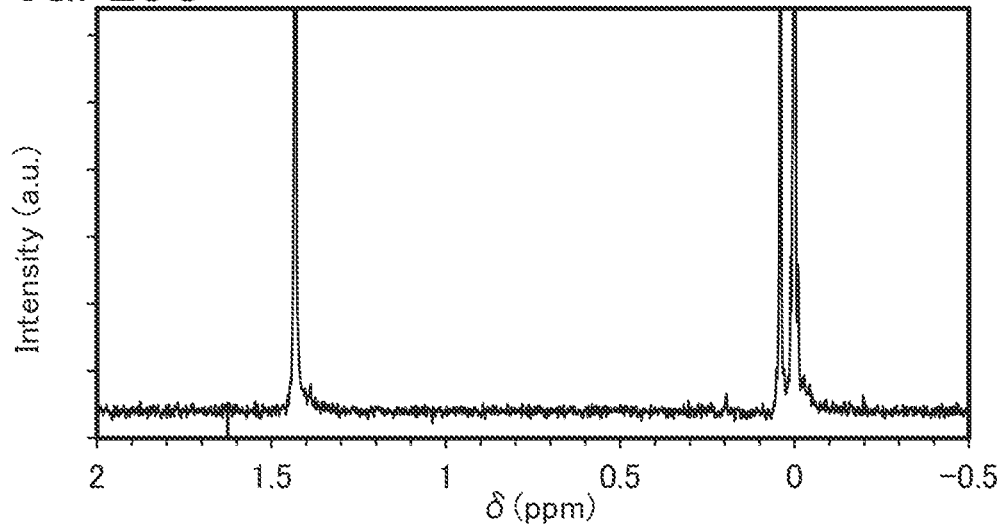

Results of $^1$H NMR measurement of the yellow solid obtained in Step 3 are shown below. Furthermore, $^1$H NMR charts are shown in FIGS. 28A to 28C. Note that FIG. 28B is an enlarged chart showing the range of 6.5 ppm to 9.0 ppm in FIG. 28A. FIG. 28C is an enlarged chart showing the range of −0.5 ppm to 2.0 ppm in FIG. 28A. The results reveal that 1,6TMSBnfAPrn (Structural Formula (145)) was obtained.

$^1$H NMR (CDCl$_3$, 300 MHz): σ=8.62 (d, J=8.8 Hz, 2H), 8.26 (d, J=9.3 Hz, 2H), 8.16-8.13 (m, 2H), 8.05-7.98 (m, 4H), 7.91-7.82 (m, 6H), 7.72-7.67 (m, 2H), 7.54-7.48 (m, 2H), 7.31-7.26 (m, 2H), 7.18-7.11 (m, 6H), 6.94-6.89 (m, 6H), 0.04 (s, 18H).

Results of measurement of absorption spectra and emission spectra of a toluene solution and a solid thin film of 1,6TMSBnfAPrn are described below. The measurement method was similar to that described in Example 1.

Figure 29A:
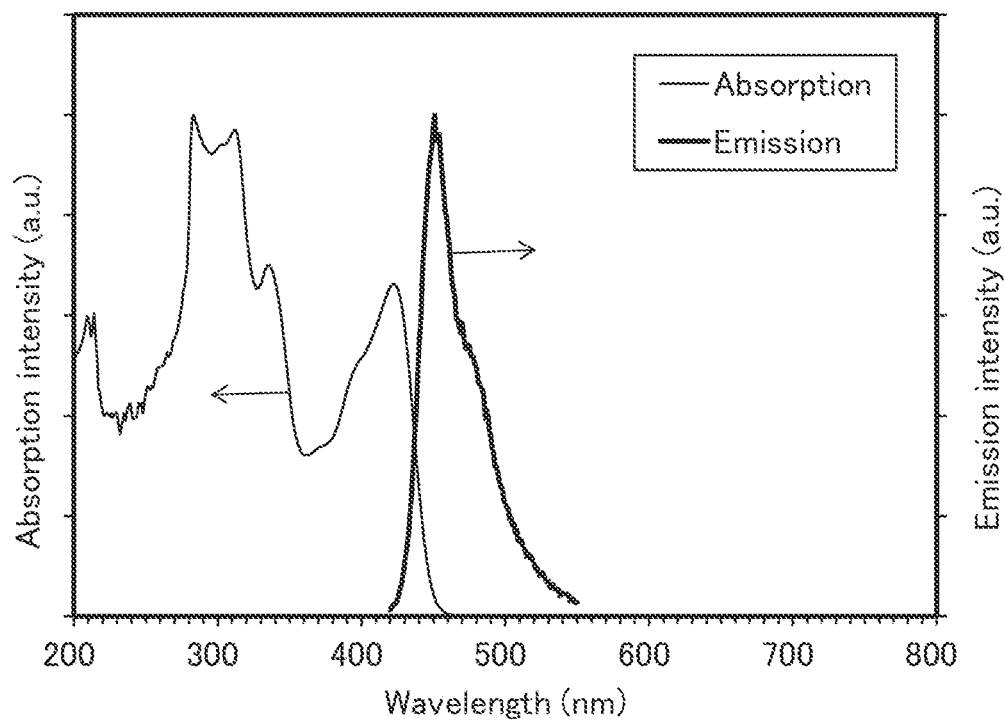
FIGS. 29A and 29B each show an ultraviolet-visible absorption spectrum and an emission spectrum of the organic compound represented by Structural Formula (145).
Figure 29B:
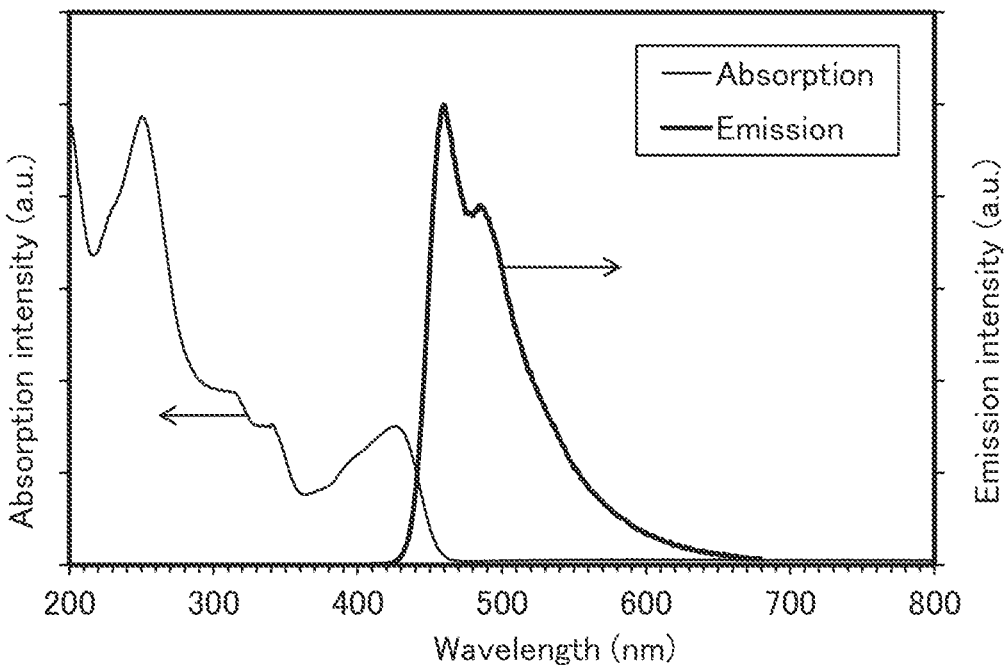

FIG. 29A shows the obtained absorption and emission spectra of the toluene solution. The horizontal axis represents wavelength and the vertical axes represent absorption intensity and emission intensity. FIG. 29B shows the obtained absorption and emission spectra of the solid thin film. The horizontal axis represents wavelength and the vertical axes represent absorption intensity and emission intensity.

As shown by the results in FIG. 29A, the toluene solution of 1,6TMSBnfAPrn exhibited an absorption peak at around 422 nm and an emission wavelength peak at 451 nm (excitation wavelength: 415 nm). Furthermore, as shown by the results in FIG. 29B, the solid thin film of 1,6TMSBn-fAPrn exhibited an absorption peak at around 428 nm and emission wavelength peaks at around 460 nm and 485 nm (excitation wavelength: 400 nm).

Example 8

Synthesis Example 7

In this example, a method for synthesizing N,N'-(3,8-dicyclohexylpyrene-1,6-diyl)bis[N-phenyl-(6-cyclohexyl-benzo[b]naphtho[1,2-d]furan)-8-amine] (abbreviation: ch-1,6chBnfAPrn), which is the organic compound of one embodiment of the present invention and which is represented by Structural Formula (142) in Embodiment 1, is described. The structure of ch-1,6chBnfAPrn is shown below.

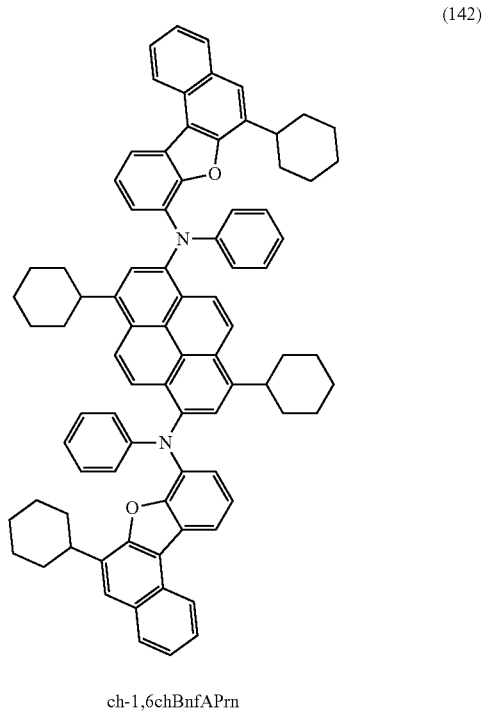 [SMILES: c1ccc(N(c2cc(C3CCCCC3)c3ccc4c(N(c5ccccc5)c5cccc6c5oc5c(C7CCCCC7)cc7ccccc7c56)cc(C5CCCCC5)c5ccc2c3c54)c2cccc3c2oc2c(C4CCCCC4)cc4ccccc4c23)cc1]

(142)

ch-1,6chBnfAPrn

Step 1: Synthesis of ch-1,6chBnfAPrn

Into a 200 mL three-neck flask were put 1.5 g (2.9 mmol) of 1,6-dibromo-3,8-dicyclohexylpyrene, 2.3 g (5.8 mmol) of N-phenyl-6-cyclohexylbenzo[b]naphtho[1,2-d]furan-8-amine, 1.1 g (11 mmol) of sodium t-butoxide, and 60 mg (0.15 mmol) of 2-dicyclohexylphosphino-2',6'-dimethoxy-1,1'-biphenyl (abbreviation: SPhos), and the air in the flask was replaced with nitrogen. To this mixture was added 30 mL of mesitylene, and the resulting mixture was degassed under reduced pressure; then, 40 mg (70 μmol) of bis(dibenzylideneacetone)palladium(0) was added to the mixture and the resulting mixture was stirred for 5.5 hours at 170° C. under a nitrogen stream.

After the stirring, 2.5 L of toluene was added and heating was performed; then, hot filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina.

A yellow solid obtained by concentration of the resulting filtrate was purified by silica gel column chromatography (a developing solvent: toluene) to give a target yellow solid. The obtained yellow solid was recrystallized with toluene to give 2.2 g of a target yellow solid in a yield of 67%.

By a train sublimation method, 1.3 g of the obtained yellow solid was purified by sublimation. In the purification by sublimation, the yellow solid was heated at 360° C. under a pressure of $2.9 \times 10^{-2}$ Pa for 15 hours. After the purification by sublimation, 1.0 g of a target yellow solid was obtained at a collection rate of 77%. A synthesis scheme of Step 1 is shown in (f-1).

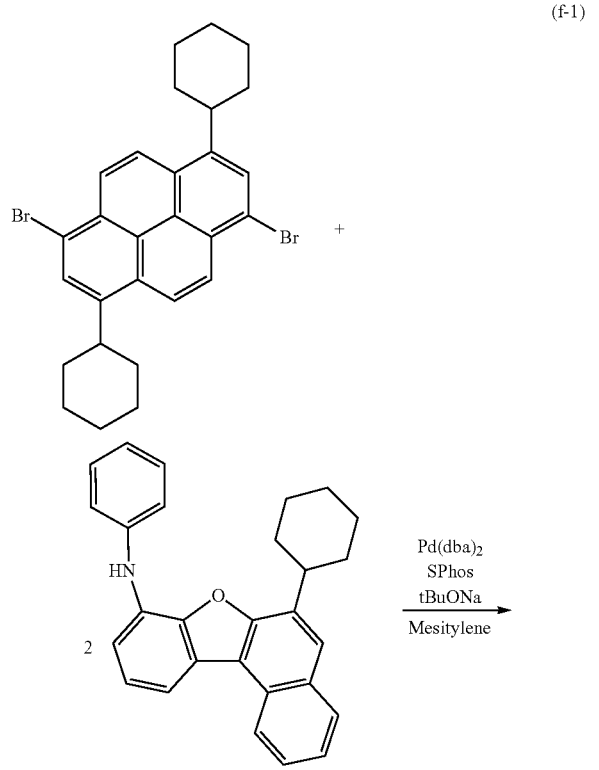

(f-1)

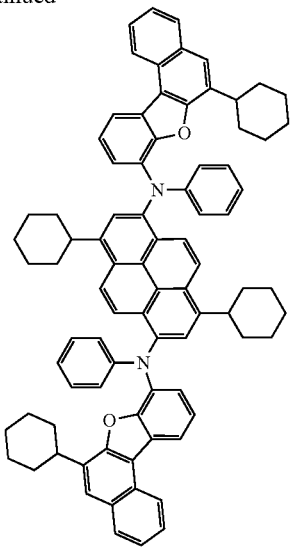

ch-1,6chBnfAPrn
(142)

Figure 30A:
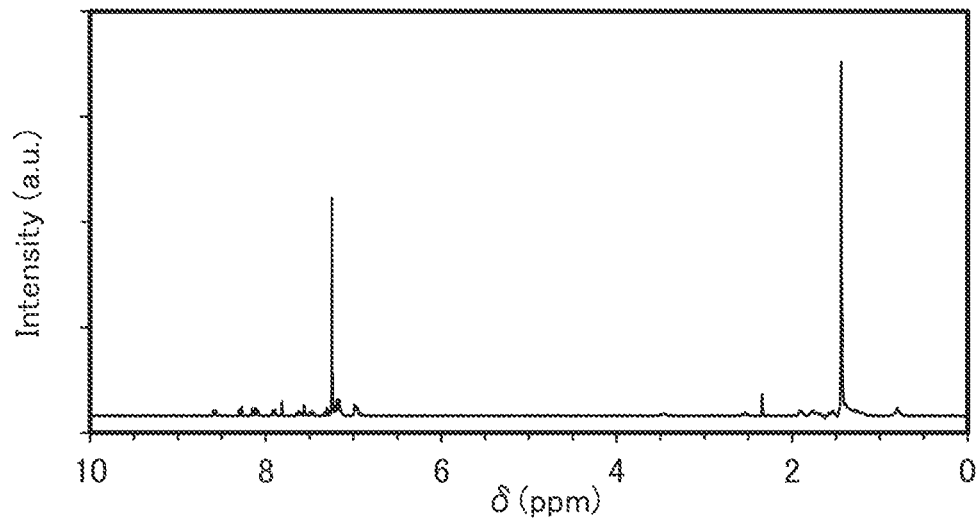
FIGS. 30A to 30C show $^1$H-NMR charts of an organic compound represented by Structural Formula (142).
Figure 30B:
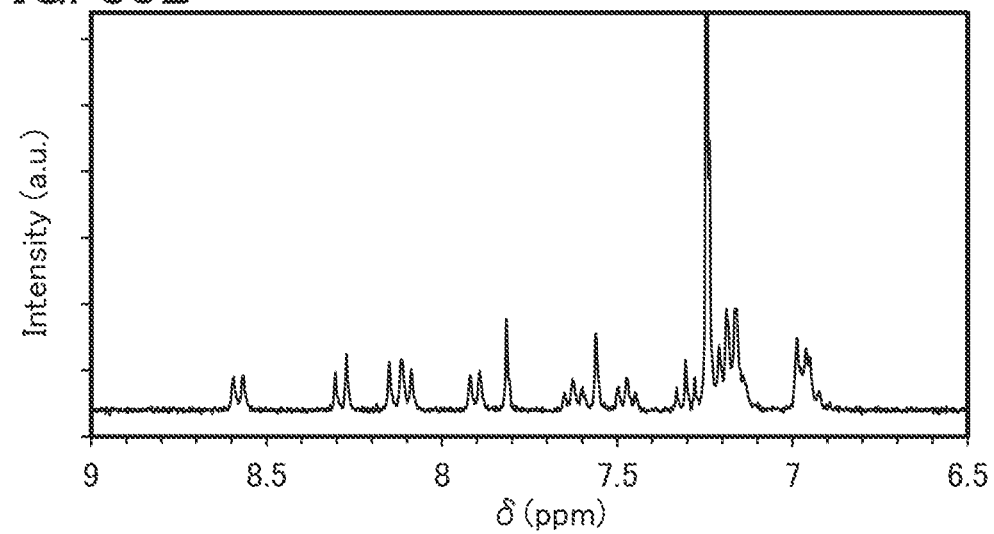
Figure 30C:
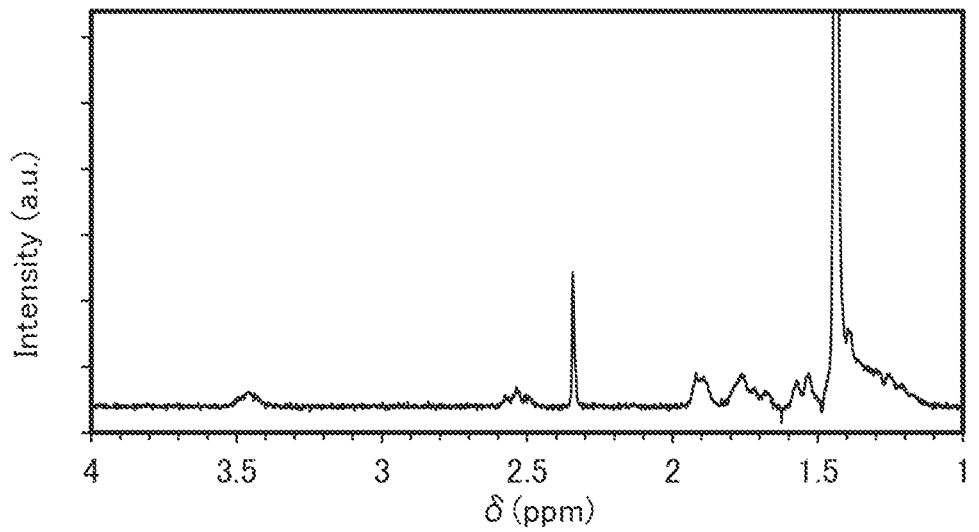

Results of $^1$H NMR measurement of the yellow solid obtained in Step 1 are shown below. Furthermore, $^1$H NMR charts are shown in FIGS. 30A to 30C. Note that FIG. 30B is an enlarged chart showing the range of 6.5 ppm to 9.0 ppm in FIG. 30A. FIG. 30C is an enlarged chart showing the range of 1.0 ppm to 4.0 ppm in FIG. 30A. The results reveal that ch-1,6chBnfAPrn (Structural Formula (142)) was obtained.

$^1$H NMR (CDCl$_3$, 300 MHz): σ=8.59 (d, J=8.3 Hz, 2H), 8.30 (d, J=9.8 Hz, 2H), 8.15-8.09 (m, 4H), 7.92 (d, J=7.8 Hz, 2H), 7.81 (s, 2H), 7.65-7.60 (m, 2H), 7.56 (s, 2H), 7.50-7.45 (m, 2H), 7.33-7.28 (m, 2H), 7.21-7.14 (m, 6H), 6.99-6.92 (m, 6H), 3.46 (m, 2H), 2.54 (m, 2H), 1.92-0.80 (m, 40H).

Results of measurement of absorption spectra and emission spectra of a toluene solution and a solid thin film of ch-1,6chBnfAPrn are described below. The measurement method was similar to that described in Example 1.

Figure 31A:
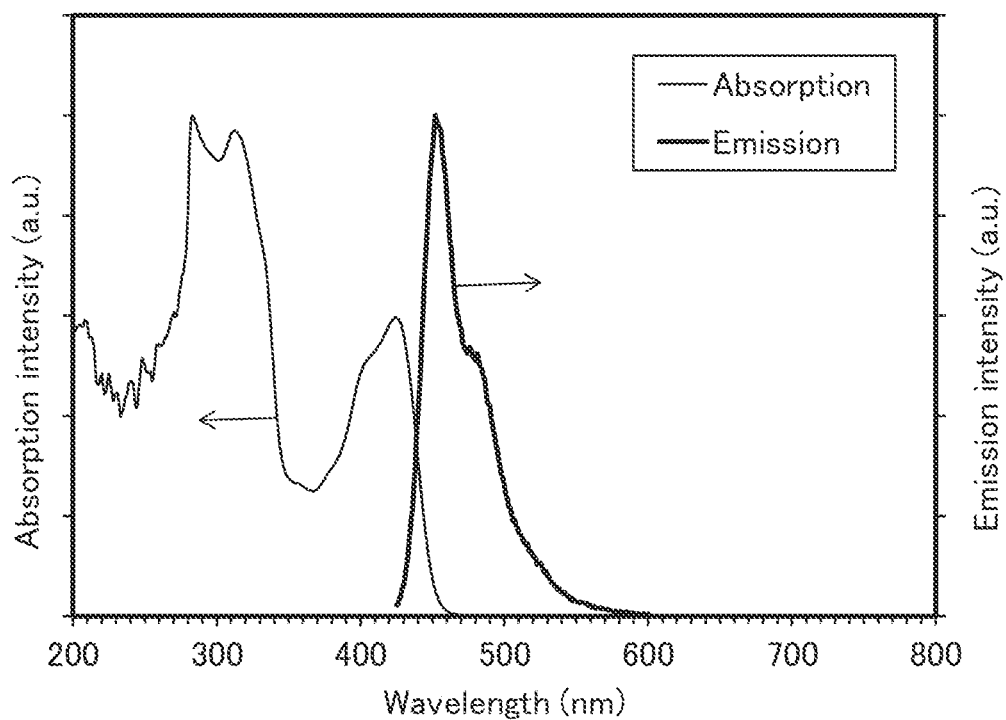
FIGS. 31A and 31B each show an ultraviolet-visible absorption spectrum and an emission spectrum of the organic compound represented by Structural Formula (142).
Figure 31B:
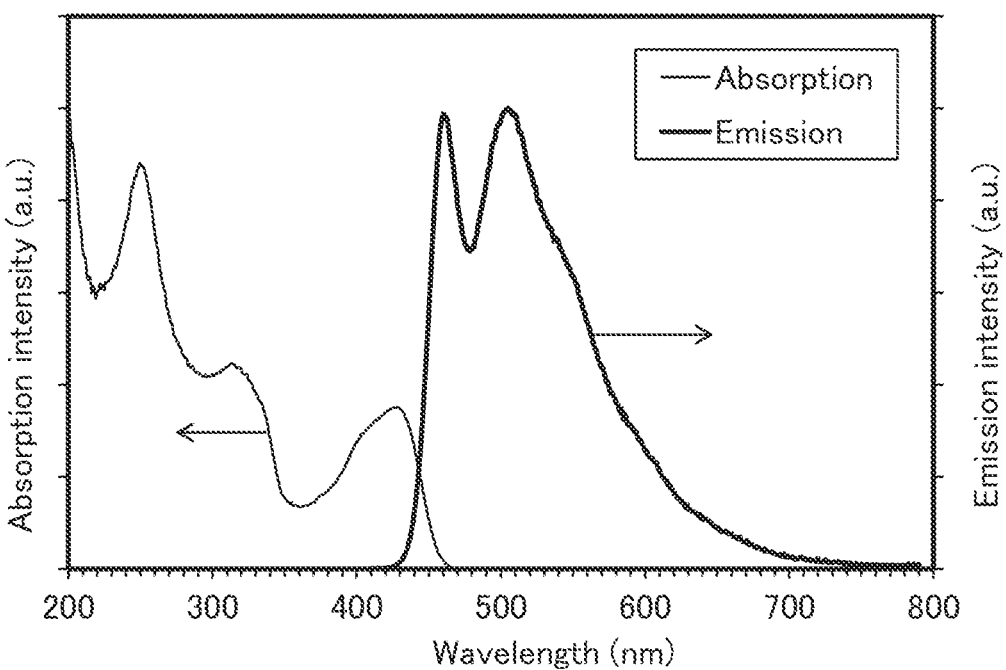

FIG. 31A shows the obtained absorption and emission spectra of the toluene solution. The horizontal axis represents wavelength and the vertical axes represent absorption intensity and emission intensity. FIG. 31B shows the obtained absorption and emission spectra of the solid thin film. The horizontal axis represents wavelength and the vertical axes represent absorption intensity and emission intensity.

As shown by the results in FIG. 31A, the toluene solution of ch-1,6chBnfAPrn exhibited an absorption peak at around 425 nm and an emission wavelength peak at 452 nm (excitation wavelength: 410 nm). Furthermore, as shown by the results in FIG. 31B, the solid thin film of ch-1,6chBnfAPrn exhibited an absorption peak at around 427 nm and emission wavelength peaks at around 460 nm and 505 nm (excitation wavelength: 400 nm).

Example 9

Synthesis Example 8

In this example, a method for synthesizing an organic compound N,N'-(3,8-dicyclohexylpyrene-1,6-diyl)bis(N-phenylbenzo[b]naphtho[1,2-d]furan-8-amine) (abbreviation: ch-1,6BnfAPrn-02) is described. The structure of ch-1,6BnfAPrn-02 is shown below.

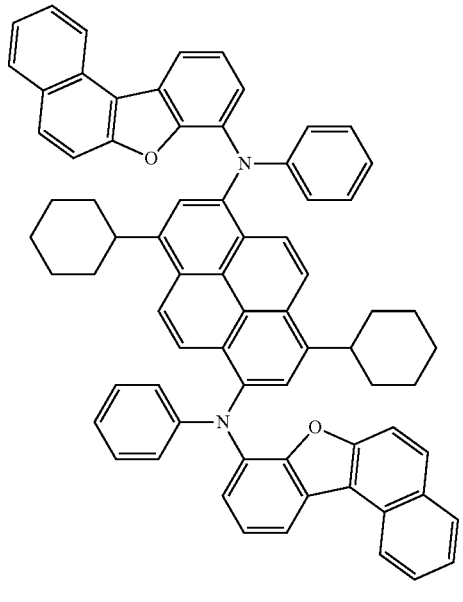

ch-1,6BnfAPrn-02

Step 1: Synthesis of 1,6-dicyclohexylpyrene

Into a 200 mL three-neck flask were put 2.0 g (5.6 mmol) of 1,6-dibromopyrene and 90 mg (0.19 mmol) of 2-dicyclohexylphosphino-2',4',6'-triisopropylbiphenyl (abbreviation: XPhos), and the air in the flask was replaced with nitrogen. Then, 30 mL of tetrahydrofuran (abbreviation: THF) was added, and the resulting mixture was degassed under reduced pressure and then stirred at 70° C. To this mixture was added 80 mg (87 μmol) of tris(dibenzylideneacetone)dipalladium(0) (abbreviation: $Pd_2(dba)_3$), and 24 mL of cyclohexylmagnesium bromide (a 1.0 mol/L tetrahydrofuran solution, 24 mmol) was dropped into the mixture; then, the resulting mixture was stirred for 6.5 hours at 70° C. under a nitrogen stream.

After the stirring, this mixture was dropped into 0° C. hydrochloric acid (1 mol/L), and an aqueous layer of the resulting mixture was subjected to extraction using toluene. The obtained solution of the extract and an organic layer were combined, and the mixture was washed with water and saturated brine. Then, the mixture was dried with magnesium sulfate. The mixture was separated by gravity filtration, and the obtained filtrate was concentrated to give a yellow oily substance.

The obtained oily substance was purified by silica gel column chromatography (a developing solvent: hexane) to give 1.47 g of a yellowish white solid. This solid was purified by recrystallization, so that 0.85 g of a target white solid was obtained in a yield of 42%. A synthesis scheme of Step 1 is shown in (g-1).

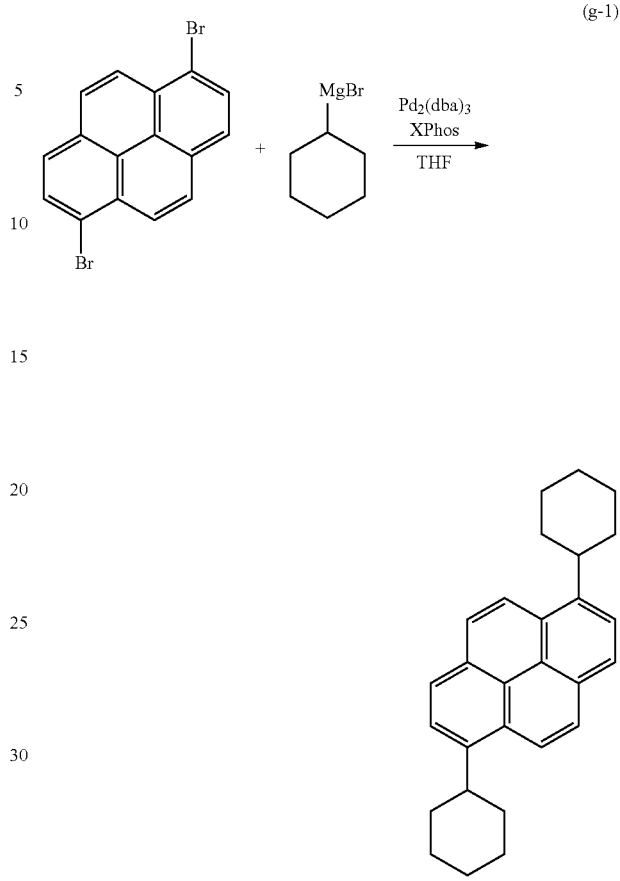

Results of $^1$H NMR measurement of the white solid obtained in Step 1 are shown below.

$^1$H NMR (CDCl$_3$, 300 MHz): σ=8.32 (d, J=9.3 Hz, 2H), 8.14 (d, J=8.3 Hz, 2H), 8.06 (d, J=9.3 Hz, 2H), 7.96 (d, J=7.8 Hz, 2H), 3.67-3.60 (m, 2H), 2.13-1.39 (m, 20H).

Step 2: Synthesis of 1,6-dibromo-3,8-dicyclohexylpyrene

Into a 300 mL three-neck flask was put 5.1 g (14 mmol) of 1,6-dicyclohexylpyrene, and the air in the flask was replaced with nitrogen. Then, 80 mL of N,N-dimethylformamide (abbreviation: DMF) was added and stirring was performed at 110° C. To the resulting mixture was added 7.7 g (43 mmol) of N-bromosuccinimide (abbreviation: NBS), and stirring was performed for 23 hours at 80° C.

After the stirring, water was added to this mixture and a precipitated solid was separated by suction filtration. The obtained brownish white solid was washed with methanol and recrystallized with toluene to give 3.1 g of a target brownish white solid in a yield of 76%. A synthesis scheme of Step 2 is shown in (g-2).

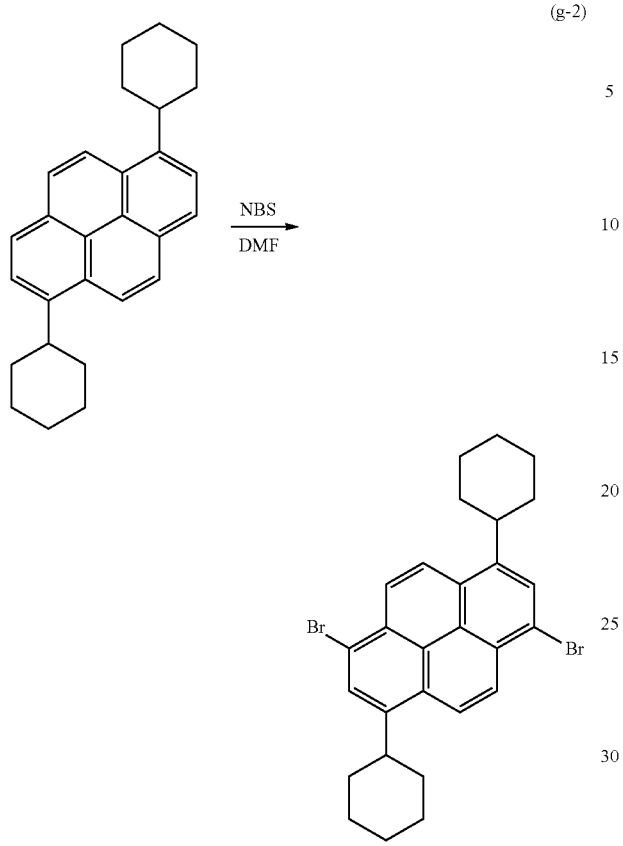

Results of ¹H NMR measurement of the brownish white solid obtained in Step 2 are shown below.

¹H NMR (CDCl₃, 300 MHz): σ=8.47 (d, J=9.8 Hz, 2H), 8.36 (d, J=9.3 Hz, 2H), 8.20 (s, 2H), 3.64-3.56 (m, 2H), 2.12-1.57 (m, 20H).

Step 3: Synthesis of N-phenyl-benzo[b]naphtho[1,2-d]furan-8-amine

Into a 200 mL three-neck flask were put 1.1 g (4.4 mmol) of 8-chlorobenzo[b]naphtho[1,2-d]furan, 0.49 g (5.3 mmol) of aniline, and 1.0 g (10 mmol) of sodium t-butoxide, and the air in the flask was replaced with nitrogen. To this mixture was added 25 mL of toluene, and the resulting mixture was degassed under reduced pressure. To this mixture were added 0.26 g (0.72 mmol) of n-butyl-diadamantylphosphine and 80 mg (0.14 mmol) of bis(dibenzylideneacetone)palladium(0) and then, stirring was performed for 10 hours at 120° C. under a nitrogen stream.

After the stirring, 300 mL of toluene was added to the resulting mixture and then, suction filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina to give a filtrate. The obtained filtrate was concentrated to give a brown oily substance.

This oily substance was purified by silica gel column chromatography (a developing solvent was a mixed solvent of hexane:toluene=4:1) to give 0.76 g of a target white solid in a yield of 57%. A synthesis scheme of Step 3 is shown in (g-3).

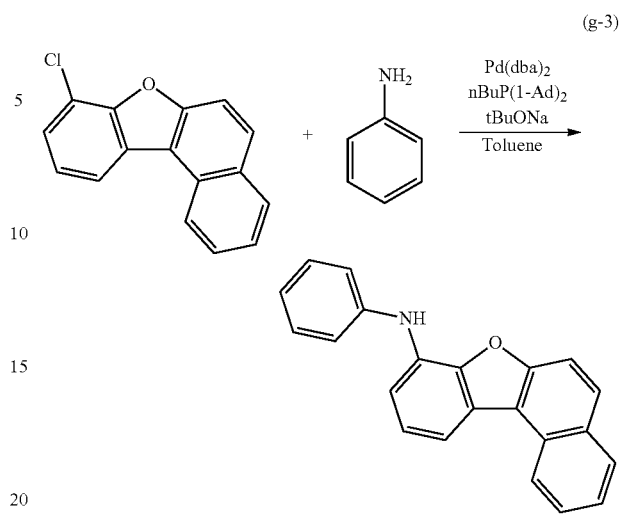

Step 4: Synthesis of ch-1,6BnfAPrn-02

Into a 200 mL three-neck flask were put 0.64 g (1.2 mmol) of 1,6-dibromo-3,8-dicyclohexylpyrene, 0.76 g (2.5 mmol) of N-phenyl-benzo[b]naphtho[1,2-d]furan-8-amine, 0.50 g (5.2 mmol) of sodium t-butoxide, and 60 mg (0.15 mmol) of 2-dicyclohexylphosphino-2',6'-dimethoxy-1,1'-biphenyl (abbreviation: SPhos), and the air in the flask was replaced with nitrogen. To this mixture was added 15 mL of mesitylene, and the resulting mixture was degassed under reduced pressure; then, 40 mg (70 μmol) of bis(dibenzylideneacetone)palladium(0) was added to the mixture and the resulting mixture was stirred for 6 hours at 170° C. under a nitrogen stream.

After the stirring, 500 mL of toluene was added and heating was performed; then, hot filtration was performed through Florisil (Catalog No. 066-05265 produced by Wako Pure Chemical Industries, Ltd.), Celite (Catalog No. 537-02305 produced by Wako Pure Chemical Industries, Ltd.), and alumina. A yellow solid obtained by concentration of the resulting filtrate was purified by silica gel column chromatography to give a target yellow solid. The obtained yellow solid was recrystallized with toluene to give 0.95 g of a target yellow solid in a yield of 79%.

By a train sublimation method, 0.95 g of the obtained yellow solid was purified by sublimation. In the purification by sublimation, the yellow solid was heated at 350° C. under a pressure of $2.3 \times 10^{-2}$ Pa for 7 hours. After the purification by sublimation, 0.65 g of a target yellow solid was obtained at a collection rate of 68%. A synthesis scheme of Step 4 is shown in (g-4).

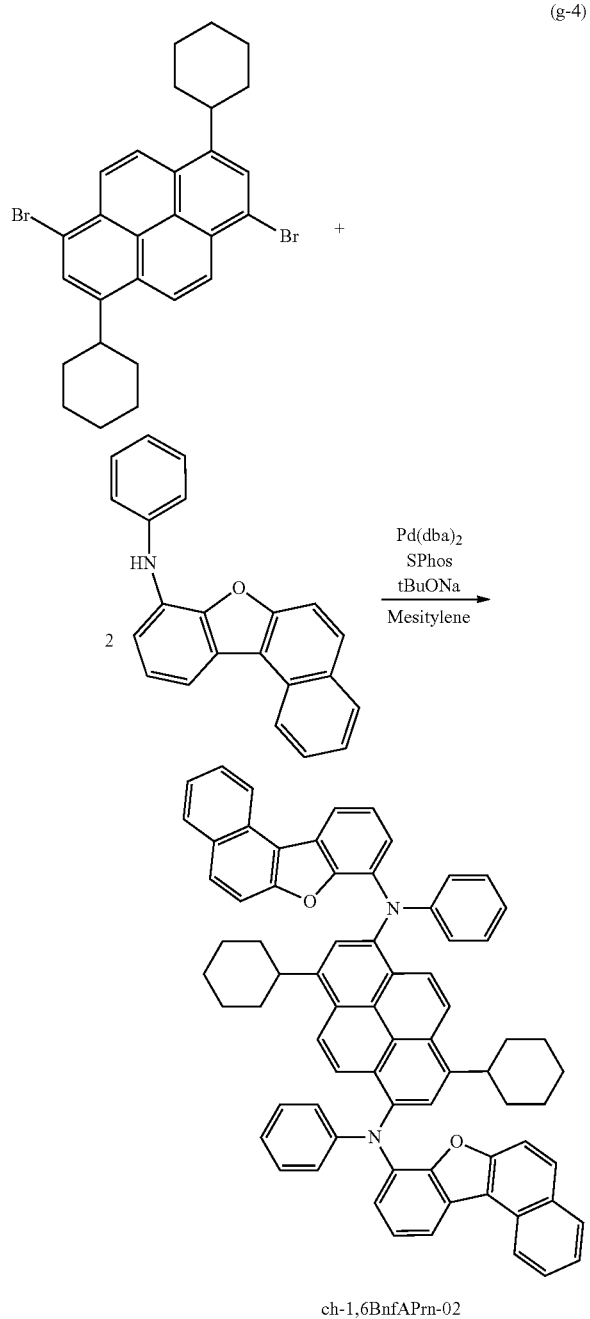

ch-1,6BnfAPrn-02

Figure 32A:
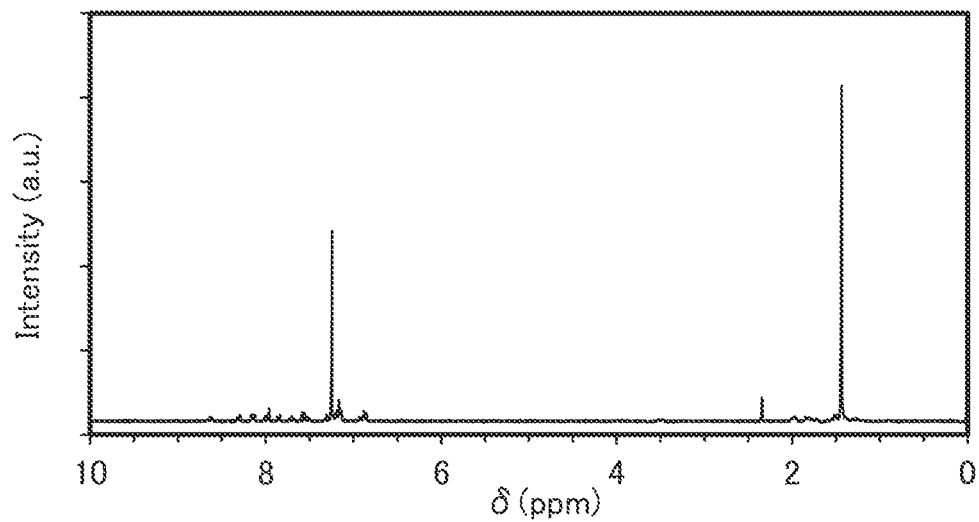
FIGS. 32A to 32C show $^1$H-NMR charts of ch-1,6BnfAPrn-02.
Figure 32B:
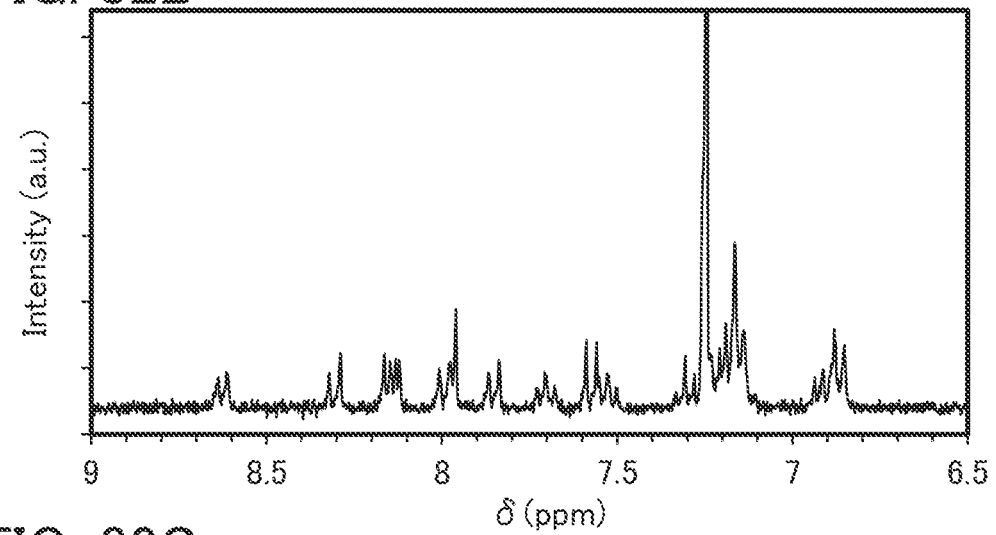
Figure 32C:
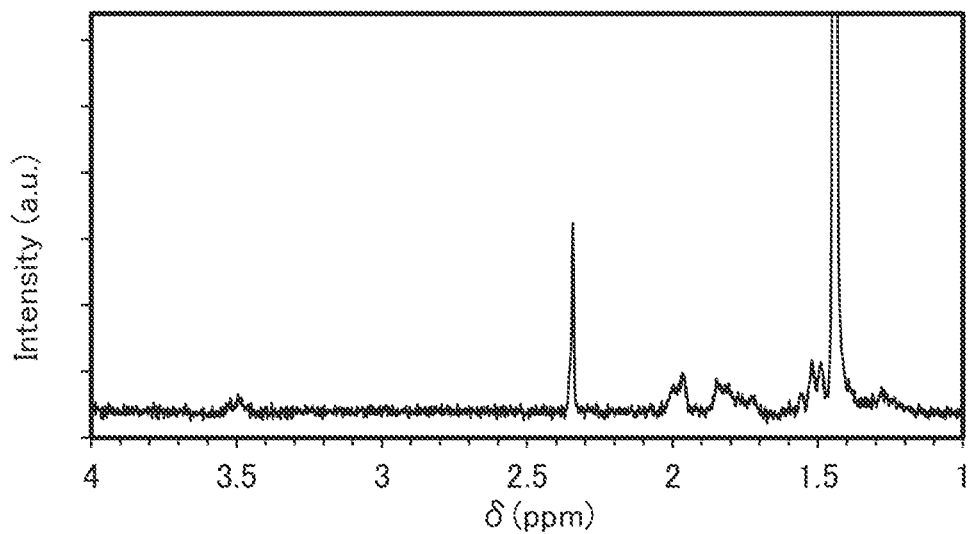

Results of $^1$H NMR measurement of the yellow solid obtained in Step 4 are shown below. Furthermore, H NMR charts are shown in FIGS. 32A to 32C. Note that FIG. 32B is an enlarged chart showing the range of 6.5 ppm to 9.0 ppm in FIG. 32A. FIG. 32C is an enlarged chart showing the range of 1.0 ppm to 4.0 ppm in FIG. 32A. The results reveal that ch-1,6BnfAPrn-02 was obtained.

$^1$H NMR (CDCl$_3$, 300 MHz): σ=8.64-8.61 (m, 2H), 8.32 (d, J=9.3 Hz, 2H), 8.16-8.12 (m, 4H), 8.01-7.96 (m, 4H), 7.87-7.84 (m, 2H), 7.73-7.68 (m, 2H), 7.59-7.50 (m, 4H), 7.33-7.28 (m, 2H), 7.21-7.14 (m, 6H), 6.94-6.85 (m, 6H), 3.49 (m, 2H), 2.01-1.28 (m, 20H).

Results of measurement of absorption spectra and emission spectra of a solid thin film and a toluene solution of ch-1,6BnfAPrn-02 are described below. The measurement method was similar to that described in Example 1.

Figure 33A:
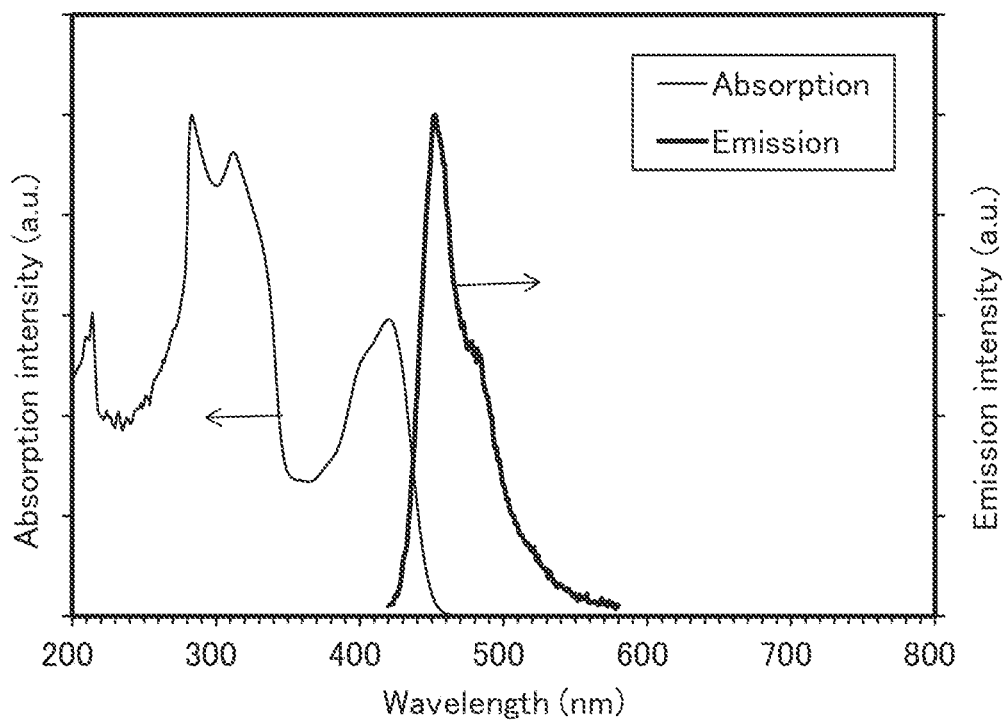
FIGS. 33A and 33B each show an ultraviolet-visible absorption spectrum and an emission spectrum of ch-1,6BnfAPrn-02.
Figure 33B:
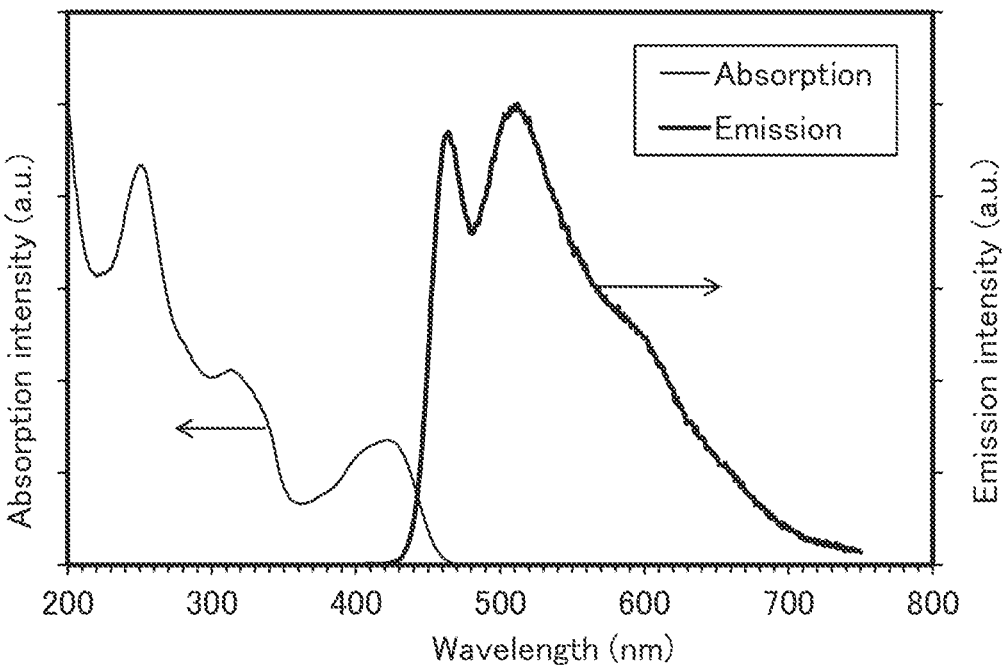
Figure 34:
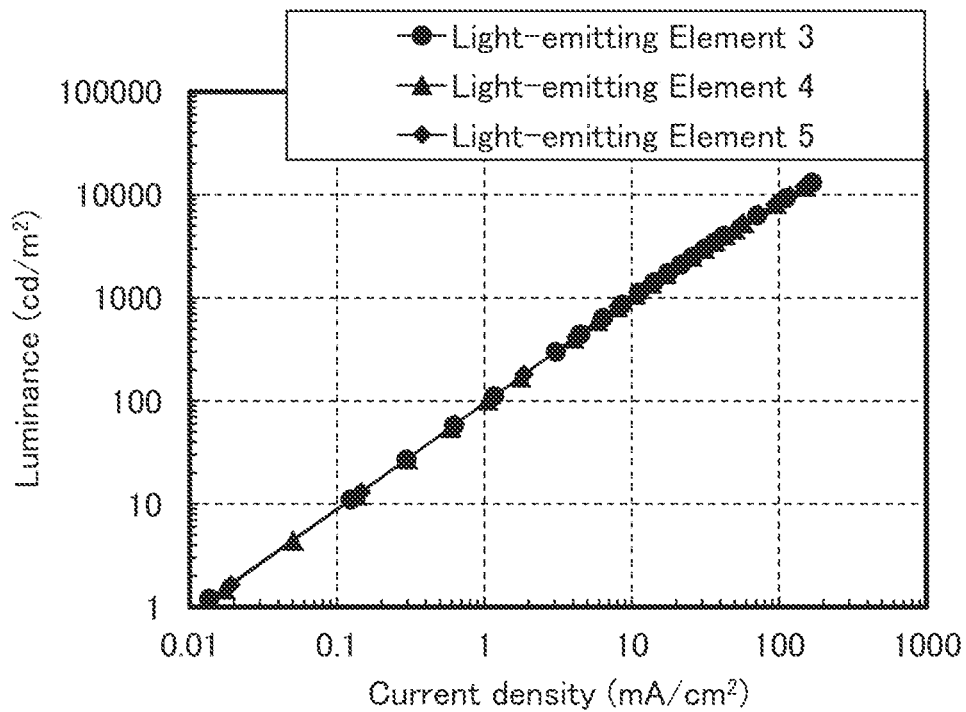
FIG. 34 shows current density-luminance characteristics of a light-emitting element 3, a light-emitting element 4, and a light-emitting element 5.
Figure 35:
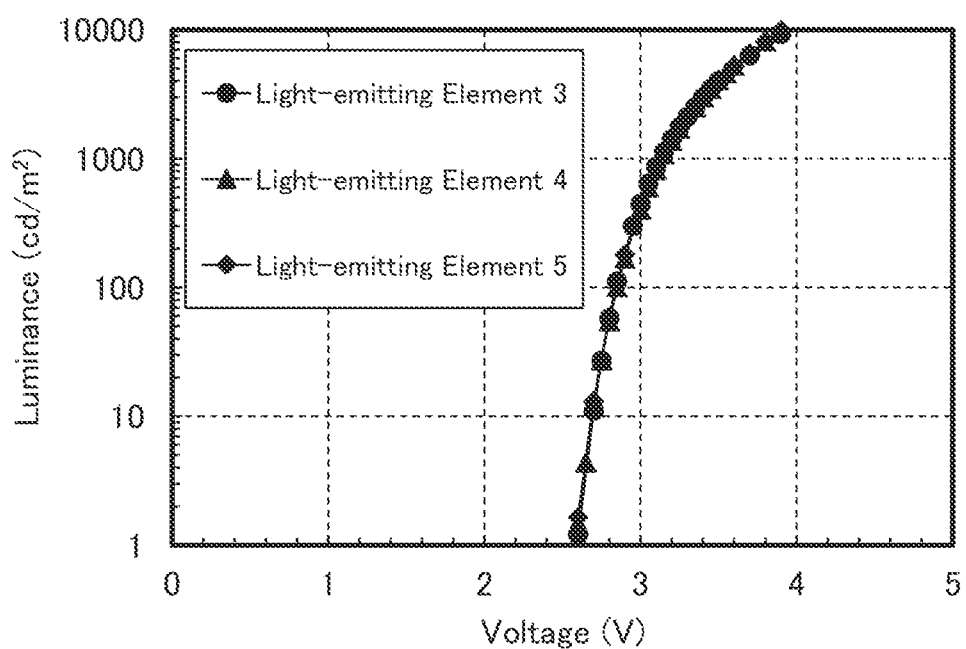
FIG. 35 shows voltage-luminance characteristics of the light-emitting element 3, the light-emitting element 4, and the light-emitting element 5.
Figure 36:
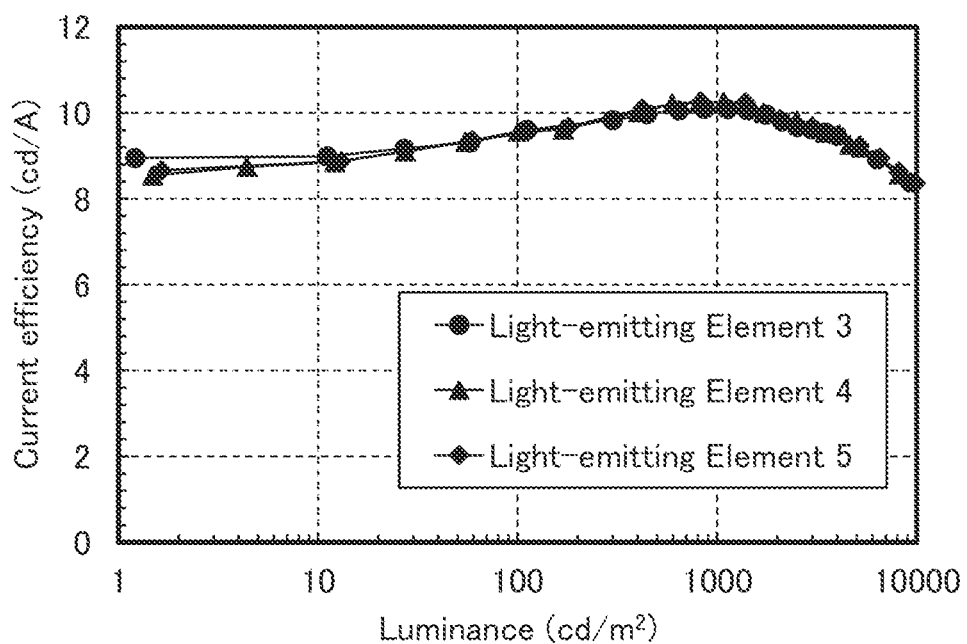
FIG. 36 shows luminance-current efficiency characteristics of the light-emitting element 3, the light-emitting element 4, and the light-emitting element 5.
Figure 37:
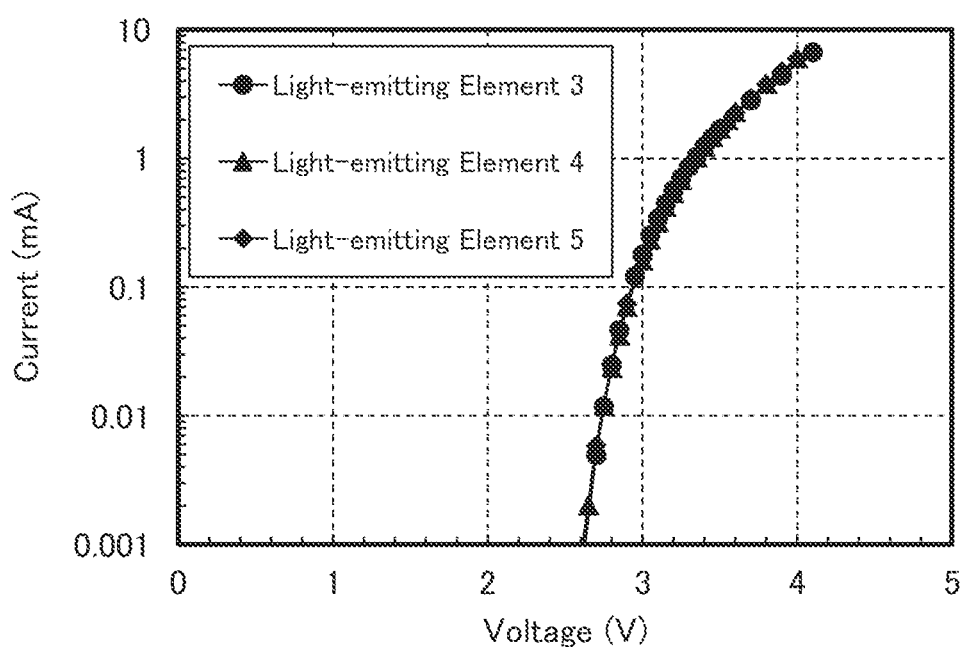
FIG. 37 shows voltage-current characteristics of the light-emitting element 3, the light-emitting element 4, and the light-emitting element 5.

FIG. 33A shows the obtained absorption and emission spectra of the toluene solution. The horizontal axis represents wavelength and the vertical axes represent absorption intensity and emission intensity. FIG. 33B shows the obtained absorption and emission spectra of the solid thin film. The horizontal axis represents wavelength and the vertical axes represent absorption intensity and emission intensity.

As shown by the results in FIG. 33A, the toluene solution of ch-1,6BnfAPrn-02 exhibited an absorption peak at around 420 nm and an emission wavelength peak at 453 nm (excitation wavelength: 415 nm). Furthermore, as shown by the results in FIG. 33B, the solid thin film of ch-1,6BnfAPrn-02 exhibited an absorption peak at around 423 nm and emission wavelength peaks at around 464 nm and 512 nm (excitation wavelength: 400 nm).

Example 10

In this example, the quantum yields of the organic compounds in Examples 1 to 3 and 5 to 9 were measured. For the measurement, the toluene solutions that were used for the measurement of the emission spectra in these examples were used. The measurement was conducted with the use of an absolute PL quantum yield measurement system (Quantaurus-QY C11347-01) manufactured by Hamamatsu Photonics K.K. The excitation wavelength was set in the range of 350 nm to 450 nm at intervals of 10 nm, and the maximum among the quantum yields obtained in the measurement range was regarded as the quantum yield of the organic compound.

Table 3 shows the measurement results. As Table 3 shows, the light-emitting materials of embodiments of the present invention have extremely high quantum yields and are thus suitable as light-emitting materials for light-emitting elements.

TABLE 3

| | Compound | Quantum yield (%) |
| --- | --- | --- |
| Synthesis Example 1 | 1,6chBnfAPrn | 82 |
| Synthesis Example 2 | 1,6oMechBnfAPrn | 85 |
| Synthesis Example 3 | 1,6iPrBnfAPrn | 72 |
| Synthesis Example 4 | 1,6nPrBnfAPrn | 86 |
| Synthesis Example 5 | 1,6tBuBnfAPrn | 86 |
| Synthesis Example 6 | 1,6TMSBnfAPrn | 84 |
| Synthesis Example 7 | ch-1,6chBnfAPrn | 94 |
| Synthesis Example 8 | ch-1,6BnfAPrn-02 | 94 |

Example 11

In this example, the HOMO levels and LUMO levels of the organic compounds synthesized in Synthesis Examples 1 to 8 in Examples 1 to 3 and 5 to 9 were calculated from cyclic voltammetry (CV) measurement results. The method and results of the calculation are as follows.

An electrochemical analyzer (ALS model 600A or 600C, produced by BAS Inc.) was used for the measurement. To prepare a solution for the CV measurement, dehydrated dimethylformamide (DMF, manufactured by Sigma-Aldrich Inc., 99.8%, catalog No. 22705-6) was used as a solvent, and tetra-n-butylammonium perchlorate (n-Bu$_4$NClO$_4$, manufactured by Tokyo Chemical Industry Co., Ltd., catalog No. T0836) as a supporting electrolyte was dissolved at a concentration of 100 mmol/L. Further, the object to be measured was dissolved at a concentration of 2 mmol/L.

A platinum electrode (PTE platinum electrode, produced by BAS Inc.) was used as a working electrode, a platinum electrode (Pt counter electrode for VC-3 (5 cm), produced by BAS Inc.) was used as an auxiliary electrode, and an Ag/Ag+ electrode (RE-7 reference electrode for nonaqueous solvent, produced by BAS Inc.) was used as a reference electrode. Note that the measurement was conducted at room temperature (20° C. to 25° C.).

In addition, the scan speed in the CV measurement was fixed to 0.1 V/sec, and an oxidation potential Ea [V] and a reduction potential Ec [V] with respect to the reference electrode were measured. The potential Ea is an intermediate potential of an oxidation-reduction wave, and the potential Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]=−4.94−Ec. Table 4 shows the measurement results.

TABLE 4

| | Compound | HOMO | LUMO |
|---|---|---|---|
| Synthesis Example 1 | 1,6chBnfAPrn | −5.46 | −2.66 |
| Synthesis Example 2 | 1,6oMechBnfAPrn | −5.36 | −2.60 |
| Synthesis Example 3 | 1,6iPrBnfAPrn | −5.47 | −2.65 |
| Synthesis Example 4 | 1,6nPrBnfAPrn | −5.45 | −2.65 |
| Synthesis Example 5 | 1,6tBuBnfAPrn | −5.48 | −2.66 |
| Synthesis Example 6 | 1,6TMSBnfAPrn | −5.44 | −2.66 |
| Synthesis Example 7 | ch-1,6chBnfAPrn | −5.40 | −2.60 |
| Synthesis Example 8 | ch-1,6BnfAPrn-02 | −5.39 | −2.62 |

From Table 4, it is found that the organic compounds of embodiments of the present invention have deeper HOMO levels than ch-1,6BnfAPrn-02, which is the organic compound synthesized as a reference in Synthesis Example 8. Unlike ch-1,6BnfAPrn-02, the organic compounds of embodiments of the present invention each have an alkyl group in a benzo[b]naphtho[1,2-d]furan skeleton and this probably led to their deeper HOMO levels and accordingly wider band gaps (BG), enabling their shorter-wavelength light emission. Note that the HOMO level of 1,6oMechBnfAPrn (one embodiment of the present invention described in Synthesis Example 2) is shallower than the HOMO levels of the compounds in the other synthesis examples probably because in 1,6oMechBnfAPrn, $Ar^1$ of General Formula (G1) has a methyl group with an electron-donating property.

Example 12

In this example, a light-emitting element 3 using 1,6TMSBnfAPrn (Structural Formula (145), Example 7) in its light-emitting layer, a light-emitting element 4 using 1,6nPrBnfAPrn (Structural Formula (118), Example 5) in its light-emitting layer, and a light-emitting element 5 using 1,6tBuBnfAPrn (Structural Formula (117), Example 6) in its light-emitting layer were fabricated as light-emitting elements of embodiments of the present invention, and their characteristics were measured.

Element structures of the light-emitting elements used in this example are similar to the element structure described in Example 4 with reference to FIG. 17, and Table 5 shows specific structures of layers in the element structures. Chemical formulae of materials used in this example are shown below.

TABLE 5

| | First electrode | Hole-injection layer | Hole-transport layer | Light-emitting layer | Electron-transport layer | Electron-injection layer | Second electrode |
|---|---|---|---|---|---|---|---|
| Light-emitting element 3 | ITSO (70 nm) | PCPPn:MoOx (4:2, 10 nm) | PCPPn (30 nm) | * | cgDBCzPA (15 nm) | NBphen (10 nm) | LiF (1 nm) | Al (200 nm) |
| Light-emitting element 4 | ITSO (70 nm) | PCPPn:MoOx (4:2, 10 nm) | PCPPn (30 nm) | ** | cgDBCzPA (15 nm) | NBphen (10 nm) | LiF (1 nm) | Al (200 nm) |
| Light-emitting element 5 | ITSO (70 nm) | PCPPn:MoOx (4:2, 10 nm) | PCPPn (30 nm) | *** | cgDBCzPA (15 nm) | NBphen (10 nm) | LiF (1 nm) | Al (200 nm) |

*cgDBCzPA:1,6TMSBnfAPr (1:0.03, 25 nm)
**cgDBCzPA:1,6nPrBnfAPrn (1:0.03, 25 nm)
***cgDBCzPA:1,6tBuBnfAPrn (1:0.03, 25 nm)

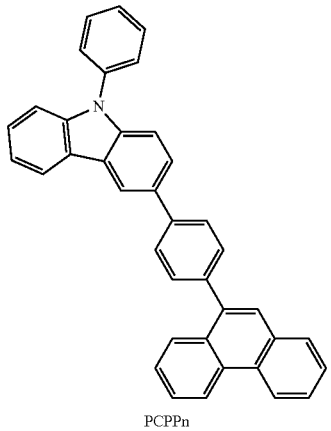 [SMILES: c1ccc(-n2c3ccccc3c3cc(-c4ccc(-c5cc6ccccc6c6ccccc56)cc4)ccc32)cc1]

PCPPn

TABLE 5-continued
| First electrode | Hole-injection layer | Hole-transport layer | Light-emitting layer | Electron-transport layer | Electron-injection layer | Second electrode |
|---|---|---|---|---|---|---|
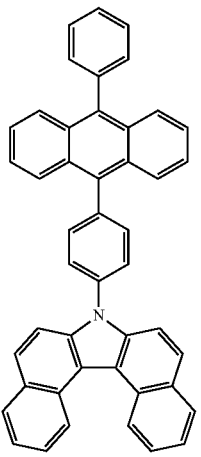
cgDBCzPA
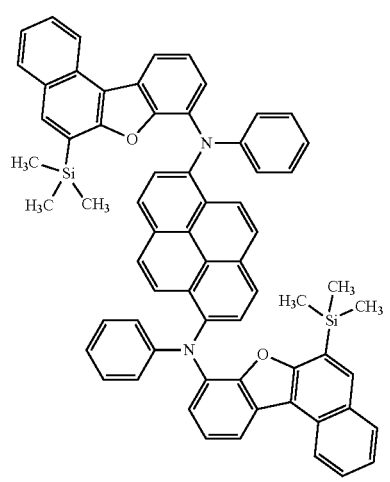
1,6TMSBnfAPrn
(145)
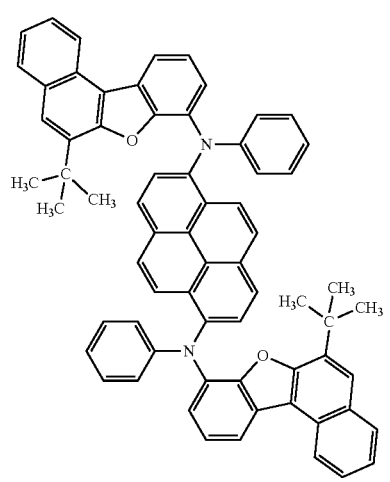
1,6tBuBnfAPrn
(117)

TABLE 5-continued

| First electrode | Hole-injection layer | Hole-transport layer | Light-emitting layer | Electron-transport layer | Electron-injection layer | Second electrode |
|---|---|---|---|---|---|---|

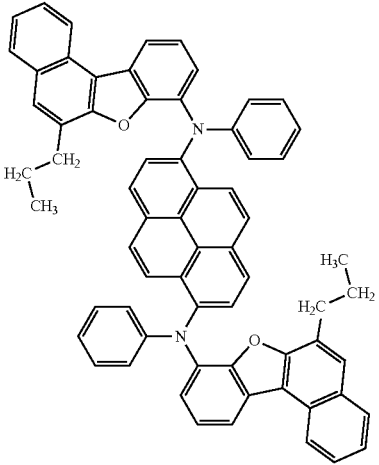

1,6nPrBnfAPrn (118)

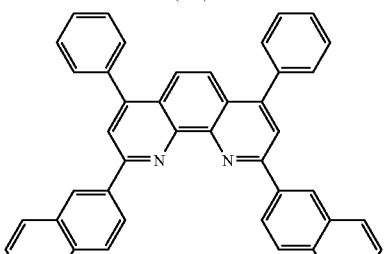

NBphen

<<Operation Characteristics of Light-Emitting Elements>>

Operation characteristics of the fabricated light-emitting elements 3 to 5 were measured. The measurement was carried out at room temperature. The results are shown in FIGS. 34 to 37.

Table 6 shows initial values of main characteristics of the light-emitting elements at a luminance of approximately 1000 cd/m².

TABLE 6

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting element 3 | 3.2 | 0.45 | 11 | (0.14, 0.12) | 1100 | 10 | 10 | 10 |
| Light-emitting element 4 | 3.2 | 0.42 | 11 | (0.14, 0.11) | 1100 | 10 | 10 | 11 |
| Light-emitting element 5 | 3.1 | 0.32 | 8.1 | (0.14, 0.11) | 830 | 10 | 10 | 11 |

The above results show that the light-emitting element 3, the light-emitting element 4, and the light-emitting element 5 fabricated in this example have an external quantum efficiency of 10% or higher and that these light-emitting elements have high efficiencies and exhibit favorable blue light emission.

Figure 38:
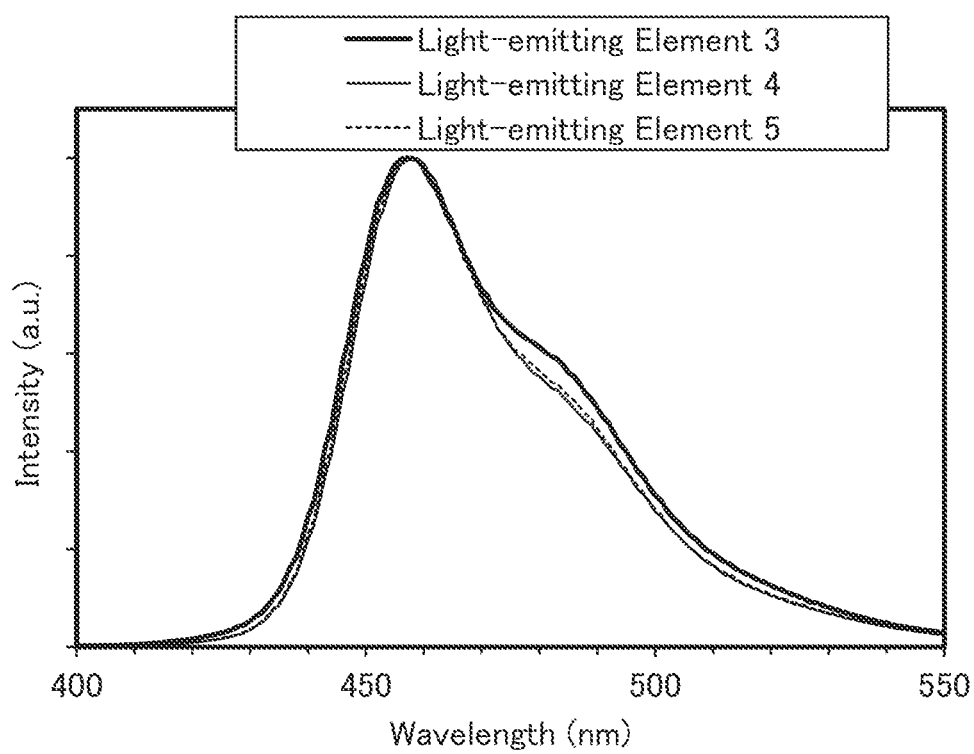
FIG. 38 shows emission spectra of the light-emitting element 3, the light-emitting element 4, and the light-emitting element 5.
Figure 39:
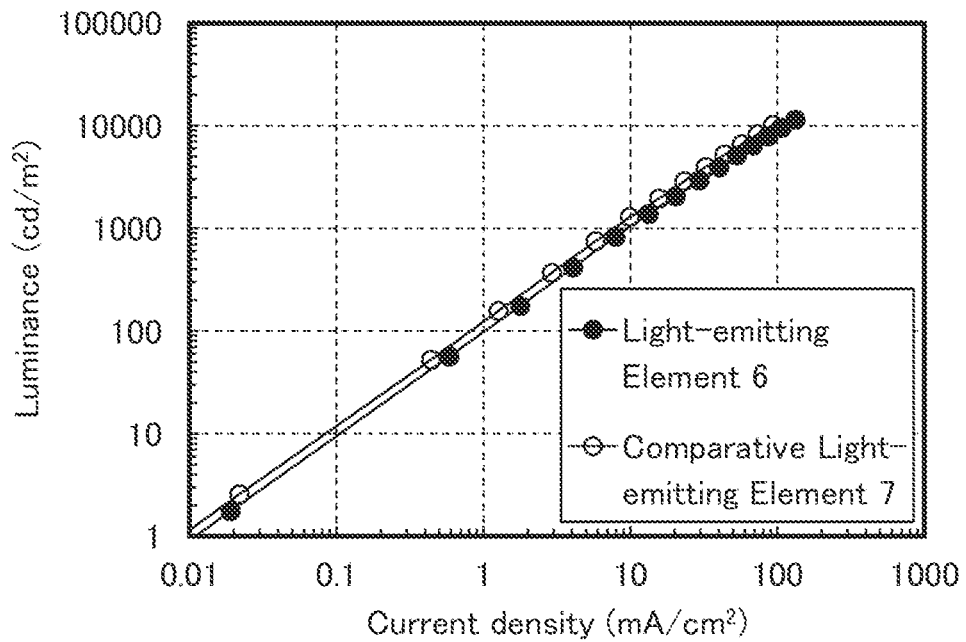
FIG. 39 shows current density-luminance characteristics of a light-emitting element 6 and a comparative light-emitting element 7.
Figure 40:
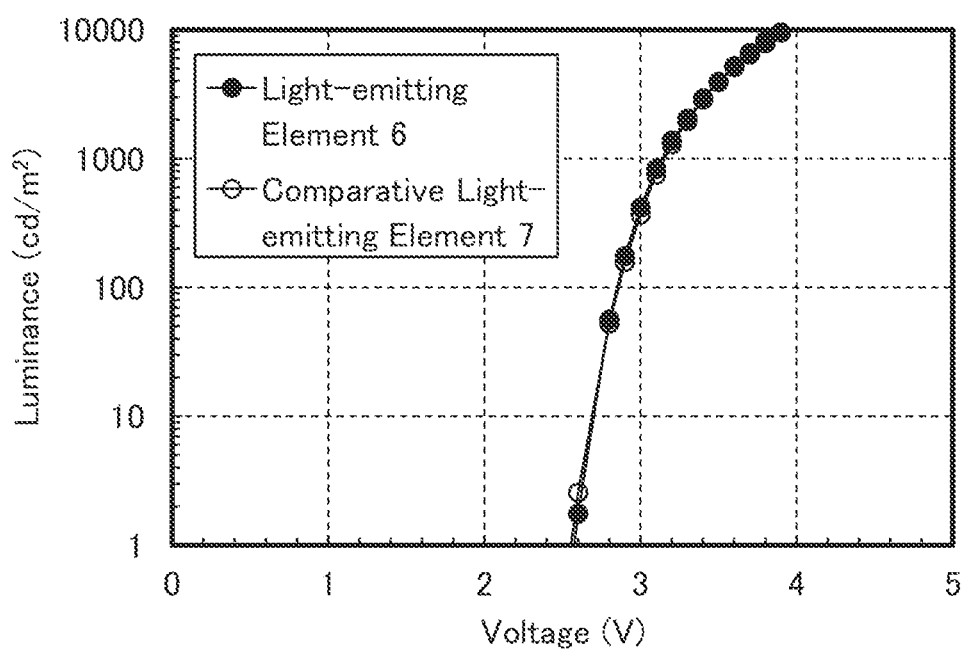
FIG. 40 shows voltage-luminance characteristics of the light-emitting element 6 and the comparative light-emitting element 7.
Figure 41:
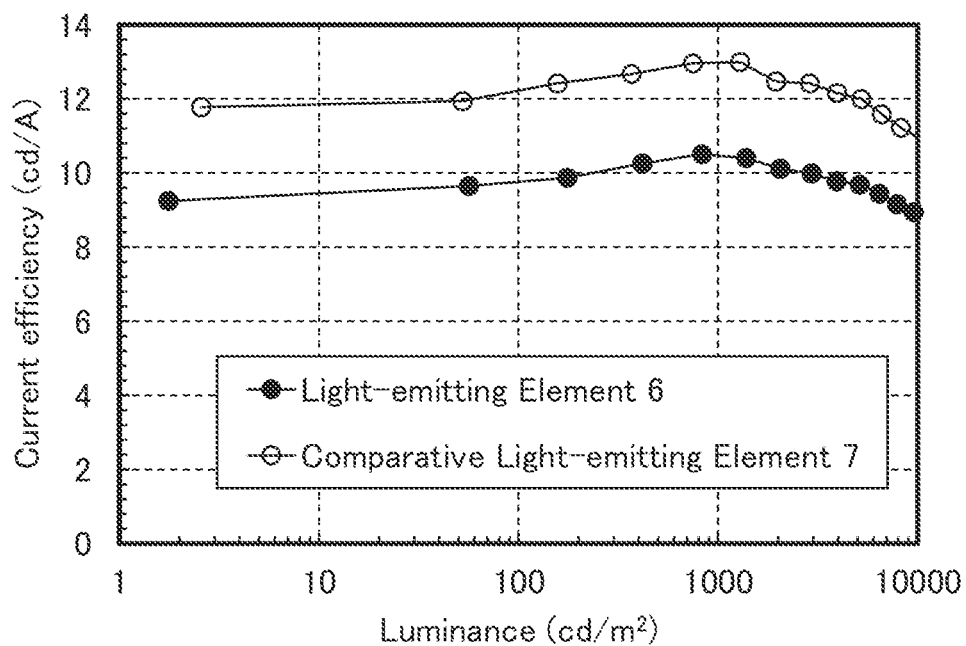
FIG. 41 shows luminance-current efficiency characteristics of the light-emitting element 6 and the comparative light-emitting element 7.
Figure 42:
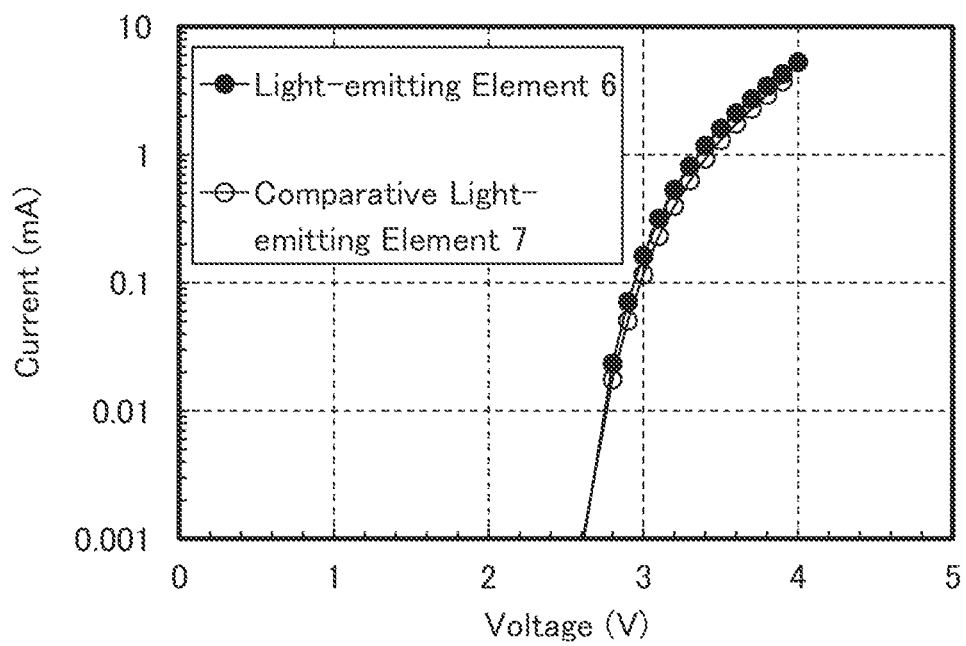
FIG. 42 shows voltage-current characteristics of the light-emitting element 6 and the comparative light-emitting element 7.

FIG. 38 shows emission spectra when current at a current density of 12.5 mA/cm² was applied to the light-emitting elements. As shown in FIG. 38, the emission spectra of the light-emitting elements have peaks at around 475 nm to 458 nm, which suggests that the peaks were derived from light emission of the light-emitting substances contained in the light-emitting layers 913. In addition, the emission spectra have half widths of 40 nm to 45 nm to have extremely sharp shapes, which means that these light-emitting elements exhibit extremely deep blue chromaticities.

Example 13

In this example, a light-emitting element 6 using ch-1,6chBnfAPrn (Structural Formula (142), Example 8) in its light-emitting layer was fabricated as a light-emitting element of one embodiment of the present invention and a comparative light-emitting element 7 using ch-1,6BnfAPrn-02 (Example 9) in its light-emitting layer was fabricated as a reference, and their characteristics were measured.

Element structures of the light-emitting elements used in this example are similar to the element structure described in Example 4 with reference to FIG. 17, and Table 7 shows specific structures of layers in the element structures. Chemical formulae of materials used in this example are shown below.

TABLE 7

| | First electrode | Hole-injection layer | Hole-transport layer | Light-emitting layer | Electron-transport layer | Electron-injection layer | Second electrode |
|---|---|---|---|---|---|---|---|
| Light-emitting element 6 | ITSO (70 nm) | PCPPn:MoOx (4:2, 10 nm) | PCPPn (30 nm) | * | cgDBCzPA (15 nm) | NBphen (10 nm) | LiF (1 nm) | Al (200 nm) |
| Comparative light-emitting element 7 | ITSO (70 nm) | PCPPn:MoOx (4:2, 10 nm) | PCPPn (30 nm) | ** | cgDBCzPA (15 nm) | NBphen (10 nm) | LiF (1 nm) | Al (200 nm) |

*cgDBCzPA:ch-1,6chBnfAPrn (1:0.03, 25 nm)
**cgDBCzPA:ch-1,6BnfAPrn-02 (1:0.03, 25 nm)

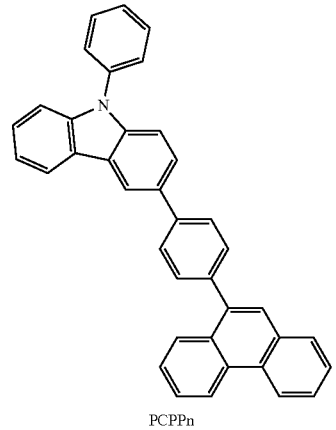 [SMILES: c1ccc(-n2c3ccccc3c3cc(-c4ccc(-c5cc6ccccc6c6ccccc56)cc4)ccc32)cc1]

PCPPn

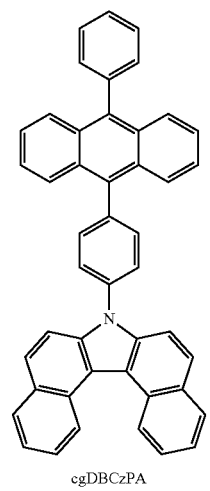 [SMILES: c1ccc(-c2c3ccccc3c(-c3ccc(-n4c5ccc6ccccc6c5c5c6ccccc6ccc54)cc3)c3ccccc23)cc1]

cgDBCzPA

TABLE 7-continued

| First electrode | Hole-injection layer | Hole-transport layer | Light-emitting layer | Electron-transport layer | Electron-injection layer | Second electrode |
| --- | --- | --- | --- | --- | --- | --- | ch-1,6chBnfAPrn
(142)

ch-1,6BnfAPrn-02

NBphen

<<Operation Characteristics of Light-Emitting Elements>>

Operation characteristics of the fabricated light-emitting element 6 and comparative light-emitting element 7 were measured. The measurement was carried out at room temperature. The results are shown in FIGS. 39 to 42.

Table 8 shows initial values of main characteristics of the light-emitting elements at a luminance of approximately 1000 cd/m$^2$.

TABLE 8

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 6 | 3.1 | 0.32 | 7.9 | (0.14, 0.12) | 830 | 11 | 11 | 11 |
| Comparative light-emitting element 7 | 3.1 | 0.23 | 5.8 | (0.14, 0.16) | 750 | 13 | 13 | 11 |

The above results show that the light-emitting element 6 of one embodiment of the present invention fabricated in this example has an external quantum efficiency higher than 10% and a chromaticity of (0.14, 0.12) and that this light-emitting element has high efficiencies and exhibits blue light emission with a high color purity.

Figure 43:
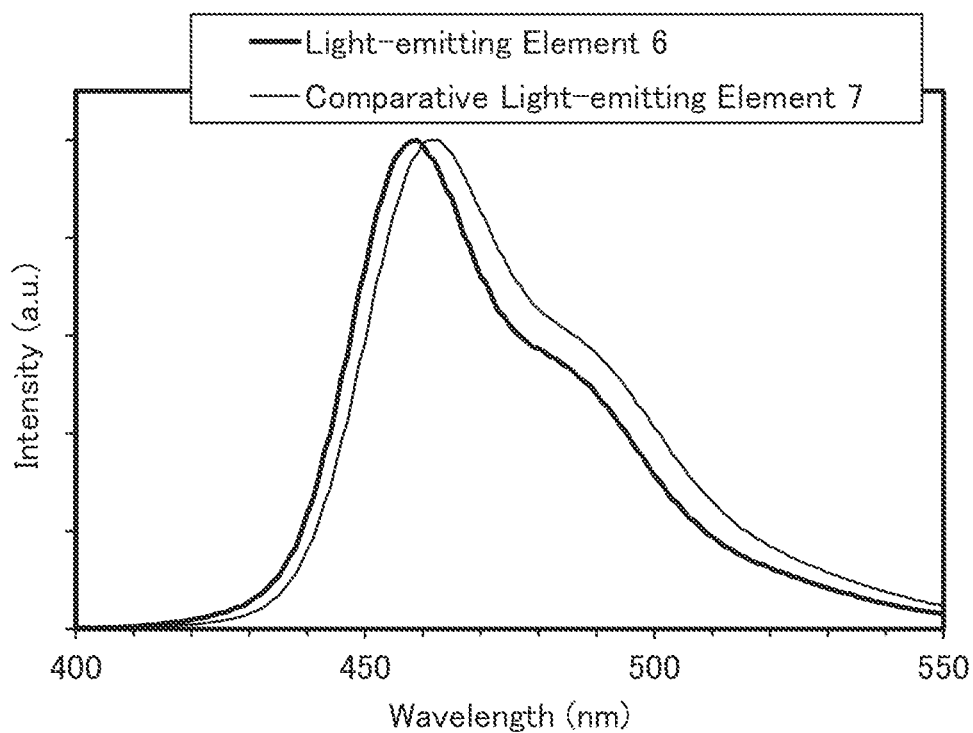
FIG. 43 shows emission spectra of the light-emitting element 6 and the comparative light-emitting element 7.

FIG. 43 shows emission spectra when current at a current density of 12.5 mA/cm$^2$ was applied to the light-emitting elements. As shown in FIG. 43, the emission spectrum of the light-emitting element 6 has a peak at around 458 nm, which suggests that the peak was derived from light emission of ch-1,6chBnfAPrn contained in the light-emitting layer 913. The emission spectrum of the light-emitting element 6 using ch-1,6chBnfAPrn whose benzo[b]naphtho[1,2-d]furan skeleton includes an alkyl group has an emission peak wavelength of 459 nm, which is shorter than the emission peak wavelength (463 nm) of the comparative light-emitting element 7 using ch-1,6BnfAPrn-02 whose benzo[b]naphtho[1,2-d]furan skeleton does not include an alkyl group. Furthermore, the emission spectrum of the light-emitting element 6 has a half width of 43 nm to be narrower than the emission spectrum of the comparative light-emitting element 7, whose half width is 46 nm. These results reveal that the light-emitting element 6 of one embodiment of the present invention exhibits blue light emission with a high color purity.

Figure 44:
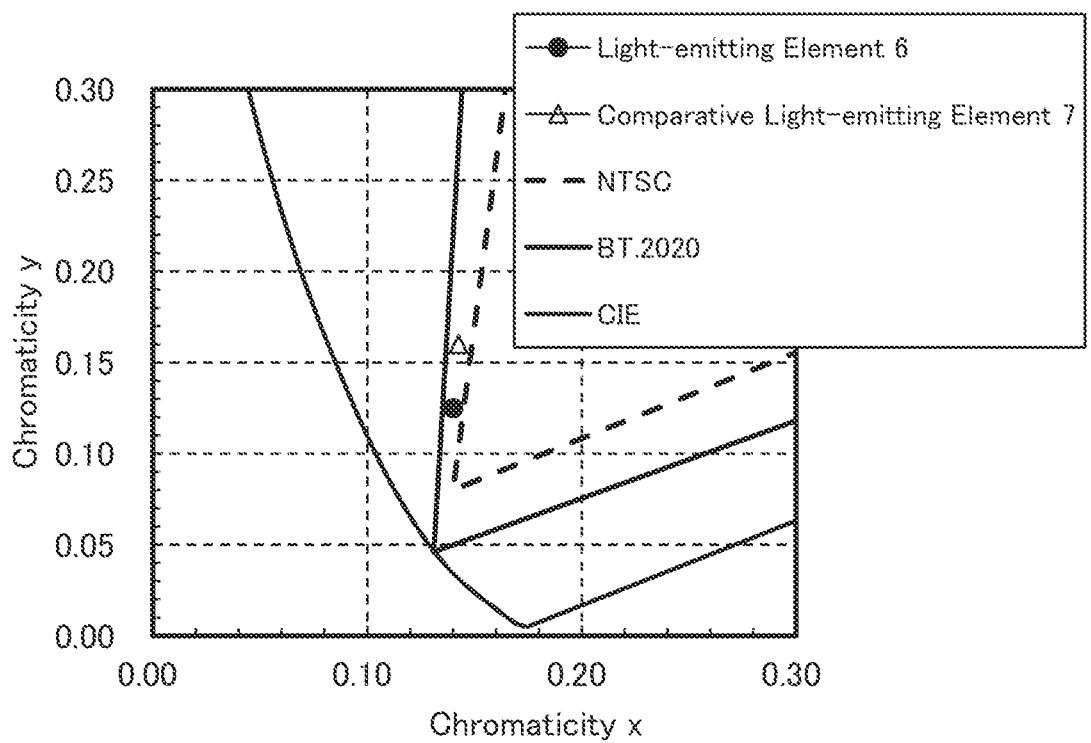
FIG. 44 shows the chromaticities of the light-emitting element 6 and the comparative light-emitting element 7.

Next, the results of measuring the chromaticities (x, y) of the light-emitting element 6 and the comparative light-emitting element 7 fabricated in this example with a luminance colorimeter (BM-5A manufactured by TOPCON CORPORATION) are shown in FIG. 44. According to the results shown in FIG. 44, the chromaticity of the light-emitting element 6 of one embodiment of the present invention represents deeper blue than that of the comparative light-emitting element 7. This proves the significant effect of the alkyl group in the benzo[b]naphtho[1,2-d]furan skeleton in improving chromaticity. Accordingly, an organic compound of one embodiment of the present invention and a light-emitting element using the organic compound can be suitably used for blue light-emitting elements for displays, especially 4K and 8K displays, for example.

REFERENCE NUMERALS

101: first electrode, 102: second electrode, 103: EL layer, 103a, 103b: EL layer, 104: charge-generation layer, 111, 111a, 111b: hole-injection layer, 112, 112a, 112b: hole-transport layer, 113, 113a, 113b: light-emitting layer, 114, 114a, 114b: electron-transport layer, 115, 115a, 115b: electron-injection layer, 201: first substrate, 202: transistor (FET), 203R, 203G, 203B, 203W: light-emitting element, 204: EL layer, 205: second substrate, 206R, 206G, 206B: color filter, 206R', 206G', 206B': color filter, 207: first electrode, 208: second electrode, 209: black layer (black matrix), 210R, 210G: conductive layer, 301: first substrate, 302: pixel portion, 303: driver circuit portion (source line driver circuit), 304a, 304b: driver circuit portion (gate line driver circuit), 305: sealant, 306: second substrate, 307: lead wiring, 308: FPC, 309: FET, 310: FET, 311: FET, 312: FET, 313: first electrode, 314: insulator, 315: EL layer, 316: second electrode, 317: light-emitting element, 318: space, 900: substrate, 901: first electrode, 902: EL layer, 903: second electrode, 911: hole-injection layer, 912: hole-transport layer, 913: light-emitting layer, 914: electron-transport layer, 915: electron-injection layer, 4000: lighting device, 4001: substrate, 4002: light-emitting element, 4003: substrate, 4004: first electrode, 4005: EL layer, 4006: second electrode, 4007: electrode, 4008: electrode, 4009: auxiliary wiring, 4010: insulating layer, 4011: sealing substrate, 4012: sealant, 4013: desiccant, 4015: diffusion plate, 4100: lighting device, 4200: lighting device, 4201: substrate, 4202: light-emitting element, 4204: first electrode, 4205: EL layer, 4206: second electrode, 4207: electrode, 4208: electrode, 4209: auxiliary wiring, 4210: insulating layer, 4211: sealing substrate, 4212: sealant, 4213: barrier film, 4214: planarization film, 4215: diffusion plate, 4300: lighting device, 5101: light, 5102: wheel cover, 5103: door, 5104: display portion, 5105: steering wheel, 5106: gear lever, 5107: seat, 5108: inner rearview mirror, 7000: housing, 7001: display portion, 7002: second display portion, 7003: speaker, 7004: LED lamp, 7005: operation key, 7006: connection terminal, 7007: sensor, 7008: microphone, 7009: switch, 7010: infrared port, 7011: recording medium reading portion, 7012: support, 7013: earphone, 7014: antenna, 7015: shutter button, 7016: image receiving portion, 7018: stand, 7020: camera, 7021: external connection portion, 7022, 7023: operation button, 7024: connection terminal, 7025: band, 7026: clasp, 7027: icon indicating time, 7028: another icon, 8001: lighting device, 8002: lighting device, 8003: lighting device, 8004: lighting device, 9310: portable information terminal, 9311: display portion, 9312: display region, 9313: hinge, and 9315: housing.

This application is based on Japanese Patent Application Serial No. 2017-091582 filed with Japan Patent Office on May 2, 2017, the entire contents of which are hereby incorporated by reference.

The invention claimed is:
1. A compound represented by any one of the below formulae:
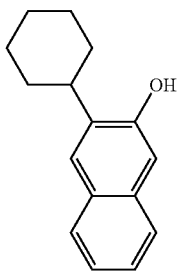 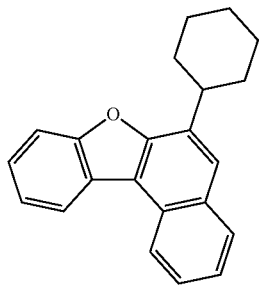
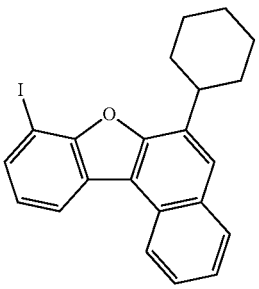
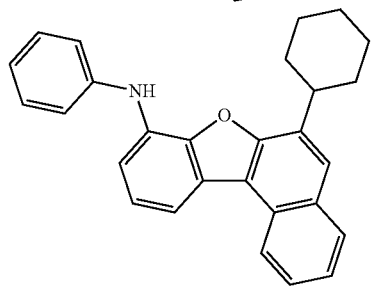
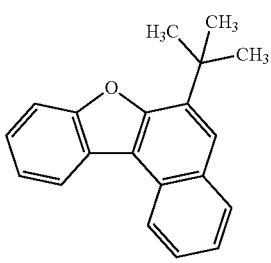
2. A compound represented by any one of the below formulae:
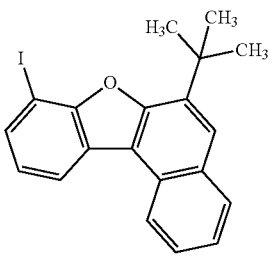
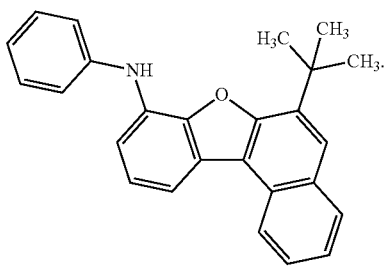
3. A compound represented by any one of the below formulae:
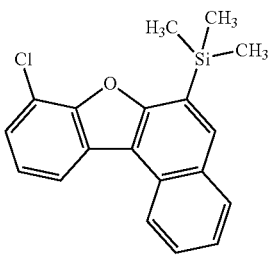
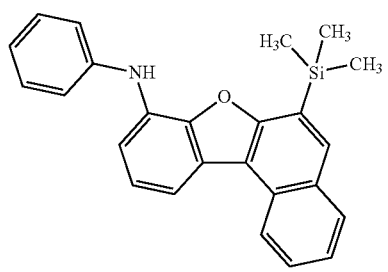
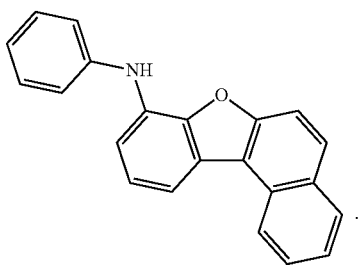
* * * * *